United States Patent
Altenbach et al.

(10) Patent No.: US 10,118,916 B2
(45) Date of Patent: *Nov. 6, 2018

(54) MODULATORS OF CYSTIC FIBROSIS TRANSMEMBRANE CONDUCTANCE REGULATOR PROTEIN

(71) Applicants: AbbVie S.à.r.l., Luxembourg (LU); Galapagos NV, Mechelen (BE)

(72) Inventors: Robert J. Altenbach, Chicago, IL (US); Andrew Bogdan, Evanston, IL (US); Vincent Chan, Evanston, IL (US); Timothy A. Grieme, Chicago, IL (US); John R. Koenig, Chicago, IL (US); Philip R. Kym, Libertyville, IL (US); Bo Liu, Waukegan, IL (US); Karine Fabienne Malagu, Saffron Walden (GB); Sachin V. Patel, Round Lake, IL (US); Marc Scanio, Libertyville, IL (US); Xenia B. Searle, Grayslake, IL (US); Shashank Shekhar, Vernon Hills, IL (US); Xueqing Wang, Northbrook, IL (US); Ming C. Yeung, Grayslake, IL (US)

(73) Assignees: AbbVie S.á.r.l., Luxembourg (LU); Galapagos NV, Mechelen (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,094

(22) Filed: Apr. 25, 2017

(65) Prior Publication Data
US 2017/0305891 A1 Oct. 26, 2017

Related U.S. Application Data

(60) Provisional application No. 62/327,669, filed on Apr. 26, 2016.

(51) Int. Cl.

| | | |
|---|---|---|
| *C07D 407/12* | (2006.01) |
| *A61K 31/36* | (2006.01) |
| *C07D 311/68* | (2006.01) |
| *A61K 31/353* | (2006.01) |
| *C07D 311/70* | (2006.01) |
| *A61K 31/352* | (2006.01) |
| *C07D 311/58* | (2006.01) |
| *C07D 311/60* | (2006.01) |
| *C07D 407/14* | (2006.01) |

(52) U.S. Cl.
CPC .......... *C07D 407/12* (2013.01); *A61K 31/352* (2013.01); *A61K 31/353* (2013.01); *A61K 31/36* (2013.01); *C07D 311/58* (2013.01); *C07D 311/60* (2013.01); *C07D 311/68* (2013.01); *C07D 311/70* (2013.01); *C07D 407/14* (2013.01)

(58) Field of Classification Search
CPC .. C07D 407/12; C07D 311/70; C07D 311/68; A61K 31/36; A61K 31/353
See application file for complete search history.

(56) References Cited

U.S. PATENT DOCUMENTS

| | | | |
|---|---|---|---|
| 8,999,976 B2 | 4/2015 | Binch et al. |
| 9,642,831 B2* | 5/2017 | Altenbach ............ A61K 31/353 |
| 2008/0176899 A1 | 7/2008 | Ruah et al. |
| 2014/0163035 A1* | 6/2014 | Hilpert ............... C07D 491/048 |
| | | | 514/248 |

FOREIGN PATENT DOCUMENTS

| | | |
|---|---|---|
| WO | 2005120497 A2 | 12/2005 |
| WO | 2006002421 A2 | 1/2006 |
| WO | 2008147952 A1 | 12/2008 |
| WO | 2009006315 A1 | 1/2009 |
| WO | 2009074575 A2 | 6/2009 |
| WO | 2009076593 A1 | 6/2009 |
| WO | 2009108657 A2 | 9/2009 |
| WO | 2010048573 A1 | 4/2010 |
| WO | 2011072241 A1 | 6/2011 |
| WO | 2011113894 A1 | 9/2011 |
| WO | 2012048181 A1 | 4/2012 |
| WO | 2012083165 A1 | 6/2012 |
| WO | 2013038373 A1 | 3/2013 |

(Continued)

OTHER PUBLICATIONS

International Search Report and Written Opinion issued in corresponding PCT Application No. PCT/IB2017/052349, dated Jun. 22, 2017, 14 pages.

(Continued)

*Primary Examiner* — Sudhakar Katakam
(74) *Attorney, Agent, or Firm* — Quarles & Brady LLP

(57) ABSTRACT

The present invention provides for compounds of formula (I)

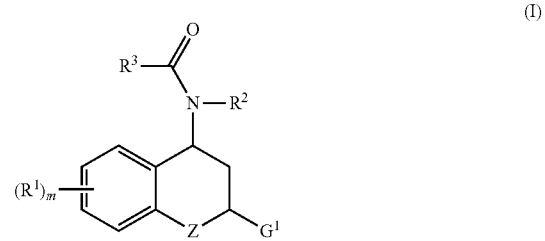

wherein $R^1$, m, Z, $G^1$, $R^2$, and $R^3$ have any of the values defined in the specification, and pharmaceutically acceptable salts thereof, that are useful as agents in the treatment of diseases and conditions mediated and modulated by CFTR, including cystic fibrosis, Sjögren's syndrome, pancreatic insufficiency, chronic obstructive lung disease, and chronic obstructive airway disease. Also provided are pharmaceutical compositions comprised of one or more compounds of formula (I).

50 Claims, No Drawings

(56) References Cited

FOREIGN PATENT DOCUMENTS

| WO | 2013038378 A1 | 3/2013 |
|---|---|---|
| WO | 2013038381 A1 | 3/2013 |
| WO | 2013038386 A1 | 3/2013 |
| WO | 2013038390 A1 | 3/2013 |
| WO | 2013043720 A1 | 3/2013 |
| WO | 2014180562 A1 | 12/2014 |
| WO | 2015018823 A1 | 2/2015 |
| WO | 2015138909 A1 | 9/2015 |
| WO | 2015138934 A1 | 9/2015 |
| WO | 2016069757 A1 | 5/2016 |
| WO | 2017009804 A1 | 1/2017 |

OTHER PUBLICATIONS

Quinton, P.M., 1990. Cystic fibrosis: a disease in electrolyte transport. FASEB J. 4, 2709-2717.

Kerem, B., Rommens, J.M., Buchanan, J.A., Markiewicz, D., Cox, T.K., Chakravarti, A., Buchwald, M., Tsui, L.C., 1989. Identification of the cystic fibrosis gene: genetic analysis. Science 245, 1073-1080.

Bobadilla, J.L., Macek, M., Jr, Fine, J.P., Farrell, P.M., 2002. Cystic fibrosis: a worldwide analysis of CFTR mutations—correlation with incidence data and application to screening. Hum. Mutat. 19, 575-606. doi:10.1002/humu.10041.

Pasyk, E.A., Foskett, J.K., 1995. Mutant (ΔF508) Cystic Fibrosis Transmembrane Conductance Regulator Cl-Channel Is Functional When Retained in Endoplasmic Reticulum of Mammalian Cells. J. Biol. Chem. 270, 12347-12350.

Morello, J.-P., Bouvier, M., Petäjä-Repo, U.E., Bichet, D.G., 2000. Pharmacological chaperones: a new twist on receptor folding. Trends Pharmacol. Sci. 21, 466-469. doi:10.1016/S0165-6147(00)01575-3.

Shastry, B.S., 2003. Neurodegenerative disorders of protein aggregation. Neurochem. Int. 43, 1-7. doi:10.1016/S0197-0186(02)00196-1.

Zhang, W., Fujii, N., Naren, A.P., 2012. Recent advances and new perspectives in targeting CFTR for therapy of cystic fibrosis and enterotoxin-induced secretory diarrheas. Future Med. Chem. 4, 329-345. doi:10.4155/fmc.12.1.

IUPAC 1974 Recommendations for Section E, Fundamental Stereochemistry, in Pure Appl. Chem., 1976, 45: 13-30.

Neuberger T, Burton B, Clark H and VanGoor F; Cystic Fibrosis, Methods in Mole Biol 741; eds. Amaral MD and Kunzelmann K, 2011.

S. M. Berge et al. J. Pharmaceutical Sciences, 1977, 66: 1-19.

Tanuwidjaja, J.; Ellman, J.A. et al. J. Org. Chem. 2007, 72, 626.

Veit Get al, (2012) Mol Biol Cell. 23(21): 4188-4202.

\* cited by examiner

MODULATORS OF CYSTIC FIBROSIS TRANSMEMBRANE CONDUCTANCE REGULATOR PROTEIN

CROSS-REFERENCE TO RELATED APPLICATION

This application claims priority to U.S. provisional application 62/327,669, filed Apr. 26, 2016, which is incorporated by reference herein.

BACKGROUND OF THE INVENTION

Technical Field

The invention relates to substituted tricyclic compounds that are modulators of the Cystic Fibrosis Transmembrane Conductance Regulator (CFTR) protein, useful in treating diseases and conditions mediated and modulated by CFTR. Additionally, the invention relates to compositions containing compounds of the invention and processes for their preparation.

Description of Related Technology

ABC transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cells types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue (Quinton, P. M., 1990. Cystic fibrosis: a disease in electrolyte transport. FASEB J. 4, 2709-2717).

The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis (CF) is caused by a defect in this gene which induces mutations in CFTR. Cystic fibrosis is the most common fatal genetic disease in humans, and affects ~0.04% of white individuals (Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi:10.1002/humu.10041), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations has been identified through sequence analysis of the CFTR gene of CF chromosomes (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). ΔF508-CFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if ΔF508-CFTR is allowed to reach the cell plasma membrane by low-temperature (27° C.) rescue where it can function as a cAMP-activated chloride channel, its activity is decreased significantly compared with WT-CFTR (Pasyk, E. A., Foskett, J. K., 1995. Mutant (&F508) Cystic Fibrosis Transmembrane Conductance Regulator Cl-Channel Is Functional When Retained in Endoplasmic Reticulum of Mammalian Cells. J. Biol. Chem. 270, 12347-12350).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, and G1349D. Mutations affecting chloride conductance have a CFTR protein that is correctly trafficked to the cell membrane but that generates reduced chloride flow (e.g. missense mutations located within the membrane-spanning domain), examples of these mutations are R117H and R334W.

In addition to cystic fibrosis, CFTR activity modulation may be beneficial for other diseases not directly caused by mutations in CFTR, such as, for example, chronic obstructive pulmonary disease (COPD), dry eye disease, and Sjögren's syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjögren's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjögren's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjögren's syndrome is also associated with rheumatoid arthritis, systemic lupus, systemic sclerosis, and polymypositis/dermatomyositis. The cause of the disease is believed to lie in defective protein trafficking, for which treatment options are limited. As a consequence, modulation of CFTR activity may help hydrating the various organs and help to elevate the associated symptoms.

In addition to CF, the defective protein trafficking induced by the ΔF508-CFTR has been shown to be the underlying basis for a wide range of other diseases, in particular diseases where the defective functioning of the endoplasmic reticulum (ER) may either prevent the CFTR protein to exit the cell, and/or the misfolded protein is degraded (Morello, J.-P., Bouvier, M., Petäjä-Repo, U. E., Bichet, D. G., 2000. Pharmacological chaperones: a new twist on receptor folding. Trends Pharmacol. Sci. 21, 466-469. doi:10.1016/S0165-6147(00)01575-3; Shastry, B. S., 2003. Neurodegenerative disorders of protein aggregation. Neurochem. Int. 43, 1-7. doi:10.1016/S0197-0186(02)00196-1; Zhang, W., Fujii, N., Naren, A. P., 2012. Recent advances and new perspectives in targeting CFTR for therapy of cystic fibrosis and enterotoxin-induced secretory diarrheas. Future Med. Chem. 4, 329-345. doi:10.4155/fmc.12.1).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurophyseal DI (vasopvessin hormoneN2-receptor), neprogenic DI (aquaporin II), Charcot-Marie Tooth syndrome (peripheral myelin protein 22), Perlizaeus-Merzbacher disease, neurodegenerative diseases such as Alzheimer's disease (APP and presenilins), Parkinson's disease, amyotrophic lateral sclerosis, progressive supranuclear palsy, Pick's disease, several polyglutamine neurological disorders such as Huntington's disease, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (prion protein processing defect), Fabry disease (lysosomal α-galactosidase A), Straussler-Scheinker syndrome, chronic obstructive pulmonary disease (COPD), dry eye disease, and Sjögren's Syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrhoeas, and results in dehydration, acidosis, impaired growth and death. Acute and chronic diarrhoeas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhoea is a dangerous condition.

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect the present invention provides for compounds of formula (I)

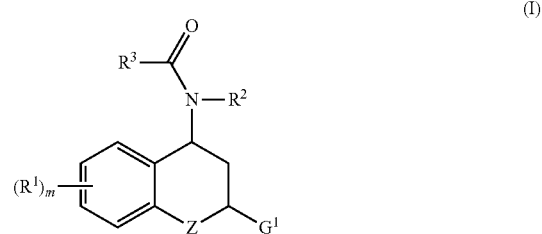

or a pharmaceutically acceptable salt thereof, wherein
Z is O or N($R^{z1}$) wherein $R^{z1}$ is hydrogen or $C_1$-$C_3$ alkyl;
$R^1$ groups are optional substituents on the benzo ring, and are each independently halogen, —CN, $C_1$-$C_3$ alkyl, $C_1$-$C_3$ haloalkyl, —$OR^j$, or —$SR^j$;
m is 0, 1, 2, 3, or 4;
$R^2$ is hydrogen or $C_1$-$C_3$ alkyl;
$R^3$ is formula (a)

wherein
$R^{3a}$ and $R^{3b}$ are each independently $C_1$-$C_3$ alkyl; or $R^{3a}$ and $R^{3b}$ together with the carbon atom to which they are attached, form a cyclopropyl, a cyclobutyl, or a cyclopentyl; wherein the cyclopropyl, the cyclobutyl, and the cyclopentyl are each optionally substituted with 1, 2, 3, or 4 substituents independently selected from the group consisting of $C_1$-$C_3$ alkyl, $C_1$-$C_3$ haloalkyl, and halogen; and $G^2$ is formula (b), phenyl, or —O-phenyl, wherein the phenyl and the phenyl moiety of —O-phenyl are each optionally substituted with 1, 2, 3, or 4 $R^x$ groups;

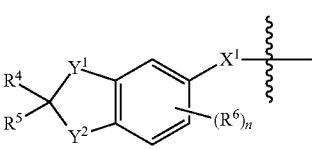

(b)

wherein
each $R^x$ is independently halogen, —CN, $C_1$-$C_6$ alkyl, $C_1$-$C_6$ haloalkyl, —$OR^j$, or —$SR^j$;
$X^1$ is a bond or O;
$Y^1$ is O, $CH_2$, or —O—$CH_2$— wherein the —O—$CH_2$- is connected to the benzo ring via the oxygen atom;
$Y^2$ is O;
$R^4$ and $R^5$ are each independently hydrogen or halogen;
$R^6$ groups are optional substituents on the benzo ring, and are each independently $C_1$-$C_3$ alkyl, $C_1$-$C_3$ haloalkyl, halogen, —CN, —$OR^j$, or —$SR^j$; and
n is 0, 1, 2, or 3;
or $R^3$ is formula (c)

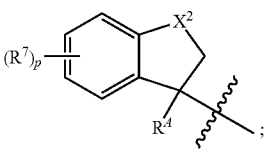

(c)

wherein
$X^2$ is O or $CH_2$;
$R^A$ is $C_1$-$C_3$ alkyl;
$R^7$ groups are optional substituents on the benzo ring, and are each independently halogen, —CN, $C_1$-$C_6$ alkyl, $C_1$-$C_6$ haloalkyl, —$OR^j$, or —$SR^j$; and
p is 0, 1, 2, 3, or 4;
or $R^3$ is formula (d)

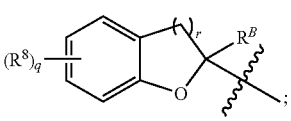

(d)

wherein
r is 1 or 2;
q is 0, 1, 2, 3, or 4;
$R^B$ is $C_1$-$C_3$ alkyl;

$R^8$ groups are optional substituents on the benzo ring, and are each independently halogen, —CN, $C_1$-$C_6$ alkyl, $C_1$-$C_6$ haloalkyl, —$OR^j$, or —$SR^j$;
$G^1$ is phenyl, monocyclic heteroaryl, or $C_3$-$C_6$ cycloalkyl; wherein each $G^1$ is optionally substituted with 1, 2, 3, or 4 $R^9$ groups;
each $R^9$ is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$ alkylenyl)-$OR^j$, —($C_1$-$C_6$ alkylenyl)-$OC(O)R^k$, —($C_1$-$C_6$ alkylenyl)-$OC(O)N(R^j)_2$, —($C_1$-$C_6$ alkylenyl)-$SR^j$, —($C_1$-$C_6$ alkylenyl)-$S(O)_2R^j$, —($C_1$-$C_6$ alkylenyl)-$S(O)_2N(R^j)_2$, —($C_1$-$C_6$ alkylenyl)-$C(O)R^j$, —($C_1$-$C_6$ alkylenyl)-$C(O)OR^j$, —($C_1$-$C_6$ alkylenyl)-$C(O)N(R^j)_2$, —($C_1$-$C_6$ alkylenyl)-$C(O)N(R^j)S(O)_2R^k$, —($C_1$-$C_6$ alkylenyl)-$N(R^j)_2$, —($C_1$-$C_6$ alkylenyl)-$N(R^j)C(O)R^k$, —($C_1$-$C_6$ alkylenyl)-$N(R^j)S(O)_2R^k$, —($C_1$-$C_6$ alkylenyl)-$N(R^j)C(O)O(R^k)$, —($C_1$-$C_6$ alkylenyl)-$N(R^j)C(O)N(R^j)_2$, or —($C_1$-$C_6$ alkylenyl)-CN;

$R^j$, at each occurrence, is independently hydrogen, $C_1$-$C_6$ alkyl, or $C_1$-$C_6$ haloalkyl; and
$R^k$, at each occurrence, is independently $C_1$-$C_6$ alkyl or $C_1$-$C_6$ haloalkyl;
with the proviso that when $R^2$ is hydrogen, Z is O, $R^3$ is formula (a), $R^{3a}$ and $R^{3b}$ together with the carbon atom to which they are attached form an unsubstituted cyclopropyl, and $G^2$ is formula (b) wherein $Y^1$ is O, $R^4$ and $R^5$ are halogen, $X^1$ is a bond, n is 0 or 1, and $R^6$ is halogen; then $G^1$ is optionally substituted pyrimidinyl, optionally substituted pyridazinyl, optionally substituted pyrazinyl, or

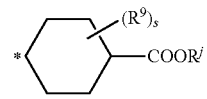

wherein * is the point of connection, $R^9$ is $C_1$-$C_3$ alkyl, $C_1$-$C_3$ haloalkyl, or halogen; and s is 0, 1, 2, or 3.

Another aspect of the invention relates to pharmaceutical compositions comprising a compound of the invention, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

Yet another aspect of the invention relates to a method for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of cystic fibrosis. In a particular aspect, the compounds of the invention are provided for use in the treatment of cystic fibrosis caused by class I, II, III, IV, V, and/or VI mutations.

The present invention also provides pharmaceutical compositions comprising a compound of the invention, and a suitable pharmaceutical carrier for use in medicine. In a particular aspect, the pharmaceutical composition is for use in the treatment of cystic fibrosis.

These and other objects of the invention are described in the following paragraphs. These objects should not be deemed to narrow the scope of the invention.

DETAILED DESCRIPTION OF THE INVENTION

Described herein are compounds of formula (I)

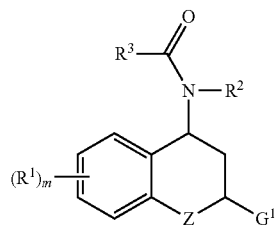

(I)

wherein $R^1$, $R^2$, $R^3$, $G^1$, m, and Z are defined above in the Summary of the Invention and below in the Detailed Description. Further, compositions comprising such compounds and methods for treating conditions and disorders using such compounds and compositions are also described.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of $C_2$-$C_6$ alkenyl include buta-1,3-dienyl, ethenyl, 2-propenyl, 2-methyl-2-propenyl, 3-butenyl, 4-pentenyl, and 5-hexenyl.

The term "alkyl" as used herein, means a saturated, straight or branched hydrocarbon chain radical. In some instances, the number of carbon atoms in an alkyl moiety is indicated by the prefix "$C_x$-$C_y$," wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —CH$_2$—, —CH$_2$CH$_2$—, —C((CH$_3$)$_2$)—CH$_2$CH$_2$CH$_2$—, —C((CH$_3$)$_2$)—CH$_2$CH$_2$—, —CH$_2$CH$_2$CH$_2$CH$_2$—, and —CH$_2$CH(CH$_3$)CH$_2$—.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited, to acetylenyl, 1-propynyl, 2-propynyl, 3-butynyl, 2-pentynyl, and 1-butynyl.

The term "$C_3$-$C_6$ cycloalkyl" as used herein, means cyclopropyl, cyclobutyl, cyclopentyl, and cyclohexyl, each of which is optionally substituted unless otherwise indicated.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "monocyclic heteroaryl" as used herein, means a 5- or 6-membered monocyclic aromatic ring. The five-membered ring contains two double bonds. The five membered ring may contain one heteroatom selected from the group consisting of O and S; or one, two, three, or four nitrogen atoms and optionally one oxygen or one sulfur atom. The six-membered ring contains three double bonds and one, two, three, or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The monocyclic heteroaryls, including exemplary rings, are optionally substituted unless otherwise indicated. The monocyclic heteroaryls are connected to the parent molecular moiety through any substitutable carbon atom or any substitutable nitrogen atom contained within the ring systems. The nitrogen atom in the heteroaryl rings may optionally be oxidized and may optionally be quarternized.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

The term 'one or more' refers to one to four. In another embodiment it refers to one to three. In a further embodiment it refers to one to two. In yet other embodiment it refers to two. In yet other further embodiment it refers to one.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G; G1349D; S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326delTC, or 4279insA mutations. More particularly, Class VI mutation(s) refers to Rescued F508del mutations.

Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments, Z is O.

In certain embodiments, Z is $N(R^{z1})$ wherein $R^{z1}$ is hydrogen.

In certain embodiments, m is 0, 1, or 2.

In certain embodiments, m is 0 or 1.

In certain embodiments, m is 0.

In certain embodiments, m is 1.

In certain embodiments, $R^1$, if present, is halogen, $C_1$-$C_3$ alkyl, $C_1$-$C_3$ haloalkyl, or —$OR^j$.

In certain embodiments, $R^1$, if present, is F, $CH_3$, $CF_3$, —$OCH_3$, —$OCHF_2$, or —$OCH_2CH_2F$.

In certain embodiments, $R^1$, if present, is —$OR^j$ wherein $R^j$ is $C_1$-$C_6$ alkyl or $C_1$-$C_6$ haloalkyl.

In certain embodiments, $R^1$, if present, is —$OCH_3$, —$OCF_3$, or —$OCHF_2$.

In certain embodiments, $R^2$ is hydrogen.

In certain embodiments, $R^2$ is $C_1$-$C_3$ alkyl. In some such embodiments, $R^2$ is methyl.

In certain embodiments, $G^1$ is phenyl, pyridinyl, pyrimidinyl, pyridazinyl, pyrazinyl, thiazolyl, thienyl, cyclopropyl, or cyclohexyl; each of which is optionally substituted with 1, 2, 3, or 4 independently selected $R^9$ groups. In some such embodiments $G^1$ is substituted.

In certain embodiments, $G^1$ is phenyl or cyclohexyl, each of which is optionally substituted with 1, 2, 3, or 4 independently selected $R^9$ groups. In some such embodiments $G^1$ is substituted.

In certain embodiments, $G^1$ is phenyl optionally substituted with 1, 2, 3, or 4 independently selected $R^9$ groups. In some such embodiments the phenyl is substituted.

In certain embodiments, $G^1$ is monocyclic heteroaryl which is optionally substituted with 1, 2, 3, or 4 independently selected $R^9$ groups. In some such embodiments the monocyclic heteroaryl is substituted.

In certain embodiments, $G^1$ is pyridinyl optionally substituted with 1, 2, 3, or 4 independently selected $R^9$ groups. In some such embodiments the pyridinyl is substituted.

In certain embodiments, $G^1$ is pyrimidinyl, pyridazinyl, or pyrazinyl; each of which is optionally substituted with 1, 2, 3, or 4 independently selected $R^9$ groups. In some such embodiments $G^1$ is substituted.

In certain embodiments, $G^1$ is $C_3$-$C_6$ cycloalkyl which is optionally substituted with 1, 2, 3, or 4 independently selected $R^9$ groups. In some such embodiments the $C_3$-$C_6$ cycloalkyl is substituted.

In certain embodiments, $G^1$ is cyclopropyl or cyclohexyl, each of which is optionally substituted with 1, 2, 3, or 4 independently selected $R^9$ groups. In some such embodiments $G^1$ is substituted.

In certain embodiments, $G^1$ is cyclohexyl optionally substituted with 1, 2, 3, or 4 independently selected $R^9$ groups. In some such embodiments the cyclohexyl is substituted.

In certain embodiments, $G^1$ is cyclopropyl optionally substituted with 1, 2, 3, or 4 independently selected $R^9$ groups. In some such embodiments the cyclopropyl is substituted.

In certain embodiments, each $G^1$ (including the exemplary rings) is optionally substituted with 1, 2, 3, or 4 $R^9$ groups.

In certain embodiments, each $G^1$ (including the exemplary rings) is unsubstituted.

In certain embodiments, each $G^1$ (including the exemplary rings) is substituted with 1, 2, 3, or 4 $R^9$ groups.

In certain embodiments, each $R^9$, when present, is independently $C_1$-$C_6$ alkyl, halogen, $C_1$-$C_6$ haloalkyl, —CN, —$OR^j$, —$SR^j$, —$S(O)_2R^j$, —$S(O)_2N(R^j)_2$, —$C(O)R^j$, —$C(O)OR^j$, —$C(O)N(R^j)_2$, or —$C(O)N(R^j)S(O)_2R^k$.

In certain embodiments, each $R^9$, when present, is independently —$OR^j$ or —$C(O)OR^j$.

In certain embodiments, $G^1$ (including specific examples) is substituted with 1, 2, 3, or 4 independently selected $R^9$ groups, wherein one of the $R^9$ groups is —$OR^j$ or —$C(O)OR^j$, and the other 1, 2, or 3 optional $R^9$ groups are independently $C_1$-$C_3$ alkyl, halogen, or $C_1$-$C_3$ haloalkyl. In some such embodiments, $R^j$ of —$C(O)OR^j$ is $C_1$-$C_6$ alkyl. In some such embodiments, $R^j$ of —$C(O)OR^j$ is hydrogen.

In certain embodiments, $G^1$ (including specific examples) is substituted with 1, 2, 3, or 4 independently selected $R^9$ groups, wherein one of the $R^9$ groups is —$C(O)OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl. In some such embodiments, $R^j$ of —$C(O)OR^j$ is hydrogen. In some such embodiments, $R^j$ of —$C(O)OR^j$ is $C_1$-$C_6$ alkyl.

In certain embodiments, $G^1$ (including specific examples) is substituted with one $R^9$ group, and $R^9$ is —$C(O)OR^j$ wherein $R^j$ is hydrogen or $C_1$-$C_6$ alkyl. In some such embodiments, $R^j$ of —$C(O)OR^j$ is hydrogen. In some such embodiments, $R^j$ of —$C(O)OR^j$ is $C_1$-$C_6$ alkyl.

In certain embodiments, $G^1$ is

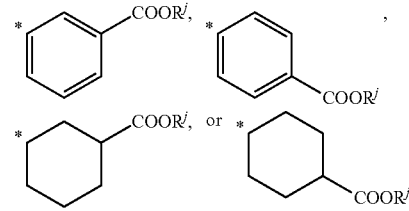

wherein * is the point of connection, and $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, the phenyl and the pyridinyl of $G^1$ is

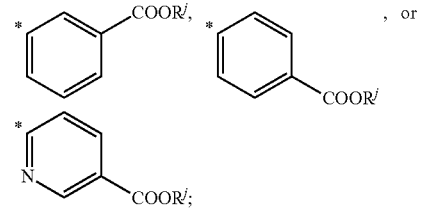

wherein * is the point of connection, and $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, the cyclohexyl of $G^1$ is

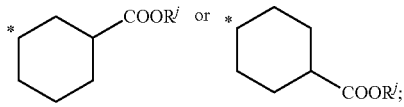

wherein * is the point of connection, and $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, the cyclohexyl of $G^1$ is

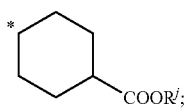

wherein * is the point of connection, and $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $R^3$ is formula (a). Thus, certain embodiments are directed to compounds of formula (I-a)

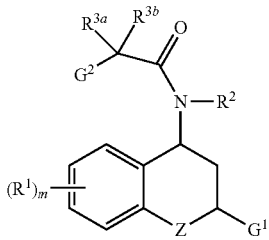

(I-a)

wherein $R^1$, m, Z, $G^1$, $R^2$, $G^2$, $R^{3a}$, and $R^{3b}$, have values as disclosed in the Summary and embodiments herein above and below.

Certain embodiments are directed to compounds of formula (I-a-i)

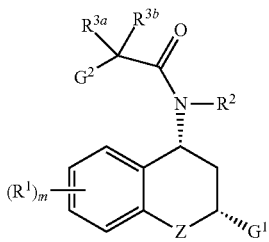

(I-a-i)

wherein $R^1$, m, Z, $G^1$, $R^2$, $G^2$, $R^{3a}$, and $R^{3b}$, have values as disclosed in the Summary and embodiments herein above and below.

In certain embodiments, $G^2$ is phenyl or —O-phenyl, wherein the phenyl and the phenyl moiety of —O-phenyl are each optionally substituted.

In certain embodiments, $G^2$ is optionally substituted phenyl.

In certain embodiments, $G^2$ is formula (b).

In certain embodiments, $G^2$ is formula (b) wherein $X^1$ is O.

In certain embodiments, $G^2$ is formula (b) wherein $X^1$ is a bond. Thus, certain embodiments are directed to compounds of formula (I-a-ii)

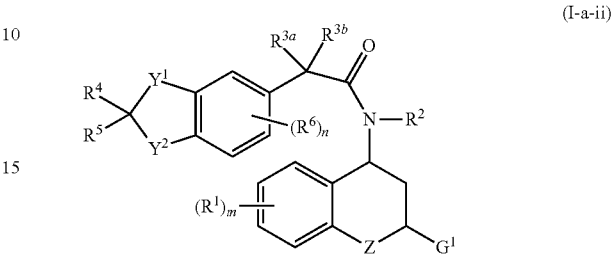

(I-a-ii)

wherein $R^1$, m, Z, $G^1$, $R^2$, $R^{3a}$, $R^{3b}$, $R^6$, n, $Y^1$, $Y^2$, $R^4$, and $R^5$ have values as disclosed in the Summary and embodiments herein above and below.

Certain embodiments are directed to compounds of formula (I-a-iii)

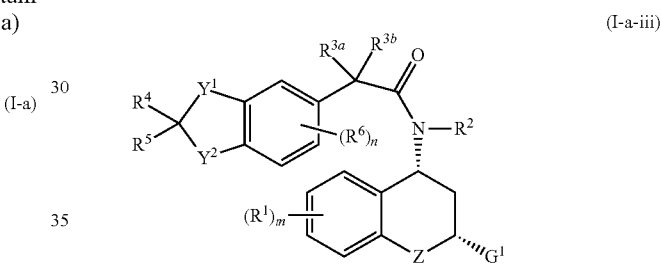

(I-a-iii)

wherein $R^1$, m, Z, $G^1$, $R^2$, $R^{3a}$, $R^{3b}$, $R^6$, n, $Y^1$, $Y^2$, $R^4$, and $R^5$ have values as disclosed in the Summary and embodiments herein above and below.

In certain embodiments, $R^{3a}$ and $R^{3b}$ are methyl; or $R^{3a}$ and $R^{3b}$ together with the carbon atom to which they are attached form an optionally substituted cyclopropyl.

In certain embodiments, $R^{3a}$ and $R^{3b}$ are each independently $C_1$-$C_3$ alkyl. In some such embodiments, $R^{3a}$ and $R^{3b}$ are each independently methyl or ethyl.

In certain embodiments, $R^{3a}$ and $R^{3b}$ are methyl.

In certain embodiments, $R^{3a}$ and $R^{3b}$ together with the carbon atom to which they are attached, form a cyclopropyl, a cyclobutyl, or a cyclopentyl; wherein the cyclopropyl, the cyclobutyl, and the cyclopentyl are each optionally substituted. In some such embodiments, $R^{3a}$ and $R^{3b}$ together with the carbon atom to which they are attached, form a cyclopropyl or a cyclobutyl; wherein the cyclopropyl and the cyclobutyl are each optionally substituted.

In certain embodiments, $R^{3a}$ and $R^{3b}$ together with the carbon atom to which they are attached form an optionally substituted cyclopropyl. In some such embodiments, the cyclopropyl is optionally substituted with one or two halogens. In some such embodiments, the cyclopropyl is optionally substituted with two halogens. In some such embodiments, the cyclopropyl is unsubstituted. In some such embodiments, the cyclopropyl is substituted. In some such embodiments, the cyclopropyl is substituted with 1 or 2 halogens. In some such embodiments, the halogen is F.

In certain embodiments, n is 0 or 1.

In certain embodiments, n is 1.

In certain embodiments, n is 0.

In certain embodiments, $R^6$ is halogen.

In certain embodiments, $R^4$ and $R^5$ are hydrogen or $R^4$ and $R^5$ are halogen.

In certain embodiments, $R^4$ and $R^5$ are hydrogen.

In certain embodiments, $R^4$ and $R^5$ are halogen.

In certain embodiments, $R^4$ and $R^5$ are F.

In certain embodiments, $Y^1$ is O.

In certain embodiments, $Y^1$ is $CH_2$.

In certain embodiments, $Y^1$ is —O—$CH_2$—.

In certain embodiments, $R^3$ is formula (c). Thus, certain embodiments are directed to compounds of formula (I-c)

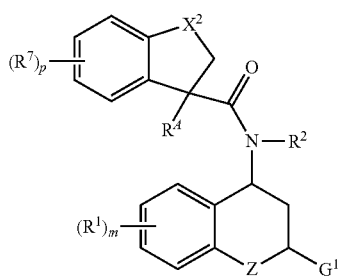

(I-c)

wherein $R^1$, m, Z, $G^1$, $R^2$, $X^2$, $R^A$, $R^7$, and p have values as disclosed in the Summary and embodiments herein above and below.

Certain embodiments are directed to compounds of formula (I-c-i)

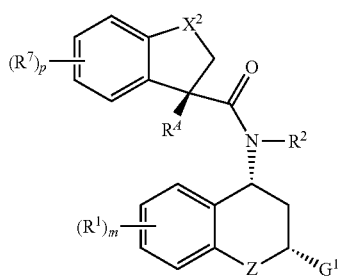

(I-c-i)

wherein $R^1$, m, Z, $G^1$, $R^2$, $X^2$, $R^A$, $R^7$, and p have values as disclosed in the Summary and embodiments herein above and below.

In certain embodiments, $X^2$ is O.

In certain embodiments, $X^2$ is $CH_2$.

In certain embodiments, $R^A$ is methyl.

In certain embodiments, p is 0, 1, or 2.

In certain embodiments, each $R^7$ is independently halogen, $C_1$-$C_6$ alkyl, $C_1$-$C_6$ haloalkyl, or —$OR^j$.

In certain embodiments, each $R^7$ is independently $CH_3$, —$OCH_3$, —$OCF_3$, or Cl.

In certain embodiments, $R^3$ is formula (d). Thus, certain embodiments are directed to compounds of formula (I-d)

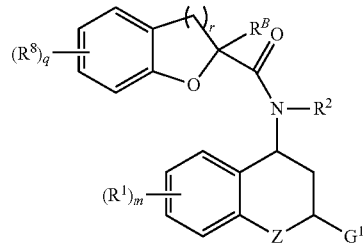

(I-d)

wherein $R^1$, m, Z, $G^1$, $R^2$, $R^B$, $R^8$, q, and r have values as disclosed in the Summary and embodiments herein above and below.

In certain embodiments, r is 1.

In certain embodiments, r is 2.

In certain embodiments, $R^B$ is methyl.

In certain embodiments, q is 0, 1, or 2.

In certain embodiments, $R^8$ is halogen.

Various embodiments of substituents Z, m, $R^1$, $R^2$, $G^1$, $R^9$, $R^{3a}$, $R^{3b}$, $G^2$, n, $X^1$, $Y^1$, $Y^2$, $R^4$, $R^5$, $R^6$, $X^2$, $R^A$, p, $R^7$, $R^4$, $R^5$, $R^6$, $R^7$, $R^8$, q, $R^9$, $R^B$, r, and $R^x$, have been discussed above. These substituents embodiments can be combined to form various embodiments of the invention. All embodiments of present compounds, formed by combining the substituent embodiments discussed above are within the scope of Applicant's invention, and some illustrative embodiments of present compounds are provided below.

In certain embodiments, the invention is directed to compounds wherein Z is O and $R^2$ is hydrogen.

In certain embodiments, the invention is directed to compounds wherein

Z is O;

$R^2$ is hydrogen;

$G^1$ is phenyl or cyclohexyl; each of which is substituted with 1, 2, 3, or 4 $R^9$ groups; wherein one of the $R^9$ groups is —C(O)$OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl;

m is 0 or 1; and $R^1$ is —$OR^j$ wherein $R^j$ is $C_1$-$C_6$ alkyl or $C_1$-$C_6$ haloalkyl.

In certain embodiments, the invention is directed to compounds of formula (I-a)

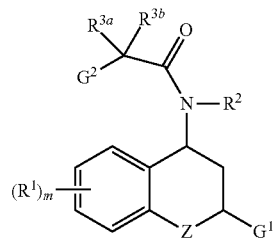

(I-a)

wherein

Z is O or N($R^{z1}$) wherein $R^{z1}$ is hydrogen or $C_1$-$C_3$ alkyl;

$R^1$ groups are optional substituents on the benzo ring, and are each independently halogen, —CN, $C_1$-$C_3$ alkyl, $C_1$-$C_3$ haloalkyl, —$OR^j$, or —$SR^j$;

m is 0, 1, 2, 3, or 4;

$R^2$ is hydrogen or $C_1$-$C_3$ alkyl;

$R^{3a}$ and $R^{3b}$ are each independently $C_1$-$C_3$ alkyl; or $R^{3a}$ and $R^{3b}$ together with the carbon atom to which they are attached, form a cyclopropyl, a cyclobutyl, or a cyclopentyl; wherein the cyclopropyl, the cyclobutyl, and the cyclopentyl are each optionally substituted with 1, 2, 3, or 4 substituents independently selected from the group consisting of $C_1$-$C_3$ alkyl, $C_1$-$C_3$ haloalkyl, and halogen;

$G^2$ is formula (b), phenyl, or —O-phenyl, wherein the phenyl and the phenyl moiety of —O-phenyl are each optionally substituted with 1, 2, 3, or 4 $R^x$ groups;

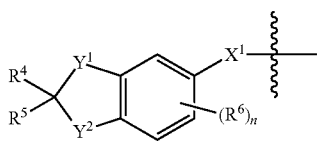

(b)

wherein
each $R^x$ is independently halogen, —CN, $C_1$-$C_6$ alkyl, $C_1$-$C_6$ haloalkyl, —$OR^j$, or —$SR^j$;
$X^1$ is O;
$Y^1$ is O, $CH_2$, or —O—$CH_2$— wherein the —O—$CH_2$— is connected to the benzo ring via the oxygen atom;
$Y^2$ is O;
$R^4$ and $R^5$ are hydrogen or $R^4$ and $R^5$ are halogen;
$R^6$ groups are optional substituents on the benzo ring, and are each independently $C_1$-$C_3$ alkyl, $C_1$-$C_3$ haloalkyl, halogen, —CN, —$OR^j$, or —$SR^j$; and
n is 0, 1, 2, or 3;

$G^1$ is phenyl, monocyclic heteroaryl, or $C_3$-$C_6$ cycloalkyl; wherein each $G^1$ is optionally substituted with 1, 2, 3, or 4 $R^9$ groups;

each $R^9$ is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$ alkylenyl)-$OR^j$, —($C_1$-$C_6$ alkylenyl)-$OC(O)R^k$, —($C_1$-$C_6$ alkylenyl)-$OC(O)N(R^j)_2$, —($C_1$-$C_6$ alkylenyl)-$SR^j$, —($C_1$-$C_6$ alkylenyl)-$S(O)_2R^j$, —($C_1$-$C_6$ alkylenyl)-$S(O)_2N(R^j)_2$, —($C_1$-$C_6$ alkylenyl)-$C(O)R^j$, —($C_1$-$C_6$ alkylenyl)-$C(O)OR^j$, —($C_1$-$C_6$ alkylenyl)-$C(O)N(R^j)_2$, —($C_1$-$C_6$ alkylenyl)-$C(O)N(R^j)S(O)_2R^k$, —($C_1$-$C_6$ alkylenyl)-$N(R^j)_2$, —($C_1$-$C_6$ alkylenyl)-$N(R^j)C(O)R^k$, —($C_1$-$C_6$ alkylenyl)-$N(R^j)S(O)_2R^k$, —($C_1$-$C_6$ alkylenyl)-$N(R^j)C(O)O(R^k)$, —($C_1$-$C_6$ alkylenyl)-$N(R^j)C(O)N(R^j)_2$, or —($C_1$-$C_6$ alkylenyl)-CN;

$R^j$, at each occurrence, is independently hydrogen, $C_1$-$C_6$ alkyl, or $C_1$-$C_6$ haloalkyl; and
$R^k$, at each occurrence, is independently $C_1$-$C_6$ alkyl or $C_1$-$C_6$ haloalkyl.

In certain embodiments, the invention is directed to compounds of formula (I-a) wherein $G^2$ is phenyl or —O-phenyl, wherein the phenyl and the phenyl moiety of —O-phenyl are each optionally substituted with 1, 2, 3, or 4 $R^x$ groups.

In certain embodiments, the invention is directed to compounds of formula (I-a) wherein $G^2$ is phenyl optionally substituted with 1, 2, 3, or 4 $R^x$ groups.

In certain embodiments, the invention is directed to compounds of formula (I-a) wherein
$G^2$ is formula (b) wherein $Y^1$ is O;
$R^4$ and $R^5$ are hydrogen; and
$R^{3a}$ and $R^{3b}$ are methyl.

In certain embodiments, the invention is directed to compounds of formula (I-a) wherein
Z is O;
$R^2$ is hydrogen; and
$R^{3a}$ and $R^{3b}$ are each independently $C_1$-$C_3$ alkyl; or $R^{3a}$ and $R^{3b}$ together with the carbon atom to which they are attached, form a cyclopropyl or a cyclobutyl; wherein the cyclopropyl and the cyclobutyl are each optionally substituted with 1, 2, 3, or 4 substituents independently selected from the group consisting of $C_1$-$C_3$ alkyl, $C_1$-$C_3$ haloalkyl, and halogen.

In some such embodiments, $R^{3a}$ and $R^{3b}$ are methyl. In some such embodiments, $R^{3a}$ and $R^{3b}$ together with the carbon atom to which they are attached, form a cyclopropyl which is optionally substituted with 1 or 2 halogens. In some such embodiments, the cyclopropyl is unsubstituted. In some such embodiments, the cyclopropyl is substituted with 2 halogens. In some such embodiments, the halogen is F.

In certain embodiments, the invention is directed to compounds of formula (I-a) wherein
$G^1$ is phenyl or cyclohexyl; each of which is substituted with 1, 2, 3, or 4 $R^9$ groups; wherein one of the $R^9$ groups is —$OR^j$ or —$C(O)OR^j$, and the other 1, 2, or 3 optional $R^9$ groups are independently $C_1$-$C_3$ alkyl, halogen, or $C_1$-$C_3$ haloalkyl;
m is 0 or 1; and
$R^1$ is —$OR^j$ wherein $R^j$ is $C_1$-$C_6$ alkyl or $C_1$-$C_6$ haloalkyl.

In certain embodiments, the invention is directed to compounds of formula (I-a) wherein
Z is O;
$R^2$ is hydrogen;
$Y^1$ is O;
$R^{3a}$ and $R^{3b}$ are methyl; or $R^{3a}$ and $R^{3b}$ together with the carbon atom to which they are attached, form a cyclopropyl or a cyclobutyl; wherein the cyclopropyl and the cyclobutyl are each optionally substituted with 1, 2, 3, or 4 substituents independently selected from the group consisting of $C_1$-$C_3$ alkyl, $C_1$-$C_3$ haloalkyl, and halogen;
$G^2$ is phenyl which is optionally substituted with 1, 2, 3, or 4 $R^x$ groups;
$G^1$ is phenyl or cyclohexyl; each of which is substituted with 1, 2, 3, or 4 $R^9$ groups; wherein one of the $R^9$ groups is —$C(O)OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl;
m is 0 or 1; and
$R^1$ is —$OR^j$ wherein $R^j$ is $C_1$-$C_6$ alkyl or $C_1$-$C_6$ haloalkyl.

In one embodiment, the invention is directed to compounds of formula (I-a-i)

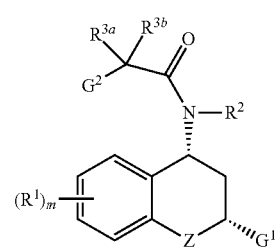

(I-a-i)

wherein
R[1] groups are optional substituents on the benzo ring, and are each independently halogen, —CN, $C_1$-$C_3$ alkyl, $C_1$-$C_3$ haloalkyl, —OR[j], or —SR[j];
m is 0, 1, 2, 3, or 4;
$G^1$ is phenyl, monocyclic heteroaryl, or $C_3$-$C_6$ cycloalkyl; wherein each $G^1$ is optionally substituted with 1, 2, 3, or 4 R[9] groups;
each R[9] is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —OR[j], —OC(O)R[k], —OC(O)N(R[j])$_2$, —SR[j], —S(O)$_2$R[j], —S(O)$_2$N(R[j])$_2$, —C(O)R[j], —C(O)OR[j], —C(O)N(R[j])$_2$, —C(O)N(R[j])S(O)$_2$R[k], —N(R[j])$_2$, —N(R[j])C(O)R[k], —N(R[j])S(O)$_2$R[k], —N(R[j])C(O)O(R[k]), —N(R[j])C(O)N(R[j])$_2$, —($C_1$-$C_6$ alkylenyl)-OR[j], —($C_1$-$C_6$ alkylenyl)-OC(O)R[k], —($C_1$-$C_6$ alkylenyl)-OC(O)N(R[j])$_2$, —($C_1$-$C_6$ alkylenyl)-SR[j], —($C_1$-$C_6$ alkylenyl)-S(O)$_2$R[j], —($C_1$-$C_6$ alkylenyl)-S(O)$_2$N(R[j])$_2$, —($C_1$-$C_6$ alkylenyl)-C(O)R[j], —($C_1$-$C_6$ alkylenyl)-C(O)OR[j], —($C_1$-$C_6$ alkylenyl)-C(O)N(R[j])$_2$, —($C_1$-$C_6$ alkylenyl)-C(O)N(R[j])S(O)$_2$R[k], —($C_1$-$C_6$ alkylenyl)-N(R[j])$_2$, —($C_1$-$C_6$ alkylenyl)-N(R[j])C(O)R[k], —($C_1$-$C_6$ alkylenyl)-N(R[j])S(O)$_2$R[k], —($C_1$-$C_6$ alkylenyl)-N(R[j])C(O)O(R[k]), —($C_1$-$C_6$ alkylenyl)-N(R[j])C(O)N(R[j])$_2$, or —($C_1$-$C_6$ alkylenyl)-CN;
R[3a] and R[3b] are each independently $C_1$-$C_3$ alkyl; or R[3a] and R[3b] together with the carbon atom to which they are attached, form a cyclopropyl, a cyclobutyl, or a cyclopentyl; wherein the cyclopropyl, the cyclobutyl, and the cyclopentyl are each optionally substituted with 1, 2, 3, or 4 substituents independently selected from the group consisting of $C_1$-$C_3$ alkyl, $C_1$-$C_3$ haloalkyl, and halogen;
$G^2$ is phenyl which is optionally substituted with 1, 2, 3, or 4 R[x] groups;
each R[x] is independently halogen, —CN, $C_1$-$C_6$ alkyl, $C_1$-$C_6$ haloalkyl, —OR[j], or —SR[j];
Z is O;
R[2] is hydrogen;
R[j], at each occurrence, is independently hydrogen, $C_1$-$C_6$ alkyl, or $C_1$-$C_6$ haloalkyl; and
R[k], at each occurrence, is independently $C_1$-$C_6$ alkyl or $C_1$-$C_6$ haloalkyl.

In certain embodiments, the invention is directed to compounds of formula (I-a-i) wherein R[3a] and R[3b] are methyl; or R[3a] and R[3b] together with the carbon atom to which they are attached, form a cyclopropyl which is optionally substituted with 1, 2, 3, or 4 substituents independently selected from the group consisting of $C_1$-$C_3$ alkyl, $C_1$-$C_3$ haloalkyl, and halogen. In some such embodiments, the cyclopropyl is substituted with 1 or 2 halogens. In some such embodiments, the cyclopropyl is unsubstituted. In some such embodiments, the halogens are F.

In certain embodiments, the invention is directed to compounds of formula (I-a-i)
R[3a] and R[3b] are methyl; or R[3a] and R[3b] together with the carbon atom to which they are attached, form a cyclopropyl which is optionally substituted with 1, 2, 3, or 4 substituents independently selected from the group consisting of $C_1$-$C_3$ alkyl, $C_1$-$C_3$ haloalkyl, and halogen; and
$G^1$ is phenyl or cyclohexyl; each of which is substituted with 1, 2, 3, or 4 R[9] groups; wherein one of the R[9] groups is —C(O)OR[j] wherein R[j] is hydrogen or $C_1$-$C_6$ alkyl, and the other 1, 2, or 3 optional R[9] groups are independently $C_1$-$C_3$ alkyl, halogen, or $C_1$-$C_3$ haloalkyl.

In some such embodiments, the cyclopropyl is substituted with 1 or 2 halogens. In some such embodiments, the cyclopropyl is unsubstituted. In some such embodiments, the halogens are F.

In certain embodiments, the invention is directed to compounds of formula (I-a-i) wherein
R[3a] and R[3b] are methyl; or R[3a] and R[3b] together with the carbon atom to which they are attached, form a cyclopropyl which is optionally substituted with 1, 2, 3, or 4 substituents independently selected from the group consisting of $C_1$-$C_3$ alkyl, $C_1$-$C_3$ haloalkyl, and halogen; and
$G^1$ is

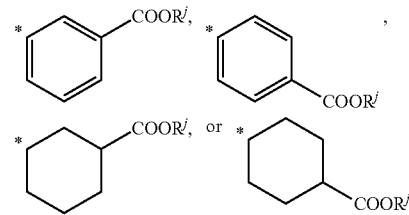

wherein * is the point of connection, and R[j] is hydrogen or $C_1$-$C_6$ alkyl.

In some such embodiments, the cyclopropyl is substituted with 1 or 2 halogens. In some such embodiments, the cyclopropyl is unsubstituted. In some such embodiments, the halogens are F.

In certain embodiments, the invention is directed to compounds of formula (I-a-i) wherein
R[3a] and R[3b] are methyl; or R[3a] and R[3b] together with the carbon atom to which they are attached, form a cyclopropyl which is optionally substituted with 1, 2, 3, or 4 substituents independently selected from the group consisting of $C_1$-$C_3$ alkyl, $C_1$-$C_3$ haloalkyl, and halogen;
$G^1$ is

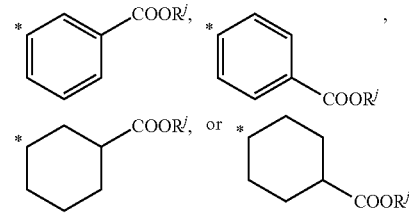

wherein * is the point of connection, and R[j] is hydrogen or $C_1$-$C_6$ alkyl
m is 0 or 1; and
R[1] is —OR[j] wherein R[j] is $C_1$-$C_6$ alkyl or $C_1$-$C_6$ haloalkyl.

In some such embodiments, the cyclopropyl is substituted with 1 or 2 halogens. In some such embodiments, the cyclopropyl is unsubstituted. In some such embodiments, the halogens are F.

In one embodiment, the invention is directed to compounds of formula (I-a-ii)

21

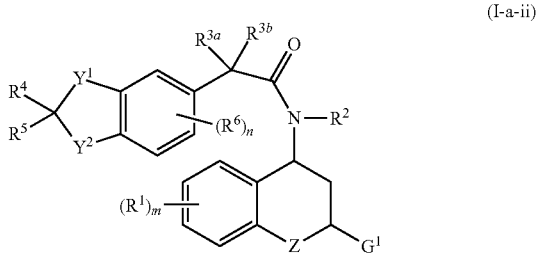
(I-a-ii)

wherein
- Z is O or N(R$^{z1}$) wherein R$^{z1}$ is hydrogen or C$_1$-C$_3$ alkyl;
- R$^1$ groups are optional substituents on the benzo ring, and are each independently halogen, —CN, C$_1$-C$_3$ alkyl, C$_1$-C$_3$ haloalkyl, —OR$^j$, or —SR$^j$;
- m is 0, 1, 2, 3, or 4;
- R$^2$ is hydrogen or C$_1$-C$_3$ alkyl;
- R$^{3a}$ and R$^{3b}$ are each independently C$_1$-C$_3$ alkyl; or R$^{3a}$ and R$^{3b}$ together with the carbon atom to which they are attached, form a cyclopropyl, a cyclobutyl, or a cyclopentyl;
  wherein the cyclopropyl, the cyclobutyl, and the cyclopentyl are each optionally substituted with 1, 2, 3, or 4 substituents independently selected from the group consisting of C$_1$-C$_3$ alkyl, C$_1$-C$_3$ haloalkyl, and halogen;
- Y$^1$ is O, CH$_2$, or —O—CH$_2$— wherein the —O—CH$_2$— is connected to the benzo ring via the oxygen atom;
- Y$^2$ is O;
- R$^4$ and R$^5$ are hydrogen, or R$^4$ and R$^5$ are halogen;
- R$^6$ groups are optional substituents on the benzo ring, and are each independently C$_1$-C$_3$ alkyl, C$_1$-C$_3$ haloalkyl, halogen, —CN, —OR$^j$, or —SR$^j$;
- n is 0, 1, 2, or 3;
- G$^1$ is phenyl, monocyclic heteroaryl, or C$_3$-C$_6$ cycloalkyl; wherein each G$^1$ is optionally substituted with 1, 2, 3, or 4 R$^9$ groups;
- each R$^9$ is independently C$_1$-C$_6$ alkyl, C$_2$-C$_6$ alkenyl, C$_2$-C$_6$ alkynyl, halogen, C$_1$-C$_6$ haloalkyl, —CN, oxo, NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^j$, —C(O)OR$^j$, —C(O)N(R$^j$)$_2$, —C(O)N(R$^j$)S(O)$_2$R$^k$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$ alkylenyl)-OR$^j$, —(C$_1$-C$_6$ alkylenyl)-OC(O)R$^k$, —(C$_1$-C$_6$ alkylenyl)-OC(O)N(R$^j$)$_2$, —(C$_1$-C$_6$ alkylenyl)-SR$^j$, —(C$_1$-C$_6$ alkylenyl)-S(O)$_2$R$^j$, —(C$_1$-C$_6$ alkylenyl)-S(O)$_2$N(R$^j$)$_2$, —(C$_1$-C$_6$ alkylenyl)-C(O)R$^j$, —(C$_1$-C$_6$ alkylenyl)-C(O)OR$^j$, —(C$_1$-C$_6$ alkylenyl)-C(O)N(R$^j$)$_2$, —(C$_1$-C$_6$ alkylenyl)-C(O)N(R$^j$)S(O)$_2$R$^k$, —(C$_1$-C$_6$ alkylenyl)-N(R$^j$)$_2$, —(C$_1$-C$_6$ alkylenyl)-N(R$^j$)C(O)R$^k$, —(C$_1$-C$_6$ alkylenyl)-N(R$^j$)S(O)$_2$R$^k$, —(C$_1$-C$_6$ alkylenyl)-N(R$^j$)C(O)O(R$^k$), —(C$_1$-C$_6$ alkylenyl)-N(R$^j$)C(O)N(R$^j$)$_2$, or —(C$_1$-C$_6$ alkylenyl)-CN;
- R$^j$, at each occurrence, is independently hydrogen, C$_1$-C$_6$ alkyl, or C$_1$-C$_6$ haloalkyl; and
- R$^k$, at each occurrence, is independently C$_1$-C$_6$ alkyl or C$_1$-C$_6$ haloalkyl;
- with the proviso that when R$^2$ is hydrogen, Z is O, R$^{3a}$ and R$^{3b}$ together with the carbon atom to which they are attached form an unsubstituted cyclopropyl, Y$^1$ is

22

O, R$^4$ and R$^5$ are halogen, n is 0 or 1, and R$^6$ is halogen, then G$^1$ is optionally substituted pyrimidinyl, optionally substituted pyridazinyl, optionally substituted pyrazinyl, or

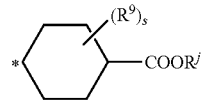

wherein * is the point of connection, R$^9$ is C$_1$-C$_3$ alkyl, C$_1$-C$_3$ haloalkyl, or halogen; and s is 0, 1, 2, or 3.

In certain embodiments, the invention is directed to compounds of formula (I-a-ii) wherein
- Z is O;
- R$^2$ is hydrogen; and
- R$^{3a}$ and R$^{3b}$ together with the carbon atom to which they are attached, form an unsubstituted cyclopropyl.

In certain embodiments, the invention is directed to compounds of formula (I-a-ii) wherein
- Z is O;
- R$^2$ is hydrogen;
- R$^{3a}$ and R$^{3b}$ together with the carbon atom to which they are attached, form an unsubstituted cyclopropyl;
- Y$^1$ is O; and
- G$^1$ is

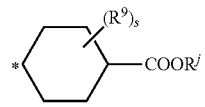

wherein * is the point of connection, R$^j$ is hydrogen or C$_1$-C$_6$ alkyl; R$^9$ is C$_1$-C$_3$ alkyl, C$_1$-C$_3$ haloalkyl, or halogen; and s is 0, 1, 2, or 3.

In some such embodiments, R$^j$ of —C(O)OR$^j$ is hydrogen.
In some such embodiments, R$^j$ of —C(O)OR$^j$ is C$_1$-C$_6$ alkyl.

In certain embodiments, the invention is directed to compounds of formula (I-a-ii) wherein
- Z is O;
- R$^2$ is hydrogen; and
- R$^{3a}$ and R$^{3b}$ are methyl; or R$^{3a}$ and R$^{3b}$ together with the carbon atom to which they are attached, form a cyclopropyl which is substituted with 1, 2, 3, or 4 substituents independently selected from the group consisting of C$_1$-C$_3$ alkyl, C$_1$-C$_3$ haloalkyl, and halogen.

In some such embodiments, the cyclopropyl formed by R$^{3a}$ and R$^{3b}$ and the carbon atom to which they are attached, is substituted with 1 or 2 halogens. In some such embodiments, the halogens are F.

In certain embodiments, the invention is directed to compounds of formula (I-a-ii) wherein
- Z is O;
- R$^2$ is hydrogen;
- R$^{3a}$ and R$^{3b}$ are methyl; or R$^{3a}$ and R$^{3b}$ together with the carbon atom to which they are attached, form a cyclopropyl which is substituted with 1, 2, 3, or 4 substituents independently selected from the group consisting of C$_1$-C$_3$ alkyl, C$_1$-C$_3$ haloalkyl, and halogen; and
- G$^1$ is phenyl or cyclohexyl; each of which is substituted with 1, 2, 3, or 4 R$^9$ groups; wherein one of the R$^9$ groups is —OR$^j$ or —C(O)OR$^j$, and the other 1, 2, or 3 optional R⁹ groups are independently $C_1$-$C_3$ alkyl, halogen, or $C_1$-$C_3$ haloalkyl.

In some such embodiments, the cyclopropyl formed by $R^{3a}$ and $R^{3b}$ and the carbon atom to which they are attached, is substituted with 1 or 2 halogens. In some such embodiments, the halogens are F.

In one embodiment, the invention is directed to compounds of formula (I-a-iii)

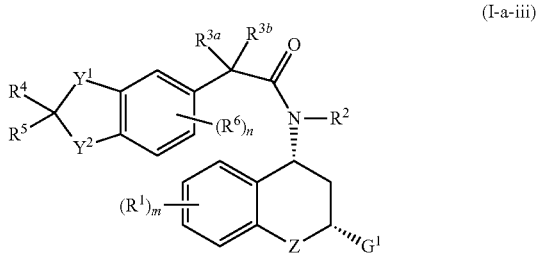

(I-a-iii)

wherein
- $R^1$ groups are optional substituents on the benzo ring, and are each independently halogen, —CN, $C_1$-$C_3$ alkyl, $C_1$-$C_3$ haloalkyl, —$OR^j$, or —$SR^j$;
- m is 0, 1, 2, 3, or 4;
- $Y^1$ and $Y^2$ are O;
- $R^4$ and $R^5$ are hydrogen, or $R^4$ and $R^5$ are halogen;
- Z is O;
- $R^2$ is hydrogen;
- $R^{3a}$ and $R^{3b}$ are each independently $C_1$-$C_3$ alkyl; or $R^{3a}$ and $R^{3b}$ together with the carbon atom to which they are attached, form a cyclopropyl, a cyclobutyl, or a cyclopentyl; wherein the cyclopropyl, the cyclobutyl, and the cyclopentyl are each optionally substituted with 1, 2, 3, or 4 substituents independently selected from the group consisting of $C_1$-$C_3$ alkyl, $C_1$-$C_3$ haloalkyl, and halogen;
- $R^6$ groups are optional substituents on the benzo ring, and are each independently $C_1$-$C_3$ alkyl, $C_1$-$C_3$ haloalkyl, halogen, —CN, —$OR^j$, or —$SR^j$; and
- n is 0, 1, 2, or 3;
- $G^1$ is phenyl, monocyclic heteroaryl, or $C_3$-$C_6$ cycloalkyl; wherein each $G^1$ is optionally substituted with 1, 2, 3, or 4 $R^9$ groups;
- each $R^9$ is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$ alkylenyl)-$OR^j$, —($C_1$-$C_6$ alkylenyl)-$OC(O)R^k$, —($C_1$-$C_6$ alkylenyl)-$OC(O)N(R^j)_2$, —($C_1$-$C_6$ alkylenyl)-$SR^j$, —($C_1$-$C_6$ alkylenyl)-$S(O)_2R^j$, —($C_1$-$C_6$ alkylenyl)-$S(O)_2N(R^j)_2$, —($C_1$-$C_6$ alkylenyl)-$C(O)R^j$, —($C_1$-$C_6$ alkylenyl)-$C(O)OR^j$, —($C_1$-$C_6$ alkylenyl)-$C(O)N(R^j)_2$, —($C_1$-$C_6$ alkylenyl)-$C(O)N(R^j)S(O)_2R^k$, —($C_1$-$C_6$ alkylenyl)-$N(R^j)_2$, —($C_1$-$C_6$ alkylenyl)-$N(R^j)C(O)R^k$, —($C_1$-$C_6$ alkylenyl)-$N(R^j)S(O)_2R^k$, —($C_1$-$C_6$ alkylenyl)-$N(R^j)C(O)O(R^k)$, —($C_1$-$C_6$ alkylenyl)-$N(R^j)C(O)N(R^j)_2$, or —($C_1$-$C_6$ alkylenyl)-CN;
- $R^j$, at each occurrence, is independently hydrogen, $C_1$-$C_6$ alkyl, or $C_1$-$C_6$ haloalkyl; and
- $R^k$, at each occurrence, is independently $C_1$-$C_6$ alkyl or $C_1$-$C_6$ haloalkyl;
- with the proviso that when $R^{3a}$ and $R^{3b}$ together with the carbon atom to which they are attached form an unsubstituted cyclopropyl, $R^4$ and $R^5$ are halogen, n is 0 or 1, and $R^6$ is halogen, then $G^1$ is optionally substituted pyrimidinyl, optionally substituted pyridazinyl, optionally substituted pyrazinyl, or

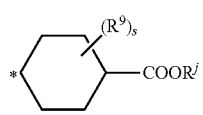

wherein * is the point of connection; $R^9$ is $C_1$-$C_3$ alkyl, $C_1$-$C_3$ haloalkyl, or halogen; and s is 0, 1, 2, or 3.

In certain embodiments, the invention is directed to compounds of formula (I-a-iii) wherein $R^{3a}$ and $R^{3b}$ together with the carbon atom to which they are attached, form an unsubstituted cyclopropyl.

In certain embodiments, the invention is directed to compounds of formula (I-a-iii) wherein
- $R^{3a}$ and $R^{3b}$ together with the carbon atom to which they are attached, form an unsubstituted cyclopropyl, and
- $G^1$ is

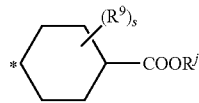

wherein * is the point of connection, $R^j$ is hydrogen or $C_1$-$C_6$ alkyl; $R^9$ is $C_1$-$C_3$ alkyl, $C_1$-$C_3$ haloalkyl, or halogen; and s is 0, 1, 2, or 3.

In some such embodiments, $R^j$ of —$C(O)OR^j$ is hydrogen. In some such embodiments, $R^j$ of —$C(O)OR^j$ is $C_1$-$C_6$ alkyl.

In certain embodiments, the invention is directed to compounds of formula (I-a-iii) wherein $R^{3a}$ and $R^{3b}$ are methyl; or $R^{3a}$ and $R^{3b}$ together with the carbon atom to which they are attached, form a cyclopropyl which is substituted with 1, 2, 3, or 4 substituents independently selected from the group consisting of $C_1$-$C_3$ alkyl, $C_1$-$C_3$ haloalkyl, and halogen.

In some such embodiments, the cyclopropyl formed by $R^{3a}$ and $R^{3b}$ together with the carbon atom to which they are attached is substituted with 1 or 2 halogens. In some such embodiments, the halogens are F.

In certain embodiments, the invention is directed to compounds of formula (I-a-iii) wherein
- $R^{3a}$ and $R^{3b}$ are methyl; or $R^{3a}$ and $R^{3b}$ together with the carbon atom to which they are attached, form a cyclopropyl which is substituted with 1, 2, 3, or 4 substituents independently selected from the group consisting of $C_1$-$C_3$ alkyl, $C_1$-$C_3$ haloalkyl, and halogen; and
- $G^1$ is phenyl or cyclohexyl; each of which is substituted with 1, 2, 3, or 4 $R^9$ groups; wherein one of the $R^9$ groups is —$C(O)OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl.

In some such embodiments, the cyclopropyl formed by $R^{3a}$ and $R^{3b}$ together with the carbon atom to which they are attached is substituted with 1 or 2 halogens. In some such embodiments, the halogens are F.

In certain embodiments, the invention is directed to compounds of formula (I-c) wherein
Z is O;
$R^2$ is hydrogen; and
$R^4$ is methyl.

In certain embodiments, the invention is directed to compounds of formula (I-c) wherein
Z is O;
$R^2$ is hydrogen;
$R^4$ is methyl; and
$G^1$ is phenyl, pyridinyl, pyrimidinyl, pyridazinyl, pyrazinyl, thiazolyl, thienyl, cyclopropyl, or cyclohexyl; each of which is optionally substituted with 1, 2, 3, or 4 independently selected $R^9$ groups.

In certain embodiments, the invention is directed to compounds of formula (I-c) wherein
Z is O;
$R^2$ is hydrogen;
$R^4$ is methyl;
$G^1$ is phenyl or cyclohexyl; each of which is substituted with 1, 2, 3, or 4 $R^9$ groups; wherein one of the $R^9$ groups is —$OR^j$ or —$C(O)OR^j$, and the other 1, 2, or 3 optional $R^9$ groups are independently $C_1$-$C_3$ alkyl, halogen, or $C_1$-$C_3$ haloalkyl;
m is 0 or 1; and
$R^1$ is —$OR^j$ wherein $R^j$ is $C_1$-$C_6$ alkyl or $C_1$-$C_6$ haloalkyl.

In one embodiment, the invention is directed to compounds of formula (I-c-i)

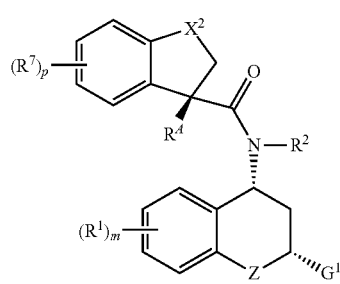

(I-c-i)

wherein
Z is O;
$R^2$ is hydrogen;
$R^4$ is methyl;
$R^1$ groups are optional substituents on the benzo ring, and are each independently halogen, —CN, $C_1$-$C_3$ alkyl, $C_1$-$C_3$ haloalkyl, —$OR^j$, or —$SR^j$;
m is 0, 1, 2, 3, or 4;
$X^2$ is O or $CH_2$;
$R^7$ groups are optional substituents on the benzo ring, and are each independently halogen, —CN, $C_1$-$C_6$ alkyl, $C_1$-$C_6$ haloalkyl, —$OR^j$, or —$SR^j$;
p is 0, 1, 2, 3, or 4;
$G^1$ is phenyl, monocyclic heteroaryl, or $C_3$-$C_6$ cycloalkyl; wherein each $G^1$ is optionally substituted with 1, 2, 3, or 4 $R^9$ groups;
each $R^9$ is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$ alkylenyl)-$OR^j$, —($C_1$-$C_6$ alkylenyl)-$OC(O)R^k$, —($C_1$-$C_6$ alkylenyl)-$OC(O)N(R^j)_2$, —($C_1$-$C_6$ alkylenyl)-$SR^j$, —($C_1$-$C_6$ alkylenyl)-$S(O)_2R^j$, —($C_1$-$C_6$ alkylenyl)-$S(O)_2N(R^j)_2$, —($C_1$-$C_6$ alkylenyl)-$C(O)R^j$, —($C_1$-$C_6$ alkylenyl)-$C(O)OR^j$, —($C_1$-$C_6$ alkylenyl)-$C(O)N(R^j)_2$, —($C_1$-$C_6$ alkylenyl)-$C(O)N(R^j)S(O)_2R^k$, —($C_1$-$C_6$ alkylenyl)-$N(R^j)_2$, —($C_1$-$C_6$ alkylenyl)-$N(R^j)C(O)R^k$, —($C_1$-$C_6$ alkylenyl)-$N(R^j)S(O)_2R^k$, —($C_1$-$C_6$ alkylenyl)-$N(R^j)C(O)O(R^k)$, —($C_1$-$C_6$ alkylenyl)-$N(R^j)C(O)N(R^j)_2$, or —($C_1$-$C_6$ alkylenyl)-CN;
$R^j$, at each occurrence, is independently hydrogen, $C_1$-$C_6$ alkyl, or $C_1$-$C_6$ haloalkyl; and
$R^k$, at each occurrence, is independently $C_1$-$C_6$ alkyl or $C_1$-$C_6$ haloalkyl.

In certain embodiments, the invention is directed to compounds of formula (I-c-i) wherein
Z is O;
$R^2$ is hydrogen; and
$R^4$ is methyl.

In certain embodiments, the invention is directed to compounds of formula (I-c-i) wherein
Z is O;
$R^2$ is hydrogen;
$R^4$ is methyl; and
$G^1$ is phenyl or cyclohexyl; each of which is substituted with 1, 2, 3, or 4 $R^9$ groups; wherein one of the $R^9$ groups is —$C(O)OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl.

In some such embodiments, $R^j$ of —$C(O)OR^j$ is hydrogen. In some such embodiments, $R^j$ of —$C(O)OR^j$ is $C_1$-$C_6$ alkyl.

In certain embodiments, the invention is directed to compounds of formula (I-c-i) wherein
Z is O;
$R^2$ is hydrogen;
$R^4$ is methyl;
$G^1$ is

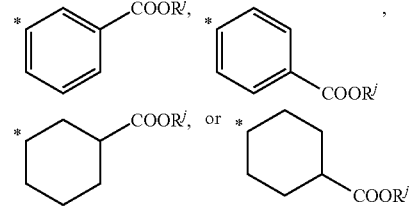

wherein
* is the point of connection; and $R^j$ is hydrogen or $C_1$-$C_6$ alkyl;
m is 0 or 1; and
$R^1$ is —$OR^j$ wherein $R^j$ is $C_1$-$C_6$ alkyl or $C_1$-$C_6$ haloalkyl.
In some such embodiments, $R^j$ of —$C(O)OR^j$ is hydrogen.
In some such embodiments, $R^j$ of —$C(O)OR^j$ is $C_1$-$C_6$ alkyl.

In certain embodiments, the invention is directed to compounds of formula (I-d) wherein
Z is O;
$R^2$ is hydrogen; and
$R^B$ is methyl.

In embodiments, the invention is directed to compounds of formula (I-d) wherein

Z is O;

R² is hydrogen;

R^B is methyl; and

G¹ is phenyl, pyridinyl, pyrimidinyl, pyridazinyl, pyrazinyl, thiazolyl, thienyl, cyclopropyl, or cyclohexyl; each of which is optionally substituted with 1, 2, 3, or 4 independently selected R⁹ groups.

In some such embodiments, G¹ is phenyl or cyclohexyl; each of which is optionally substituted with 1, 2, 3, or 4 independently selected R⁹ groups.

In certain embodiments, the invention is directed to compounds of formula (I-d) wherein Z is O;

R² is hydrogen;

R^B is methyl;

G¹ is phenyl or cyclohexyl; each of which is substituted with 1, 2, 3, or 4 R⁹ groups; wherein one of the R⁹ groups is —OR^j or —C(O)OR^j, and the other 1, 2, or 3 optional R⁹ groups are independently $C_1$-$C_3$ alkyl, halogen, or $C_1$-$C_3$ haloalkyl;

m is 0 or 1; and

R¹ is —OR^j wherein R^j is $C_1$-$C_6$ alkyl or $C_1$-$C_6$ haloalkyl.

Exemplary compounds include, but are not limited to:

4-{(2R,4R)-4-[2-(2,2-difluoro-2H-1,3-benzodioxol-5-yl)-2-methylpropanamido]-7-methoxy-3,4-dihydro-2H-1-benzopyran-2-yl}benzoic acid;

4-[(2R,4R)-4-{[1-(3,4-dichlorophenyl)cyclopropane-1-carbonyl]amino}-7-methoxy-3,4-dihydro-2H-1-benzopyran-2-yl]benzoic acid;

4-[(2R,4R)-7-methoxy-4-({1-[4-(trifluoromethoxy)phenyl]cyclopropane-1-carbonyl}amino)-3,4-dihydro-2H-1-benzopyran-2-yl]benzoic acid;

4-[(2R,4R)-4-{[1-(4-bromophenyl)cyclopropane-1-carbonyl]amino}-7-methoxy-3,4-dihydro-2H-1-benzopyran-2-yl]benzoic acid;

4-[(2R,4R)-7-methoxy-4-({1-[4-(trifluoromethyl)phenyl]cyclopropane-1-carbonyl}amino)-3,4-dihydro-2H-1-benzopyran-2-yl]benzoic acid;

4-[(2R,4R)-7-methoxy-4-{[1-(4-methylphenyl)cyclopropane-1-carbonyl]amino}-3,4-dihydro-2H-1-benzopyran-2-yl]benzoic acid;

4-{(2R,4R)-4-[(1,5-dimethyl-2,3-dihydro-1H-indene-1-carbonyl)amino]-7-methoxy-3,4-dihydro-2H-1-benzopyran-2-yl}benzoic acid;

3-[(2R,4R)-4-{[(1S)-1,5-dimethyl-2,3-dihydro-1H-indene-1-carbonyl]amino}-7-methoxy-3,4-dihydro-2H-1-benzopyran-2-yl]benzoic acid;

4-[(2R,4R)-4-{[(1S)-1,5-dimethyl-2,3-dihydro-1H-indene-1-carbonyl]amino}-7-methoxy-3,4-dihydro-2H-1-benzopyran-2-yl]benzoic acid;

ethyl trans-4-[(2R,4R)-4-{[1-(2,2-difluoro-2H-1,3-benzodioxol-5-yl)cyclopropane-1-carbonyl]amino}-7-methoxy-3,4-dihydro-2H-1-benzopyran-2-yl]cyclohexane-1-carboxylate;

trans-4-[(2R,4R)-4-{[1-(2,2-difluoro-2H-1,3-benzodioxol-5-yl)cyclopropane-1-carbonyl]amino}-7-methoxy-3,4-dihydro-2H-1-benzopyran-2-yl]cyclohexane-1-carboxylic acid;

ethyl trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylate;

trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylic acid;

methyl cis-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylate;

methyl trans-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylate;

cis-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylic acid;

trans-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylic acid;

N-[2-(3,4-dimethoxyphenyl)-7-methoxy-3,4-dihydro-2H-1-benzopyran-4-yl]-3,3-difluoro-1-phenylcyclobutane-1-carboxamide;

1-(3,4-difluorophenyl)-N-[2-(3,4-dimethoxyphenyl)-7-methoxy-3,4-dihydro-2H-1-benzopyran-4-yl]cyclobutane-1-carboxamide;

2-(4-chlorophenoxy)-N-[2-(3,4-dimethoxyphenyl)-7-methoxy-3,4-dihydro-2H-1-benzopyran-4-yl]-2-methylpropanamide;

N-[2-(3,4-dimethoxyphenyl)-7-methoxy-3,4-dihydro-2H-1-benzopyran-4-yl]-1-(3-fluorophenyl)cyclopropane-1-carboxamide;

N-[2-(3,4-dimethoxyphenyl)-7-methoxy-3,4-dihydro-2H-1-benzopyran-4-yl]-1-(4-fluorophenyl)cyclopropane-1-carboxamide;

1-(4-chlorophenyl)-N-[2-(3,4-dimethoxyphenyl)-7-methoxy-3,4-dihydro-2H-1-benzopyran-4-yl]cyclopropane-1-carboxamide;

2-(4-chlorophenyl)-N-[2-(3,4-dimethoxyphenyl)-7-methoxy-3,4-dihydro-2H-1-benzopyran-4-yl]-2-methylpropanamide;

N-[2-(3,4-dimethoxyphenyl)-7-methoxy-3,4-dihydro-2H-1-benzopyran-4-yl]-2-(4-methoxyphenyl)-2-methylpropanamide;

3-{(2R,4S)-7-methoxy-4-[2-(4-methoxyphenyl)-2-methylpropanamido]-3,4-dihydro-2H-1-benzopyran-2-yl}benzoic acid;

3-{(2R,4R)-7-methoxy-4-[2-(4-methoxyphenyl)-2-methylpropanamido]-3,4-dihydro-2H-1-benzopyran-2-yl}benzoic acid;

3-[(2R,4R)-4-{[(2R)-5-chloro-2-methyl-2,3-dihydro-1-benzofuran-2-carbonyl]amino}-3,4-dihydro-2H-1-benzopyran-2-yl]benzoic acid;

3-[(2R,4R)-4-{[(2S)-5-chloro-2-methyl-2,3-dihydro-1-benzofuran-2-carbonyl]amino}-3,4-dihydro-2H-1-benzopyran-2-yl]benzoic acid;

methyl 3-[(2R,4R)-4-{[(1R)-5-methoxy-1-methyl-2,3-dihydro-1H-indene-1-carbonyl]amino}-3,4-dihydro-2H-1-benzopyran-2-yl]benzoate;

methyl 3-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoate;

methyl 3-[(2R,4R)-4-{[(1S)-5-methoxy-1-methyl-2,3-dihydro-1H-indene-1-carbonyl]amino}-3,4-dihydro-2H-1-benzopyran-2-yl]benzoate;

methyl 3-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoate;

3-[(2R,4R)-4-{[(1R)-5-methoxy-1-methyl-2,3-dihydro-1H-indene-1-carbonyl]amino}-3,4-dihydro-2H-1-benzopyran-2-yl]benzoic acid;

3-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoic acid;

3-[(2R,4R)-4-{[(1S)-5-methoxy-1-methyl-2,3-dihydro-1H-indene-1-carbonyl]amino}-3,4-dihydro-2H-1-benzopyran-2-yl]benzoic acid;

3-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoic acid;

3-{(2R,4R)-4-[(5-chloro-1-methyl-2,3-dihydro-1H-indene-1-carbonyl)amino]-7-methoxy-3,4-dihydro-2H-1-benzopyran-2-yl}benzoic acid;

3-[(2R,4R)-7-methoxy-4-{2-methyl-2-[4-(2-methylpropoxy)phenyl]propanamido}-3,4-dihydro-2H-1-benzopyran-2-yl]benzoic acid;

3-{(2R,4R)-4-[2-(2H-1,3-benzodioxol-5-yl)-2-methylpropanamido]-7-methoxy-3,4-dihydro-2H-1-benzopyran-2-yl}benzoic acid;

3-{(2R,4R)-4-[2-(2,3-dihydro-1,4-benzodioxin-6-yl)-2-methylpropanamido]-7-methoxy-3,4-dihydro-2H-1-benzopyran-2-yl}benzoic acid;

3-[(2R,4R)-7-methoxy-4-{2-methyl-2-[4-(trifluoromethoxy)phenyl]propanamido}-3,4-dihydro-2H-1-benzopyran-2-yl]benzoic acid;

3-[(2R,4R)-7-methoxy-4-({1-[4-(trifluoromethoxy)phenyl]cyclopropane-1-carbonyl}amino)-3,4-dihydro-2H-1-benzopyran-2-yl]benzoic acid;

3-[(2R,4R)-4-{[1-(4-chlorophenyl)cyclopropane-1-carbonyl]amino}-7-methoxy-3,4-dihydro-2H-1-benzopyran-2-yl]benzoic acid;

3-[(2R,4R)-4-{[1-(4-bromophenyl)cyclopropane-1-carbonyl]amino}-7-methoxy-3,4-dihydro-2H-1-benzopyran-2-yl]benzoic acid;

3-[(2R,4R)-7-methoxy-4-{[1-(4-methoxyphenyl)cyclopropane-1-carbonyl]amino}-3,4-dihydro-2H-1-benzopyran-2-yl]benzoic acid;

3-{(2R,4R)-4-[2-(4-chlorophenoxy)-2-methylpropanamido]-7-methoxy-3,4-dihydro-2H-1-benzopyran-2-yl}benzoic acid;

3-[(2R,4R)-4-{[(1S)-7-methoxy-1-methyl-2,3-dihydro-1H-indene-1-carbonyl]amino}-3,4-dihydro-2H-1-benzopyran-2-yl]benzoic acid;

3-[(2R,4R)-4-{[(1S)-6-methoxy-1-methoxy-1-methyl-2,3-dihydro-1H-indene-1-carbonyl]amino}-3,4-dihydro-2H-1-benzopyran-2-yl]benzoic acid;

3-[(2R,4R)-4-{[(1R)-6-methoxy-1-methyl-2,3-dihydro-1H-indene-1-carbonyl]amino}-3,4-dihydro-2H-1-benzopyran-2-yl]benzoic acid;

3-{(2R,4R)-4-[2-methyl-2-(2-methylphenyl)propanamido]-3,4-dihydro-2H-1-benzopyran-2-yl}benzoic acid;

3-[(2R,4R)-4-{[(1R)-7-methoxy-1-methyl-2,3-dihydro-1H-indene-1-carbonyl]amino}-3,4-dihydro-2H-1-benzopyran-2-yl]benzoic acid;

3-[(2R,4R)-4-{2-methyl-2-[4-(trifluoromethyl)phenyl]propanamido}-3,4-dihydro-2H-1-benzopyran-2-yl]benzoic acid;

3-{(2R,4R)-4-[2-(2,4-dichlorophenyl)-2-methylpropanamido]-3,4-dihydro-2H-1-benzopyran-2-yl}benzoic acid;

3-[(2R,4R)-4-{[(1R)-6-chloro-1-methyl-2,3-dihydro-1H-indene-1-carbonyl]amino}-3,4-dihydro-2H-1-benzopyran-2-yl]benzoic acid;

3-[(2R,4R)-4-{[(1S)-6-chloro-1-methyl-2,3-dihydro-1H-indene-1-carbonyl]amino}-3,4-dihydro-2H-1-benzopyran-2-yl]benzoic acid;

3-[(2R,4R)-4-{[1-methyl-5-(trifluoromethoxy)-2,3-dihydro-1H-indene-1-carbonyl]amino}-3,4-dihydro-2H-1-benzopyran-2-yl]benzoic acid;

3-{(2R,4R)-4-[(6-methoxy-3-methyl-2,3-dihydro-1-benzofuran-3-carbonyl)amino]-3,4-dihydro-2H-1-benzopyran-2-yl}benzoic acid;

methyl 3-[(2R,4R)-7-methoxy-4-{[1-methyl-6-(trifluoromethoxy)-2,3-dihydro-1H-indene-1-carbonyl]amino}-3,4-dihydro-2H-1-benzopyran-2-yl]benzoate;

3-[(2R,4R)-7-methoxy-4-{[1-methyl-6-(trifluoromethoxy)-2,3-dihydro-1H-indene-1-carbonyl]amino}-2H-1-benzopyran-2-yl]benzoic acid;

methyl 4-[(2R,4R)-4-{[(2R)-6-chloro-2-methyl-3,4-dihydro-2H-1-benzopyran-2-carbonyl]amino}-3,4-dihydro-2H-1-benzopyran-2-yl]benzoate;

4-[(2R,4R)-4-{[(2R)-6-chloro-2-methyl-3,4-dihydro-2H-1-benzopyran-2-carbonyl]amino}-3,4-dihydro-2H-1-benzopyran-2-yl]benzoic acid;

methyl 4-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoate;

4-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoic acid;

methyl 3-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoate;

3-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoic acid;

3-[(2R,4R)-4-{[(2R)-6-chloro-2-methyl-3,4-dihydro-2H-1-benzopyran-2-carbonyl]amino}-3,4-dihydro-2H-1-benzopyran-2-yl]benzoic acid;

4-[(2R,4R)-7-methoxy-4-{[1-methyl-5-(trifluoromethoxy)-2,3-dihydro-1H-indene-1-carbonyl]amino}-3,4-dihydro-2H-1-benzopyran-2-yl]benzoic acid;

4-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoic acid;

4-[(2R,4R)-7-methoxy-4-({1-[4-(trifluoromethoxy)phenyl]cyclobutane-1-carbonyl}amino)-3,4-dihydro-2H-1-benzopyran-2-yl]benzoic acid;

4-{(2R,4R)-4-[2-(2,3-dihydro-1-benzofuran-5-yl)-2-methylpropanamido]-7-methoxy-3,4-dihydro-2H-1-benzopyran-2-yl}benzoic acid;

4-{(2R,4R)-4-[(3,3-difluoro-1-phenylcyclobutane-1-carbonyl)amino]-7-methoxy-3,4-dihydro-2H-1-benzopyran-2-yl}benzoic acid;

4-{(2R,4R)-4-[2-(3-chlorophenoxy)-2-methylpropanamido]-7-methoxy-3,4-dihydro-2H-1-benzopyran-2-yl}benzoic acid;

4-[(2R,4R)-7-methoxy-4-{[1-(4-methoxyphenyl)cyclopropane-1-carbonyl]amino}-3,4-dihydro-2H-1-benzopyran-2-yl]benzoic acid;

4-{(2R,4R)-7-methoxy-4-[(1-phenylcyclopropane-1-carbonyl)amino]-3,4-dihydro-2H-1-benzopyran-2-yl}benzoic acid;

4-[(2R,4R)-4-{[1-(4-chlorophenyl)cyclobutane-1-carbonyl]amino}-7-methoxy-3,4-dihydro-2H-1-benzopyran-2-yl]benzoic acid;

4-{(2R,4R)-4-[2-(4-chloro-3-methylphenoxy)-2-methylpropanamido]-7-methoxy-3,4-dihydro-2H-1-benzopyran-2-yl}benzoic acid;

4-[(2R,4R)-7-methoxy-4-{2-methyl-2-[3-(trifluoromethyl)phenoxy]propanamido}-3,4-dihydro-2H-1-benzopyran-2-yl]benzoic acid;

4-[(2R,4R)-4-(2-ethyl-2-phenylbutanamido)-7-methoxy-3,4-dihydro-2H-1-benzopyran-2-yl]benzoic acid;

4-{(2R,4R)-4-[(3,3-difluoro-1-phenylcyclopentane-1-carbonyl)amino]-7-methoxy-3,4-dihydro-2H-1-benzopyran-2-yl}benzoic acid;

4-[(2R,4R)-4-{[1-(3,4-difluorophenyl)cyclobutane-1-carbonyl]amino}-7-methoxy-3,4-dihydro-2H-1-benzopyran-2-yl]benzoic acid;

4-[(2R,4R)-7-methoxy-4-({1-[2-(trifluoromethyl)phenyl]cyclobutane-1-carbonyl}amino)-3,4-dihydro-2H-1-benzopyran-2-yl]benzoic acid;

4-[(2R,4R)-7-methoxy-4-({1-[3-(trifluoromethoxy)phenyl]cyclobutane-1-carbonyl}amino)-3,4-dihydro-2H-1-benzopyran-2-yl]benzoic acid;

4-[(2R,4R)-4-{[1-(4-fluorophenyl)cyclopropane-1-carbonyl]amino}-7-methoxy-3,4-dihydro-2H-1-benzopyran-2-yl]benzoic acid;

4-[(2R,4R)-4-{[1-(3-fluorophenyl)cyclopropane-1-carbonyl]amino}-7-methoxy-3,4-dihydro-2H-1-benzopyran-2-yl]benzoic acid;

4-[(2R,4R)-7-methoxy-4-{[1-(3-methoxy-4-methylphenyl)cyclopropane-1-carbonyl]amino}-3,4-dihydro-2H-1-benzopyran-2-yl]benzoic acid;

4-[(2R,4R)-4-{[1-(3-cyanophenyl)cyclopropane-1-carbonyl]amino}-7-methoxy-3,4-dihydro-2H-1-benzopyran-2-yl]benzoic acid;

4-[(2R,4R)-4-{[1-(3-bromophenyl)cyclopropane-1-carbonyl]amino}-7-methoxy-3,4-dihydro-2H-1-benzopyran-2-yl]benzoic acid;

4-[(2R,4R)-4-{[1-(2-bromophenyl)cyclopropane-1-carbonyl]amino}-7-methoxy-3,4-dihydro-2H-1-benzopyran-2-yl]benzoic acid;

4-[(2R,4R)-4-{[1-(3-fluorophenyl)cyclopentane-1-carbonyl]amino}-7-methoxy-3,4-dihydro-2H-1-benzopyran-2-yl]benzoic acid;

4-[(2R,4R)-4-{[1-(2-fluorophenyl)cyclopentane-1-carbonyl]amino}-7-methoxy-3,4-dihydro-2H-1-benzopyran-2-yl]benzoic acid;

4-[(2R,4R)-4-{[1-(4-cyanophenyl)cyclopropane-1-carbonyl]amino}-7-methoxy-3,4-dihydro-2H-1-benzopyran-2-yl]benzoic acid;

4-[(2R,4R)-4-{[1-(4-fluorophenyl)cyclopentane-1-carbonyl]amino}-7-methoxy-3,4-dihydro-2H-1-benzopyran-2-yl]benzoic acid;

4-[(2R,4R)-4-{[1-(2-bromophenyl)cyclobutane-1-carbonyl]amino}-7-methoxy-3,4-dihydro-2H-1-benzopyran-2-yl]benzoic acid;

4-[(2R,4R)-4-{[1-(3,4-dichlorophenyl)cyclobutane-1-carbonyl]amino}-7-methoxy-3,4-dihydro-2H-1-benzopyran-2-yl]benzoic acid;

4-[(2R,4R)-4-{[1-(2-chlorophenyl)cyclobutane-1-carbonyl]amino}-7-methoxy-3,4-dihydro-2H-1-benzopyran-2-yl]benzoic acid;

4-{(2R,4R)-7-methoxy-4-[(1-phenylcyclopentane-1-carbonyl)amino]-3,4-dihydro-2H-1-benzopyran-2-yl}benzoic acid;

4-[(2R,4R)-4-{[1-(4-chlorophenyl)cyclopentane-1-carbonyl]amino}-7-methoxy-3,4-dihydro-2H-1-benzopyran-2-yl]benzoic acid;

4-[(2R,4R)-4-{2-[(2H-1,3-benzodioxol-5-yl)oxy]-2-methylpropanamido}-7-methoxy-3,4-dihydro-2H-1-benzopyran-2-yl]benzoic acid;

4-{(2R,4R)-7-methoxy-4-{[(1R)-5-methoxy-1-methyl-2,3-dihydro-1H-indene-1-carbonyl]amino}-3,4-dihydro-2H-1-benzopyran-2-yl}benzoic acid;

4-[(2R,4R)-4-{[1-(3-chlorophenyl)cyclopropane-1-carbonyl]amino}-7-methoxy-3,4-dihydro-2H-1-benzopyran-2-yl]benzoic acid;

4-{(2R,4R)-7-methoxy-4-[(1-phenylcyclobutane-1-carbonyl)amino]-3,4-dihydro-2H-1-benzopyran-2-yl}benzoic acid;

4-[(2R,4R)-7-methoxy-4-{[1-(2-methoxyphenyl)cyclopropane-1-carbonyl]amino}-3,4-dihydro-2H-1-benzopyran-2-yl]benzoic acid;

4-[(2R,4R)-4-{[1-(4-bromophenyl)cyclobutane-1-carbonyl]amino}-7-methoxy-3,4-dihydro-2H-1-benzopyran-2-yl]benzoic acid;

4-{(2R,4R)-4-[(2,2-difluoro-1-phenylcyclopropane-1-carbonyl)amino]-7-methoxy-3,4-dihydro-2H-1-benzopyran-2-yl}benzoic acid;

4-[(2R,4R)-4-{[1-(2-fluorophenyl)cyclopropane-1-carbonyl]amino}-7-methoxy-3,4-dihydro-2H-1-benzopyran-2-yl]benzoic acid;

4-{(2R,4R)-4-[2-(4-cyanophenoxy)-2-methylpropanamido]-7-methoxy-3,4-dihydro-2H-1-benzopyran-2-yl}benzoic acid;

4-[(2R,4R)-4-{[1-(4-chlorophenyl)cyclopropane-1-carbonyl]amino}-7-methoxy-3,4-dihydro-2H-1-benzopyran-2-yl]benzoic acid;

4-[(2R,4R)-7-methoxy-4-{2-methyl-2-[4-(trifluoromethoxy)phenyl]propanamido}-3,4-dihydro-2H-1-benzopyran-2-yl]benzoic acid;

4-{(2R,4R)-4-[2-(4-chlorophenyl)-2-methylpropanamido]-7-methoxy-3,4-dihydro-2H-1-benzopyran-2-yl}benzoic acid;

4-{(2R,4R)-4-[2-(4-fluorophenyl)-2-methylpropanamido]-7-methoxy-3,4-dihydro-2H-1-benzopyran-2-yl}benzoic acid;

4-{(2R,4R)-4-[2-(2,3-dihydro-1,4-benzodioxin-6-yl)-2-methylpropanamido]-7-methoxy-3,4-dihydro-2H-1-benzopyran-2-yl}benzoic acid;

4-{(2R,4R)-4-[2-(3-fluoro-4-methoxyphenyl)-2-methylpropanamido]-7-methoxy-3,4-dihydro-2H-1-benzopyran-2-yl}benzoic acid;

4-[(2R,4R)-7-methoxy-4-{[1-(4-methoxyphenyl)cyclopentane-1-carbonyl]amino}-3,4-dihydro-2H-1-benzopyran-2-yl]benzoic acid;

4-[(2R,4R)-7-methoxy-4-{[1-(4-methoxyphenyl)cyclobutane-1-carbonyl]amino}-3,4-dihydro-2H-1-benzopyran-2-yl]benzoic acid;

4-[(2R,4R)-4-{[1-(3,4-dimethoxyphenyl)cyclobutane-1-carbonyl]amino}-7-methoxy-3,4-dihydro-2H-1-benzopyran-2-yl]benzoic acid;

4-{(2R,4R)-4-[2-(2-fluoro-4-methoxyphenyl)-2-methylpropanamido]-7-methoxy-3,4-dihydro-2H-1-benzopyran-2-yl}benzoic acid;

4-{(2R,4R)-4-[2-(4-fluorophenoxy)-2-methylpropanamido]-7-methoxy-3,4-dihydro-2H-1-benzopyran-2-yl}benzoic acid;

4-{(2R,4R)-4-[2-(4-chlorophenoxy)-2-methylpropanamido]-7-methoxy-3,4-dihydro-2H-1-benzopyran-2-yl}benzoic acid;

4-{(2R,4R)-4-[2-(2H-1,3-benzodioxol-5-yl)-2-methylpropanamido]-7-methoxy-3,4-dihydro-2H-1-benzopyran-2-yl}benzoic acid;

4-{(2R,4R)-7-methoxy-4-[2-(4-methoxyphenyl)-2-methylpropanamido]-3,4-dihydro-2H-1-benzopyran-2-yl}benzoic acid;

3-{(2R,4R)-4-[(1,5-dimethyl-2,3-dihydro-1H-indene-1-carbonyl)amino]-7-methoxy-3,4-dihydro-2H-1-benzopyran-2-yl}benzoic acid;

methyl 3-{(2R,4R)-4-[(1,5-dimethyl-2,3-dihydro-1H-indene-1-carbonyl)amino]-7-methoxy-3,4-dihydro-2H-1-benzopyran-2-yl}benzoate;

methyl 4-{(2R,4R)-4-[(1,5-dimethyl-2,3-dihydro-1H-indene-1-carbonyl)amino]-7-methoxy-3,4-dihydro-2H-1-benzopyran-2-yl}benzoate;

3-[(2R,4R)-4-{[(1R)-1,5-dimethyl-2,3-dihydro-1H-indene-1-carbonyl]amino}-7-methoxy-3,4-dihydro-2H-1-benzopyran-2-yl]benzoic acid; and 4-[(2R,4R)-4-{[(1R)-1,5-dimethyl-2,3-dihydro-1H-indene-1-carbonyl]amino}-7-methoxy-3,4-dihydro-2H-1-benzopyran-2-yl]benzoic acid.

Compound of the invention are named by using Name 2015 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I), (I-a), (I-a-i), (I-a-ii), (I-a-iii), (I-c), (I-c-i), and (I-d), wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula (I), (I-a), (I-a-i), (I-a-ii), (I-a-iii), (I-c), (I-c-i), and (I-d), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I), (I-a), (I-a-i), (I-a-ii), (I-a-iii), (I-c), (I-c-i), and (I-d), may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of formula (I), (I-a), (I-a-i), (I-a-ii), (I-a-iii), (I-c), (I-c-i), and (I-d) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I), (I-a), (I-a-i), (I-a-ii), (I-a-iii), (I-c), (I-c-i), and (I-d) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid, and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, refers to derivatives of the compounds of the invention which have cleavable groups. Such derivatives become, by solvolysis or under physiological conditions, the compounds of the invention which are pharmaceutically active in vivo. Prodrugs of the compounds of the invention are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of formula (I), (I-a), (I-a-i), (I-a-ii), (I-a-iii), (I-c), (I-c-i), and (I-d) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds of the invention can be better understood in connection with the following synthetic schemes and methods which illustrate a means by which the compounds may be prepared.

The compounds of this invention can be prepared by a variety of synthetic procedures. Representative procedures are shown in, but are not limited to, Schemes 1-7. In Schemes 1-7, the variables $R^1$, $R^2$, $R^3$, $R^{3a}$, $R^{3b}$, $R^7$, $R^8$, $R^A$, $R^B$, Z, $G^1$, $G^2$, $X^2$, m, p, and q are as described in the Summary.

Abbreviations used in the descriptions of the schemes and the specific examples have the following meanings: APCI for atmospheric pressure chemical ionization; DMSO for dimethylsulfoxide, HATU for N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N'N'-tetramethyluronium hexafluorophosphate or 1-[bis(dimethylamino)methylene]-1H-1,2,3-triazolo[4,5-b]pyridinium 3-oxid hexafluorophosphate, HPLC for high-performance liquid chromatography; LC/MS for liquid chromatography/mass spectrometry; MS for mass spectrometry; NMR for nuclear magnetic resonance, psi for pounds per square inch; and SFC for supercritical fluid chromatography.

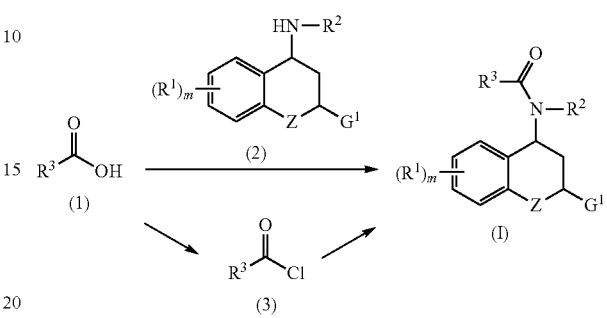

Scheme 1

As shown in Scheme 1, compounds of formula (I) may be prepared from compounds of formula (1). Carboxylic acids of formula (1) may be coupled with amines of formula (2) or the corresponding acid salts thereof under amide bond forming conditions to give compounds of formula (I). Examples of conditions known to generate amides from a mixture of a carboxylic acid and an amine include, but are not limited to, those in the presence of a coupling reagent such as, but not limited to, N-(3-dimethylaminopropyl)-N'-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may be added to facilitate the coupling reaction. Auxiliary coupling reagents that are often used in the coupling reactions include, but are not limited to, (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine, N,N-diisopropylethylamine, or pyridine. The coupling reaction may be carried out in a solvent such as, but not limited to, tetrahydrofuran, N,N-dimethylformamide, N,N-dimethylacetamide, dimethyl sulfoxide, dichloromethane, or ethyl acetate, or mixtures thereof. The reactions may be carried out at ambient temperature or at elevated temperature. The reaction mixture may be heated either conventionally or with microwave irradiation.

Alternatively, carboxylic acids of formula (1) may be converted to the corresponding acid chlorides of formula (3) by reaction with thionyl chloride, $PCl_3$, $PCl_5$, cyanuric chloride, or oxalyl chloride. The reactions with thionyl chloride and oxalyl chloride may be catalyzed with N,N-dimethylformamide at ambient temperature in a solvent such as dichloromethane. The resultant acid chlorides of formula (3) may then reacted with amines of formula (1) optionally in the presence of a base such as, but not limited to, a tertiary amine base (for example, triethylamine or N,N-diisopropylethylamine) or an aromatic base such as pyridine, at room temperature or heated in a solvent such as dichloromethane to give amides of formula (I).

Scheme 2

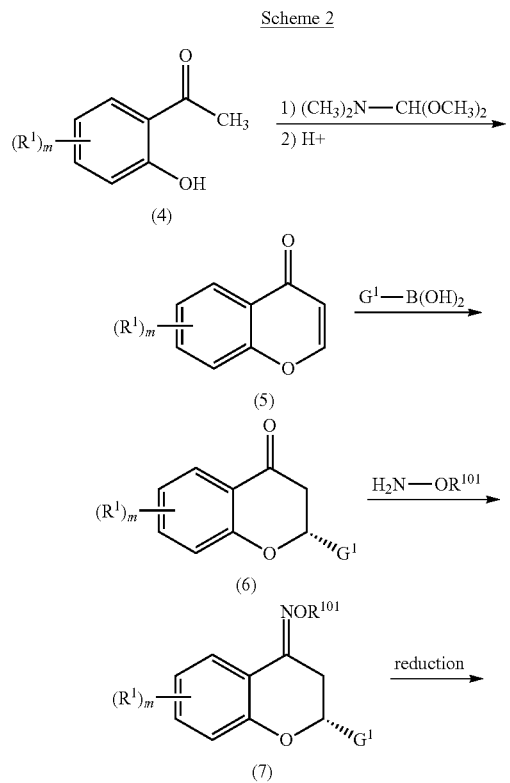

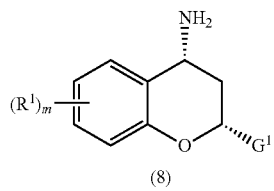

As shown in Scheme 2, compounds of formula (8) may be prepared from compounds of formula (4). Methyl ketones of general formula (4) may be treated with N,N-dimethylformamide dimethyl acetal at elevated temperature (about 100° C. to about 120° C.) or under microwave irradiation to obtain intermediate enamines. The intermediate enamines may be treated with an acid, such as hydrochloric acid, in refluxing dichloromethane to give chromenones of formula (5). Treatment of chromenones of formula (5) with a boronic acid (or esters thereof) of formula $G^1$-$B(OH)_2$ in a heated solvent such as dichloroethane in the presence of (S)-4-(tert-butyl)-2-(pyridin-2-yl)-4,5-dihydrooxazole, ammonium hexafluorophosphate(V), and a catalyst such as bis(2,2,2-trifluroacetoxy)palladium provides the chiral chromanones of formula (6). Chromanones of formula (6) may be reacted with hydroxylamines or alkoxyamines of formula $H_2N$—$OR^{101}$ wherein $R^{101}$ is hydrogen, $C_1$-$C_6$ alkyl, or benzyl; in heated pyridine to give oximes of formula (7). Stereoselective hydrogenolysis of oximes of formula (7) may be achieved in the presence of a catalyst such as platinum on carbon or platinum(IV) oxide/acetic acid. The reduction provides selectively a single enantiomer of formula (8). Amines of formula (8) are representative of amines of formula (2) in Scheme 1.

Scheme 3

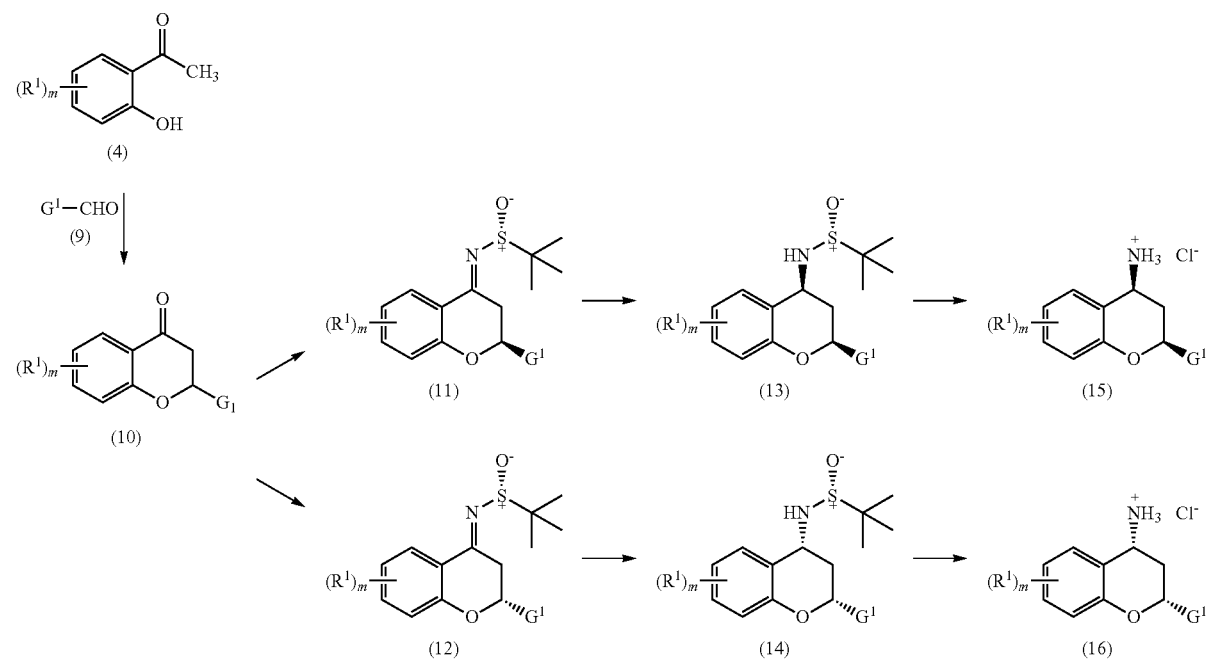

As shown in Scheme 3, compounds of formula (15) and formula (16) may be prepared from compounds of formula (4). Compounds of formula (4) may be reacted with aldehydes of formula (9) in the presence of pyrrolidine and optionally, acetic acid, to provide compounds of formula (10). The reaction is typically performed at an elevated temperature, for example, at about 70° C., and in a solvent, such as, but not limited to, toluene.

The hydrochloride salts of the chiral amines (15) and (16) may be prepared from ketones of formula (10) according to the general procedure described by Ellman and co-workers (Tanuwidjaja, J.; Ellman, J. A. et al. *J. Org. Chem.* 2007, 72, 626) as illustrated in Scheme 3. Chromanones (10) may be condensed with a chiral sulfinamide such as tert-butanesulfinamide in the presence of a Lewis acid such as titanium (IV) ethoxide to provide N-sulfinyl imine intermediates (11) and (12). The diastereomeric mixture of (11) and (12) may be separated via chromatography. The respective N-sulfinyl imine intermediates (11) and (12) may undergo a subsequent reduction with reagents such as sodium borohydride to provide sulfinamides of general formula (13) and (14). Treatment of the sulfinamides (13) and (14) with HCl or acetyl chloride/methanol provides the hydrochloride salts of amines (15) and (16). Amine salts of formula (15) and (16) are salts of representative of amines of formula (2) in Scheme 1.

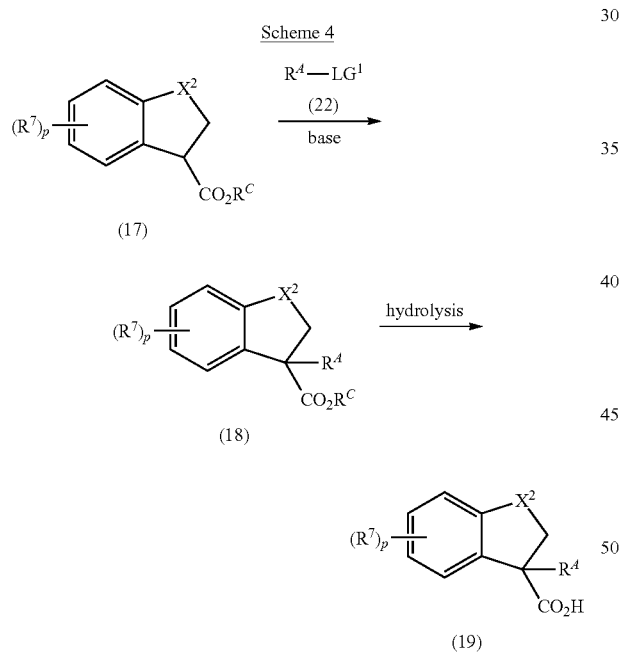

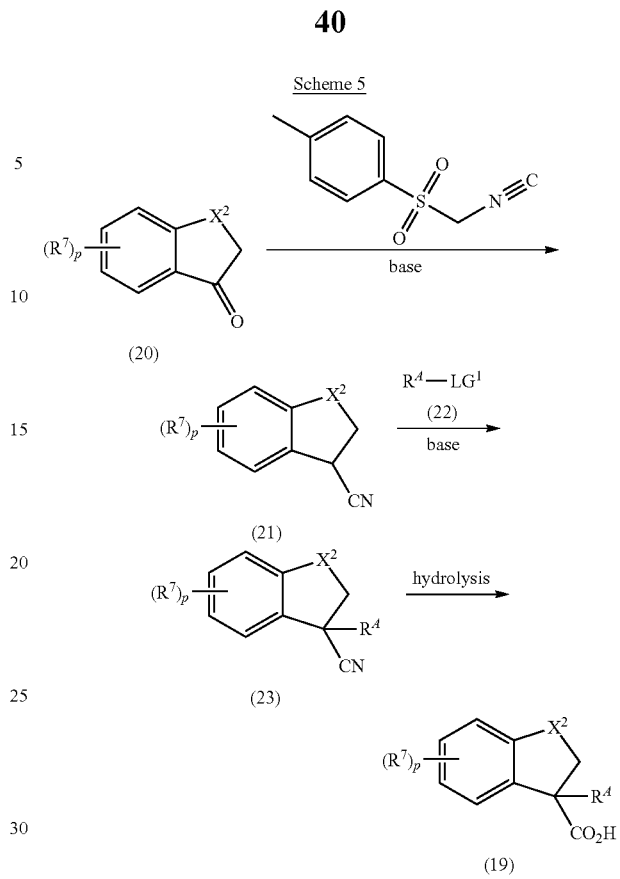

Alternatively, compounds of formula (20) may be reacted with 1-((isocyanomethyl)sulfonyl)-4-methylbenzene in the presence of a base such as but not limited to potassium tert-butoxide to give nitriles of formula (21). Nitriles of formula (21) may be alkylated with $R^4$-$LG^1$ (22) in the presence of a base such as, but not limited, to n-butyllithium, wherein $LG^1$ is a leaving group selected from chlorine, bromine, iodine or a sulfonate, to give compounds of formula (23). Nitriles of formula (23) may be hydrolyzed in a heated hydroxide solution to give compounds of formula (19).

As illustrated in Scheme 4, compounds of formula (19) may be prepared from compounds of formula (17) or (20). Compounds of formula (17), wherein $R^C$ is typically an alkyl group, may be alkylated with $R^4$-$LG^1$ (22) in the presence of a base such as but not limited to n-butyllithium wherein $LG^1$ is a leaving group selected from chlorine, bromine, iodine or a sulfonate, to give compounds of formula (18). Esters of formula (18) can be hydrolyzed in a heated hydroxide solution to give compounds of formula (19). Compounds of formula (19) are representative of acids of formula (1) in Scheme 1.

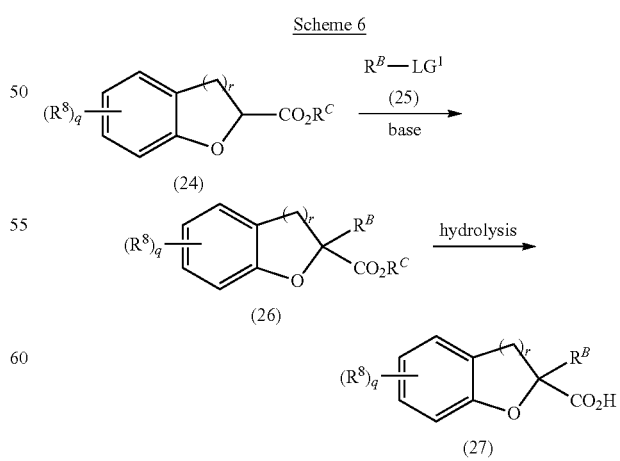

As shown in Scheme 6, compounds of formula (27) may be prepared from compounds of formula (24). Compounds of formula (24), wherein $R^C$ is typically an alkyl group, may be alkylated with $R^B$-$LG^1$ (25) in the presence of a base such as but not limited to n-butyllithium, wherein $LG^1$ is a leaving group selected from chlorine, bromine, iodine or a sulfonate, to give compounds of formula (26). Esters of formula (26) may be hydrolyzed in a heated hydroxide solution to give compounds of formula (27). Compounds of formula (27) are representative of acids of formula (1) in Scheme 1.

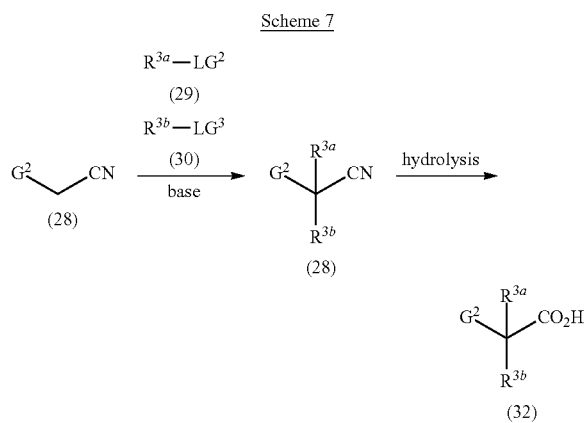

Scheme 7

As illustrated in Scheme 7, compounds of formula (32) may be prepared from compounds of formula (28). Compounds of formula (28) may be alkylated with $R^{3a}$-$LG^2$ (29) and/or $R^{3b}$-$LG^3$ (30) wherein $R^{3a}$ and $R^{3b}$ are each independently $C_1$-$C_3$ alkyl and are the same or different, in the presence of a base such as, but not limited to, sodium hydroxide, wherein $LG^2$ and $LG^3$ are leaving groups selected from chlorine, bromine, iodine or a sulfonate, to give compounds of formula (31). Nitriles of formula (31) may be hydrolyzed in a heated hydroxide solution to give compounds of formula (32). Compounds of formula (32) are representative of acids of formula (1) in Scheme 1.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

When employed as a pharmaceutical, a compound of the invention is typically administered in the form of a pharmaceutical composition. Such compositions can be prepared in a manner well known in the pharmaceutical art and comprise a therapeutically effective amount of a compound of formula (I), (I-a), (I-a-i), (I-a-ii), (I-a-iii), (I-c), (I-c-i), or (I-d), or a pharmaceutically acceptable salt thereof together with a pharmaceutically acceptable carrier. The phrase "pharmaceutical composition" refers to a composition suitable for administration in medical or veterinary use.

The pharmaceutical compositions that comprise a compound of formula (I), (I-a), (I-a-i), (I-a-ii), (I-a-iii), (I-c), (I-c-i), or (I-d), alone or in combination with further therapeutically active ingredient, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous diluents, solvents, or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it may be desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In certain embodiments, solid dosage forms may contain from 1% to 95% (w/w) of a compound of the invention. In certain embodiments, the present compounds or pharmaceutically acceptable salts thereof, may be present in the solid dosage form in a range of from 5% to 70% (w/w). In such solid dosage forms, the active compound may be mixed with at least one inert, pharmaceutically acceptable carrier, such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

A compound of the invention may also be administered in sustained release forms or from sustained release drug delivery systems.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's Syndrome (SS), chronic obstructive lung disease (COLD), or chronic obstructive airway disease (COAD) in a subject, wherein the method comprises the step of administering to said subject a therapeutically effective amount of a compound of formula (I), (I-a), (I-a-i), (I-a-ii), (I-a-iii), (I-c), (I-c-i), or (I-d), or a pharmaceutically acceptable salt thereof, or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

One embodiment is directed to a compound of the invention or a pharmaceutically acceptable salt thereof, or pharmaceutical compositions comprising a compound of the invention for use in medicine. One embodiment is directed to a compound of the invention or a pharmaceutically acceptable salt thereof, or pharmaceutical compositions thereof, for use in the treatment of cystic fibrosis, pancreatic insufficiency, Sjögren's Syndrome (SS), chronic obstructive lung disease (COLD) or chronic obstructive airway disease (COAD). In a more particular embodiment, the present invention provides compounds of the invention or pharmaceutically acceptable salts thereof, or pharmaceutical compositions comprising thereof, for use in the treatment of cystic fibrosis. In a more particular embodiment, the cystic fibrosis is caused by a Class I, II, III, IV, V, and/or VI mutation.

One embodiment is directed to the use of a compound according to formula (I), (I-a), (I-a-i), (I-a-ii), (I-a-iii), (I-c), (I-c-i), or (I-d) or a pharmaceutically acceptable salt thereof in the preparation of a medicament. The medicament optionally can comprise one or more additional therapeutic agents.

In some embodiments, the medicament is for use in the treatment of cystic fibrosis, pancreatic insufficiency, Sjögren's Syndrome (SS), chronic obstructive lung disease (COLD) or chronic obstructive airway disease (COAD). In a particular embodiment, the medicament is for use in the treatment of cystic fibrosis. In a more particular embodiment, the cystic fibrosis is caused by a Class I, II, III, IV, V, and/or VI mutation.

This invention also is directed to the use of a compound according to formula (I), (I-a), (I-a-i), (I-a-ii), (I-a-iii), (I-c), (I-c-i), or (I-d) or a pharmaceutically acceptable salt thereof in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of a compound according to formula (I), (I-a), (I-a-i), (I-a-ii), (I-a-iii), (I-c), (I-c-i), or (I-d) or a pharmaceutically acceptable salt thereof in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention or a pharmaceutically acceptable salt thereof, and one or more additional therapeutic agents. In a particular embodiment, the other therapeutic agent is a cystic fibrosis treatment agent. In a more particular embodiment, the cystic fibrosis is caused by a Class I, II, III, IV, V, and/or VI mutation.

The present compounds or pharmaceutically acceptable salts thereof may be administered as the sole active agent or it may be co-administered with other therapeutic agents, including other compounds or a pharmaceutically acceptable salt thereof that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), CFTR stabilizers, and CFTR amplifiers. In one embodiment, the CFTR mediated disease is cystic fibrosis, chronic obstructive pulmonary disease (COPD), dry eye disease, pancreatic insufficiency, or Sjögren's Syndrome. In one embodiment, the CFTR mediated disease is cystic fibrosis. In one embodiment, the compounds of the invention or pharmaceutically acceptable salts thereof may be co-administered with one or two CFTR modulators and one CFTR stabilizer. In one embodiment, the compounds of the invention or pharmaceutically acceptable salts thereof may be co-administered with one or two CFTR modulators, one CFTR stabilizer, and one CFTR amplifier. In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator and one corrector. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, N-(3-carbamoyl-5,5,7,7-tetramethyl-5,7-dihydro-4H-thieno[2,3-c]pyran-2-yl)-1H-pyrazole-5-carboxamide, and 3-amino-N-[(2S)-2-hydroxypropyl]-5-{[4-(trifluoromethoxy)phenyl]sulfonyl}pyridine-2-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823; and U.S. Applications 62/169,881.

In one embodiment, the potentiator can be selected from the group consisting of
Ivacaftor (VX-770, N-(2,4-di-tert-butyl-5-hydroxyphenyl)-4-oxo-1,4-dihydroquinoline-3-carboxamide);
CTP-656;
NVS-QBW251:
FD1860293;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide
2-(1-hydroxycyclopropanecarboxamido)-5,5,7,7-tetramethyl-5,7-dihydro-4H-thieno[2,3-c]pyran-3-carboxamide;

5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5, 5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;
2-[[(2R)-2-hydroxy-3,3-dimethyl-butanoyl]amino]-5,5,7,7-tetramethyl-4H-thieno[2,3-c]pyran-3-carboxamide;
2-[(2-hydroxy-2,3,3-trimethyl-butanoyl)amino]-5,5,7,7-tetramethyl-4H-thieno[2,3-c]pyran-3-carboxamide;
[5-[(3-carbamoyl-5,5,7,7-tetramethyl-4H-thieno[2,3-c]pyran-2-yl)carbamoyl]pyrazol-1-yl]methyl dihydrogen phosphate;
[3-[(3-carbamoyl-5,5,7,7-tetramethyl-4H-thieno[2,3-c]pyran-2-yl)carbamoyl]pyrazol-1-yl]methyl dihydrogen phosphate;
N-(3-carbamoyl-5,5,7,7-tetramethyl-4H-thieno[2,3-c]pyran-2-yl)-4-(1,4-dioxan-2-yl)-1H-pyrazole-3-carboxamide;
5,5,7,7-tetramethyl-2-[[(2S)-3,3,3-trifluoro-2-hydroxy-2-methyl-propanoyl]amino]-4H-thieno[2,3-c]pyran-3-carboxamide;
2-[[(2S)-2-hydroxypropanoyl]amino]-5,5,7,7-tetramethyl-4H-thieno[2,3-c]pyran-3-carboxamide;
3-amino-N-(2-hydroxy-2-methylpropyl)-5-{[4-(trifluoromethoxy)phenyl]sulfonyl}pyridine-2-carboxamide;
3-amino-N-[(4-hydroxy-1-methylpiperidin-4-yl)methyl]-5-{[4-(trifluoromethoxy)phenyl]sulfonyl}pyridine-2-carboxamide;
3-amino-N-(3-hydroxy-2,2-dimethylpropyl)-5-{[4-(trifluoromethoxy)phenyl]sulfonyl}pyridine-2-carboxamide;
3-amino-5-[(4-fluorophenyl)sulfonyl]-N-[(1-hydroxycyclopropyl)methyl]pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-5-[(4-fluorophenyl)sulfonyl]-N-(2-hydroxy-2-methylpropyl)pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(azetidin-1-yl)methanone;
(3-amino-5-{[4-(trifluoromethoxy)phenyl]sulfonyl}pyridin-2-yl)[3-(hydroxymethyl)azetidin-1-yl]methanone;
(3-amino-5-{[4-(trifluoromethoxy)phenyl]sulfonyl}pyridin-2-yl)(3-fluoroazetidin-1-yl)methanone;
3-amino-N-[(2R)-2-hydroxy-3-methoxypropyl]-5-{[4-(trifluoromethyl)phenyl]sulfonyl}pyridine-2-carboxamide;
(3-amino-5-{[2-fluoro-4-(trifluoromethoxy)phenyl]sulfonyl}pyridin-2-yl)(3-hydroxyazetidin-1-yl)methanone;
(3-amino-5-{[2-(trifluoromethoxy)phenyl]sulfonyl}pyridin-2-yl)(3,3-difluoroazetidin-1-yl)methanone;
rac-3-amino-N-[(3R,4S)-4-hydroxytetrahydro-2H-pyran-3-yl]-5-{[2-(trifluoromethoxy)phenyl]sulfonyl}pyridine-2-carboxamide;
3-amino-5-[(4,4-difluoropiperidin-1-yl)sulfonyl]-N-(3,3,3-trifluoro-2-hydroxypropyl)pyridine-2-carboxamide;
(3-amino-5-{[2-(trifluoromethoxy)phenyl]sulfonyl}pyridin-2-yl)[3-hydroxy-3-(trifluoromethyl)azetidin-1-yl]methanone;
3-amino-N-(2-hydroxy-4-methylpentyl)-5-{[4-(trifluoromethoxy)phenyl]sulfonyl}pyridine-2-carboxamide;
(3-amino-5-{[4-(trifluoromethyl)phenyl]sulfonyl}pyridin-2-yl)(3-hydroxy-3-methylazetidin-1-yl)methanone;
3-amino-N-(3,3,3-trifluoro-2-hydroxypropyl)-5-{[4-(trifluoromethyl)piperidin-1-yl]sulfonyl}pyridine-2-carboxamide;
3-amino-N-[2-hydroxy-1-(4-methoxyphenyl)ethyl]-5-{[4-(trifluoromethoxy)phenyl]sulfonyl}pyridine-2-carboxamide;
3-amino-5-[(3,3-difluoroazetidin-1-yl)sulfonyl]-N-(3,3,3-trifluoro-2-hydroxypropyl)pyridine-2-carboxamide;
3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;

3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
(3-amino-5-{[2-fluoro-4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3S)-tetrahydrofuran-3-ylmethyl]pyridine-2-carboxamide;
3-amino-5-{[2-fluoro-4-(trifluoromethoxy)phenyl]sulfonyl}-N-[(3S)-tetrahydrofuran-3-ylmethyl]pyridine-2-carboxamide;
3-amino-N-[2-hydroxy-3-(2,2,2-trifluoroethoxy)propyl]-5-{[4-(trifluoromethyl)phenyl]sulfonyl}pyridine-2-carboxamide;
3-amino-N-(3-tert-butoxy-2-hydroxypropyl)-5-{[2-fluoro-4-(trifluoromethyl)phenyl]sulfonyl}pyridine-2-carboxamide;
[3-amino-5-(phenylsulfonyl)pyridin-2-yl][3-hydroxy-3-(trifluoromethyl)azetidin-1-yl]methanone;
{3-amino-5-[(3-fluorophenyl)sulfonyl]pyridin-2-yl}[3-hydroxy-3-(trifluoromethyl)azetidin-1-yl]methanone; and
3-amino-N-[(2S)-2-hydroxypropyl]-5-{[4-(trifluoromethoxy)phenyl]sulfonyl}pyridine-2-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2222, GLPG2665, GLPG2737, GLPG2851, GLPG3221, VX-152, VX-440, VX-659, VX-445, FDL169, FDL304, FD2052160, and FD2035659. Examples of correctors are also disclosed in U.S. application Ser. Nos. 14/925,649, 14/926,727, 62/193,391, 62/299,633, 62/239,475, 62/239,647, and 62/309,794.

In one embodiment, the corrector(s) can be selected from the group consisting of
Lumacaftor (VX-809);
1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);
VX-983;
GLPG2665;
GLPG3221;
VX-152;
VX-440;
VX-659;
VX-445;
FDL169
FDL304;
FD2052160;
FD2035659;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;
3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;
3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;
3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;
4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;
4-[(2R,4R)-4-({[1-(2,2-difluoro-1,3-benzodioxol-5-yl)cyclopropyl]carbonyl}amino)-3,4-dihydro-2H-chromen-2-yl]benzoic acid;
4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
rac-3-[(2R,4S)-4-({[1-(2,2-difluoro-1,3-benzodioxol-5-yl)cyclopropyl]carbonyl}amino)tetrahydro-2H-pyran-2-yl]benzoic acid;
rac-4-[(2R,4S)-4-({[1-(2,2-difluoro-1,3-benzodioxol-5-yl)cyclopropyl]carbonyl}amino)tetrahydro-2H-pyran-2-yl]benzoic acid;
3-[(2S,4R)-4-({[1-(2,2-difluoro-1,3-benzodioxol-5-yl)cyclopropyl]carbonyl}amino)tetrahydro-2H-pyran-2-yl]benzoic acid;
3-[(2R,4S)-4-({[1-(2,2-difluoro-1,3-benzodioxol-5-yl)cyclopropyl]carbonyl}amino)tetrahydro-2H-pyran-2-yl]benzoic acid;
rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)
cyclopropyl]carbonyl}amino)-6-phenyltetrahydro-2H-
pyran-2-yl]benzoic acid;
3-[(2R,4S,6S)-4-({[1-(2,2-difluoro-1,3-benzodioxol-5-yl)
cyclopropyl]carbonyl}amino)-6-phenyltetrahydro-2H-
pyran-2-yl]benzoic acid;
4-[(2R,4S)-4-({[1-(2,2-difluoro-1,3-benzodioxol-5-yl)cy-
clopropyl]carbonyl}amino)tetrahydro-2H-pyran-2-yl]
benzoic acid;
4-[6-(4-cyanopiperidin-1-yl)pyridin-3-yl]-3-cyclobutyl-N-
(methanesulfonyl)-1-phenyl-1H-pyrazolo[3,4-b]pyri-
dine-6-carb oxamide;
3-cyclobutyl-N-(methanesulfonyl)-4-[4-(methoxymethyl)
piperidin-1-yl]-1-phenyl-1H-pyrazolo[3,4-b]pyridine-6-
carb oxamide;
4-[6-(4-cyanopiperidin-1-yl)pyridin-3-yl]-3-cyclobutyl-N-
(methanesulfonyl)-1-[2-(morpholin-4-yl)pyridin-4-yl]-
1H-pyrazolo[3,4-b]pyridine-6-carboxamide;
N-(methanesulfonyl)-4-[4-(methoxymethyl)piperidin-1-yl]-
1-[2-(morpholin-4-yl)pyridin-4-yl]-3-(propan-2-yl)-1H-
pyrazolo[3,4-b]pyridine-6-carboxamide;
3-cyclobutyl-4-[4-(methoxymethyl)piperidin-1-yl]-N-[2-
(morpholin-4-yl)ethanesulfonyl]-1-phenyl-1H-pyrazolo
[3,4-b]pyridine-6-carboxamide;
3-cyclobutyl-N-[2-(dimethylamino)ethanesulfonyl]-4-[4-
(methoxymethyl)piperidin-1-yl]-1-phenyl-1H-pyrazolo
[3,4-b]pyridine-6-carboxamide;
1-(4-fluorophenyl)-N-(methanesulfonyl)-4-(1'-methyl[4,4'-
bipiperidin]-1-yl)-3-(propan-2-yl)-1H-pyrazolo[3,4-b]
pyridine-6-carboxamide;
3-cyclobutyl-N-(methanesulfonyl)-4-{4-[2-(morpholin-4-
yl)ethyl]piperidin-1-yl}-1-phenyl-1H-pyrazolo[3,4-b]
pyridine-6-carb oxamide;
3-cyclobutyl-4-[4-(methoxymethyl)piperidin-1-yl]-N-(oxo-
lane-3-sulfonyl)-1-phenyl-1H-pyrazolo[3,4-b]pyridine-6-
carboxamide;
3-cyclobutyl-N-(dimethylsulfamoyl)-1-(4-fluorophenyl)-4-
(4-methoxy[1,4'-bipiperidin]-1'-yl)-1H-pyrazolo[3,4-b]
pyridine-6-carboxamide;
3-cyclobutyl-N-(morpholine-4-sulfonyl)-4-[4-(morpholin-
4-yl)piperidin-1-yl]-1-phenyl-1H-pyrazolo[3,4-b]pyri-
dine-6-carboxamide;
3-cyclobutyl-N-(morpholine-4-sulfonyl)-1-phenyl-4-{4-
[(pyrrolidin-1-yl)methyl]piperidin-1-yl}-1H-pyrazolo[3,
4-b]pyridine-6-carboxamide;
3-cyclobutyl-N-(methanesulfonyl)-4-[4-(morpholin-4-yl)pi-
peridin-1-yl]-1-phenyl-1H-pyrazolo[3,4-b]pyridine-6-
carboxamide;
3-cyclobutyl-4-[4-(morpholin-4-yl)piperidin-1-yl]-1-phe-
nyl-1H-pyrazolo[3,4-b]pyridine-6-carboxylic acid;
3-cyclobutyl-1-phenyl-4-{4-[(pyrrolidin-1-yl)methyl]pip-
eridin-1-yl}-1H-pyrazolo[3,4-b]pyridine-6-carboxylic
acid;
5-[(2R,4R)-4-{[(7R)-2,2-difluoro-7-methyl-6,7-dihydro-
2H-furo[2,3-f][1,3]benzodioxole-7-carbonyl]amino}-7-
methoxy-3,4-dihydro-2H-1-benzopyran-2-yl]pyrazine-2-
carboxylic acid;
6-[(2R,4R)-4-{[(7R)-2,2-difluoro-7-methyl-6,7-dihydro-
2H-furo[2,3-f][1,3]benzodioxole-7-carbonyl]amino}-7-
(trifluoromethoxy)-3,4-dihydro-2H-1-benzopyran-2-yl]
pyridine-3-carboxylic acid;
trans-4-[(2S,4S)-4-{[(7R)-2,2-difluoro-7-methyl-6,7-di-
hydro-2H-furo[2,3-f][1,3]benzodioxole-7-carbonyl]
amino}-7-(trifluoromethoxy)-3,4-dihydro-2H-1-benzo-
pyran-2-yl]cyclohexane-1-carboxylic acid;
6-[(2R,4R)-7-(difluoromethoxy)-4-{[(7R)-2,2-difluoro-7-
methyl-6,7-dihydro-2H-furo[2,3-f][1,3]benzodioxole-7-
carbonyl]amino}-3,4-dihydro-2H-1-benzopyran-2-yl]
pyridine-3-carboxylic acid;
trans-4-[(2S,4S)-4-{[(7R)-2,2-difluoro-7-methyl-6,7-di-
hydro-2H-furo[2,3-f][1,3]benzodioxole-7-carbonyl]
amino}-7-methoxy-3,4-dihydro-2H-1-benzopyran-2-yl]
cyclohexane-1-carboxylic acid;
ethyl trans-4-[(2S,4S)-7-(difluoromethoxy)-4-{[(7R)-2,2-
difluoro-7-methyl-6,7-dihydro-2H-furo[2,3-f][1,3]benzo-
dioxole-7-carbonyl]amino}-3,4-dihydro-2H-1-benzopy-
ran-2-yl]cyclohexane-1-carboxylate;
cis-4-[(2R,4R)-4-{[(7R)-2,2-difluoro-7-methyl-6,7-di-
hydro-2H-furo[2,3-f][1,3]benzodioxole-7-carbonyl]
amino}-7-(trifluoromethoxy)-3,4-dihydro-2H-1-benzo-
pyran-2-yl]cyclohexane-1-carboxylic acid;
trans-4-[(2S,4S)-7-(difluoromethoxy)-4-{[(7R)-2,2-dif-
luoro-7-methyl-6,7-dihydro-2H-furo[2,3-f][1,3]benzodi-
oxole-7-carbonyl]amino}-3,4-dihydro-2H-1-benzopyran-
2-yl]cyclohexane-1-carboxylic acid;
1-[(2R,4R)-4-{[(7R)-2,2-difluoro-7-methyl-6,7-dihydro-
2H-furo[2,3-f][1,3]benzodioxole-7-carbonyl]amino}-7-
(trifluoromethoxy)-3,4-dihydro-2H-1-benzopyran-2-yl]
cyclopropane-1-carboxylic acid;
trans-4-[(2R,4R)-4-{[(5S)-2,2-difluoro-5-methyl-6,7-di-
hydro-2H,5H-indeno[5,6-d][1,3]dioxole-5-carbonyl]
amino}-7-(trifluoromethoxy)-3,4-dihydro-2H-1-benzo-
pyran-2-yl]cyclohexane-1-carboxylic acid;
trans-4-[(2R,4R)-4-{[(5S)-2,2-difluoro-5-methyl-6,7-di-
hydro-2H,5H-indeno[5,6-d][1,3]dioxole-5-carbonyl]
amino}-7-methoxy-3,4-dihydro-2H-1-benzopyran-2-yl]
cyclohexane-1-carboxylic acid;
trans-4-[(2R,4R)-4-{[(7R)-2,2-difluoro-7-methyl-6,7-di-
hydro-2H-furo[2,3-f][1,3]benzodioxole-7-carbonyl]
amino}-7-methoxy-3,4-dihydro-2H-1-benzopyran-2-yl]
cyclohexane-1-carboxylic acid;
trans-4-[(2R,4R)-7-(difluoromethoxy)-4-{[(7R)-2,2-dif-
luoro-7-methyl-6,7-dihydro-2H-furo[2,3-f][1,3]benzodi-
oxole-7-carbonyl]amino}-3,4-dihydro-2H-1-benzopyran-
2-yl]cyclohexane-1-carboxylic acid; and
trans-4-[(2R,4R)-4-{[(7R)-2,2-difluoro-7-methyl-6,7-di-
hydro-2H-furo[2,3-f][1,3]benzodioxole-7-carbonyl]
amino}-7-(trifluoromethoxy)-3,4-dihydro-2H-1-benzo-
pyran-2-yl]cyclohexane-1-carboxylic acid.

In one embodiment, the additional therapeutic agent is a CFTR amplifier. CFTR amplifiers enhance the effect of known CFTR modulators, such as potentiators and correctors. Examples of CFTR amplifier include PTI130 and PTI-428. Examples of amplifiers are also disclosed in publications: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is Cavosonstat (N91115). Examples of stabilizers are also disclosed in publications: WO2012048181 and WO2012083165.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in PCT Publication Nos. WO2009/074575 and WO2013/043720; and U.S. Pat. No. 8,999,976.

In one embodiment, the ENaC inhibitor is VX-371.

In one embodiment, the ENaC inhibitor is SPX-101 (S18).

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

Further benefits of Applicants' invention will be apparent to one skilled in the art from reading this patent application.

The following Examples may be used for illustrative purposes and should not be deemed to narrow the scope of the invention.

EXAMPLES

All reagents were of commercial grade and were used as received without further purification, unless otherwise stated. Commercially available anhydrous solvents were used for reactions conducted under inert atmosphere. Reagent grade solvents were used in all other cases, unless otherwise specified. Chemical shifts (δ) for $^1$H NMR spectra were reported in parts per million (ppm) relative to tetramethylsilane (δ 0.00) or the appropriate residual solvent peak, i.e. $CHCl_3$ (δ 7.27), as internal reference. Multiplicities were given as singlet (s), doublet (d), triplet (t), quartet (q), quintuplet (quin), multiplet (m) and broad (br). Microwave heating was performed with a Biotage® Initiator.

Example 1

4-{(2R,4R)-4-[2-(2,2-difluoro-2H-1,3-benzodioxol-5-yl)-2-methylpropanamido]-7-methoxy-3,4-dihydro-2H-1-benzopyran-2-yl}benzoic acid Example 1A methyl 4-[(2R)-7-methoxy-4-oxo-3,4-dihydro-2H-1-benzopyran-2-yl]benzoate A 250-mL round-bottomed flask was charged with (4-(methoxycarbonyl)phenyl)boronic acid (30.6 g, 170 mmol), ammonium hexafluorophosphate(V) (4.16 g, 25.5 mmol), bis(2,2,2-trifluoroacetoxy)palladium (2.123 g, 6.39 mmol), and (S)-4-(tert-butyl)-2-(pyridin-2-yl)-4,5-dihydrooxazole (1.565 g, 7.66 mmol). 1,2-Dichloroethane (85 mL) was added. The resulting suspension was stirred at ambient temperature for 10 minutes, at which point Example 7D (15 g, 85.0 mmol) was added, followed by water (7.67 g, 426 mmol) and an additional 85 mL of 1,2-dichloroethane to rinse the sides of the flask. The reaction mixture was heated at 60° C. (internal temperature) in a sand bath for 36 hours. The flask was cooled to room temperature, and the suspension was filtered through a 1-inch pad of silica, eluting with dichloromethane. The filtrates were concentrated to give a crude solid. tert-Butyl methyl ether (100 mL) and heptanes (100 mL) were added, and the solids were broken up with a spatula. The resulting suspension was heated at 60° C. for 1 hour while stirring vigorously. The mixture was then cooled to ambient temperature, and the resulting solid was collected via filtration through a fritted funnel to give 10.54 g of the title compound (39% yield). $^1$H NMR (400 MHz, $CDCl_3$) δ ppm 8.10 (d, J=8.3 Hz, 2H), 7.87 (d, J=8.9 Hz, 1H), 7.56 (d, J=8.3 Hz, 2H), 6.64 (dd, J=8.8, 2.3 Hz, 1H), 6.52 (d, J=2.4 Hz, 1H), 5.53 (dd, J=13.0, 3.2 Hz, 1H), 3.94 (s, 3H), 3.85 (s, 3H), 2.99 (dd, J=16.9, 13.0 Hz, 1H), 2.86 (dd, J=16.8, 3.2 Hz, 1H); MS (ESI+) m/z 312.8 (M+H)$^+$.

Example 1B methyl 4-{(2R)-4-[(benzyloxy)imino]-7-methoxy-3,4-dihydro-2H-1-benzopyran-2-yl}benzoate Example 1A (2 g, 6.40 mmol) was dissolved in 15 mL of dry pyridine. O-Benzylhydroxylamine hydrochloride (1.073 g, 6.72 mmol) was added, and the solution was heated at 50° C. for 16 hours. The reaction mixture was cooled to ambient temperature and concentrated. The residue was partitioned between tert-butyl methyl ether and saturated aqueous ammonium chloride. The organic extracts were concentrated in vacuo and purified via flash chromatography, eluting with 10-40% ethyl acetate/heptanes over 20 minutes on an 80 g silica gel column to give the title compound (10:1 mixture of E and Z oximes, 2.57 g, 96% yield). Analytical data for the major isomer: $^1$H NMR (501 MHz, $CDCl_3$) δ ppm 8.06 (d, J=8.3 Hz, 2H), 7.84 (d, J=8.8 Hz, 1H), 7.54-7.46 (m, 2H), 7.40-7.28 (m, 5H), 6.57 (dd, J=8.8, 2.5 Hz, 1H), 6.48 (d, J=2.5 Hz, 1H), 5.19 (d, J=2.0 Hz, 2H), 5.11 (dd, J=12.3, 3.2 Hz, 1H), 3.92 (s, 3H), 3.78 (s, 3H), 3.48 (dd, J=17.2, 3.2 Hz, 1H), 2.67 (dd, J=17.2, 12.2 Hz, 1H); MS (ESI+) m/z 418.1 (M+H)$^+$.

Example 1C methyl 4-[(2R,4R)-4-amino-7-methoxy-3,4-dihydro-2H-1-benzopyran-2-yl]benzoate Acetic acid (300 mL) was added to Example 1B (20 g 47.9 mmol) and 5% Pt/C wet (1.5 g wet weight, 58.9% water, 0.884 g or 4.42% dry basis) in a 300-mL stainless steel reactor. The headspace was inerted with argon and then pressurized to 30 psi with hydrogen. The mixture was shaken at ambient temperature under 30 psi of hydrogen for 18 hours. The reactor was vented and the reaction mixture was filtered through 0.45 μm GHP Acrodisc® membrane. The filtrate was concentrated in vacuo to give 60 g of crude material. The crude material was heated at 70° C. in 250 mL of 4:1 tert-butyl methyl ether:heptanes until a clear solution resulted. HCl (3 M in cyclopentyl methyl ether, 47.9 mL, 144 mmol) was added dropwise at the same temperature, and a solid precipitated from the reaction mixture. The flask was allowed to cool to ambient temperature over 1 hour, and the resulting precipitate was collected by filtration. The solid was washed with tert-butyl methyl ether (2×100 mL) and dried in the funnel. The resulting solid was further heated at 70° C. in toluene (20 mL) for 30 minutes to remove additional impurities. After cooling to ambient temperature, the resulting solid was collected by filtration, washed with 75 mL of toluene and 100 mL of heptanes, and then dried to constant weight to give 19.8 g of the title compound (79% yield) as the hydrochloride salt. $^1$H NMR (400 MHz, dimethyl sulfoxide-$d_6$) δ ppm 8.67 (s, 3H), 8.08-7.95 (m, 2H), 7.58 (dd, J=8.4, 6.1 Hz, 3H), 6.62 (dd, J=8.7, 2.6 Hz, 1H), 6.50 (d, J=2.5 Hz, 1H), 5.33 (dd, J=11.8, 1.6 Hz, 1H), 4.70

(dd, J=11.1, 6.2 Hz, 1H), 3.84 (s, 3H), 3.70 (s, 3H), 2.60-2.50 (m, 1H), 1.96 (q, J=11.8 Hz, 1H); MS (ESI+) m/z 297.1 (M−NH$_3$+H)$^+$.

Example 1D 2-(2,2-difluorobenzo[d][1,3]dioxol-5-yl)-2-methylpropanenitrile

Iodomethane (3.96 g, 27.9 mmol) was added dropwise to a stirred mixture of 2-(2,2-difluorobenzo[d][1,3]dioxol-5-yl)acetonitrile (1.375 g, 6.97 mmol) and sodium hydroxide (1.116 g, 27.9 mmol) in dimethyl sulfoxide (12 mL) and water (1.9 mL) at 0° C. The reaction mixture was allowed to warm to room temperature overnight. The reaction mixture was poured into ice water (60 mL) and extracted with 300 mL of methyl tert-butyl ether. The organic extracts were washed with brine and then concentrated with heptane to provide a brownish pink solid. $^1$H NMR (400 MHz, dimethyl sulfoxide-d$_6$) δ 7.61 (d, J=1.9 Hz, 1H), 7.43 (d, J=8.5 Hz, 1H), 7.36 (dd, J=8.5, 2.0 Hz, 1H), 1.68 (s, 6H).

Example 1E 2-(2,2-difluorobenzo[d][1,3]dioxol-5-yl)-2-methylpropanoic acid

To an aqueous solution of sodium hydroxide (5 mmol, 10.4 mL, 52.0 mmol) was added Example 1D (0.698 g, 3.10 mmol) followed by methanol (6.9 mL). The reaction tube was sealed and warmed to 100° C. overnight. The aqueous layer was washed with ethyl acetate. Concentrated HCl was added dropwise to the aqueous layer in an ice bath until it was acidic. The mixture was filtered and washed with water to give 75 mg of the title compound. The organic layer was acidified with concentrated HCl, and diluted with ethyl acetate and water. The organic layers were washed with brine and dried over sodium sulfate. After filtration and removal of the solvent in vacuo, the residue was precipitated from toluene (2 mL) and triturated with pentane to give 0.20 g of the crude title compound. The crude title compound was washed with heptane, which triturated to give precipitated additional product. The combined solids were washed with heptanes and dried in vacuo to provide the title compound. $^1$H NMR (400 MHz, dimethyl sulfoxide-d$_6$) δ 12.43 (s, 1H), 7.39 (d, J=1.9 Hz, 1H), 7.33 (d, J=8.5 Hz, 1H), 7.15 (dd, J=8.5, 1.9 Hz, 1H), 1.46 (s, 6H).

Example 1F methyl 4-{(2R,4R)-4-[2-(2,2-difluoro-2H-1,3-benzodioxol-5-yl)-2-methylpropanamido]-7-methoxy-3,4-dihydro-2H-1-benzopyran-2-yl}benzoate Example 1E (32.1, 0.131 mmol), Example 1C (36.8 mg, 0.105 mmol) and N-(3-dimethylaminopropyl)-N'-ethylcarbodiimide hydrochloride (44.0 mg, 0.230 mmol) were dissolved in N,N-dimethylformamide (0.5 mL) and pyridine (0.5 mL). The reaction mixture was stirred at 60° C. for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (22.1 mg, 39%). $^1$H NMR (500 MHz, dimethyl sulfoxide-d$_6$) δ ppm 8.04-7.96 (m, 2H), 7.59 (dd, J=8.7, 5.0 Hz, 3H), 7.39 (d, J=1.8 Hz, 1H), 7.35 (d, J=8.5 Hz, 1H), 7.16 (dd, J=8.5, 1.9 Hz, 1H), 6.79 (dt, J=7.8, 1.3 Hz, 1H), 6.47-6.39 (m, 2H), 5.42-5.28 (m, 2H), 3.87 (s, 3H), 3.69 (s, 3H), 2.12 (ddd, J=13.0, 6.1, 2.0 Hz, 1H), 1.98 (dt, J=13.1, 11.6 Hz, 1H), 1.51 (s, 3H), 1.50 (s, 3H); MS (ESI−) m/z 538 (M−H)$^−$.

Example 1G

4-{(2R,4R)-4-[2-(2,2-difluoro-2H-1,3-benzodioxol-5-yl)-2-methylpropanamido]-7-methoxy-3,4-dihydro-2H-1-benzopyran-2-yl}benzoic acid Example 1F (19.5 mg, 0.036 mmol) and potassium trimethylsilanolate (18.9 mg, 90% purity, 0.133 mmol) were dissolved in tetrahydrofuran (1 mL) and stirred at ambient temperature for 2 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (13.5 mg, 71%). $^1$H NMR (400 MHz, dimethyl sulfoxide-d$_6$) δ ppm 12.95 (s, 1H), 8.00-7.94 (m, 2H), 7.59 (d, J=8.8 Hz, 1H), 7.57-7.53 (m, 2H), 7.39 (d, J=1.8 Hz, 1H), 7.35 (d, J=8.5 Hz, 1H), 7.16 (dd, J=8.5, 1.9 Hz, 1H), 6.79 (d, J=8.2 Hz, 1H), 6.43 (d, J=8.1 Hz, 2H), 5.42-5.25 (m, 2H), 3.69 (s, 3H), 2.11 (ddd, J=13.1, 6.2, 2.1 Hz, 1H), 1.98 (dt, J=13.0, 11.6 Hz, 1H), 1.51 (s, 3H), 1.50 (s, 3H); MS (ESI−) m/z 524.2 (M−H)$^−$.

Example 2

4-[(2R,4R)-4-{[1-(3,4-dichlorophenyl)cyclopropane-1-carbonyl]amino}-7-methoxy-3,4-dihydro-2H-1-benzopyran-2-yl]benzoic acid A 4 mL vial was charged with a stir bar, and 1-(3,4-dichlorophenyl) cyclopropanecarboxylic acid monomer (23 mg, 0.10 mmol) in dimethyl acetamide (0.25 mL), 1-[bis(dimethylamino)methylene]-1H-1,2,3-triazolo[4,5-b]pyridinium3-oxid hexafluorophosphate (30 mg, 0.08 mmol) in dimethyl acetamide (0.3 mL), and neat diisopropyl ethyl amine (35 μL, 3 eq, 0.21 mmol) were added. A solution of Example 1C (21 mg, 0.07 mmol) in dimethylacetamide (0.3 mL) was added. The mixture was allowed to stir at room temperature overnight. The mixture was analyzed for completion using LC/MS. Upon completion, the mixture was filtered and concentrated to dryness. The residue was dissolved in 1:1 dimethyl sulfoxide/CH$_3$OH and purified by reverse phase HPLC (TFA method, purified by preparative HPLC on a Phenomenex Luna C8(2) 5 μm 100 Å AXIA column (30 mm×150 mm). A gradient of CH$_3$CN (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A). The fractions collected were concentrated. The residue was dissolved in 500 μL of tetrahydrofuran and potassium trimethylsilanolate (2.5 equivalents, 26 mg, 0.2 mmol) was added. The mixture was allowed to heat at 35° C. for 2 hours and was diluted with 500 μL of 1M aqueous HCl and followed by the addition of 200 μL acetonitrile. The mixture was analyzed for completion using LC/MS. Upon completion, the mixture was filtered and concentrated to dryness. The residue was dissolved in 1:1 dimethyl sulfoxide/CH$_3$OH and was purified by reverse phase HPLC (TFA method, purified by preparative HPLC on a Phenomenex Luna C8(2) 5 μm 100 Å AXIA column (30 mm×150 mm). A gradient of CH$_3$CN (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A) to provide the title compound. $^1$H NMR (400 MHz, dimethyl sulfoxide-d$_6$) δ 7.97 (d, J=1.8 Hz, 1H), 7.58-7.52 (m, 4H), 7.41-7.32 (m, 2H), 6.95 (d, J=1.0 Hz, 1H), 6.54 (d, J=2.5 Hz, 1H), 6.39 (s, 1H), 5.32 (d, J=2.9 Hz, 1H), 3.68 (s, 3H), 2.13-2.03 (m, 2H), 1.49 (ddd, J=10.1, 6.3, 3.4 Hz, 1H), 1.43-1.32 (m, 1H), 1.15-1.00 (m, 2H); MS (APCI+) m/z 512.3 (M+H)$^+$.

Example 3

4-[(2R,4R)-7-methoxy-4-({1-[4-(trifluoromethoxy)phenyl]cyclopropane-1-carbonyl}amino)-3,4-dihydro-2H-1-benzopyran-2-yl]benzoic acid A 4 mL vial was charged with a stir bar, and 1-(4-(trifluoromethoxy)phenyl)cyclopropanecarboxylic acid monomer (25 mg, 0.10 mmol) in dimethyl acetamide (0.25 mL), 1-[bis(dimethylamino)methylene]-1H-1,2,3-triazolo[4,5-b]pyridinium3-oxid hexafluorophosphate (30 mg, 0.08 mmol) in dimethyl acetamide (0.3 mL), and neat diisopropyl ethyl amine (35 μL, 3 equivalents, 0.21 mmol) were added. To the mixture was added a solution of Example 1C (21 mg, 0.07 mmol) in dimethylacetamide (0.3 mL). The mixture was allowed to stir at room temperature overnight. The mixture was analyzed in LC/MS for completion. Upon completion, the mixture was filtered and concentrated to dryness. The residue was dissolved in 1:1 dimethyl sulfoxide/CH$_3$OH and purified by reverse phase HPLC (TFA method, samples were purified by preparative HPLC on a Phenomenex Luna C8(2) 5 μm 100 Å AXIA column (30 mm×150 mm). A gradient of CH$_3$CN (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A)). The residue was dissolved in 500 μL of tetrahydrofuran and potassium trimethylsilanolate (2.5 equivalents, 26 mg, 0.2 mmol) was added. The mixture was allowed to heat at 35° C. for 2 hours and was diluted with 500 μL of 1M aqueous HCl and 200 μL of acetonitrile. The mixture was analyzed for completion using LC/MS. Upon completion, the mixture was filtered and concentrated to dryness. The residue was dissolved in 1:1 dimethyl sulfoxide/CH$_3$OH and was purified by reverse phase HPLC (TFA method, samples were purified by preparative HPLC on a Phenomenex Luna C8(2) 5 μm 100 Å AXIA column (30 mm×150 mm). A gradient of CH$_3$CN (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A) to provide the title compound. $^1$H NMR (400 MHz, dimethyl sulfoxide-d$_6$) δ 7.96 (d, J=6.5 Hz, 2H), 7.59-7.53 (m, 2H), 7.51-7.44 (m, 2H), 7.31-7.22 (m, 3H), 6.91 (dd, J=8.6, 1.0 Hz, 1H), 6.56-6.50 (m, 1H), 6.39 (d, J=2.6 Hz, 1H), 5.35-5.26 (m, 2H), 3.70 (s, 3H), 2.17-1.98 (m, 2H), 1.47 (ddd, J=9.9, 5.8, 3.0 Hz, 1H), 1.37 (dt, J=9.9, 5.9 Hz, 1H), 1.04 (dtq, J=15.6, 6.3, 3.4 Hz, 2H); MS (APCI+) m/z 528.4 (M+H)$^+$.

Example 4

4-[(2R,4R)-4-{[1-(4-bromophenyl)cyclopropane-1-carbonyl]amino}-7-methoxy-3,4-dihydro-2H-1-benzopyran-2-yl]benzoic acid A 4 mL vial was charged with a stir bar, and 1-(4-bromophenyl)cyclopropanecarboxylic acid monomer (25 mg, 0.10 mmol) in dimethyl acetamide (0.25 mL), 1-[bis(dimethylamino)methylene]-1H-1,2,3-triazolo[4,5-b]pyridinium3-oxid hexafluorophosphate (30 mg, 0.08 mmol) in dimethyl acetamide (0.3 mL), and neat diisopropyl ethyl amine (35 μL, 3 equivalents, 0.21 mmol) were added. To the mixture was added a solution of Example 1C (21 mg, 0.07 mmol) in dimethylacetamide (0.3 mL). The mixture was allowed to stir at room temperature overnight. The mixture was analyzed for completion using LC/MS. Upon completion, the mixture was filtered and concentrated to dryness. The residue was dissolved in 1:1 dimethyl sulfoxide/CH$_3$OH and purified by reverse phase HPLC (TFA method, samples were purified by preparative HPLC on a Phenomenex Luna C8(2) 5 μm 100 Å AXIA column (30 mm×150 mm). A gradient of CH$_3$CN (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A)). The residue was dissolved in 500 μL of tetrahydrofuran and potassium trimethylsilanolate (2.5 equivalents, 26 mg, 0.2 mmol) was added. The mixture was allowed to heat at 35° C. for 2 hours and was diluted with 500 μL of 1M aqueous HCl and followed by addition of 200 μL acetonitrile. The mixture was analyzed for completion using LC/MS. Upon completion, the mixture was filtered and concentrated to dryness. The fractions collected were concentrated. The residue was dissolved in 1:1 dimethyl sulfoxide/CH$_3$OH and purified by reverse phase HPLC (TFA method, samples were purified by preparative HPLC on a Phenomenex Luna C8(2) 5 μm 100 Å AXIA column (30 mm×150 mm). A gradient of CH$_3$CN (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A) to provide the title compound. $^1$H NMR (400 MHz, dimethyl sulfoxide-d$_6$) δ 7.96 (d, J=8.4 Hz, 2H), 7.56-7.52 (m, 2H), 7.51-7.44 (m, 2H), 7.34-7.27 (m, 2H), 7.16 (d, J=8.9 Hz, 1H), 6.92 (dd, J=8.6, 1.0 Hz, 1H), 6.52 (dd, J=8.6, 2.6 Hz, 1H), 6.39 (d, J=2.6 Hz, 1H), 5.35-5.26 (m, 2H), 3.68 (s, 3H), 2.14-2.01 (m, 2H), 1.47 (td, J=6.6, 6.2, 2.9 Hz, 1H), 1.40-1.31 (m, 1H), 1.01 (dqt, J=15.6, 6.3, 3.4 Hz, 2H); MS (APCI+) m/z 524.3 (M+H)$^+$.

Example 5

4-[(2R,4R)-7-methoxy-4-({1-[4-(trifluoromethyl)phenyl]cyclopropane-1-carbonyl}amino)-3,4-dihydro-2H-1-benzopyran-2-yl]benzoic acid A 4 mL vial was charged with a stir bar, and (1-(4-(trifluoromethyl)phenyl)cyclopropanecarboxylic acid monomer (24 mg, 0.10 mmol) in dimethyl acetamide (0.25 mL), (1-[bis(dimethylamino)methylene]-1H-1,2,3-triazolo[4,5-b]pyridinium3-oxid hexafluorophosphate) (30 mg, 0.08 mmol) in dimethyl acetamide (0.3 mL), and neat diisopropyl ethyl amine (35 μL, 3 equivalents, 0.21 mmol) were added. To the mixture was added a solution of Example 1C (21 mg, 0.07 mmol) in dimethylacetamide (0.3 mL). The mixture was allowed to stir at room temperature overnight. The mixture was analyzed for completion using LC/MS. Upon completion, the mixture was filtered and concentrated to dryness. The residue was dissolved in 1:1 dimethyl sulfoxide/$CH_3OH$ and purified by reverse phase HPLC (TFA method, samples were purified by preparative HPLC on a Phenomenex Luna C8(2) 5 um 100 Å AXIA column (30 mm×150 mm). A gradient of $CH_3CN$ (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A)). The fractions collected were concentrated. The residue was dissolved in 500 μL of tetrahydrofuran, and potassium trimethylsilanolate (2.5 equivalents, 26 mg, 0.2 mmol) was added to the reaction mixture. The mixture was allowed to heat at 35° C. for 2 hours and was diluted with 500 μL of 1M HCl and 200 μL acetonitrile. The mixture was analyzed for completion using LC/MS. Upon completion, the mixture was filtered and concentrated to dryness. The residue was dissolved in 1:1 dimethyl sulfoxide/$CH_3OH$ and was purified by reverse phase HPLC (TFA method, samples were purified by preparative HPLC on a Phenomenex Luna C8(2) 5 um 100 Å AXIA column (30 mm×150 mm). A gradient of $CH_3CN$ (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A) to provide the title compound. $^1$H NMR (400 MHz, dimethyl sulfoxide-$d_6$) δ 8.02-7.94 (m, 2H), 7.66 (s, 1H), 7.61-7.50 (m, 4H), 7.34 (d, J=9.0 Hz, 1H), 6.94 (dd, J=8.6, 1.0 Hz, 1H), 6.54 (ddd, J=13.4, 8.6, 2.5 Hz, 1H), 6.39 (d, J=2.6 Hz, 1H), 5.38-5.28 (m, 2H), 3.68 (s, 3H), 2.22-1.99 (m, 2H), 1.50 (dd, J=6.3, 3.5 Hz, 1H), 1.44-1.37 (m, 1H), 1.20-1.03 (m, 2H); MS (APCI+) m/z 512.4 (M+H)$^+$.

Example 6

4-[(2R,4R)-7-methoxy-4-{[1-(4-methylphenyl)cyclopropane-1-carbonyl]amino}-3,4-dihydro-2H-1-benzopyran-2-yl]benzoic acid A 4 mL vial was charged with a stir bar, and 1-(p-tolyl)cyclopropanecarboxylic acid (22 mg, 0.10 mmol) in dimethyl acetamide (0.25 mL), 1-[bis(dimethylamino)methylene]-1H-1,2,3-triazolo[4,5-b]pyridinium3-oxid hexafluorophosphate (30 mg, 0.08 mmol) in dimethyl acetamide, (0.3 mL) and neat diisopropyl ethyl amine (35 μL, 3 equivalents, 0.21 mmol) were added. To the mixture was added a solution of Example 1C (21 mg, 0.07 mmol) in dimethylacetamide (0.3 mL). The mixture was allowed to stir at room temperature overnight. The mixture was analyzed for completion using LC/MS. Upon completion, the mixture was filtered and concentrated to dryness. The residue was dissolved in 1:1 dimethyl sulfoxide/$CH_3OH$ and purified by reverse phase HPLC (TFA method, samples were purified by preparative HPLC on a Phenomenex Luna C8(2) 5 μm 100 Å AXIA column (30 mm×150 mm). A gradient of $CH_3CN$ (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A)). The fractions collected were concentrated. The residue was dissolved in 500 μL of tetrahydrofuran and potassium trimethylsilanolate (2.5 equivalents, 26 mg, 0.2 mmol) was added to the mixture. The mixture was allowed to heat at 35° C. for 2 hours and was diluted with 500 μL of 1M aqueous HCl and 200 μL of acetonitrile. The mixture was analyzed for completion using LC/MS. Upon completion, the mixture was filtered and concentrated to dryness. The residue was dissolved in 1:1 dimethyl sulfoxide/$CH_3OH$ and was purified by reverse phase HPLC (TFA method, samples were purified by preparative HPLC on a Phenomenex Luna C8(2) 5 μm 100 Å AXIA column (30 mm×150 mm). A gradient of $CH_3CN$ (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A)) to provide the title compound. $^1$H NMR (400 MHz, dimethyl sulfoxide-$d_6$) δ 7.95 (d, J=8.4 Hz, 2H), 7.53 (d, J=8.4 Hz, 2H), 7.21 (d, J=8.1 Hz, 2H), 7.11 (s, 2H), 6.91 (dd, J=8.6, 1.0 Hz, 1H), 6.56-6.49 (m, 1H), 6.38 (d, J=2.5 Hz, 1H), 5.33 (d, J=2.1 Hz, 1H), 5.31-5.24 (m, 1H), 3.68 (s, 3H), 2.24 (s, 3H), 2.18-1.95 (m, 2H), 1.44 (ddd, J=9.8, 6.1, 3.0 Hz, 1H), 1.31 (td, J=6.2, 3.2 Hz, 1H), 1.07-0.92 (m, 2H); MS (APCI+) m/z 458.4 (M+H)$^+$.

Example 7

4-{(2R,4R)-4-[(1,5-dimethyl-2,3-dihydro-1H-indene-1-carbonyl)amino]-7-methoxy-3,4-dihydro-2H-1-benzopyran-2-yl}benzoic acid Example 7A 5-methyl-2,3-dihydro-1H-indene-1-carbonitrile To a stirred suspension of 5-methyl-2,3-dihydro-1H-inden-1-one (0.869 g, 5.95 mmol) and 1-((isocyanomethyl)sulfonyl)-4-methylbenzene (1.29 g, 6.61 mmol) in 1,2-dimethoxyethane (20 mL) cooled to 0° C. with an ice bath, was added dropwise a warm solution of potassium tert-butoxide (1.34 g, 11.94 mmol) in tert-butanol (8 mL) over about 10 minutes. The stirring was continued with cooling for another 15 minutes, after which the ice bath was removed. After a further 95 minutes, aqueous ammonium chloride was added and the mixture was extracted with ethyl acetate (twice). The combined organic layers were dried ($MgSO_4$), filtered, concentrated under reduced pressure, and purified by flash chromatography using Biotage® SNAP 100 g silica column, eluting with 10-13% ethyl acetate in iso-hexane to provide the title compound. $^1$H NMR (400 MHz, $CDCl_3$) δ ppm 7.31 (d, J=7.5 Hz, 1H), 7.08 (d, J=8.5 Hz, 2H), 4.06 (t, J=8.0 Hz, 1H), 3.05 (ddd, J=4.6, 8.6, 16.0 Hz, 1H), 2.96-2.87 (m, 1H), 2.60-2.51 (m, 1H), 2.41-2.36 (m, 3H), 2.35 (s, 1H).

Example 7B 1,5-dimethyl-2,3-dihydro-1H-indene-1-carbonitrile

To a stirred solution of Example 7A (307 mg, 1.95 mmol) in anhydrous tetrahydrofuran (8 mL) cooled to −60° C. with an acetone-dry ice bath, was added a solution of n-butyl lithium in hexanes (1.0 mL, 2.34 mmol, 2.4M). The mixture darkened and was stirred for a further 5 minutes at −60° C., after which the acetone-dry ice bath was swapped for an ice bath. Methyl iodide (0.15 mL, 2.30 mmol) was added. The resulting mixture became clearer and was left to warm up to room temperature over 17 hours. Aqueous 1N hydrochloric acid was added until aqueous layer was acidic, and the mixture was extracted twice with diethyl ether. The combined organic layers were dried (MgSO$_4$), filtered, and concentrated under reduced pressure to provide the title compound. $^1$H NMR (400 MHz, CDCl$_3$) δ ppm 7.26 (d, J=8.1 Hz, 1H), 7.09-7.07 (m, 2H), 3.10-2.91 (m, 2H), 2.64 (ddd, J=6.1, 8.2, 12.8 Hz, 1H), 2.34 (s, 3H), 2.14 (ddd, J=6.3, 7.9, 12.8 Hz, 1H), 1.63 (s, 3H).

Example 7C 1,5-dimethyl-2,3-dihydro-1H-indene-1-carboxylic acid

A suspension of Example 7B (144 mg, 0.84 mmol) and potassium hydroxide (381 mg, 6.8 mmol) in diethylene glycol (3.4 mL) was stirred at 120° C. for 70 hours. Water was added to the reaction mixture, and it was extracted twice with ethyl acetate. The combined organic layers were dried (MgSO$_4$), filtered, and concentrated under reduced pressure to provide the title compound. $^1$H NMR (400 MHz, CDCl$_3$) δ ppm 7.20 (d, J=7.9 Hz, 1H), 7.05-7.00 (m, 2H), 3.08-2.99 (m, 1H), 2.87 (ddd, J=4.3, 8.7, 15.8 Hz, 1H), 2.70 (ddd, J=4.3, 8.5, 12.9 Hz, 1H), 2.32 (s, 3H), 1.93 (ddd, J=7.7, 8.6, 12.9 Hz, 1H), 1.53 (s, 3H).

Example 7D 7-methoxy-4H-1-benzopyran-4-one 1-(2-Hydroxy-4-methoxyphenyl)ethanone (47 g, 283 mmol) was dissolved in N,N-dimethylformamide dimethyl acetal (47 mL, 351 mmol), and the solution was heated at >100° C. in a sand bath for 10 minutes, at which point a solid mass formed. The flask was cooled to ambient temperature, and 200 mL of heptanes were added. The solids were broken up with a spatula and collected by filtration with a fritted funnel. The solid material was crushed with a pestle and washed with heptanes. The solid was dried on the filter to give about 60 g of the crude intermediate. The intermediate was dissolved in dichloromethane (1 L) and stirred with 150 mL of concentrated HCl at 40° C. for 30 minutes. The flask was cooled to ambient temperature, and about 100 mL of water was added. The layers were separated, and the aqueous layer was extracted with dichloromethane (2×100 mL). The combined organic extracts were washed with saturated sodium bicarbonate (100 mL) and brine (100 mL) and dried over sodium sulfate. The mixture was filtered, and the filtrate was concentrated in vacuo to give a solid. The solid was taken into 500 mL of 1:1 cyclopentyl methyl ether:heptanes and the precipitate was collected to provide the title compound (35 g, 70% yield). $^1$H NMR (400 MHz, CDCl$_3$) δ ppm 8.11 (d, J=8.9 Hz, 1H), 7.77 (d, J=6.0 Hz, 1H), 6.97 (dd, J=8.9, 2.4 Hz, 1H), 6.84 (d, J=2.4 Hz, 1H), 6.28 (d, J=6.0 Hz, 1H), 3.90 (s, 3H); MS(ESI+) m/z 176.9 (M+H)$^+$.

Example 7E methyl 4-[(2R)-7-methoxy-4-oxo-3,4-dihydro-2H-1-benzopyran-2-yl]benzoate A 250-mL round-bottomed flask was charged with (4-(methoxycarbonyl)phenyl)boronic acid (30.6 g, 170 mmol), ammonium hexafluorophosphate(V) (4.16 g, 25.5 mmol), bis(2,2,2-trifluoroacetoxy)palladium (2.123 g, 6.39 mmol), and (S)-4-(tert-butyl)-2-(pyridin-2-yl)-4,5-dihydrooxazole (1.565 g, 7.66 mmol); and 1,2-dichloroethane (85 mL) was added. The resulting suspension was stirred at ambient temperature for 10 minutes, at which point Example 7D (15 g, 85.0 mmol) was added, followed by water (7.67 g, 426 mmol) and an additional 85 mL of 1,2-dichloroethane to rinse the sides of the flask. The reaction mixture was heated at 60° C. in a sand bath (internal temperature) for 36 hours. The flask was cooled to room temperature, and the suspension was filtered through a 1-inch pad of silica, eluting with dichloromethane. The filtrates were concentrated to give a crude solid. tert-Butyl methyl ether (100 mL) and heptanes (100 mL) were added, and the solids were broken up with a spatula. The resulting suspension was heated at 60° C. for 1 hour while stirring vigorously. The mixture was cooled to ambient temperature, and the resulting solid was collected via filtration through a fritted funnel to provide 10.54 g of the title compound (39% yield). $^1$H NMR (400 MHz, CDCl$_3$) δ ppm 8.10 (d, J=8.3 Hz, 2H), 7.87 (d, J=8.9 Hz, 1H), 7.56 (d, J=8.3 Hz, 2H), 6.64 (dd, J=8.8, 2.3 Hz, 1H), 6.52 (d, J=2.4 Hz, 1H), 5.53 (dd, J=13.0, 3.2 Hz, 1H), 3.94 (s, 3H), 3.85 (s, 3H), 2.99 (dd, J=16.9, 13.0 Hz, 1H), 2.86 (dd, J=16.8, 3.2 Hz, 1H); MS (ESI+); m/z 312.8 (M+H)$^+$.

Example 7F methyl 4-{(2R)-4-[(benzyloxy)imino]-7-methoxy-3,4-dihydro-2H-1-benzopyran-2-yl}benzoate Example 7E (2 g, 6.40 mmol) was dissolved in 15 mL of dry pyridine. O-Benzylhydroxylamine hydrochloride (1.073 g, 6.72 mmol) was added, and the solution was heated at 50° C. for 16 hours. The reaction mixture was cooled to ambient temperature and concentrated. The residue was partitioned between tert-butyl methyl ether and saturated aqueous ammonium chloride. The organic extracts were concentrated in vacuo and purified via flash chromatography, eluting with 10-40% ethyl acetate/heptanes over 20 minutes on an 80 g silica gel column to give the title compound (10:1 mixture of E and Z oximes, 2.57 g, 96% yield). Analytical data for the major isomer: $^1$H NMR (501 MHz, CDCl$_3$) δ ppm 8.06 (d, J=8.3 Hz, 2H), 7.84 (d, J=8.8 Hz, 1H), 7.54-7.46 (m, 2H), 7.40-7.28 (m, 5H), 6.57 (dd, J=8.8, 2.5 Hz, 1H), 6.48 (d, J=2.5 Hz, 1H), 5.19 (d, J=2.0 Hz, 2H), 5.11 (dd, J=12.3, 3.2 Hz, 1H), 3.92 (s, 3H), 3.78 (s, 3H), 3.48 (dd, J=17.2, 3.2 Hz, 1H), 2.67 (dd, J=17.2, 12.2 Hz, 1H); MS (ESI+) m/z 418.1 (M+H)$^+$.

Example 7G methyl 4-[(2R,4R)-4-amino-7-methoxy-3,4-dihydro-2H-1-benzopyran-2-yl]benzoate Acetic acid (300 mL) was added to Example 7F (20 g 47.9 mmol) and 5% Pt/C wet (1.5 g wet weight, 58.9% water, 0.884 g or 4.42% dry basis) in a 300-mL stainless steel reactor. The headspace was inerted with argon and pressurized to 30 psig with hydrogen. The mixture was shaken at ambient temperature under 30 psig of hydrogen for 18 hours. The reactor was vented and the reaction mixture was filtered through a 0.45 μm GHP Acrodisc® membrane. The filtrate was concentrated in vacuo to give 60 g of crude material. The crude material was heated at 70° C. in 250 mL of 4:1 tert-butyl methyl ether:heptanes until a clear solution resulted. HCl (3 M in cyclopentyl methyl ether, 47.9 mL, 144 mmol) was added dropwise at the same temperature, and a solid precipitated from the reaction mixture. The flask was allowed to cool to ambient temperature over 1 hour, and the resulting precipitate was collected by filtration. The solid was washed with tert-butyl methyl ether (2×100 mL) and dried in the funnel. The resulting solid was further heated at 70° C. in toluene (20 mL) for 30 minutes to remove additional impurities. After cooling to ambient temperature, the resulting solid was collected by filtration, washed with 75 mL of toluene and 100 mL of heptanes, and dried to a constant weight to provide 19.8 g of the title compound (79% yield) as the hydrochloride salt. $^1$H NMR (400 MHz, dimethyl sulfoxide-$d_6$) δ ppm 8.67 (s, 3H), 8.08-7.95 (m, 2H), 7.58 (dd, J=8.4, 6.1 Hz, 3H), 6.62 (dd, J=8.7, 2.6 Hz, 1H), 6.50 (d, J=2.5 Hz, 1H), 5.33 (dd, J=11.8, 1.6 Hz, 1H), 4.70 (dd, J=11.1, 6.2 Hz, 1H), 3.84 (s, 3H), 3.70 (s, 3H), 2.60-2.50 (m, 1H), 1.96 (q, J=11.8 Hz, 1H); MS (ESI+); m/z 297.1 (M−NH$_3$+H)$^+$.

Example 7H methyl 4-{(2R,4R)-4-[(1,5-dimethyl-2,3-dihydro-1H-inden-1-carbonyl)amino]-7-methoxy-3,4-dihydro-2H-1-benzopyran-2-yl}benzoate Example 7C (0.057 g, 0.3 mmol), Example 7G (0.121 g, 0.345 mmol), and 1-ethyl-3-[3-(dimethylamino)propyl]-carbodiimide hydrochloride (EDCI, 0.115 g, 0.600 mmol) were stirred in N,N-dimethylformamide (1 mL) and pyridine (1 mL) at 60° C. overnight. The reaction mixture was concentrated in vacuo; and the remaining crude oil was dissolved in ethyl acetate and washed three times with water and once with brine. The organic layer was dried over Na$_2$SO$_4$, filtered, and concentrated. The residue was purified by silica gel chromatography, eluting with 0 to 40% ethyl acetate/heptanes to provide the title compound as a white solid (0.098 g, 67% yield). $^1$H NMR (400 MHz, CDCl$_3$) δ 8.10-7.96 (m, 2H), 7.52-7.39 (m, 2H), 7.19-6.84 (m, 4H), 6.58-6.38 (m, 2H), 5.46-5.34 (m, 2H), 5.22 (dd, J=11.0, 2.0 Hz, 1H), 3.93 (s, 1.5H), 3.92 (s, 1.5H), 3.76 (s, 1.5H), 3.75 (s, 1.5H), 2.95-2.74 (m, 2H), 2.64 (ddd, J=12.2, 7.6, 4.4 Hz, 1H), 2.67-2.44 (m, 2H), 2.31 (s, 3H), 2.16-1.96 (m, 1H), 1.62 (m, 1H), 1.59 (s, 1.5H), 1.54 (s, 1.5H); MS (ESI$^+$) m/z 485.9 (M+H).

Example 7I

4-{(2R,4R)-4-[(1,5-dimethyl-2,3-dihydro-1H-inden-1-carbonyl)amino]-7-methoxy-3,4-dihydro-2H-1-benzopyran-2-yl}benzoic acid Example 7H (0.098 g, 0.202 mmol) in tetrahydrofuran (2.5 mL) was treated with potassium trimethylsilanolate (0.057 g, 0.444 mmol) in one portion, and the reaction mixture was stirred overnight at room temperature. The reaction mixture was treated with 2.6 mL CH$_2$Cl$_2$ and 1.3 mL 1N aqueous HCl and was stirred vigorously at room temperature for 30 minutes. The mixture was diluted with ethyl acetate, and the phases were separated. The organic layer was washed twice with water and once with brine, dried over Na$_2$SO$_4$, filtered, and concentrated in vacuo. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a white solid (41 mg, 43% yield). $^1$H NMR (400 MHz, dimethyl sulfoxide-$d_6$) δ 12.96 (br, 1H), 8.03-7.92 (m, 2H), 7.62-7.47 (m, 3H), 7.20 (t, J=7.5 Hz, 1H), 7.07-6.90 (m, 2.5H), 6.78 (m, 0.5 H), 6.58-6.39 (m, 2H), 5.43-5.25 (m, 2H), 3.71 (s, 1.5H), 3.70 (s, 1.5H), 2.97-2.74 (m, 2H), 2.63 (m, 1H), 2.27 (s, 1.5H), 2.24 (s, 1.5H), 2.20-2.00 (m, 2H), 1.86 (m, 1H), 1.44 (s, 1.5H), 1.43 (s, 1.5H); MS (ESI$^+$) m/z 471.9 (M+H)$^+$.

Example 8

3-[(2R,4R)-4-{[(1S)-1,5-dimethyl-2,3-dihydro-1H-inden-1-carbonyl]amino}-7-methoxy-3,4-dihydro-2H-1-benzopyran-2-yl]benzoic acid Example 8A methyl 3-[(2R)-7-methoxy-4-oxo-3,4-dihydro-2H-1-benzopyran-2-yl]benzoate A 4 mL vial was charged with bis(2,2,2-trifluoroacetoxy)palladium (9.44 mg, 0.028 mmol), (S)-4-(tert-butyl)-2-(pyridin-2-yl)-4,5-dihydrooxazole (6.96 mg, 0.034 mmol), ammonium hexafluorophosphate(V) (27.8 mg, 0.170 mmol), and 3-methoxycarbonylphenylboronic acid (204 mg, 1.135 mmol), and the mixture was stirred in dichloroethane (1.0 mL) for 5 minutes. To the mixture was added Example 7D (100 mg, 0.568 mmol) and water (0.051 mL, 2.84 mmol), and the sides of the vial were washed with more dichloroethane (1.0 mL). The vial was capped and the mixture stirred at 60° C. overnight. The mixture was filtered through a plug of silica gel, and eluted with dichloromethane and ethyl acetate. The filtrate was concentrated, and the crude material was chromatographed using a 12 g silica gel cartridge with a gradient of 5-50% ethyl acetate/heptanes over 20 minutes to provide the title compound (133 mg, 0.426 mmol, 75% yield). $^1$H NMR (400 MHz, dimethyl sulfoxide-$d_6$) δ ppm 8.15 (t, J=1.8 Hz, 1H), 7.98 (dt, J=7.8, 1.4 Hz, 1H), 7.84 (dt, J=7.9, 1.5 Hz, 1H), 7.74 (d, J=8.5 Hz, 1H), 7.61 (t, J=7.8 Hz, 1H), 6.69 (d, J=8.6 Hz, 2H), 5.77 (dd, J=12.9, 2.9 Hz, 1H), 3.88 (s, 3H), 3.83 (s, 3H), 3.17 (dd, J=16.8, 13.0 Hz, 1H), 2.80 (dd, J=16.8, 3.0 Hz, 1H); MS (ESI+) m/z 313 (M+H)$^+$.

Example 8B methyl 3-[(2R)-7-methoxy-4-(methoxyimino)-3,4-dihydro-2H-1-benzopyran-2-yl]benzoate Example 8A (100 mg, 0.320 mmol) and O-methylhydroxylamine hydrochloride (29.4 mg, 0.352 mmol) were stirred in pyridine (640 μL) at 60° C. overnight. An additional 0.3 equivalents (7 mg) of O-methylhydroxylamine hydrochloride was added with continued heating at 60° C. for 12 hours. The mixture was concentrated, and the residue was diluted with ethyl acetate. The ethyl acetate mixture was washed sequentially with saturated aqueous sodium bicarbonate and saturated aqueous ammonium chloride. The organic layer was concentrated, and the crude material was purified using a 12 g silica gel cartridge eluting with 5-20% ethyl acetate/heptanes over 20 minutes to provide the title compound (107 mg, 0.313 mmol). $^1$H NMR (400 MHz, CDCl$_3$) δ ppm 8.15 (t, J=1.9 Hz, 1H), 8.03 (dt, J=7.7, 1.5 Hz, 1H), 7.84 (d, J=8.8 Hz, 1H), 7.77-7.63 (m, 1H), 7.49 (t, J=7.7 Hz, 1H), 6.59 (dd, J=8.8, 2.6 Hz, 1H), 6.50 (d, J=2.5 Hz, 1H), 5.12 (dd, J=12.5, 3.1 Hz, 1H), 3.96 (s, 3H), 3.94 (s, 3H), 3.80 (s, 3H), 3.48 (dd, J=17.2, 3.1 Hz, 1H), 2.65 (dd, J=17.1, 12.5 Hz, 1H); MS (ESI+) m/z 342.0 (M+H)$^+$.

Example 8C methyl 3-[(2R,4R)-4-amino-7-methoxy-3,4-dihydro-2H-1-benzopyran-2-yl]benzoate hydrochloride A 250-mL round bottom flask was charged with Example 8B (3.74 g, 10.96 mmol) and platinum (IV) oxide (0.343 g, 1.510 mmol) suspended in acetic acid (27.4 mL). The flask was purged with a balloon of $H_2$ and was stirred under 1 atmosphere of $H_2$ for 7 hours. The reaction seemed to stall after 6 hours. An additional 5 mol % of platinum (IV) oxide was added, and the reaction was run for an additional hour at ambient temperature. The mixture was diluted with ethyl acetate, filtered, and concentrated. The residue was dissolved in tert-butyl methyl ether (35 mL) and treated with HCl (4 M in dioxane, 5.48 mL, 21.91 mmol) dropwise at ambient temperature. The resulting suspension was stirred vigorously at ambient temperature for 1 hour, and the resultant solid was collected by filtration and washed with tert-butyl methyl ether (2×5 mL). The solid was heated at 50° C. for 1 hour in a mixture of 30 mL of tert-butyl methyl ether and 4 mL of dioxane. The solid was collected by filtration and dried in a vacuum oven at 40° C. to afford the title compound (2.27 g, 59%). $^1$H NMR (501 MHz, dimethyl sulfoxide-$d_6$) δ ppm 8.69 (s, 3H), 8.05 (t, J=1.7 Hz, 1H), 7.98 (d, J=7.9 Hz, 1H), 7.74 (dt, J=7.7, 1.4 Hz, 1H), 7.62 (d, J=7.7 Hz, 1H), 7.58 (d, J=8.7 Hz, 1H), 6.65 (dd, J=8.7, 2.6 Hz, 1H), 6.53 (d, J=2.5 Hz, 1H), 5.35 (dd, J=11.8, 1.6 Hz, 1H), 4.73 (dd, J=11.1, 6.3 Hz, 1H), 3.87 (s, 3H), 3.73 (s, 3H), 2.55 (ddd, J=13.0, 6.4, 1.8 Hz, 1H), 2.01 (dt, J=13.0, 11.5 Hz, 1H); MS (ESI+) m/z 297 (M−$NH_3$+H)$^+$.

Example 8D methyl 3-{(2R,4R)-4-[(1,5-dimethyl-2,3-dihydro-1H-inden-1-carbonyl)amino]-7-methoxy-3,4-dihydro-2H-1-benzopyran-2-yl}benzoate Example 7C (0.133 g, 0.7 mmol), Example 8C (0.282 g, 0.805 mmol), and 1-ethyl-3-[3-(dimethylamino)propyl]-carbodiimide hydrochloride (EDCI, 0.268 g, 1.400 mmol) were stirred in N,N-dimethylformamide (1.7 mL) and pyridine (1.7 mL) at 60° C. overnight. The mixture was concentrated, and the residue was dissolved in ethyl acetate and washed three times with water and once with brine. The organic solution was dried over $Na_2SO_4$, filtered, and concentrated in vacuo. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a tan solid (107 mg, 32% yield). $^1$H NMR (400 MHz, dimethyl sulfoxide-$d_6$) δ 8.05-7.93 (m, 2H), 7.55 (m, 3H), 7.19 (m, 1H), 7.05-6.89 (m, 2.5H), 6.77 (m, 0.5H), 6.57-6.38 (m, 2H), 5.43-5.24 (m, 2H), 3.86 (s, 3H), 3.69 (s, 3H), 2.85 (dq, J=22.8, 9.0, 8.5 Hz, 2H), 2.68-2.55 (m, 1H), 2.25 (s, 1.5H), 2.23 (s, 1.5H), 2.20-1.96 (m, 2H), 1.93-1.77 (m, 1H), 1.42 (s, 3H). MS (ESI$^+$) m/z 485.9 (M+H)$^+$.

Example 8E

3-[(2R,4R)-4-{[(1S)-1, 5-dimethyl-2,3-dihydro-1H-inden-1-carbonyl]amino}-7-methoxy-3,4-dihydro-2H-1-benzopyran-2-yl]benzoic acid Example 8D (0.107 g, 0.220 mmol) and potassium trimethylsilanolate (0.062 g, 0.485 mmol) were stirred in tetrahydrofuran (3 mL) at room temperature overnight. The mixture was treated with 3 mL $CH_2Cl_2$ and 1.5 mL 1N aqueous HCl, and the mixture was stirred vigorously at room temperature for 30 minutes. The mixture was diluted with ethyl acetate, washed twice with water and once with brine, dried over $Na_2SO_4$, filtered, and concentrated in vacuo. The residue was purified by reverse-phase preparative HPLC on a Phenomenex® Luna® C8(2) 5 m 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The mixture of (1S) and (1R) epimers thus provided was separated by chiral supercritical fluid chromatography using a Whelk-O S,S column (21×250 mm, 5 micron), eluted with 40% methanol (0.1% diethylamine) in $CO_2$, at a 70 mL/minute flow rate, 100 bar, and ambient temperature. The diethylamine salt of the title compound was obtained as the first eluting isomer (7.4 mg, 6.2% yield). Analytical chiral SFC analysis of the compound thus provided (Whelk-O1 S,S column, eluting with 5 to 50% $CH_3OH$ (0.1% diethylamine):$CO_2$ over 10 minutes, 3 mL/minute, 150 bar) indicated ee>99%. The chirality of the carbon atom bearing the methyl group was assigned arbitrarily. $^1$H NMR (400 MHz, dimethyl sulfoxide-$d_6$) δ 7.91 (d, J=7.9 Hz, 2H), 7.53 (d, J=8.9 Hz, 1H), 7.43 (d, J=7.9 Hz, 2H), 7.21 (d, J=7.7 Hz, 1H), 7.04-6.90 (m, 3H), 6.56-6.38 (m, 2H), 5.31 (m, 2H), 3.70 (s, 3H), 2.86 (m, 1H), 2.76 (m, 4H), 2.62 (m, 1H), 2.24 (s, 3H), 2.05 (m, 1H), 1.84 (m, 1H), 1.43 (s, 3H), 1.10 (t, J=7.2 Hz, 6H). MS (ESI$^+$) m/z 472.0 (M+H)$^+$.

Example 9

4-[(2R,4R)-4-{[(1S)-1, 5-dimethyl-2,3-dihydro-1H-inden-1-carbonyl]amino}-7-methoxy-3,4-dihydro-2H-1-benzopyran-2-yl]benzoic acid The mixture of (1S) and (1R) epimers provided by reverse-phase preparative HPLC in Example 71 was separated by chiral supercritical fluid chromatography using a Whelk-O S,S column (21×250 mm, 5 micron), eluting with 40% methanol in $CO_2$, at a 70 mL/minute flow rate, 100 bar, and ambient temperature. The title compound was obtained as the first eluting isomer. Analytical chiral SFC analysis of the compound thus provided (ChiralCel OD-H column, eluting with 5 to 50% $CH_3OH$:$CO_2$ over 10 minutes, 3 mL/minute, 150 bar) indicated ee>99%. The chirality of the carbon bearing the methyl group was assigned arbitrarily. $^1$H NMR (400 MHz, dimethyl sulfoxide-$d_6$) δ 7.91 (d, J=7.7 Hz, 2H), 7.54-7.42 (m, 3H), 7.21 (d, J=7.8 Hz, 1H), 7.04-6.90 (m, 3H), 6.56-6.38 (m, 2H), 5.31 (m, 2H), 3.70 (s, 3H), 2.92-2.78 (m, 2H), 2.62 (m, 2H), 2.24 (s, 3H), 2.08 (m, 1H), 1.86 (m, 1H), 1.43 (s, 3H); ESI$^+$ (m/z) 471.9 (M+H)$^+$.

Example 10 ethyl trans-4-[(2R,4R)-4-{[1-(2,2-difluoro-2H-1,3-benzodioxol-5-yl)cyclopropane-1-carbonyl]amino}-7-methoxy-3,4-dihydro-2H-1-benzopyran-2-yl]cyclohexane-1-carboxylate

Example 10A methyl trans-4-(7-methoxy-4-oxo-3,4-dihydro-2H-1-benzopyran-2-yl)cyclohexane-1-carboxylate A solution of 1-(2-hydroxy-4-methoxyphenyl)ethanone (0.703 g, 4.23 mmol) and methyl trans-4-formylcyclohexane-1-carboxylate (0.72 g, 4.23 mmol) in methanol (15 mL) was treated with pyrrolidine (0.700 mL, 8.46 mmol), and the mixture was stirred at 60° C. for 90 minutes. The mixture was concentrated to dryness and the residue was partitioned between ethyl acetate (30 mL) and 1 M aqueous HCl (20 mL). The ethyl acetate layer was washed with saturated aqueous NaHCO$_3$ solution and brine, dried (MgSO$_4$), filtered, and concentrated. The residue was chromatographed on silica gel, eluting with a gradient of 10% to 30% ethyl acetate in heptanes to provide the title compound as the second eluting isomer. $^1$H NMR (400 MHz, CDCl$_3$) δ 7.80 (d, J=8.8 Hz, 1H), 6.56 (dd, J=8.8, 2.3 Hz, 1H), 6.40 (d, J=2.3 Hz, 1H), 4.19 (ddd, J=12.7, 6.0, 3.2 Hz, 1H), 3.83 (s, 3H), 3.67 (s, 3H), 2.68 (dd, J=16.6, 12.8 Hz, 1H), 2.58 (dd, J=16.6, 3.2 Hz, 1H), 2.29 (tt, J=12.2, 3.4 Hz, 1H), 2.15-2.05 (m, 3H), 1.90-1.82 (m, 1H), 1.79-1.65 (m, 1H), 1.57-1.39 (m, 2H), 1.31-1.11 (m, 2H); LC/MS (ESI+) m/z 319 (M+H)$^+$.

Example 10B ethyl trans-4-[(2S,4E)-7-methoxy-4-{[(R)-2-methyl-propane-2-sulfinyl]imino}-3,4-dihydro-2H-1-benzo-pyran-2-yl]cyclohexane-1-carboxylate and ethyl trans-4-[(2R,4E)-7-methoxy-4-{[(R)-2-methylpropane-2-sulfinyl]imino}-3,4-dihydro-2H-1-benzopyran-2-yl]cyclohexane-1-carboxylate A mixture of Example 10A (0.78 g, 2.450 mmol) and (R)-(+)-2-methyl-2-propanesulfinamide (0.297 g, 2.450 mmol) in toluene (25 mL) was treated with titanium(IV) ethoxide (2.235 g, 9.80 mmol), stirred at 90° C. for 5 hours, heated at 110° C. for 4 hours, and cooled to room temperature. The reaction mixture was diluted with ethyl acetate (25 mL), treated with water (25 mL), stirred for 5 minutes, and filtered through diatomaceous earth to remove the solids. The ethyl acetate layer washed with brine, dried (MgSO$_4$), filtered, and concentrated. The residue was chromatographed on silica gel, eluting with a gradient of 10% to 50% ethyl acetate in heptanes. The chromatography only partially separated the isomers, and provided 0.34 g of a product enriched in ethyl trans-4-[(2S,4E)-7-methoxy-4-{[(R)-2-methylpropane-2-sulfinyl]imino}-3,4-dihydro-2H-1-benzopyran-2-yl]cyclohexane-1-carboxylate as the first eluting isomer, and 0.42 g of a product enriched in ethyl trans-4-[(2R,4E)-7-methoxy-4-{[(R)-2-methylpropane-2-sulfinyl]imino}-3,4-dihydro-2H-1-benzopyran-2-yl]cyclohexane-1-carboxylate as the second eluting isomer. Analytical Data for the first eluting isomer: $^1$H NMR (400 MHz, CDCl$_3$) δ 7.88 (d, J=8.9 Hz, 1H), 6.53 (dd, J=8.9, 2.3 Hz, 1H), 6.37 (d, J=2.5 Hz, 1H), 4.12 (q, J=7.1 Hz, 2H), 3.96 (ddd, J=12.5, 6.0, 2.7 Hz, 1H), 3.81 (s, 3H), 3.44 (dd, J=17.2, 2.6 Hz, 1H), 2.97 (dd, J=17.2, 12.6 Hz, 1H), 2.25 (tt, J=12.0, 3.2 Hz, 1H), 2.13-2.02 (m, 3H), 1.95-1.87 (m, 1H), 1.74-1.65 (m, 1H), 1.54-1.38 (m, 2H), 1.34-1.12 (m, 14H); LC/MS (ESI+) m/z 436 (M+H)$^+$]; Analytical Data for the second eluting isomer: $^1$H NMR (400 MHz, CDCl$_3$) δ 7.92 (d, J=8.9 Hz, 1H), 6.54 (dd, J=8.9, 2.4 Hz, 1H), 6.37 (d, J=2.4 Hz, 1H), 4.12 (q, J=7.1 Hz, 2H), 4.02 (ddd, J=12.2, 6.1, 2.7 Hz, 1H), 3.81 (s, 3H), 3.76 (dd, J=16.7, 2.7 Hz, 1H), 2.66 (dd, J=16.7, 12.2 Hz, 1H), 2.26 (tt, J=12.1, 3.3 Hz, 1H), 2.12-2.02 (m, 3H), 1.91-1.83 (m, 1H), 1.72-1.65 (m, 1H), 1.53-1.37 (m, 2H), 1.33-1.12 (m, 14H); LC/MS (ESI+) m/z 436 (M+H)$^+$.

Example 10C ethyl trans-4-[(2R,4R)-7-methoxy-4-{[(R)-2-methyl-propane-2-sulfinyl]amino}-3,4-dihydro-2H-1-benzo-pyran-2-yl]cyclohexane-1-carboxylate A solution of the product from Example 10B enriched in ethyl trans-4-[(2R,4E)-7-methoxy-4-{[(R)-2-methylpropane-2-sulfinyl]imino}-3,4-dihydro-2H-1-benzopyran-2-yl] cyclohexane-1-carboxylate (0.42 g, 0.964 mmol) in ethanol (10 mL) was cooled to 0° C., treated with NaBH$_4$ (0.073 g, 1.928 mmol), stirred at 0° C. for 30 minutes, stirred at room temperature for 45 minutes, treated with more NaBH$_4$ (50 mg), and stirred overnight. The mixture was partitioned between ethyl acetate (50 mL) and saturated NaHCO$_3$ solution (15 mL). The layers were separated and the aqueous layer was extracted with ethyl acetate (25 mL). The combined ethyl acetate layers were washed with brine, dried (MgSO$_4$), filtered, concentrated and chromatographed on silica gel eluting with a gradient of 0%-50% ethyl acetate in [9:1 CH$_2$Cl$_2$:ethyl acetate] to provide the title compound (191 mg, 0.436 mmol, 45.3% yield) as the first eluting isomer. $^1$H NMR (400 MHz, CDCl$_3$) δ 7.50 (d, J=8.7 Hz, 1H), 6.52 (dd, J=8.6, 2.6 Hz, 1H), 6.34 (d, J=2.6 Hz, 1H), 4.61 (dt, J=11.3, 6.7 Hz, 1H), 4.13 (q, J=7.1 Hz, 2H), 3.86 (dd, J=10.5, 5.6 Hz, 1H), 3.76 (s, 3H), 3.47 (d, J=7.3 Hz, 1H), 2.32-2.16 (m, 2H), 2.11-2.04 (m, 3H), 1.90-1.84 (m, 1H), 1.84-1.73 (m, 1H), 1.68-1.55 (m, 1H), 1.54-1.39 (m, 2H), 1.32-1.12 (m, 14H); LC/MS (ESI+) m/z 317 (100%) (M−tBuSONH$_2$)$^+$, 438 (30%) (M+H)$^+$.

Example 10D ethyl trans-4-[(2R,4R)-4-amino-7-methoxy-3,4-di-hydro-2H-1-benzopyran-2-yl]cyclohexane-1-car-boxylate A solution of Example 10C (191 mg, 0.436 mmol) in ethanol (11 mL) was cooled to 0° C., treated with 4 M HCl in dioxane (1091 µL, 4.36 mmol), stirred at room temperature for 20 minutes, diluted with ethyl acetate (30 mL) and washed with saturated aqueous NaHCO$_3$ solution (15 mL). The ethyl acetate layer was washed with brine, dried (MgSO$_4$), filtered, and concentrated. The residue was dissolved in CH$_2$Cl$_2$ (1.5 mL). After standing overnight, the residue contained a solid. The residue was treated with CH$_2$Cl$_2$ (3 mL) and filtered through diatomaceous earth to remove the solid. The filtrate was concentrated to dryness to provide the title compound. $^1$H NMR (400 MHz, CDCl$_3$) δ 7.32 (d, J=8.6 Hz, 1H), 6.50 (dd, J=8.6, 2.6 Hz, 1H), 6.34 (d, J=2.6 Hz, 1H), 4.13 (q, J=7.2 Hz, 2H), 4.07 (dd, J=11.3, 6.0 Hz, 1H), 3.86 (dd, J=11.5, 5.5 Hz, 1H), 3.76 (s, 3H), 2.26 (tt, J=12.2, 3.3 Hz, 1H), 2.21-2.15 (m, 1H), 2.12-2.02 (m, 5H), 1.90-1.83 (m, 1H), 1.65-1.55 (m, 1H), 1.54-1.40 (m, 3H), 1.31-1.12 (m, 5H); LC/MS (ESI+) m/z 317 (M−NH$_3$)$^+$.

Example 10E 1-(2,2-difluorobenzo[d][1,3]dioxol-5-yl)cyclopro-pane-1-carbonyl chloride A solution of 1-(2,2-difluorobenzo[d][1,3]dioxol-5-yl)cyclopropanecarboxylic acid (0.78 g, 3.22 mmol) in CH$_2$Cl$_2$ (7 mL) at 0° C. was treated with oxalyl chloride (1.410 mL, 16.10 mmol), treated with a small amount of N,N-dimethylformamide (about 1 drop), stirred at room temperature for 2 hours, and concentrated to provide the title compound. $^1$H NMR (501 MHz, CDCl$_3$) δ 7.10-7.07 (m, 2H), 7.04-7.01 (m, 1H), 2.03-1.92 (m, 2H), 1.52-1.43 (m, 2H).

Example 10F ethyl trans-4-[(2R,4R)-4-{[1-(2,2-difluoro-2H-1,3-benzodioxol-5-yl)cyclopropane-1-carbonyl]amino}-7-methoxy-3,4-dihydro-2H-1-benzopyran-2-yl]cyclohexane-1-carboxylate A solution of Example 10D (39 mg, 0.117 mmol) and triethylamine (32.6 µL, 0.234 mmol) in CH$_2$Cl$_2$ (0.5 mL) at 0° C. under N$_2$ was treated with a solution of Example 10E (45.7 mg, 0.175 mmol) in CH$_2$Cl$_2$ (0.5 mL). The mixture was stirred for 1 hour at room temperature, treated with saturated NH$_4$OH solution (10 drops), and stirred for 10 minutes. The mixture was partitioned between ethyl acetate (30 mL) and 1 M aqueous HCl (10 mL). The ethyl acetate layer was washed with saturated NaHCO$_3$ solution (10 mL) and brine, dried (MgSO$_4$), filtered, concentrated, and chromatographed on silica gel eluting with a gradient of 10% to 30% ethyl acetate in heptane to provide the title compound (43.6 mg, 0.078 mmol, 66.9% yield). $^1$H NMR (400 MHz, CDCl$_3$) δ 7.16 (dd, J=8.3, 1.5 Hz, 1H), 7.12 (d, J=1.6 Hz, 1H), 7.02 (d, J=8.2 Hz, 1H), 6.88 (d, J=8.6 Hz, 1H), 6.43 (dd, J=8.6, 2.5 Hz, 1H), 6.31 (d, J=2.5 Hz, 1H), 5.32 (d, J=8.8 Hz, 1H), 5.25-5.17 (m, 1H), 4.12 (q, J=7.1 Hz, 2H), 3.87 (dd, J=10.9, 5.5 Hz, 1H), 3.73 (s, 3H), 2.29-2.20 (m, 2H), 2.10-1.98 (m, 3H), 1.86-1.79 (m, 1H), 1.73 (dd, J=9.6, 3.6 Hz, 1H), 1.66 (dd, J=10.1, 3.3 Hz, 1H), 1.50-1.34 (m, 3H), 1.32-1.11 (m, 6H), 1.10-1.06 (m, 2H); LC/MS (ESI+) m/z 317 (100%) (M−C$_{11}$H$_9$F$_2$NO$_3$)$^+$, 558.2 (5%) (M+H)$^+$.

Example 11 trans-4-[(2R,4R)-4-{[1-(2,2-difluoro-2H-1,3-benzodioxol-5-yl)cyclopropane-1-carbonyl]amino}-7-methoxy-3,4-dihydro-2H-1-benzopyran-2-yl]cyclohexane-1-carboxylic acid A solution of Example 10F (37.4 mg, 0.067 mmol) in tetrahydrofuran (1.5 mL) was diluted with methanol (1.5 mL), treated with 1 M aqueous NaOH (about 1 mL), heated at 60° C. for 30 minutes, cooled, acidified with 1 M aqueous HCl (3 mL), and extracted with ethyl acetate (30 mL). The ethyl acetate layer was washed with brine, dried (MgSO$_4$), filtered and concentrated to provide the title compound (33.5 mg, 0.063 mmol, 94% yield). $^1$H NMR (400 MHz, CDCl$_3$) δ 7.16 (d, J=8.2 Hz, 1H), 7.12 (s, 1H), 7.02 (d, J=8.1 Hz, 1H), 6.88 (d, J=8.6 Hz, 1H), 6.43 (dd, J=8.6, 2.0 Hz, 1H), 6.31 (d, J=2.0 Hz, 1H), 5.34 (d, J=8.8 Hz, 1H), 5.26-5.18 (m, 1H), 3.88 (dd, J=11.4, 5.3 Hz, 1H), 3.73 (s, 3H), 2.35-2.20 (m, 2H), 2.13-1.98 (m, 3H), 1.88-1.80 (m, 1H), 1.74 (dd, J=9.6, 3.2 Hz, 1H), 1.66 (dd, J=10.0, 2.9 Hz, 1H), 1.50-1.35 (m, 3H), 1.30-1.12 (m, 3H), 1.12-1.05 (m, 2H); LC/MS (ESI+) m/z 289 (100%) (M−C$_{11}$H$_9$F$_2$NO$_3$)$^+$, 530.5 (5%) (M+H)$^+$.

Example 12 ethyl trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylate Example 12A 1-(2-hydroxy-4-(trifluoromethoxy)phenyl)ethan-1-one A solution of 2'-methoxy-4'-(trifluoromethoxy)acetophenone (5 g, 21.35 mmol) in CH$_2$Cl$_2$ (50 mL) under N$_2$ was cooled to −25° C., and treated dropwise with 1 M boron trichloride in CH$_2$Cl$_2$ (21.35 mL, 21.35 mmol) over 5 minutes. The reaction mixture was quenched by pouring into ice. The mixture was allowed to warm and was extracted with CH$_2$Cl$_2$ (twice). The combined CH$_2$Cl$_2$ layers were dried (MgSO$_4$), filtered, and concentrated to provide the title compound (4.50 g, 20.44 mmol, 96% yield). $^1$H NMR (400 MHz, CDCl$_3$) δ 12.47 (s, 1H), 7.77 (d, J=8.8 Hz, 1H), 6.81 (s, 1H), 6.76-6.66 (m, 1H), 2.63 (s, 3H).

Example 12B methyl cis-4-[4-oxo-7-(trifluoromethoxy)-3,4-dihydro-2H-1-benzopyran-2-yl]cyclohexane-1-carboxylate To a vial containing a solution of Example 12A (2.39 g, 10.86 mmol) in toluene (4 mL) was added trans methyl 4-formylcyclohexanecarboxylate (1.848 g, 10.86 mmol), acetic acid (0.746 mL, 13.03 mmol), and pyrrolidine (0.898 mL, 10.86 mmol). The mixture was stirred overnight at 70° C. The mixture was cooled to room temperature, diluted with ethyl acetate (100 mL), washed with 1 M aqueous HCl (30 mL), washed with saturated NaHCO$_3$ solution (15 mL), washed with brine, dried (MgSO$_4$), filtered, and concentrated. The residue was chromatographed on silica gel, eluting with a gradient of 10% to 30% ethyl acetate in heptanes. Mixed fractions of the isomers were collected and concentrated. The residue was rechromatographed on silica gel eluting with a gradient of 10% to 50% ethyl acetate in heptanes. The title compound (0.81 g, 20% yield) was provided as the first eluting isomer. $^1$H NMR (400 MHz, CDCl$_3$) δ 7.90 (d, J=8.4 Hz, 1H), 6.86-6.80 (m, 2H), 4.30 (dt, J=9.2, 6.6 Hz, 1H), 3.70 (s, 3H), 2.73-2.62 (m, 3H), 2.21-2.09 (m, 2H), 1.89-1.76 (m, 2H), 1.70-1.53 (m, 3H), 1.53-1.38 (m, 2H); LC/MS (ESI+) m/z 414 (M+CH$_3$CN)$^+$.

Example 12C methyl trans-4-[4-oxo-7-(trifluoromethoxy)-3,4-dihydro-2H-1-benzopyran-2-yl]cyclohexane-1-carboxylate The title compound (2.88 g, 71% yield) was provided as the second eluting isomer from the chromatography separation described in Example 12B. $^1$H NMR (501 MHz, CDCl$_3$) δ 7.90 (dd, J=8.5, 0.5 Hz, 1H), 6.85-6.81 (m, 2H), 4.25 (ddd, J=12.9, 5.9, 3.1 Hz, 1H), 3.68 (s, 3H), 2.74 (dd, J=16.7, 12.9 Hz, 1H), 2.66 (dd, J=16.7, 3.2 Hz, 1H), 2.30 (tt, J=12.3, 3.3 Hz, 1H), 2.13-2.07 (m, 3H), 1.90-1.83 (m, 1H), 1.78-1.71 (m, 1H), 1.55-1.42 (m, 2H), 1.31-1.16 (m, 2H); LC/MS (ESI+) m/z 414 (M+CH$_3$CN)$^+$.

Example 12D ethyl trans-4-[(2S,4E)-4-{[(S)-2-methylpropane-2-sulfinyl]imino}-7-(trifluoromethoxy)-3,4-dihydro-2H-1-benzopyran-2-yl]cyclohexane-1-carboxylate and ethyl trans-4-[(2R,4E)-4-{[(S)-2-methylpropane-2-sulfinyl]imino}-7-(trifluoromethoxy)-3,4-dihydro-2H-1-benzopyran-2-yl]cyclohexane-1-carboxylate A mixture of Example 12C (0.21 g, 0.564 mmol) and (S)-(−)-2-methyl-2-propanesulfinamide (0.137 g, 1.128 mmol) in toluene (5 mL) was treated with titanium(IV) ethoxide (0.515 g, 2.256 mmol). The mixture was stirred at 90° C. for 6 hours, cooled, diluted with ethyl acetate (50 mL), treated with water (50 mL), stirred for 5 minutes, and filtered through diatomaceous earth to remove the solids. The ethyl acetate layer of the filtrate was washed with brine, dried (MgSO$_4$), filtered and concentrated to provide the title compound. $^1$H NMR (500 MHz, CDCl$_3$) δ 7.98 (d, J=8.8 Hz, 0.5H), 7.95 (d, J=8.8 Hz, 0.5H), 6.79 (d, J=8.8 Hz, 1H), 6.77-6.75 (m, 1H), 4.11 (q, J=7.1 Hz, 2H), 4.06 (ddd, J=12.2, 6.1, 2.6 Hz, 0.5H), 3.99 (ddd, J=12.5, 6.0, 2.5 Hz, 0.5H), 3.88 (dd, J=16.8, 2.6 Hz, 0.5H), 3.55 (dd, J=17.3, 2.6 Hz, 0.5H), 3.00 (dd, J=17.3, 12.6 Hz, 0.5H), 2.71 (dd, J=16.8, 12.2 Hz, 0.5H), 2.32-2.19 (m, 1H), 2.11-2.01 (m, 3H), 1.93-1.82 (m, 1H), 1.72-1.64 (m, 1H), 1.53-1.37 (m, 2H), 1.34-1.14 (m, 14H); LC/MS (ESI+) m/z 490 (M+H)$^+$.

Example 12E ethyl trans-4-[(2S,4S)-4-{[(S)-2-methylpropane-2-sulfinyl]amino}-7-(trifluoromethoxy)-3,4-dihydro-2H-1-benzopyran-2-yl]cyclohexane-1-carboxylate A solution of Example 12D (274 mg, 0.56 mmol) in ethanol (5 mL) was cooled to 0° C. and treated with NaBH$_4$ (42.4 mg, 1.120 mmol). The mixture was stirred at 0° C. for 45 minutes, diluted with CH$_2$Cl$_2$, treated with silica gel (approximately 1.5 g) and concentrated. The silica gel suspension was chromatographed on a silica gel column, eluting with a gradient of 0% to 100% [1:1 ethyl acetate:CH$_2$Cl$_2$] in [9:1 CH$_2$Cl$_2$:ethyl acetate] to provide the title compound (59.9 mg, 0.122 mmol, 21.76% yield) as the first eluting isomer. $^1$H NMR (501 MHz, CDCl$_3$) δ 7.67 (dd, J=8.6, 1.0 Hz, 1H), 6.77 (ddd, J=8.6, 2.3, 0.9 Hz, 1H), 6.66 (dd, J=2.3, 1.0 Hz, 1H), 4.64 (dt, J=11.5, 6.7 Hz, 1H), 4.13 (q, J=7.1 Hz, 2H), 3.91 (ddd, J=11.6, 5.6, 1.3 Hz, 1H), 3.50 (d, J=7.9 Hz, 1H), 2.31-2.19 (m, 2H), 2.06 (ddt, J=9.8, 6.1, 3.4 Hz, 3H), 1.89-1.77 (m, 2H), 1.61 (s, 1H), 1.53-1.40 (m, 2H), 1.32-1.12 (m, 14H); LC/MS (ESI+) m/z 492 (M+H)$^+$.

Example 12F ethyl trans-4-[(2R,4R)-4-{[(S)-2-methylpropane-2-sulfinyl]amino}-7-(trifluoromethoxy)-3,4-dihydro-2H-1-benzopyran-2-yl]cyclohexane-1-carboxylate The title compound (75.2 mg, 0.153 mmol, 27.3% yield) was provided as the second eluting isomer from the chromatography separation as described in Example 12E. $^1$H NMR (400 MHz, CDCl$_3$) δ 7.39 (dd, J=8.5, 0.7 Hz, 1H), 6.74 (dd, J=8.6, 1.2 Hz, 1H), 6.67 (d, J=1.1 Hz, 1H), 4.57 (td, J=11.0, 6.0 Hz, 1H), 4.12 (q, J=7.1 Hz, 2H), 3.94 (dd, J=10.7, 5.3 Hz, 1H), 3.27 (d, J=10.8 Hz, 1H), 2.61 (ddd, J=13.4, 5.8, 1.2 Hz, 1H), 2.24 (tt, J=12.2, 3.4 Hz, 1H), 2.10-1.99 (m, 3H), 1.87 (d, J=12.2 Hz, 1H), 1.82-1.72 (m, 1H), 1.66-1.56 (m, 1H), 1.44 (dtt, J=18.1, 8.6, 4.3 Hz, 2H), 1.33-1.13 (m, 14H); LC/MS (ESI+) m/z 492 (M+H)$^+$.

Example 12G ethyl trans-4-[(2R,4R)-4-amino-7-(trifluoromethoxy)-3,4-dihydro-2H-1-benzopyran-2-yl]cyclohexane-1-carboxylate A solution of Example 12F (74 mg, 0.151 mmol) in ethanol (3 mL) was treated with 4 M HCl in dioxane (376 µL, 1.505 mmol), stirred at room temperature for 30 minutes, diluted with ethyl acetate (30 mL) and washed with saturated NaHCO$_3$ solution (15 mL). The ethyl acetate layer was washed with brine, dried (MgSO$_4$), filtered, and concentrated. The residue was chromatographed on silica gel eluting with a gradient of 0% to 100% [10:1:1 ethyl acetate:HCOOH:H$_2$O] in [200:1:1 ethyl acetate:HCOOH:H$_2$O]. Fractions containing the product were combined, washed with saturated NaHCO$_3$ solution to remove the formic acid, washed with brine, dried (MgSO$_4$), filtered, and concentrated to provide the title compound (52.2 mg, 0.135 mmol, 90% yield). $^1$H NMR (400 MHz, CDCl$_3$) δ 7.44 (dd, J=8.6, 0.6 Hz, 1H), 6.78-6.74 (m, 1H), 6.67-6.65 (m, 1H), 4.17-4.06 (m, 3H), 3.91 (ddd, J=11.6, 5.5, 1.1 Hz, 1H), 2.33-2.16 (m, 4H), 2.11-2.02 (m, 3H), 1.90-1.82 (m, 1H), 1.68-1.56 (m, 2H), 1.55-1.39 (m, 2H), 1.32-1.11 (m, 5H); LC/MS (ESI+) m/z 371 (M−NH$_3$)$^+$.

Example 12H ethyl trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylate A solution of Example 12G (40 mg, 0.094 mmol) and triethylamine (26.3 µL, 0.189 mmol) in CH$_2$Cl$_2$ (0.5 mL) at 0° C. under N$_2$ was treated with a solution of Example 10E (36.9 mg, 0.142 mmol) in CH$_2$Cl$_2$ (0.5 mL). The mixture was stirred for 1 hour at room temperature. The mixture was treated with saturated NH$_4$OH solution (10 drops) and stirred for 10 minutes. The mixture was partitioned between ethyl acetate (30 mL) and 1 M aqueous HCl (10 mL). The ethyl acetate layer was isolated, washed with saturated aqueous NaHCO$_3$ solution (10 mL), washed with brine, dried (MgSO$_4$), filtered, concentrated and chromatographed on silica gel eluting with a gradient of 10% to 30% ethyl acetate in heptane to provide the title compound (51.7 mg, 0.085 mmol, 90% yield). $^1$H NMR (500 MHz, CDCl$_3$) δ 7.16 (dd, J=8.2, 1.7 Hz, 1H), 7.12 (d, J=1.6 Hz, 1H), 7.04 (d, J=8.2 Hz, 1H), 6.99 (dd, J=8.5, 0.9 Hz, 1H), 6.71-6.68 (m, 1H), 6.63 (dd, J=2.2, 0.9 Hz, 1H), 5.34 (d, J=9.0 Hz, 1H), 5.30-5.24 (m, 1H), 4.12 (q, J=7.1 Hz, 2H), 3.91 (ddd, J=11.4, 5.4, 1.1 Hz, 2H), 2.28-2.19 (m, 2H), 2.08-1.98 (m, 3H), 1.84-1.78 (m, 1H), 1.75-1.72 (m, 1H), 1.69-1.66 (m, 1H), 1.50-1.39 (m, 3H), 1.27-1.08 (m, 7H); LC/MS (ESI+) m/z 612.6 (M+H)$^+$.

Example 13 trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylic acid A solution of Example 12H (42.5 mg, 0.069 mmol) in tetrahydrofuran (1.5 mL) was diluted with methanol (1.5 mL), treated with 1 M aqueous NaOH (about 1 mL), heated at 60° C. for 30 minutes, cooled, acidified with 1 M aqueous HCl (3 mL), and extracted with ethyl acetate (30 mL). The ethyl acetate layer was washed with brine, dried (MgSO$_4$), filtered, concentrated, and chromatographed on silica gel eluting with a gradient of 25%-100% [200:1:1 ethyl acetate:HCOOH:H$_2$O] in heptane to provide the title compound (37.5 mg, 0.064 mmol, 92% yield). $^1$H NMR (500 MHz, CDCl$_3$) δ 7.19 (dd, J=8.2, 1.7 Hz, 1H), 7.15 (d, J=1.7 Hz, 1H), 7.07 (d, J=8.2 Hz, 1H), 7.02 (dd, J=8.5, 0.9 Hz, 1H), 6.76-6.69 (m, 1H), 6.66 (dd, J=2.2, 0.9 Hz, 1H), 5.38 (d, J=9.0 Hz, 1H), 5.30 (ddd, J=11.4, 5.5, 1.0 Hz, 1H), 3.95 (ddd, J=11.6, 5.5, 1.1 Hz, 1H), 2.32 (tt, J=12.2, 3.5 Hz, 1H), 2.25 (ddd, J=12.8, 5.9, 1.2 Hz, 1H), 2.15-2.10 (m, 2H), 2.07-2.02 (m, 1H), 1.88-1.83 (m, 1H), 1.79-1.69 (m, 2H), 1.64-1.55 (m, 1H), 1.53-1.42 (m, 3H), 1.34-1.09 (m, 4H); LC/MS (ESI+) m/z 584 (M+H)$^+$.

Example 14A methyl 4-{(2R)-4-oxo-7-[(propan-2-yl)oxy]-3,4-dihydro-2H-1-benzopyran-2-yl}benzoate In a 20 mL vial was charged with bis(2,2,2-trifluoroacetoxy)palladium (0.197 g, 0.594 mmol), (S)-4-(tert-butyl)-2-(pyridin-2-yl)-4,5-dihydrooxazole (0.146 g, 0.713 mmol), ammonium hexafluorophosphate(V) (0.581 g, 3.56 mmol) and (4-(methoxycarbonyl)phenyl)boronic acid (2.138 g, 11.88 mmol). The mixture was stirred in dichloroethane (5 mL) for 5 minutes. To this suspension was added 7-(difluoromethoxy)-4H-chromen-4-one (1.26 g, 5.94 mmol) and water (0.256 mL, 14.19 mmol) and the sides of the vial washed with more dichloroethane (5 mL). The vial was capped and the mixture stirred at 60° C. overnight. The reaction gradually turned black, with Pd plated out on the sides of the vial. The mixture was filtered through a plug of silica gel and diatomaceous earth and eluted with ethyl acetate to give a red solution. The solvent was removed in vacuo and the crude material was chromatographed on a 40 g silica gel cartridge, eluting with a gradient of 5-50% ethyl acetate/heptanes to yield the title compound (860 mg, 2.469 mmol, 41.6% yield). MS (APCI+) m/z 349.3 (M+H)$^+$.

Example 14B methyl 4-[(2R)-4-[(benzyloxy)imino]-7-(difluoromethoxy)-3,4-dihydro-2H-1-benzopyran-2-yl]benzoate A 40 mL vial was charged with Example 14A (577 mg, 1.657 mmol) and pyridine (5.7 mL). O-benzylhydroxylamine hydrochloride (278 mg, 1.739 mmol) was added and the reaction was heated at 50° C. for over 1 hour. The reaction mixture was cooled to room temperature and then concentrated, and the residue was taken into ethyl acetate. The mixture was washed with saturated aqueous NH$_4$Cl, 1M HCl, and brine. The organic layer was concentrated and the residue (2.1 mg) was dissolved in ethyl acetate followed by dropwise addition of 5 mL heptanes. The resulting white solid was collected by filtration and washed with heptanes. The solid was dried under vacuum to yield the title compound (430.7 mg). $^1$H NMR (400 MHz, CDCl$_3$) δ 8.03-7.96 (m, 2H), 7.89-7.82 (m, 1H), 7.47-7.39 (m, 2H), 7.35-7.18 (m, 5H), 6.71-6.60 (m, 2H), 6.44 (t, J=73.5 Hz, 1H), 5.14 (d, J=1.2 Hz, 2H), 5.06 (dd, J=12.2, 3.2 Hz, 1H), 3.90-3.83 (m, 3H), 3.43 (ddd, J=17.4, 3.3, 1.0 Hz, 1H), 2.62 (ddd, J=17.3, 12.2, 1.1 Hz, 1H).

Example 14C methyl 4-[(2R,4R)-4-amino-7-(difluoromethoxy)-3,4-dihydro-2H-1-benzopyran-2-yl]cyclohexane-1-carboxylate hydrochloride A 50-mL Parr reactor was charged with methyl Example 14B (1.55 g, 3.42 mmol) and platinum (IV) oxide (0.124 g, 0.305 mmol). The solids were suspended in methanol (23 mL) and 2,2,2-trifluoroacetic acid (2.62 mL, 34.2 mmol). The reactor was sealed and purged with argon (60 psig, 4×) and then with H$_2$ (100 psig, 4×). The reactor was pressurized to 150 psig of H$_2$, warmed to 50° C. and stirred for 6 hours. The mixture was cooled to 23° C. and then carefully vented the pressure in the reactor. The contents of the reactor were then purged with argon (60 psig, 3×). The slurry was filtered to remove the catalyst, rinsed with ethyl acetate (2×30 mL), and washed with 10 wt % aqueous K$_3$PO$_4$ (18 mL, 3×), then concentrated (about 12 mL). 4 M HCl in cyclopentylmethylether (3.42 mL, 13.7 mmol) was added. The mixture was stirred for three hours and concentrated to provide the title compound. $^1$H NMR (400 MHz, CDCl$_3$) δ 7.42 (d, J=8.0 Hz, 2H), 6.69-6.66 (m, 2H), 6.55 (m, 2H), 6.47 (br s, 1H), 6.29 (s, 0.3H), 4.06-4.01 (m, 2H), 3.97-3.89 (m, 2H), 3.70 (s, 3H), 3.68 (s, 3H), 2.32-2.06 (m, 10H), 1.88-1.38 (m, 22H), 1.30-1.11 (m, 4H). $^{13}$C NMR (100 MHz, CDCl$_3$) δ 176.3, 175.6, 155.7, 151.0, 127.8, 124.8, 116.0 (t, J=257 Hz), 111.4, 107.3, 79.8, 79.1, 51.5, 47.0, 46.9, 43.2, 41.5, 41.1, 39.6, 36.4, 28.6, 27.4, 27.0, 26.5, 24.9, 24.7. $^{19}$F NMR (376 MHz, CDCl$_3$) δ −76.0, −80.7.

Example 14D methyl cis-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylate Example 14C (0.50 g, 1.407 mmol) was mixed with 2-(3H-[1,2,3]triazolo[4,5-b]pyridin-3-yl)-1,1,3,3-tetramethylisouronium hexafluorophosphate(V) (0.59 g, 1.548 mmol) and 1-(2,2-difluorobenzo[d][1,3]dioxol-5-yl)cyclopropane-1-carboxylic acid (0.36 g, 1.477 mmol) in ethyl acetate (5 mL) and cooled to 0° C. N-ethyl-N-isopropylpropan-2-amine (0.86 mL, 4.92 mmol) was added and the mixture was stirred overnight at 0° C. The reaction mixture was filtered and then washed with 5% sodium bicarbonate solution (2.5 mL), and concentrated. The residue was purified by preparative HPLC on a Chiralpak IC SFC column (30×25 mm, 5 um), and eluted with an isocratic mixture of 93% hexane: 7% ethanol at a flow rate of 30 mL/min to provide the title compound (100 mg, 0.172 mmol, 12% yield) as the first eluted isomer. $^1$H NMR (700 MHz, DMSO-d$_6$) δ 7.44 (d, J=1.7 Hz, 1H), 7.35 (d, J=8.3 Hz, 1H), 7.28-7.22 (m, 2H), 7.18 (t, J=74.3 Hz, 1H), 7.02 (dd, J=8.5, 1.1 Hz, 1H), 6.67 (dd, J=8.5, 2.5 Hz, 1H), 6.53 (d, J=2.5 Hz, 1H), 5.20-5.12 (m, 1H), 4.03 (ddd, J=11.8, 5.9, 1.6 Hz, 1H), 3.64 (s, 3H), 2.67 (p, J=4.4 Hz, 1H), 2.02 (ddd, J=13.8, 9.1, 4.3 Hz, 2H), 1.86 (ddd, J=12.9, 6.0, 1.7 Hz, 1H), 1.78-1.66 (m, 2H), 1.64-1.49 (m, 6H), 1.39 (ddd, J=9.9, 6.7, 3.6 Hz, 1H), 1.35-1.28 (m, 2H), 1.14-1.00 (m, 2H).

Example 14E methyl trans-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylate The title compound (65 mg, 0.112 mmol, 8% yield) was obtained as the second eluting isomer from the chromatography separation as described in Example 14D. $^1$H NMR (700 MHz, DMSO-d$_6$) δ 7.44 (d, J=1.7 Hz, 1H), 7.35 (d, J=8.3 Hz, 1H), 7.28-7.22 (m, 2H), 7.18 (t, J=74.2 Hz, 1H), 7.02 (dd, J=8.5, 1.1 Hz, 1H), 6.68 (dd, J=8.5, 2.5 Hz, 1H), 6.55 (d, J=2.5 Hz, 1H), 5.21-5.13 (m, 1H), 4.06-3.96 (m, 1H), 2.29 (tt, J=12.1, 3.6 Hz, 1H), 1.94 (dd, J=30.1, 12.3 Hz, 3H), 1.90-1.84 (m, 1H), 1.81 (t, J=12.0 Hz, 1H), 1.79-1.72 (m, 1H), 1.53 (dtd, J=19.7, 7.2, 6.6, 3.5 Hz, 2H), 1.42-1.32

(m, 3H), 1.24-1.12 (m, 3H), 1.10 (ddd, J=9.9, 6.6, 3.2 Hz, 1H), 1.05 (ddd, J=10.8, 7.1, 3.9 Hz, 1H).

Example 15A cis-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylic acid A solution of Example 14D (30 mg, 0.052 mmol) in acetonitrile (0.06 mL) and methanol (0.24 mL) was treated with a solution of LiOH (10.0 mg, 0.238 mmol) in water (0.06 mL). The mixture was heated at 45° C. for 4 hours and then cooled, followed by the addition of water (0.25 mL) and extracted with isopropyl acetate (0.4 mL). The isopropyl acetate layer was washed with 1N aqueous HCl (0.25 mL) twice, water (0.25 mL), and brine (0.25 mL). The isopropyl acetate solution was then concentrated to provide the title compound (27 mg, 0.048 mmol, 92% yield). $^1$H NMR (400 MHz, DMSO-$d_6$) δ 12.12 (s, 1H), 7.42 (d, J=1.7 Hz, 1H), 7.32 (d, J=8.3 Hz, 1H), 7.28-7.20 (m, 2H), 7.16 (s, 1H), 6.99 (dd, J=8.5, 1.1 Hz, 1H), 6.65 (dd, J=8.5, 2.5 Hz, 1H), 6.50 (d, J=2.5 Hz, 1H), 5.14 (dt, J=10.1, 7.8 Hz, 1H), 4.01 (ddd, J=11.3, 5.8, 1.8 Hz, 1H), 2.06-1.97 (m, 2H), 1.87-1.62 (m, 3H), 1.61-1.40 (m, 5H), 1.41-1.24 (m, 4H), 1.03 (dddd, J=22.5, 16.2, 9.6, 3.2 Hz, 3H).

Example 15B trans-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylic acid A solution of Example 14E (25 mg, 0.043 mmol) in acetonitrile (0.05 mL) and methanol (0.2 mL) was treated with a solution of LiOH (8.3 mg, 0.198 mmol) in water (0.05 mL). The mixture was heated at 45° C. for 2 hours and then cooled, followed by the addition of water (0.25 mL) and extracted with isopropyl acetate (0.4 mL). The isopropyl acetate layer was washed with 1N aqueous HCl (0.25 mL) twice, water (0.25 mL), and brine (0.25 mL). The isopropyl acetate solution was then concentrated to provide the title compound (19 mg, 0.034 mmol, 78% yield). $^1$H NMR (400 MHz, DMSO-$d_6$) δ 7.41 (d, J=1.8 Hz, 1H), 7.34 (d, J=1.5 Hz, 1H), 7.32 (s, 1H), 7.27-7.19 (m, 2H), 7.18-7.14 (m, 1H), 7.03-6.93 (m, 1H), 6.65 (dd, J=8.4, 2.5 Hz, 1H), 6.52 (d, J=2.5 Hz, 1H), 5.14 (td, J=10.4, 6.5 Hz, 1H), 3.98 (ddd, J=11.3, 5.4, 2.0 Hz, 1H), 2.19-2.06 (m, 1H), 1.95-1.66 (m, 6H), 1.49 (ddd, J=9.7, 6.2, 2.9 Hz, 2H), 1.41-1.24 (m, 4H), 1.15-0.94 (m, 5H).

Example 16

N-[2-(3,4-dimethoxyphenyl)-7-methoxy-3,4-dihydro-2H-1-benzopyran-4-yl]-3,3-difluoro-1-phenylcyclobutane-1-carboxamide A stock solution of 2-(3,4-dimethoxyphenyl)-7-methoxychroman-4-amine and diisopropylethylamine (0.17 M and 0.47 M in N,N-dimethylacetamide, respectively, 300 µL, 0.051 mmol 2-(3,4-dimethoxyphenyl)-7-methoxychroman-4-amine (1.0 equivalent) and 0.14 mmol diisopropylethylamine (3.0 equivalents)), 3,3-difluoro-1-phenylcyclobutanecarboxylic acid (0.40 M in N,N-dimethylacetamide, 190 µL, 0.076 mmol, 1.5 equivalents), and HATU (0.20 M in N,N-dimethylacetamide, 300 µL, 0.06 mmol, 1.2 equivalents) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction mixture was loaded directly into an injection loop and purified using preparative LC (TFA method, purified by preparative HPLC on a Phenomenex Luna C8(2) 5 µm 100 Å AXIA column (30 mm×150 mm). A gradient of CH$_3$CN (A) and 0.1% trifluoroacetic acid in water (B) was used, at a flow rate of 30 mL/minute (0-0.5 min 5% A, 0.5-6.5 min linear gradient 5-100% A, 6.5-8.5 min 100% A, 8.5-9.0 min linear gradient 100-5% A, 9.0-10 min 5% A) to provide the title compound. $^1$H NMR (400 MHz, DMSO-$d_6$) δ 7.77-7.70 (m, 1H), 7.45-7.25 (m, 4H), 7.02-6.93 (m, 3H), 6.56 (d, J=8.5 Hz, 1H), 6.40-6.28 (m, 2H), 5.25-5.07 (m, 2H), 3.77 (s, 6H), 3.68 (s, 3H), 3.51-3.33 (m, 2H), 3.11-2.91 (m, 2H), 2.14-1.93 (m, 2H); MS (APCI+) m/z 510.1 (M+H)$^+$.

Example 17

1-(3,4-difluorophenyl)-N-[2-(3,4-dimethoxyphenyl)-7-methoxy-3,4-dihydro-2H-1-benzopyran-4-yl]cyclobutane-1-carboxamide Example 17 was prepared according to the procedure described in Example 16, substituting 1-(3,4-difluorophenyl)cyclobutanecarboxylic acid (CAS 633317-58-5) for 3,3-difluoro-1-phenylcyclobutanecarboxylic acid. $^1$H NMR (400 MHz, DMSO-$d_6$) δ 7.54-7.46 (m, 1H), 7.39-7.26 (m, 2H), 7.22-7.05 (m, 1H), 7.03-6.88 (m, 3H), 6.66 (d, J=8.1 Hz, 1H), 6.37 (d, J=8.1 Hz, 2H), 5.22 (td, J=9.8, 8.8, 6.1 Hz, 1H), 5.12 (dd, J=10.9, 2.8 Hz, 1H), 3.78 (s, 6H), 3.69 (s, 3H), 2.85-2.65 (m, 2H), 2.46-2.29 (m, 2H), 2.15-1.97 (m, 2H), 1.94-1.73 (m, 2H). MS (APCI+) m/z 510.1 (M+H)$^+$.

Example 18

2-(4-chlorophenoxy)-N-[2-(3,4-dimethoxyphenyl)-7-methoxy-3,4-dihydro-2H-1-benzopyran-4-yl]-2-methylpropanamide Example 18 was prepared according to the procedure described in Example 16, substituting 2-(4-chlorophenoxy)-2-methyl-propionic acid (CAS 882-09-7) for 3,3-difluoro-1-phenylcyclobutanecarboxylic acid. $^1$H NMR (400 MHz, DMSO-$d_6$) δ 7.84 (d, J=8.8 Hz, 1H), 7.33-7.23 (m, 2H), 7.06-6.85 (m, 6H), 6.46 (dd, J=8.5, 2.6 Hz, 1H), 6.38 (d, J=2.6 Hz, 1H), 5.35-5.23 (m, 1H), 5.21-5.11 (m, 1H), 3.80-3.74 (m, 6H), 3.71 (s, 3H), 2.24-2.12 (m, 2H), 1.53 (s, 3H), 1.47 (s, 3H). MS (APCI+) m/z 512.1 (M+H)$^+$.

Example 19

N-[2-(3,4-dimethoxyphenyl)-7-methoxy-3,4-dihydro-2H-1-benzopyran-4-yl]-1-(3-fluorophenyl)cyclopropane-1-carboxamide Example 19 was prepared according to the procedure described in Example 16, substituting 1-(3-fluorophenyl)cyclopropanecarboxylic acid (CAS 248588-33-2) for 3,3-difluoro-1-phenylcyclobutanecarboxylic acid. $^1$H NMR (400 MHz, DMSO-$d_6$) δ 7.40-7.30 (m, 1H), 7.20 (dt, J=7.7, 1.3 Hz, 1H), 7.13 (dt, J=10.3, 2.2 Hz, 1H), 7.07-6.87 (m, 5H), 6.78 (d, J=8.6 Hz, 1H), 6.48 (dd, J=8.6, 2.6 Hz, 1H), 6.35 (d, J=2.6 Hz, 1H), 5.30-5.18 (m, 1H), 5.12 (dd, J=11.3, 2.3 Hz, 1H), 3.80-3.74 (m, 6H), 3.70 (s, 3H), 2.21-2.11 (m, 1H), 2.10-1.98 (m, 1H), 1.53-1.44 (m, 1H), 1.43-1.33 (m, 1H), 1.14-0.98 (m, 2H). MS (APCI+) m/z 478.1 (M+H)+.

Example 20

N-[2-(3,4-dimethoxyphenyl)-7-methoxy-3,4-dihydro-2H-1-benzopyran-4-yl]-1-(4-fluorophenyl)cyclopropane-1-carb oxamide Example 20 was prepared according to the procedure described in Example 16, substituting 1-(4-fluorophenyl)cyclopropanecarboxylic acid (CAS 773100-29-1) for 3,3-difluoro-1-phenylcyclobutanecarboxylic acid. $^1$H NMR (400 MHz, DMSO-d$_6$) δ 7.45-7.34 (m, 2H), 7.15-7.03 (m, 2H), 7.02-6.86 (m, 4H), 6.48 (dd, J=8.6, 2.6 Hz, 1H), 6.35 (d, J=2.5 Hz, 1H), 5.22 (dd, J=10.9, 6.1 Hz, 1H), 5.12 (dd, J=11.1, 2.2 Hz, 1H), 3.80-3.74 (m, 6H), 3.70 (s, 3H), 2.21-2.10 (m, 1H), 2.10-1.96 (m, 1H), 1.53-1.43 (m, 1H), 1.42-1.32 (m, 1H), 1.09-0.94 (m, 2H). MS (APCI+) m/z 478.1 (M+H)+.

Example 21

1-(4-chlorophenyl)-N-[2-(3,4-dimethoxyphenyl)-7-methoxy-3,4-dihydro-2H-1-benzopyran-4-yl]cyclopropane-1-carboxamide Example 21 was prepared according to the procedure described in Example 16, substituting 1-(4-chlorophenyl)cyclopropanecarboxylic acid (CAS 72934-37-3) for 3,3-difluoro-1-phenylcyclobutanecarboxylic acid. $^1$H NMR (400 MHz, DMSO-d$_6$) δ 7.55-7.29 (m, 4H), 7.08-6.86 (m, 4H), 6.48 (dd, J=8.6, 2.6 Hz, 1H), 6.35 (d, J=2.6 Hz, 1H), 5.23 (dd, J=10.9, 6.2 Hz, 1H), 5.12 (dd, J=11.1, 2.3 Hz, 1H), 3.83-3.74 (m, 6H), 3.70 (s, 3H), 2.21-1.92 (m, 2H), 1.60-1.44 (m, 1H), 1.44-1.25 (m, 1H), 1.10-0.93 (m, 2H). MS (APCI+) m/z 494.1 (M+H)+.

Example 22

2-(4-chlorophenyl)-N-[2-(3,4-dimethoxyphenyl)-7-methoxy-3,4-dihydro-2H-1-benzopyran-4-yl]-2-methylpropanamide Example 22 was prepared according to the procedure described in Example 16, substituting 2-(4-chlorophenyl)-2-methyl-propionic acid (CAS 6258-30-6) for 3,3-difluoro-1-phenylcyclobutanecarboxylic acid. $^1$H NMR (400 MHz, DMSO-d$_6$) δ 7.41-7.30 (m, 4H), 7.16-7.08 (m, 1H), 7.03-6.94 (m, 3H), 6.87-6.80 (m, 1H), 6.44 (dd, J=8.6, 2.6 Hz, 1H), 6.35 (d, J=2.6 Hz, 1H), 5.32-5.21 (m, 1H), 5.13 (dd, J=11.0, 2.6 Hz, 1H), 3.78 (s, 6H), 3.70 (s, 3H), 2.18-1.99 (m, 2H), 1.53-1.46 (m, 6H). MS (APCI+) m/z 496.1 (M+H)+.

Example 23

N-[2-(3,4-dimethoxyphenyl)-7-methoxy-3,4-dihydro-2H-1-benzopyran-4-yl]-2-(4-methoxyphenyl)-2-methylpropanamide Example 23 was prepared according to the procedure described in Example 16, substituting 2-(4-methoxyphenyl)-2-methyl-propionic acid (CAS 2955-46-6) for 3,3-difluoro-1-phenylcyclobutanecarboxylic acid. $^1$H NMR (400 MHz, DMSO-d$_6$) δ 7.32-7.23 (m, 2H), 7.02-6.79 (m, 7H), 6.42 (dd, J=8.5, 2.6 Hz, 1H), 6.35 (d, J=2.6 Hz, 1H), 5.31-5.19 (m, 1H), 5.13 (dd, J=11.0, 2.5 Hz, 1H), 3.80-3.75 (m, 6H), 3.74 (s, 3H), 3.69 (s, 3H), 2.18-1.98 (m, 2H), 1.51-1.44 (m, 6H). MS (APCI+) m/z 492.4 (M+H)+.

Example 24

3-{(2R,4S)-7-methoxy-4-[2-(4-methoxyphenyl)-2-methylpropanamido]-3,4-dihydro-2H-1-benzopyran-2-yl}benzoic acid Example 24A methyl 3-[(2R)-7-methoxy-4-oxo-3,4-dihydro-2H-1-benzopyran-2-yl]benzoate A 20 mL vial was charged with bis(2,2,2-trifluoroacetoxy)palladium (0.377 g, 1.135 mmol) [CAS 42196-31-6], (S)-4-(tert-butyl)-2-(pyridin-2-yl)-4,5-dihydrooxazole (0.278 g, 1.362 mmol) [CAS 117408-98-7], ammonium hexafluorophosphate(V) (1.110 g, 6.81 mmol) [CAS 16941-11-0] and (3-(methoxycarbonyl)phenyl)boronic acid (4.09 g, 22.71 mmol) [CAS 99769-19-4] were stirred in dichloroethane (5 mL) for 5 min, and a pale yellow color was observed. To this suspension was added 7-methoxy-4H-chromen-4-one (2 g, 11.35 mmol)[AK 104798] and water (0.256 mL, 14.19 mmol) and the sides of the vial washed with more dichloroethane (5 mL). The vial was capped and the mixture stirred at 60° C. for overnight. The mixture was filtered through a plug of silica gel and celite and washed with DCM to give a red solution. The solvent was removed in vacuo and the crude material was purified via chromatography on a 40 g silica gel cartridge, eluting with ethyl acetate/heptanes in 5-50% gradient to give title compound (900 mg, 25.4%) and some of SM was recovered. $^1$H NMR (400 MHz, DMSO-d$_6$) δ 8.13 (t, J=1.8 Hz, 1H), 7.96 (dt, J=7.8, 1.5 Hz, 1H), 7.82 (dt, J=7.8, 1.6 Hz, 1H), 7.72 (dd, J=8.4, 0.7 Hz, 1H), 7.59 (t, J=7.7 Hz, 1H), 6.71-6.63 (m, 2H), 5.75 (dd, J=13.0, 2.9 Hz, 1H), 3.86 (s, 3H), 3.81 (s, 3H), 3.15 (dd, J=16.8, 13.0 Hz, 1H), 2.78 (dd, J=16.8, 3.0 Hz, 1H); MS (ESI+) m/z=208 (M+H)+.

Example 24B methyl 3-[(2R,4Z)-4-(hydroxyimino)-7-methoxy-3,4-dihydro-2H-1-benzopyran-2-yl]benzoate Example 24A (554 mg, 1.774 mmol), hydroxylamine, hydrochloric acid (247 mg, 3.55 mmol) and anhydrous sodium acetate (291 mg, 3.55 mmol) in methanol (10 mL) was stirred at 60° C. for overnight. Solvent was removed under pressure and the residue washed with water, filtered and dried to give title compound (537 mg, 92%) as white solid. HTP-TFA (APCI+) 328 (M+1)+.

Example 24C methyl 3-[(2R)-4-amino-7-methoxy-3,4-dihydro-2H-1-benzopyran-2-yl]benzoate, hydrochloric acid Example 24B (536 mg, 1.637 mmol) and acetic acid (6 mL) in a 25 mL pressure bottle was added 5% Pt/C wet, RD0585 (120 mg, 0.25 mmol). The mixture was stirred at 30 psi and ambient temperature for 40 hours. Solvent was removed under pressure and the residue dissolved in tert-butyl ethyl ether. To the mixture was added 4M HCl (1 mL)

in dioxane. The mixture was stirred at ambient temperature for 2 hours. The white solid precipitated was collected by filtration and dried to yield title compound (462 mg, 81%). HTP-TFA/(APCI+) 297 (M–NH$_2$)$^+$.

Example 24D methyl 3-{(2R,4S)-7-methoxy-4-[2-(4-methoxyphenyl)-2-methylpropanamido]-3,4-dihydro-2H-1-benzopyran-2-yl}benzoate and Example 24E methyl 3-{(2R,4R)-7-methoxy-4-[2-(4-methoxyphenyl)-2-methylpropanamido]-3,4-dihydro-2H-1-benzopyran-2-yl}benzoate To 2-(4-methoxyphenyl)-2-methylpropanoic acid (53.3 mg, 0.274 mmol) in N,N-dimethylformamide (1 mL) was added HATU (139 mg, 0.366 mmol). The mixture was stirred for 5 minutes at room temperature, followed by the addition of Example 24C (80 mg, 0.229 mmol) and N-ethyl-N-isopropylpropan-2-amine (0.120 mL, 0.686 mmol). The mixture was stirred at room temperature for 2 hours. The reaction mixture was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The fractions collected was concentrated and the residue purified by chromatography, eluting with 5-20% tert-butyl methyl ether in heptane. Example 24D was obtained as the first eluting isomer. (28 mg, 25.01%). $^1$H NMR (400 MHz, CDCl$_3$) δ 8.09-8.00 (m, 2H), 7.58-7.45 (m, 2H), 7.37-7.30 (m, 2H), 7.03 (d, J=8.5 Hz, 1H), 6.98-6.91 (m, 2H), 6.53 (dd, J=8.5, 2.5 Hz, 1H), 6.46 (d, J=2.5 Hz, 1H), 5.49 (d, J=6.8 Hz, 1H), 5.00 (dt, J=6.8, 3.0 Hz, 1H), 4.71 (dd, J=11.7, 2.0 Hz, 1H), 3.98 (s, 3H), 3.82 (s, 3H), 3.78 (d, J=1.1 Hz, 3H), 2.33 (dt, J=14.2, 2.3 Hz, 1H), 2.17-2.05 (m, 1H), 1.62 (s, 3H), 1.59 (s, 3H); MS(ESI+): m/z=489.8 (M+H); analytical chiral SFC analysis of the compound (column: ChiralCel OJ-H, eluting with 5-30% methanol:CO$_2$ over 10 minutes, 3 mL/min, 150 bar) showed single peak at 3.77 minutes. Example 24 E (35 mg, 31.3%) was obtained as the second eluting isomer. Chiral SFC showed single peak at 5.047 min. HTP-TFA/(APCI+) 490 (M+1)$^+$.

Example 24F

3-{(2R,4S)-7-methoxy-4-[2-(4-methoxyphenyl)-2-methylpropanamido]-3,4-dihydro-2H-1-benzopyran-2-yl}benzoic acid Example 24D (25 mg, 0.051 mmol) in methanol (1 mL) and 6N lithium hydroxide (0.25 mL) was stirred at ambient temperature for 2 hours, LC/MS showed completion of reaction. The pH of the mixture was adjusted to about 1 with the addition of 2N HCl. The mixture was purified by reverse-phase preparative HPLC on a Phenomenex® Luna® C8(2) 5 m 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (22 mg, 91%). $^1$H NMR (400 MHz, CDCl$_3$) δ 8.14 (s, 2H), 7.00 (d, J=147.5 Hz, 7H), 6.35 (s, 2H), 5.49 (s, 1H), 4.86 (s, 1H), 4.52 (s, 1H), 3.71 (s, 3H), 3.55 (d, J=45.6 Hz, 3H), 2.45-1.92 (m, 2H), 1.92-0.98 (m, 6H); MS (ESI–) m/z=474.2 (M–H)$^-$.

Example 25

3-{(2R,4R)-7-methoxy-4-[2-(4-methoxyphenyl)-2-methylpropanamido]-3,4-dihydro-2H-1-benzopyran-2-yl}benzoic acid Example 25 (27.5 mg, 88%) was prepared according the procedure described in Example 24F, substituting Example 24E for Example 24D. 1H NMR (400 MHz, CDCl$_3$) δ 8.20 (s, 1H), 8.14-8.05 (m, 1H), 7.62 (dd, J=24.4, 7.7 Hz, 1H), 7.50 (q, J=7.5 Hz, 1H), 7.30 (t, J=4.3 Hz, 2H), 6.97-6.82 (m, 3H), 6.57-6.41 (m, 2H), 5.55-5.40 (m, 1H), 5.33-5.19 (m, 1H), 4.69 (s, 1H), 3.80 (d, J=6.0 Hz, 3H), 3.76 (d, J=2.1 Hz, 3H), 2.60-2.51 (m, 1H), 2.38-2.05 (m, 1H), 1.63 (d, J=15.2 Hz, 3H), 1.58 (s, 3H); MS(ESI–) m/z=474.2 (M–H)$^-$.

Example 26

3-[(2R,4R)-4-{[(2R)-5-chloro-2-methyl-2,3-dihydro-1-benzofuran-2-carbonyl]amino}-3,4-dihydro-2H-1-benzopyran-2-yl]benzoic acid Example 26A methyl 2,3-dihydrobenzofuran-2-carboxylate To a solution of 2,3-dihydro-1-benzofuran-2-carboxylic acid (1.033 g, 6.29 mmol) (Oakwood, CAS 1914-60-9) in diethyl ether (31.5 mL) was added (trimethylsilyl)diazomethane (3.15 mL, 6.29 mmol) dropwise. The reaction was stirred at room temperature for 30 minutes. The solvent was removed and the crude material was purified using a 40 g silica gel cartridge, eluting with a gradient of 5-100% ethyl acetate/heptanes to provide the title compound (0.562 g, 3.15 mmol, 50.1% yield). $^1$H NMR (501 MHz, DMSO-d$_6$) δ 7.21 (dq, J=7.3, 1.3 Hz, 1H), 7.12 (td, J=7.6, 1.2 Hz, 1H), 6.89-6.80 (m, 2H), 5.33 (dd, J=10.8, 6.1 Hz, 1H), 3.69 (s, 3H), 3.62-3.50 (m, 1H), 3.27 (dd, J=16.1, 6.1 Hz, 1H).

Example 26B methyl 2-methyl-2,3-dihydrobenzofuran-2-carboxylate

To a solution of Example 26A (0.562 g, 3.15 mmol) in tetrahydrofuran (15.77 mL) cooled in a dry ice/acetone bath was added 1M lithium bis(trimethylsilyl)amide (4.73 mL, 4.73 mmol) in tetrahydrofuran, followed by dropwise addition of methyl iodide (0.296 mL, 4.73 mmol). The reaction was allowed to warm up to room temperature overnight, then diluted with 150 mL of ethyl acetate and quenched with saturated aqueous ammonium chloride. The aqueous layer was removed and the organics was washed with water and brine. The organic phase was dried over sodium sulfate, filtered, and concentrated. The crude material was chromatographed on a 40 g silica gel cartridge, eluting with a gradient of 5-100% ethyl acetate/heptanes to provide the title compound (166 mg, 0.777 mmol, 24.64% yield). $^1$H NMR (400 MHz, DMSO-d$_6$) δ 7.16 (dd, J=7.3, 1.3 Hz, 1H), 7.08 (td, J=7.7, 1.2 Hz, 1H), 6.82 (td, J=7.5, 1.0 Hz, 1H), 6.77 (d, J=8.0 Hz, 1H), 3.65 (s, 3H), 3.50 (d, J=16.2 Hz, 1H), 3.15 (d, J=16.2 Hz, 1H), 1.58 (s, 3H).

Example 26C methyl 5-chloro-2-methyl-2,3-dihydrobenzofuran-2-carboxylate

To a solution of Example 26B (166 mg, 0.864 mmol) in N,N-dimethylformamide (864 µL) was added N-chlorosuccinimide (115 mg, 0.864 mmol) and the reaction stirred at 60° C. for 3 hours. The mixture was then diluted with 50 mL of ethyl acetate and quenched with 4 mL of water, washed with 2×4 mL of water and brine, dried over sodium sulfate, and filtered. The solvent was removed in vacuo and the crude material purified on a 24 g silica gel cartridge, eluting with a gradient of 1-40% tert-butyl methyl ether/heptanes over 20 minutes to provide the title compound (156 mg, 0.688 mmol, 80% yield). $^1$H NMR (400 MHz, DMSO-$d_6$) δ 7.29-7.23 (m, 1H), 7.16 (dd, J=8.5, 2.3 Hz, 1H), 6.83 (d, J=8.5 Hz, 1H), 3.69 (s, 3H), 3.55 (d, J=16.6 Hz, 1H), 3.21 (d, J=16.6 Hz, 1H), 1.62 (s, 3H).

Example 26D (S)-5-chloro-2-methyl-2,3-dihydrobenzofuran-2-carboxylic acid and

Example 26E (R)-5-chloro-2-methyl-2,3-dihydrobenzofuran-2-carboxylic acid

To a solution of Example 26C (202 mg, 0.891 mmol) in tetrahydrofuran (1188 µL) and water (594 µL) was added lithium hydroxide (64.0 mg, 2.67 mmol). The reaction was stirred at 45° C. for 3 hours. The solvent was reduced under a stream of nitrogen and the reaction made acidic by the addition of 2.75 mL of 1N aqueous HCl. The solvent was reduced under a stream of nitrogen. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The mixture of (S) and (R) enantiomers thus provided was separated by chiral supercritical fluid chromatography using a Chiralpak IC column (21×250 mm, 5 micron), eluted with 15% 2-propanol (0.1% diethylamine) in CO$_2$, at a 70 mL/minute flow rate, 100 bar, and ambient temperature. The diethylamine salt of (S)-5-chloro-2-methyl-2,3-dihydrobenzofuran-2-carboxylic acid (18 mg, 0.085 mmol) was obtained as the first eluting isomer (18 mg, 0.085 mmol): $^1$H NMR (400 MHz, DMSO-$d_6$) δ 7.13 (d, J=2.2 Hz, 1H), 7.03 (dd, J=8.5, 2.4 Hz, 1H), 6.66 (d, J=8.4 Hz, 1H), 3.46 (d, J=16.3 Hz, 1H), 2.92 (d, J=16.3 Hz, 1H), 2.82 (q, J=7.3 Hz, 4H), 1.44 (s, 3H), 1.10 (t, J=7.2 Hz, 6H). Diethyl amine salt of (R)-5-chloro-2-methyl-2,3-dihydrobenzofuran-2-carboxylic acid (18 mg, 0.085 mmol) was obtained as the second eluting isomer: $^1$H NMR (400 MHz, DMSO-$d_6$) δ 7.18 (d, J=2.2 Hz, 1H), 7.08 (dd, J=8.5, 2.3 Hz, 1H), 6.71 (d, J=8.5 Hz, 1H), 3.49 (d, J=16.3 Hz, 1H), 2.98 (d, J=16.3 Hz, 1H), 2.87 (q, J=7.2 Hz, 4H), 1.49 (s, 3H), 1.14 (t, J=7.2 Hz, 6H). Absolute stereochemistry was confirmed by X-ray diffraction studies of the first eluting isomer, Example 26D.

Example 26F methyl 3-[(2R,4R)-4-amino-3,4-dihydro-2H-1-benzopyran-2-yl]benzoate hydrochloride The title compound was prepared according to the procedures as described in Example 8A-8C, substituting 4H-chromen-4-one for 7-methoxy-4H-chromen-4-one.

Example 26G methyl 3-[(2R,4R)-4-{[(2R)-5-chloro-2-methyl-2,3-dihydro-1-benzofuran-2-carbonyl]amino}-3,4-dihydro-2H-1-benzopyran-2-yl]benzoate To Example 26E (18 mg, 0.085 mmol) in N,N-dimethylformamide (0.3 mL) was added HATU (41.8 mg, 0.110 mmol). The mixture was stirred for 5 minutes at ambient temperature, followed by the addition of Example 26F (27.1 mg, 0.085 mmol) and dropwise addition of triethylamine (0.047 mL, 0.339 mmol) for 30 minutes. The solvent was reduced in volume and the mixture was quenched with saturated aqueous sodium bicarbonate, the aqueous layer removed, the resulting oil was dissolved in dichloromethane and purified on a 4 g silica gel cartridge, eluting with a gradient of 5-100% ethyl acetate/heptanes to give the title compound (25 mg, 0.052 mmol, 61.8% yield). 1H NMR (500 MHz, DMSO-$d_6$) δ 8.49 (d, J=9.1 Hz, 1H), 8.03 (t, J=1.8 Hz, 1H), 7.92 (dt, J=7.7, 1.5 Hz, 1H), 7.70 (dt, J=7.8, 1.4 Hz, 1H), 7.55 (t, J=7.7 Hz, 1H), 7.24 (d, J=2.2 Hz, 1H), 7.20 (td, J=7.7, 1.6 Hz, 1H), 7.14-7.09 (m, 2H), 6.97 (td, J=7.4, 1.2 Hz, 1H), 6.88 (dd, J=8.1, 1.2 Hz, 1H), 6.79 (d, J=8.5 Hz, 1H), 5.46-5.36 (m, 2H), 3.86 (s, 3H), 3.50 (d, J=16.6 Hz, 1H), 3.16 (d, J=16.5 Hz, 1H), 2.19 (dt, J=12.8, 11.5 Hz, 1H), 2.07 (ddd, J=13.0, 6.2, 2.0 Hz, 1H), 1.67 (s, 3H); MS (ESI+) m/z 478 (M+H)$^+$.

Example 26H

3-[(2R,4R)-4-{[(2R)-5-chloro-2-methyl-2,3-dihydro-1-benzofuran-2-carbonyl]amino}-3,4-dihydro-2H-1-benzopyran-2-yl]benzoic acid To a suspension of Example 26G (25 mg, 0.052 mmol) in tetrahydrofuran (174 µL) and water (87 µL) was added lithium hydroxide (2.5 mg, 0.104 mmol). The reaction was stirred at room temperature for four hours. The solvent was removed under a stream of nitrogen and the reaction was quenched with 10 drops of 1N aqueous HCl and this crude material was chromatographed directly on a 4 g silica gel cartridge with a gradient of 5-100% ethyl acetate/heptane to give the title compound (10 mg, 0.022 mmol, 41.2% yield). $^1$H NMR (500 MHz, DMSO-$d_6$) δ 8.49 (d, J=9.1 Hz, 1H), 8.02 (t, J=1.8 Hz, 1H), 7.89 (d, J=7.7 Hz, 1H), 7.64 (d, J=7.7 Hz, 1H), 7.50 (t, J=7.7 Hz, 1H), 7.24 (d, J=2.3 Hz, 1H), 7.22-7.15 (m, 1H), 7.16-7.08 (m, 2H), 6.96 (t, J=7.3 Hz, 1H), 6.88 (d, J=8.1 Hz, 1H), 6.79 (d, J=8.4 Hz, 1H), 5.45-5.36 (m, 2H), 3.51 (d, J=16.5 Hz, 1H), 3.16 (d, J=16.5 Hz, 1H), 2.20 (q, J=12.0 Hz, 1H), 2.06 (ddd, J=13.0, 6.1, 2.0 Hz, 1H), 1.99 (s, 1H), 1.67 (s, 3H); MS (ESI+) m/z 464 (M+H)$^+$.

Example 27

3-[(2R,4R)-4-{[(2S)-5-chloro-2-methyl-2,3-dihydro-1-benzofuran-2-carbonyl]amino}-3,4-dihydro-2H-1-benzopyran-2-yl]benzoic acid

Example 27A methyl 3-[(2R,4R)-4-{[(2S)-5-chloro-2-methyl-2,3-dihydro-1-benzofuran-2-carbonyl]amino}-3,4-dihydro-2H-1-benzopyran-2-yl]benzoate To Example 26D (18 mg, 0.085 mmol) in N,N-dimethylformamide (0.3 mL) was added HATU (41.8 mg, 0.110 mmol). The mixture was stirred for 5 minutes at ambient temperature, followed by the addition of Example 26F (27.1 mg, 0.085 mmol), and dropwise addition of triethylamine (0.047 mL, 0.339 mmol). After 30 minutes, the solvent was reduced in volume and the mixture was quenched with saturated aqueous sodium bicarbonate, the aqueous layer removed, the resulting oil was dissolved in dichloromethane and purified on a 4 g silica gel cartridge, eluting with a gradient of 5-100% ethyl acetate/heptanes to give the title compound (24 mg, 0.050 mmol, 59.3% yield). $^1$H NMR (501 MHz, DMSO-$d_6$) δ 8.40 (d, J=9.1 Hz, 1H), 8.07 (t, J=1.7 Hz, 1H), 7.94 (dt, J=7.7, 1.5 Hz, 1H), 7.73 (dt, J=7.8, 1.4 Hz, 1H), 7.58 (t, J=7.7 Hz, 1H), 7.31 (dd, J=2.3, 1.2 Hz, 1H), 7.16 (dd, J=8.5, 2.4 Hz, 1H), 7.11 (td, J=7.7, 1.8 Hz, 1H), 6.83 (dd, J=8.2, 1.1 Hz, 1H), 6.79 (d, J=8.5 Hz, 1H), 6.77-6.68 (m, 2H), 5.46-5.35 (m, 2H), 3.87 (s, 3H), 3.62 (d, J=16.4 Hz, 1H), 3.18 (d, J=16.4 Hz, 1H), 2.30 (dt, J=12.9, 11.5 Hz, 1H), 2.19 (ddd, J=12.9, 6.3, 2.1 Hz, 1H), 1.59 (s, 3H); MS (ESI+) m/z 478 (M+H)$^+$.

Example 27B

3-[(2R,4R)-4-{[(2S)-5-chloro-2-methyl-2,3-dihydro-1-benzofuran-2-carbonyl]amino}-3,4-dihydro-2H-1-benzopyran-2-yl]benzoic acid To a suspension of Example 27A (24 mg, 0.050 mmol) in tetrahydrofuran (167 μL) and water (84 μL) was added lithium hydroxide (2.8 mg, 0.117 mmol). The reaction was stirred at room temperature. After 2 hours, more lithium hydroxide (2.8 mg, 0.117 mmol) was added and the reaction was stirred at ambient temperature overnight. The reaction was quenched with 9 drops of 1N aqueous HCl and the solvent was removed under a stream of nitrogen. This crude material was chromatographed directly on a 4 g silica gel cartridge, eluting with a gradient of 5-100% ethyl acetate/heptane to give the title compound (12 mg, 0.026 mmol, 51.5% yield). 1H NMR (400 MHz, DMSO-$d_6$) δ 13.02 (s, 1H), 8.40 (d, J=9.1 Hz, 1H), 8.06 (t, J=1.7 Hz, 1H), 7.93 (dt, J=7.7, 1.4 Hz, 1H), 7.70 (d, J=7.8 Hz, 1H), 7.55 (t, J=7.7 Hz, 1H), 7.33 (d, J=2.3 Hz, 1H), 7.17 (dd, J=8.3, 2.1 Hz, 1H), 7.15-7.08 (m, 1H), 6.85-6.69 (m, 4H), 5.41 (td, J=10.3, 9.1, 3.0 Hz, 2H), 3.63 (d, J=16.5 Hz, 1H), 3.19 (d, J=16.5 Hz, 1H), 2.37-2.25 (m, 1H), 2.24-2.16 (m, 1H), 1.60 (s, 3H). MS (ESI+) m/z 464 (M+H)$^+$.

Example 28 methyl 3-[(2R,4R)-4-{[(1R)-5-methoxy-1-methyl-2,3-dihydro-1H-indene-1-carbonyl]amino}-3,4-dihydro-2H-1-benzopyran-2-yl]benzoate

Example 28A (R)-methyl 5-methoxy-1-methyl-2,3-dihydro-1H-indene-1-carboxylate and

Example 28B (S)-methyl 5-methoxy-1-methyl-2,3-dihydro-1H-indene-1-carboxylate Methyl 5-methoxy-2,3-dihydro-1H-indene-1-carboxylate (4.7 g, 22.79 mmol) was dissolved in tetrahydrofuran (45.6 mL), and the solution was cooled to <−70 OC in a dry ice-acetone bath. A solution of potassium tert-butoxide (1M, 27.3 mL, 27.3 mmol) in tetrahydrofuran was added dropwise, maintaining a temperature <−65° C., and the reaction was stirred for 10 minutes at the same temperature. Iodomethane (1.995 mL, 31.9 mmol) was added dropwise, and the flask was removed from the bath and was stirred at room temperature for 15 minutes. The reaction mixture was quenched with saturated ammonium chloride and the layers were separated. The organic layer was washed with saturated ammonium chloride, saturated sodium bicarbonate, and brine. The extracts were dried over sodium sulfate, filtered, and concentrated in vacuo. The resulting residue was purified via flash chromatography, eluting with 100:0 to 70:30 heptanes:ethyl acetate on a 220 g silica gel column. The collected fractions were concentrated and the resulting racemic mixture was separated using chiral chromatography (Whelk-O S,S, column, 21×250 mm ID, 5 micron, sample concentration 100 mg/mL in methanol. Flow rate: 49 mL/min $CO_2$, 21 mL/min modifier (methanol), oven temperature 40° C.) to give Example 28A (1.4 g) as the first eluent, and Example 28B (1.5 g) as the second eluent. $^1$H NMR (501 MHz, $CDCl_3$) δ ppm 7.23-7.15 (m, 1H), 6.78-6.70 (m, 2H), 3.78 (s, 3H), 3.65 (s, 3H), 3.10-2.96 (m, 1H), 2.89 (ddd, J=15.8, 8.6, 4.6 Hz, 1H), 2.72 (ddd, J=13.0, 8.5, 4.6 Hz, 1H), 1.94 (ddd, J=12.8, 8.6, 7.4 Hz, 1H), 1.52 (s, 3H). m/z 237.9 (M+$NH_3$)$^+$.

Example 28C (R)-5-methoxy-1-methyl-2,3-dihydro-1H-indene-1-carboxylic acid

Example 28A (1.4 g, 6.36 mmol) was dissolved in tetrahydrofuran (31.8 mL), and potassium trimethylsilanolate (2.446 g, 19.07 mmol) was added. The resulting yellow solution was heated at 60° C. in a sealed 20-mL scintillation vial for 45 minutes, at which point LC/MS indicated complete consumption of the starting material. The reaction was cooled to room temperature, diluted with 3 mL of water and extracted with methyl tert-butyl ether (3×2 mL). The aqueous layer was acidified with 6M HCl to pH=2, and the product was extracted into dichloromethane (3×3 mL). The combined dichloromethane extracts were dried over sodium sulfate, filtered, and concentrated to give the title compound (1.275 g, 97%). $^1$H NMR (501 MHz, $CDCl_3$) δ ppm 7.29-7.10 (m, 1H), 6.75 (d, J=7.4 Hz, 2H), 3.78 (s, 3H), 3.05 (dt, J=16.0, 8.1 Hz, 1H), 2.88 (ddd, J=15.9, 8.6, 4.1 Hz, 1H), 2.71 (ddd, J=12.8, 8.4, 4.2 Hz, 1H), 2.01-1.90 (m, 1H), 1.53

(s, 3H). m/z 224.0 (M+NH$_3$)$^+$. The absolute stereochemistry was confirmed by X-Ray analysis.

Example 28D methyl 3-[(2R,4R)-4-{[(1R)-5-methoxy-1-methyl-2,3-dihydro-1H-indene-1-carbonyl]amino}-3,4-dihydro-2H-1-benzopyran-2-yl]benzoate To Example 28C (70 mg, 0.339 mmol) in N,N-dimethylformamide (1 mL) was added HATU (181 mg, 0.475 mmol) at room temperature. The solution was stirred for 15 minutes and Example 26F (109 mg, 0.339 mmol) was added followed by the addition of triethylamine (0.142 mL, 1.018 mmol). The mixture was stirred at ambient temperature for 5 hours. Added water (4 mL), filtered the resulting brown precipitate, which was purified by flash chromatography (12 g cartridge, 5-50% ethyl acetate/heptane over 20 minutes) to provide the title compound (112 mg, 0.238 mmol, 70.0% yield). $^1$H NMR (400 MHz, DMSO-d$_6$) δ 8.05 (t, J=1.7 Hz, 1H), 7.94 (dt, J=7.7, 1.5 Hz, 1H), 7.72 (dt, J=7.9, 1.5 Hz, 1H), 7.58 (q, J=8.5, 7.7 Hz, 2H), 7.21 (d, J=8.3 Hz, 1H), 7.17-7.10 (m, 1H), 6.91-6.81 (m, 3H), 6.78 (d, J=2.4 Hz, 1H), 6.71 (dd, J=8.4, 2.5 Hz, 1H), 5.45-5.34 (m, 2H), 3.86 (s, 3H), 3.71 (s, 3H), 2.96-2.77 (m, 2H), 2.63 (ddd, J=13.0, 8.3, 5.0 Hz, 1H), 2.14 (td, J=8.0, 2.2 Hz, 2H), 1.88 (ddd, J=12.6, 8.4, 7.1 Hz, 1H), 1.44 (s, 3H); MS (ESI+) m/z 472 (M+H)$^+$.

Example 29 methyl 3-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoate To Example 28C (70 mg, 0.339 mmol) in N,N-dimethylformamide (1 mL) was added HATU (181 mg, 0.475 mmol) at room temperature. The solution was stirred for 15 minutes and Example 8C (119 mg, 0.339 mmol) was added followed by triethylamine (0.142 mL, 1.018 mmol). The mixture was stirred at ambient temperature for 5 hours. Added water (10 mL), filtered the resulting brown precipitate, which was purified by flash chromatography (12 g cartridge, 5-60% ethyl acetate/heptane over 20 minutes) to provide the title compound (156 mg, 0.311 mmol, 92% yield). $^1$H NMR (400 MHz, DMSO-d$_6$) δ 8.06 (t, J=1.5 Hz, 1H), 7.95 (dt, J=7.9, 1.4 Hz, 1H), 7.75-7.70 (m, 1H), 7.57 (t, J=7.7 Hz, 1H), 7.51 (d, J=8.8 Hz, 1H), 7.21 (d, J=8.3 Hz, 1H), 6.81-6.76 (m, 2H), 6.72 (dd, J=8.4, 2.5 Hz, 1H), 6.46 (dd, J=8.5, 2.6 Hz, 1H), 6.43 (d, J=2.5 Hz, 1H), 5.39 (dd, J=9.2, 4.3 Hz, 1H), 5.32 (q, J=8.9 Hz, 1H), 3.87 (s, 3H), 3.72 (s, 3H), 3.70 (s, 3H), 2.97-2.77 (m, 2H), 2.63 (ddd, J=13.1, 8.3, 5.0 Hz, 1H), 2.16-2.07 (m, 2H), 1.93-1.83 (m, 1H), 1.44 (s, 3H); MS (ESI+) m/z 502 (M+H)$^+$.

Example 30 methyl 3-[(2R,4R)-4-{[(1S)-5-methoxy-1-methyl-2,3-dihydro-1H-indene-1-carbonyl]amino}-3,4-dihydro-2H-1-benzopyran-2-yl]benzoate Example 30A (S)-5-methoxy-1-methyl-2,3-dihydro-1H-indene-1-carboxylic acid Example 30A was prepared according to Example 28C, substituting Example 28B for Example 28A.

Example 30B methyl 3-[(2R,4R)-4-{[(1S)-5-methoxy-1-methyl-2,3-dihydro-1H-indene-1-carbonyl]amino}-3,4-dihydro-2H-1-benzopyran-2-yl]benzoate To Example 30A (70 mg, 0.339 mmol) in N,N-dimethylformamide (1 mL) was added HATU (181 mg, 0.475 mmol) at room temperature. The solution was stirred for 15 minutes and Example 26F (109 mg, 0.339 mmol) was added followed by triethylamine (0.142 mL, 1.018 mmol). The mixture was stirred at room temperature for 5 hours. Added water (4 mL), filtered the resulting brown precipitate, which was purified by flash chromatography (12 g cartridge, 5-50% ethyl acetate/heptane over 20 minutes) to provide the title compound (125 mg, 0.265 mmol, 78% yield). $^1$H NMR (400 MHz, DMSO-d$_6$) δ 8.04 (t, J=1.8 Hz, 1H), 7.93 (dt, J=7.7, 1.4 Hz, 1H), 7.71 (dt, J=7.9, 1.5 Hz, 1H), 7.62-7.53 (m, 2H), 7.23 (d, J=8.3 Hz, 1H), 7.18-7.11 (m, 1H), 7.06 (dt, J=7.7, 1.4 Hz, 1H), 6.90 (td, J=7.4, 1.2 Hz, 1H), 6.84 (dd, J=8.2, 1.2 Hz, 1H), 6.76 (d, J=2.4 Hz, 1H), 6.71 (dd, J=8.4, 2.5 Hz, 1H), 5.44-5.35 (m, 2H), 3.86 (s, 3H), 3.69 (s, 3H), 2.96-2.76 (m, 2H), 2.62 (ddd, J=12.5, 8.5, 5.5 Hz, 1H), 2.20-2.02 (m, 2H), 1.87 (ddd, J=12.5, 8.4, 6.5 Hz, 1H), 1.43 (s, 3H); MS (ESI+) m/z 472 (M+H)$^+$.

Example 31 methyl 3-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoate To Example 30A (70 mg, 0.339 mmol) in N,N-dimethylformamide (1 mL) was added HATU (181 mg, 0.475 mmol) at room temperature. The solution was stirred for 15 minutes and Example 8C (119 mg, 0.339 mmol) was added followed by triethylamine (0.142 mL, 1.018 mmol). The mixture was stirred at room temperature for 5 hours. Added water (4 mL), filtered the resulting brown precipitate, which was purified by flash chromatography (12 g cartridge, 5-50% ethyl acetate/heptane over 20 minutes) to provide the title compound (152 mg, 0.303 mmol, 89% yield). $^1$H NMR (400 MHz, DMSO-d$_6$) δ 8.05 (t, J=1.7 Hz, 1H), 7.94 (dt, J=7.8, 1.4 Hz, 1H), 7.71 (dt, J=7.8, 1.4 Hz, 1H), 7.57 (t, J=7.7 Hz, 1H), 7.51 (d, J=8.9 Hz, 1H), 7.23 (d, J=8.3 Hz, 1H), 6.96 (dd, J=8.5, 1.0 Hz, 1H), 6.77 (d, J=2.3 Hz, 1H), 6.71 (dd, J=8.3, 2.5 Hz, 1H), 6.52 (dd, J=8.6, 2.5 Hz, 1H), 6.44 (d, J=2.6 Hz, 1H), 5.38 (dd, J=10.8, 2.9 Hz, 1H), 5.35-5.28 (m, 1H), 3.87 (s, 3H), 3.70 (d, J=2.1 Hz, 6H), 2.96-2.77 (m, 2H), 2.62 (ddd, J=12.4, 8.5, 5.6 Hz, 1H), 2.17-2.03 (m, 2H), 1.87 (ddd, J=12.6, 8.4, 6.6 Hz, 1H), 1.43 (s, 3H); MS (ESI+) m/z 502 (M+H)$^+$.

Example 32

3-[(2R,4R)-4-{[(1R)-5-methoxy-1-methyl-2,3-dihydro-1H-indene-1-carbonyl]amino}-3,4-dihydro-2H-1-benzopyran-2-yl]benzoic acid To a solution of Example 28 (95 mg, 0.201 mmol) in ethanol (1 mL) was added 3 N aqueous sodium hydroxide (0.269 mL, 0.806 mmol). The reaction was stirred at room temperature for 16 hours. The reaction was quenched with 0.9 mL of 1 N aqueous HCl and added 2 mL water to give a pale precipitate. The precipitate was filtered and washed with water to provide the title compound (86 mg, 0.188 mmol, 93% yield). $^1$H NMR (400 MHz, DMSO-d$_6$) δ 8.04

(s, 1H), 7.92 (d, J=7.7 Hz, 1H), 7.68 (d, J=7.7 Hz, 1H), 7.64-7.49 (m, 2H), 7.26-7.10 (m, 2H), 6.93-6.77 (m, 4H), 6.73 (dd, J=8.4, 2.5 Hz, 1H), 5.40 (td, J=10.4, 9.5, 6.9 Hz, 2H), 3.72 (s, 3H), 2.99-2.77 (m, 2H), 2.64 (ddd, J=13.0, 8.3, 5.0 Hz, 1H), 2.20-2.11 (m, 2H), 1.89 (dt, J=12.6, 7.7 Hz, 1H), 1.45 (s, 3H); MS (ESI+) m/z 458 (M+H)$^+$.

Example 33

3-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoic acid To a solution of Example 29 (138 mg, 0.275 mmol) in ethanol (1.3 mL) was added 3 N aqueous sodium hydroxide (0.367 mL, 1.101 mmol). The reaction was stirred at room temperature for 16 hours. The reaction was quenched with 1.2 mL of 1 N aqueous HCl and added 2 mL water to give a pale precipitate. The precipitate was filtered and washed with water to provide the title compound (128 mg, 0.263 mmol, 95% yield). $^1$H NMR (400 MHz, DMSO-d$_6$) δ 13.03 (bs, 1H), 8.04 (s, 1H), 7.92 (d, J=7.7 Hz, 1H), 7.68 (d, J=7.7 Hz, 1H), 7.54 (t, J=7.8 Hz, 1H), 7.50 (d, J=8.9 Hz, 1H), 7.21 (d, J=8.3 Hz, 1H), 6.81-6.76 (m, 2H), 6.72 (dd, J=8.4, 2.5 Hz, 1H), 6.46 (dd, J=8.5, 2.6 Hz, 1H), 6.43 (d, J=2.5 Hz, 1H), 5.40-5.34 (m, 1H), 5.34-5.28 (m, 1H), 3.72 (s, 3H), 3.70 (s, 3H), 2.97-2.77 (m, 2H), 2.63 (ddd, J=13.0, 8.3, 5.0 Hz, 1H), 2.16-2.08 (m, 2H), 1.88 (dt, J=12.6, 7.8 Hz, 1H), 1.44 (s, 3H); MS (ESI+) m/z 488 (M+H)$^+$.

Example 34

3-[(2R,4R)-4-{[(1S)-5-methoxy-1-methyl-2,3-dihydro-1H-indene-1-carbonyl]amino}-3,4-dihydro-2H-1-benzopyran-2-yl]benzoic acid To a solution of Example 30B (109 mg, 0.231 mmol) in ethanol (1.1 mL) was added 3 N aqueous sodium hydroxide (0.308 mL, 0.925 mmol). The reaction was stirred at room temperature for 16 hours. The reaction was quenched with 1 mL of 1 N aqueous HCl and added 2 mL water to give a pale precipitate. The precipitate was filtered and washed with water to provide the title compound (103 mg, 0.225 mmol, 97% yield). $^1$H NMR (400 MHz, DMSO-d$_6$) δ 8.02 (s, 1H), 7.90 (dt, J=7.8, 1.5 Hz, 1H), 7.66 (d, J=7.7 Hz, 1H), 7.60 (d, J=8.9 Hz, 1H), 7.52 (t, J=7.7 Hz, 1H), 7.23 (d, J=8.3 Hz, 1H), 7.18-7.11 (m, 1H), 7.06 (d, J=7.7 Hz, 1H), 6.90 (t, J=7.4 Hz, 1H), 6.84 (d, J=8.1 Hz, 1H), 6.76 (d, J=2.4 Hz, 1H), 6.71 (dd, J=8.4, 2.5 Hz, 1H), 5.39 (tt, J=7.4, 4.5 Hz, 2H), 3.69 (s, 3H), 2.97-2.77 (m, 2H), 2.63 (ddd, J=13.6, 8.5, 5.6 Hz, 1H), 2.15 (q, J=11.9 Hz, 1H), 2.07 (ddd, J=13.2, 6.4, 2.4 Hz, 1H), 1.87 (ddd, J=12.7, 8.3, 6.5 Hz, 1H), 1.43 (s, 3H); MS (ESI+) m/z 458 (M+H)$^+$.

Example 35

3-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoic acid To a solution of Example 31 (135 mg, 0.269 mmol) in ethanol (1.3 mL) was added 3 N aqueous sodium hydroxide (0.359 mL, 1.077 mmol). The reaction was stirred at room temperature for 16 hours. The reaction was quenched with 1.1 mL of 1 N aqueous HCl and added 2 mL water to give a pale precipitate. The precipitate was filtered and washed with water to provide the title compound (128 mg, 0.263 mmol, 98% yield). $^1$H NMR (400 MHz, DMSO-d$_6$) δ 8.02 (s, 1H), 7.90 (dt, J=7.7, 1.5 Hz, 1H), 7.67-7.62 (m, 1H), 7.55-7.47 (m, 2H), 7.22 (d, J=8.3 Hz, 1H), 6.94 (d, J=8.5 Hz, 1H), 6.76 (d, J=2.4 Hz, 1H), 6.70 (dd, J=8.4, 2.5 Hz, 1H), 6.50 (dd, J=8.6, 2.6 Hz, 1H), 6.43 (d, J=2.6 Hz, 1H), 5.39-5.26 (m, 2H), 3.69 (d, J=1.7 Hz, 6H), 2.96-2.74 (m, 2H), 2.62 (ddd, J=13.6, 8.5, 5.6 Hz, 1H), 2.18-2.01 (m, 2H), 1.86 (ddd, J=12.5, 8.4, 6.6 Hz, 1H), 1.42 (s, 3H); MS (ESI+) m/z 488 (M+H)$^+$.

Example 36

3-{(2R,4R)-4-[(5-chloro-1-methyl-2,3-dihydro-1H-indene-1-carbonyl)amino]-7-methoxy-3,4-dihydro-2H-1-benzopyran-2-yl}benzoic acid Example 36A methyl 5-chloro-2,3-dihydro-1H-indene-1-carboxylate The title compound was prepared using the conditions described in Example 53A, substituting 5-chloro-2,3-dihydro-1H-indene-1-carboxylic acid for 6-chloro-2,3-dihydro-1H-indene-1-carboxylic acid. $^1$H NMR (400 MHz, CDCl$_3$) δ ppm 7.30-7.27 (m, 1H), 7.22-7.21 (m, 1H), 7.17-7.14 (m, 1H), 4.03-3.99 (m, 1H), 3.73 (s, 3H), 3.12-3.03 (m, 1H), 2.94-2.85 (m, 1H), 2.50-2.30 (m, 2H).

Example 36B methyl 5-chloro-1-methyl-2,3-dihydro-1H-indene-1-carboxylate

The title compound was prepared using the conditions described in Example 53B, substituting Example 36A for Example 53A, except that the crude material was used in the next step without flash chromatography. $^1$H NMR (400 MHz, CDCl$_3$) δ ppm 7.23-7.15 (m, 3H), 3.66 (s, 3H), 3.08-2.99 (m, 1H), 2.94-2.85 (m, 1H), 2.76-2.69 (m, 1H), 2.00-1.92 (m, 1H), 1.52 (s, 3H).

Example 36C 5-chloro-1-methyl-2,3-dihydro-1H-indene-1-carboxylic acid

The title compound was prepared using the conditions described in Example 53C, substituting Example 36B for Example 53B using slightly modified conditions. The reaction was carried out at 90° C. for 2 hours. $^1$H NMR (400 MHz, CDCl$_3$) δ ppm 7.24 (s, 1H), 7.21-7.15 (m, 2H), 3.10-3.00 (m, 1H), 2.94-2.86 (m, 1H), 2.77-2.69 (m, 1H), 2.02-1.93 (m, 1H), 1.54 (s, 3H).

Example 36D

3-{(2R,4R)-4-[(5-chloro-1-methyl-2,3-dihydro-1H-indene-1-carbonyl)amino]-7-methoxy-3,4-dihydro-2H-1-benzopyran-2-yl}benzoic acid A 4 mL vial was charged with a stir bar, and 5-chloro-1-methyl-2,3-dihydro-1H-indene-1-carboxylic acid monomer (21.7 mg, 0.10 mmol), 1-[bis(dimethylamino)methylene]-1H-1,2,3-triazolo[4,5-b]pyridinium3-oxid hexafluorophosphate (30 mg, 0.08 mmol) in dimethyl acetamide (0.3 mL), and neat diisopropyl ethyl amine (35 µL, 3 eq, 0.21 mmol)

were added. A solution of Example 8C (21.5 mg, 0.07 mmol) in dimethylacetamide (0.3 mL) was added. The mixture was allowed to stir at room temperature overnight. The reaction was directly injected on a preparative reverse phase HPLC/MS and purified via reverse phase (TFA method, purified by preparative HPLC on a Phenomenex Luna C8(2) 5 μm 100 Å AXIA column (30 mm×150 mm). A gradient of CH$_3$CN (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A). The fractions collected were concentrated. The residue was dissolved in 1 mL of methanol and potassium hydroxide (4.0 M in methanol, 370 μL, 1.48 mmol, 25 equivalents) was added. The mixture was allowed to heat at 50° C. for 10 minutes. The reaction mixture was concentrated under a stream of nitrogen. The residue was dissolved in CH$_3$CN (1 mL) and diluted with 4 M HCl in dioxane (370 μL). The reaction was directly injected on a preparative reverse phase HPLC/MS and purified via reverse phase (TFA method, purified by preparative HPLC on a Phenomenex Luna C8(2) 5 μm 100 Å AXIA column (30 mm×150 mm). A gradient of CH$_3$CN (A) and 0.1% trifluoroacetic acid in water (B) was used, at a flow rate of 30 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10 min 35% A) to provide the title compound. $^1$H NMR (400 MHz, DMSO-d$_6$) δ 8.12-8.02 (m, 1H), 7.98-7.91 (m, 1H), 7.74-7.64 (m, 2H), 7.60-7.52 (m, 1H), 7.41-7.18 (m, 3H), 7.03-6.73 (m, 1H), 6.62-6.36 (m, 2H), 5.46-5.25 (m, 2H), 3.71-3.70 (m, 3H), 3.00-2.84 (m, 2H), 2.66-2.57 (m, 1H), 2.18-2.09 (m, 2H), 2.01-1.90 (m, 1H), 1.60-1.38 (m, 3H). MS (APCI+) m/z 492.4 (M+H)$^+$.

Example 37

3-[(2R,4R)-7-methoxy-4-{2-methyl-2-[4-(2-methylpropoxy)phenyl]propanamido}-3,4-dihydro-2H-1-benzopyran-2-yl]benzoic acid Example 37 was prepared according to the procedure described in Example 36D, substituting 2-(4-isobutoxyphenyl)-2-methylpropanoic acid for 5-chloro-1-methyl-2,3-dihydro-1H-indene-1-carboxylic acid. $^1$H NMR (400 MHz, DMSO-d$_6$) δ 8.06-8.00 (m, 1H), 7.97-7.89 (m, 1H), 7.72-7.65 (m, 1H), 7.56 (t, J=7.7 Hz, 1H), 7.49-7.42 (m, 1H), 7.30-7.21 (m, 2H), 6.91-6.85 (m, 2H), 6.80 (d, J=8.5 Hz, 1H), 6.44 (dd, J=8.5, 2.6 Hz, 1H), 6.39 (d, J=2.5 Hz, 1H), 5.38-5.26 (m, 2H), 3.71-3.66 (m, 5H), 2.12-2.04 (m, 2H), 2.03-1.90 (m, 1H), 1.47 (s, 6H), 0.99-0.92 (m, 6H). MS (APCI+) m/z 518.5 (M+H)$^+$.

Example 38

3-{(2R,4R)-4-[2-(2H-1,3-benzodioxol-5-yl)-2-methylpropanamido]-7-methoxy-3,4-dihydro-2H-1-benzopyran-2-yl}benzoic acid Example 38 was prepared according to the procedure described in Example 36D, substituting 2-(benzo[d][1,3]dioxol-5-yl)-2-methylpropanoic acid for 5-chloro-1-methyl-2,3-dihydro-1H-indene-1-carboxylic acid. $^1$H NMR (400 MHz, DMSO-d$_6$) δ 8.06-8.00 (m, 1H), 7.97-7.89 (m, 1H), 7.72-7.65 (m, 1H), 7.56 (t, J=7.7 Hz, 1H), 7.49-7.42 (m, 1H), 7.30-7.21 (m, 2H), 6.91-6.85 (m, 2H), 6.80 (d, J=8.5 Hz, 1H), 6.44 (dd, J=8.5, 2.6 Hz, 1H), 6.39 (d, J=2.5 Hz, 1H), 5.38-5.26 (m, 2H), 3.71-3.66 (m, 5H), 2.12-2.04 (m, 2H), 2.03-1.90 (m, 1H), 1.47 (s, 6H), 0.99-0.92 (m, 6H). MS (APCI+) m/z 518.5 (M+H)$^+$.

Example 39

3-{(2R,4R)-4-[2-(2,3-dihydro-1,4-benzodioxin-6-yl)-2-methylpropanamido]-7-methoxy-3,4-dihydro-2H-1-benzopyran-2-yl}benzoic acid Example 39 was prepared according to the procedure described in Example 36D, substituting 2-(2,3-dihydrobenzo[b][1,4]dioxin-6-yl)-2-methylpropanoic acid for 5-chloro-1-methyl-2,3-dihydro-1H-indene-1-carboxylic acid. $^1$H NMR (400 MHz, DMSO-d$_6$) δ 8.06-8.00 (m, 1H), 7.98-7.90 (m, 1H), 7.73-7.66 (m, 1H), 7.56 (t, J=7.7 Hz, 1H), 7.50 (d, J=8.8 Hz, 1H), 6.84-6.76 (m, 4H), 6.49-6.37 (m, 2H), 5.41-5.25 (m, 2H), 4.20 (s, 4H), 3.69 (s, 3H), 2.13-2.03 (m, 2H), 1.44 (s, 6H). MS (APCI+) m/z 504.4 (M+H)$^+$.

Example 40

3-[(2R,4R)-7-methoxy-4-{2-methyl-2-[4-(trifluoromethoxy)phenyl]propanamido}-3,4-dihydro-2H-1-benzopyran-2-yl]benzoic acid Example 40 was prepared according to the procedure described in Example 36D, substituting 2-methyl-2-[4-(trifluoromethoxy)phenyl]propanoic acid for 5-chloro-1-methyl-2,3-dihydro-1H-indene-1-carboxylic acid. $^1$H NMR (400 MHz, DMSO-d$_6$) δ 8.06-8.00 (m, 1H), 7.98-7.90 (m, 1H), 7.73-7.62 (m, 2H), 7.56 (t, J=7.7 Hz, 1H), 7.51-7.43 (m, 2H), 7.33 (d, J=8.4 Hz, 2H), 6.76 (d, J=8.3 Hz, 1H), 6.48-6.37 (m, 2H), 5.39-5.28 (m, 2H), 3.69 (s, 3H), 2.17-1.99 (m, 2H), 1.55-1.48 (m, 6H). MS (APCI+) m/z 530.3 (M+H)$^+$.

Example 41

3-[(2R,4R)-7-methoxy-4-({1-[4-(trifluoromethoxy)phenyl]cyclopropane-1-carbonyl}amino)-3,4-dihydro-2H-1-benzopyran-2-yl]benzoic acid Example 41 was prepared according to the procedure described in Example 36D, substituting 1-(4-trifluoromethoxyphenyl)-cyclopropanecarboxylic acid (CAS 1260741-41-0) for 5-chloro-1-methyl-2,3-dihydro-1H-indene-1-carboxylic acid. $^1$H NMR (400 MHz, DMSO-d$_6$) δ 8.04-7.99 (m, 1H), 7.97-7.89 (m, 1H), 7.71-7.64 (m, 1H), 7.55 (t, J=7.7 Hz, 1H), 7.52-7.44 (m, 2H), 7.33-7.22 (m, 3H), 6.97-6.89 (m, 1H), 6.52 (dd, J=8.6, 2.6 Hz, 1H), 6.40 (d, J=2.5 Hz, 1H), 5.39-5.26 (m, 2H), 3.70 (s, 3H), 2.15-2.03 (m, 2H), 1.54-1.45 (m, 1H), 1.43-1.33 (m, 1H), 1.13-0.98 (m, 2H). MS (APCI+) m/z 528.4 (M+H)$^+$.

Example 42

3-[(2R,4R)-4-{[1-(4-chlorophenyl)cyclopropane-1-carbonyl]amino}-7-methoxy-3,4-dihydro-2H-1-benzopyran-2-yl]benzoic acid Example 42 was prepared according to the procedure described in Example 36D, substituting 1-(4-chlorophenyl)-cyclopropanecarboxylic acid (CAS 72934-37-3) for 5-chloro-1-methyl-2,3-dihydro-1H-indene-1-carboxylic acid. $^1$H NMR (400 MHz, DMSO-d$_6$) δ 8.04-7.98 (m, 1H), 7.97-7.89 (m, 1H), 7.71-7.63 (m, 1H), 7.55 (t, J=7.7 Hz, 1H), 7.41-7.32 (m, 4H), 7.17 (d, J=8.9 Hz, 1H), 6.94 (d, J=8.4 Hz, 1H), 6.53 (dd, J=8.6, 2.6 Hz, 1H), 6.40 (d, J=2.5 Hz, 1H), 5.37-5.25 (m, 2H), 3.70 (s, 3H), 2.18-2.03 (m, 2H), 1.54-1.44 (m, 1H), 1.41-1.31 (m, 1H), 1.10-0.95 (m, 2H). MS (APCI+) m/z 478.4 (M+H)+.

Example 43

3-[(2R,4R)-4-{[1-(4-bromophenyl)cyclopropane-1-carbonyl]amino}-7-methoxy-3,4-dihydro-2H-1-benzopyran-2-yl]benzoic acid Example 43 was prepared according to the procedure described in Example 36D, substituting 1-(4-bromophenyl)-cyclopropanecarboxylic acid (CAS 1257213-52-7) for 5-chloro-1-methyl-2,3-dihydro-1H-indene-1-carboxylic acid. $^1$H NMR (400 MHz, DMSO-$d_6$) δ 8.04-7.98 (m, 1H), 7.97-7.89 (m, 1H), 7.67 (dd, J=7.9, 1.5 Hz, 1H), 7.63-7.45 (m, 3H), 7.36-7.28 (m, 2H), 7.19 (d, J=8.8 Hz, 1H), 6.94 (d, J=8.6 Hz, 1H), 6.54 (dd, J=8.6, 2.6 Hz, 1H), 6.40 (d, J=2.5 Hz, 1H), 5.37-5.26 (m, 2H), 3.70 (s, 3H), 2.18-2.03 (m, 2H), 1.54-1.44 (m, 1H), 1.41-1.31 (m, 1H), 1.10-0.95 (m, 2H). MS (APCI+) m/z 522.3 (M+H)+.

Example 44

3-[(2R,4R)-7-methoxy-4-{[1-(4-methoxyphenyl)cyclopropane-1-carbonyl]amino}-3,4-dihydro-2H-1-benzopyran-2-yl]benzoic acid Example 44 was prepared according to the procedure described in Example 36D, substituting 1-(4-methoxyphenyl)-cyclopropanecarboxylic acid (CAS 16728-01-1) for 5-chloro-1-methyl-2,3-dihydro-1H-indene-1-carboxylic acid. $^1$H NMR (400 MHz, DMSO-$d_6$) δ 8.03-7.97 (m, 1H), 7.96-7.89 (m, 1H), 7.71-7.63 (m, 1H), 7.55 (t, J=7.7 Hz, 1H), 7.33-7.23 (m, 2H), 6.94 (s, 1H), 6.91-6.85 (m, 2H), 6.85-6.79 (m, 1H), 6.53 (dd, J=8.6, 2.6 Hz, 1H), 6.39 (d, J=2.5 Hz, 1H), 5.39-5.22 (m, 2H), 3.72 (s, 3H), 3.69 (s, 3H), 2.14-2.01 (m, 2H), 1.50-1.41 (m, 1H), 1.36-1.27 (m, 1H), 1.05-0.90 (m, 2H). MS (APCI+) m/z 474.4 (M+H)+.

Example 45

3-{(2R,4R)-4-[2-(4-chlorophenoxy)-2-methylpropanamido]-7-methoxy-3,4-dihydro-2H-1-benzopyran-2-yl}benzoic acid Example 45 was prepared according to the procedure described in Example 36D, substituting 2-(4-chloro-phenoxy)-2-methyl-propionic acid (CAS 882-09-7) for 5-chloro-1-methyl-2,3-dihydro-1H-indene-1-carboxylic acid. $^1$H NMR (400 MHz, DMSO-$d_6$) δ 8.37 (d, J=8.9 Hz, 1H), 8.04 (d, J=1.7 Hz, 1H), 7.94 (dt, J=7.7, 1.4 Hz, 1H), 7.70 (dt, J=7.7, 1.5 Hz, 1H), 7.57 (t, J=7.7 Hz, 1H), 7.37-7.27 (m, 2H), 6.94 (d, J=2.3 Hz, 1H), 6.86 (d, J=8.6 Hz, 1H), 6.47 (dd, J=8.6, 2.6 Hz, 1H), 6.42 (d, J=2.5 Hz, 1H), 5.35 (td, J=10.4, 5.7 Hz, 2H), 3.70 (s, 3H), 2.24-2.07 (m, 2H), 1.54 (s, 3H), 1.46 (s, 3H). MS (APCI+) m/z 496.4 (M+H)+.

Example 46

3-[(2R,4R)-4-{[(1S)-7-methoxy-1-methyl-2,3-dihydro-1H-indene-1-carbonyl]amino}-3,4-dihydro-2H-1-benzopyran-2-yl]benzoic acid Example 46A 7-methoxy-2,3-dihydro-1H-indene-1-carbonitrile Example 46A was prepared using the conditions described in Example 7A substituting for commercially available 7-methoxy-2,3-dihydro-1H-inden-1-one for 5-methyl-2,3-dihydro-1H-inden-1-one. $^1$H NMR (400 MHz, CDCl$_3$) δ ppm 7.28-7.23 (m, 1H), 6.87 (d, J=7.5 Hz, 1H), 6.73 (d, J=8.2 Hz, 1H), 4.11 (dd, J=5.1, 8.5 Hz, 1H), 3.89 (s, 3H), 3.21-3.12 (m, 1H), 2.97 (ddd, J=5.3, 8.3, 15.9 Hz, 1H), 2.56-2.40 (m, 2H).

Example 46B 7-methoxy-1-methyl-2,3-dihydro-1H-indene-1-carbonitrile

Example 46B was prepared using the conditions described in Example 7B, substituting 7A for Example 46A. $^1$H NMR (400 MHz, CDCl$_3$) δ ppm 7.26-7.21 (1H, m), 6.84-6.81 (1H, m), 6.74 (1H, d, J=8.2 Hz), 3.89 (3H, s), 3.04-2.97 (2H, m), 2.66 (1H, ddd, J=7.4, 8.8, 13.0 Hz), 2.24-2.17 (1H, m), 1.67 (3H, s).

Example 46C 7-methoxy-1-methyl-2,3-dihydro-1H-indene-1-carboxylic acid

To a stirred solution of Example 46B (2.41 g, 12.9 mmol) in 1,4-dioxane (17 mL) at room temperature was added concentrated sulfuric acid (17 mL, 9M). The heterogenous mixture was heated at 120° C. overnight. The reaction was cooled to room temperature, diluted with water and extracted with ethyl acetate. The compound was then extracted into NaOH (1N solution). The aqueous layer was acidified with aqueous HCl to pH=2, and the product was back extracted into ethyl acetate (2×). The combined organic extracts were dried over magnesium sulfate, filtered, and concentrated to give the title compound (1.73 g, 66%). $^1$H NMR (400 MHz, CDCl$_3$) δ ppm 7.20 (1H, dd, J=7.8, 7.8 Hz), 6.85 (1H, d, J=7.5 Hz), 6.71 (1H, d, J=8.2 Hz), 3.83 (3H, s), 3.04-2.98 (2H, m), 2.69-2.60 (1H, m), 2.10-2.00 (1H, m), 1.54 (3H, s).

Example 46D (S)-7-methoxy-1-methyl-2,3-dihydro-1H-indene-1-carboxylic acid

Example 46C (1700 mg, 8.25 mmol) was dissolved in methanol (30 mL) and was purified by supercritical fluid chromatography. 45 injections were carried out using a YMC amylose-C column, 5% methanol in CO$_2$, at a 100 mL/minute flow rate, 120 bar and 40° C. The title compound was obtained as the second eluted enantiomer. Chirality was confirmed by X-ray diffraction study. $^1$H NMR (400 MHz, CDCl$_3$) δ ppm 7.19 (1H, dd, J=7.8, 7.8 Hz), 6.84 (1H, d, J=7.5 Hz), 6.70 (1H, d, J=8.2 Hz), 3.81 (3H, s), 3.04-2.98 (2H, m), 2.65-2.56 (1H, m), 2.09-2.00 (1H, m), 1.52 (3H, s); 94.6% ee.

Example 46E

3-[(2R,4R)-4-{[(1S)-7-methoxy-1-methyl-2,3-dihydro-1H-indene-1-carbonyl]amino}-3,4-dihydro-2H-1-benzopyran-2-yl]benzoic acid To Example 46D (70 mg, 0.34 mmol) and Example 26F (96 mg, 0.34 mmol) in dichloromethane (2.3 mL) was added HATU (194 mg, 0.51 mmol) and diisopropylethylamine (0.178 mL, 0.51 mmol). The mixture was stirred at room temperature for 15 hours, LC/MS showed the reaction was complete. The reaction mixture was diluted with dichloromethane and saturated sodium bicarbonate aqueous solution was added. The phases were separated and the aqueous phase was extracted with dichloromethane. The combined organic layers were passed through a hydrophobic frit and the filtrate was concentrated under reduced pressure. The crude residue was dissolved in tetrahydrofuran (1.5 mL) and water (1.5 mL), and lithium hydroxide (42 mg, 1.0 mmol) was added. The reaction was stirred at 40° C. for 18 hours, after which LC/MS showed the reaction was complete. The tetrahydrofuran was removed under vacuum and the reaction mixture was partitioned between 1N aqueous HCl and dichloromethane. The phases were separated and the aqueous phase was extracted with dichloromethane. The combined organic layers were passed through a hydrophobic frit and the filtrate was concentrated under reduced pressure. The residue was purified by reverse-phase preparative HPLC on a Phenomenex® Luna® Phenyl-Hexyl C18(2) 10 μm column (150×21.2 mm). A gradient of methanol and 0.1% formic acid (A) in water and 0.1% formic acid (B) was used, at a flow rate of 20 mL/minute (0-1 minute linear gradient 5-40% A, 1-3.5 minutes 40% A, 3.5-16 minutes linear gradient 40-100% A, 16-23.5 minutes 100% A), to provide a first batch of the title compound, 86.7% purity by HPLC. Further purification by reverse-phase preparative HPLC on a Waters Sunfire™ C18 column (150×19 mm id 10 μm) eluting using an isocratic eluent of 47% acetonitrile in 0.1% aqueous formic acid at a flow rate of 20 mL/minute for 30 minutes to provide the title compound, 98.8% purity by HPLC (41.7 mg, 27%). $^1$H NMR (400 MHz, DMSO-d$_6$) δ 8.02 (t, J=1.8 Hz, 1H), 7.90 (dt, J=7.7, 1.5 Hz, 1H), 7.65 (dt, J=7.8, 1.5 Hz, 1H), 7.51 (t, J=7.7 Hz, 1H), 7.26-7.08 (m, 4H), 6.92 (td, J=7.4, 1.2 Hz, 1H), 6.85-6.73 (m, 3H), 5.41 (ddd, J=18.4, 10.8, 4.2 Hz, 2H), 3.79 (s, 3H), 2.91 (dd, J=8.5, 6.5 Hz, 2H), 2.38 (dt, J=12.8, 8.6 Hz, 1H), 2.17 (dt, J=13.0, 11.4 Hz, 1H), 2.07 (ddd, J=13.0, 6.4, 2.2 Hz, 1H), 1.91 (dt, J=12.8, 6.4 Hz, 1H), 1.40 (s, 3H).

Example 47

3-[(2R,4R)-4-{[(1S)-6-methoxy-1-methyl-2,3-dihydro-1H-indene-1-carbonyl]amino}-3,4-dihydro-2H-1-benzopyran-2-yl]benzoic acid

Example 47A 6-methoxy-2,3-dihydro-1H-indene-1-carbonitrile

Example 47A was prepared using the conditions described in Example 7A, substituting commercially available 6-methoxy-2,3-dihydro-1H-inden-1-one for 5-methyl-2,3-dihydro-1H-inden-1-one. $^1$H NMR (400 MHz, CDCl$_3$) δ ppm 7.16 (d, J=8.3 Hz, 1H), 6.96 (d, J=2.0 Hz, 1H), 6.83 (ddd, J=0.7, 2.5, 8.3 Hz, 1H), 4.07 (ddd, J=8.2, 8.2, 0.8 Hz, 1H), 3.81 (s, 3H), 3.01 (ddd, J=4.2, 8.7, 15.6 Hz, 1H), 2.88 (ddd, J=7.9, 7.9, 15.7 Hz, 1H), 2.62-2.53 (m, 1H), 2.38 (ddd, J=8.3, 12.8, 16.9 Hz, 1H).

Example 47B 6-methoxy-1-methyl-2,3-dihydro-1H-indene-1-carbonitrile

Example 47B was prepared using the conditions described in Example 7B, substituting Example 47A for Example 7A. $^1$H NMR (400 MHz, CDCl$_3$) δ ppm 7.14 (d, J=8.3 Hz, 1H), 6.90 (d, J=2.4 Hz, 1H), 6.82 (dd, J=2.4, 8.3 Hz, 1H), 3.81 (s, 3H), 3.04-2.87 (m, 2H), 2.65 (ddd, J=6.4, 8.3, 12.8 Hz, 1H), 2.17 (ddd, J=5.9, 7.7, 12.6 Hz, 1H), 1.63 (s, 3H).

Example 47C 6-methoxy-1-methyl-2,3-dihydro-1H-indene-1-carboxylic acid

Example 47C was prepared using the conditions described in Example 7C, substituting Example 47B for Example 7B. $^1$H NMR (400 MHz, CDCl$_3$) δ ppm 7.11 (d, J=8.2 Hz, 1H), 6.87 (d, J=2.4 Hz, 1H), 6.77 (dd, J=2.4, 8.2 Hz, 1H), 3.79 (s, 3H), 3.05-2.96 (m, 1H), 2.90-2.81 (m, 1H), 2.72 (ddd, J=4.5, 8.4, 12.9 Hz, 1H), 1.97 (td, J=8.0, 13.0 Hz, 1H), 1.54 (s, 3H).

Example 47D (S)-6-methoxy-1-methyl-2,3-dihydro-1H-indene-1-carboxylic acid

Example 47C (1300 mg, 6.30 mmol) was dissolved in methanol (25 mL) and was purified by supercritical fluid chromatography. 52 injections were carried out using a YMC amylose-C column, 20% methanol in CO$_2$, at a 100 mL/minute flow rate, 120 bar and 40° C. The title compound was obtained as the second eluted enantiomer. Chirality was arbitrarily assigned. $^1$H NMR (400 MHz, CDCl$_3$) δ ppm 7.11 (d, J=8.3 Hz, 1H), 6.87 (d, J=2.4 Hz, 1H), 6.77 (dd, J=2.4, 8.2 Hz, 1H), 3.79 (s, 3H), 3.00 (td, J=7.7, 15.5 Hz, 1H), 2.90-2.81 (m, 1H), 2.72 (ddd, J=4.5, 8.3, 12.8 Hz, 1H), 1.96 (ddd, J=7.5, 8.4, 12.9 Hz, 1H), 1.54 (s, 3H); 98.4% ee.

Example 47E

3-[(2R,4R)-4-{[(1S)-6-methoxy-1-methyl-2,3-dihydro-1H-indene-1-carbonyl]amino}-3,4-dihydro-2H-1-benzopyran-2-yl]benzoic acid The title compound was prepared using the conditions described in Example 46E, substituting Example 47D for Example 46D. The titled compound was purified by reversed-phase HPLC on a Waters Sunfire™ C18 column (150×19 mm id 10 μm), eluted using a gradient of about 20-80% acetonitrile in 0.1% aqueous formic acid at a flow rate of 20 mL/minute with a total run time of 28 minutes to give a first batch of title compound of 92% purity by HPLC, which was then further purified by reversed-phase HPLC to afford the title compound in 97.4% purity by HPLC on a Waters Sunfire™ C18 column (150×19 mm id, 10 μm), eluting with an isocratic eluent of 47% acetonitrile in 0.1% aqueous formic acid at a flow rate of 20 mL/minute. ¹H NMR (400 MHz, DMSO-d$_6$) δ ppm 13.04 (broad s, 1H), 8.04 (s, 1H), 7.92 (d, J=7.8 Hz, 1H), 7.70-7.66 (m, 2H), 7.54 (t, J=7.7 Hz, 1H), 7.19-7.08 (m, 3H), 6.96-6.85 (m, 3H), 6.72 (dd, J=2.5, 8.3 Hz, 1H), 5.47-5.38 (m, 2H), 3.70 (s, 3H), 2.90-2.76 (m, 2H), 2.68-2.60 (m, 1H), 2.22-2.06 (m, 2H), 1.90 (ddd, J=6.2, 8.3, 12.6 Hz, 1H), 1.47 (s, 3H); MS (ESI) m/z 458 (M+H)⁺.

Example 48

3-[(2R,4R)-4-{[(1R)-6-methoxy-1-methyl-2,3-dihydro-1H-indene-1-carbonyl]amino}-3,4-dihydro-2H-1-benzopyran-2-yl]benzoic acid Example 48A (R)-6-methoxy-1-methyl-2,3-dihydro-1H-indene-1-carboxylic acid Example 48A was isolated as the first eluting fraction from the supercritical fluid chromatography as described in Example 47D.

Example 48B

3-[(2R,4R)-4-{[(1R)-6-methoxy-1-methyl-2,3-dihydro-1H-indene-1-carbonyl]amino}-3,4-dihydro-2H-1-benzopyran-2-yl]benzoic acid Example 48B was prepared using the conditions described in Example 46E, substituting Example 48A for Example 46D. ¹H NMR (400 MHz, DMSO-d$_6$) δ 8.05 (t, J=1.8 Hz, 1H), 7.92 (dt, J=7.7, 1.5 Hz, 1H), 7.76-7.65 (m, 2H), 7.54 (t, J=7.7 Hz, 1H), 7.20-7.08 (m, 2H), 6.97-6.79 (m, 4H), 6.76 (dd, J=8.2, 2.5 Hz, 1H), 5.47-5.36 (m, 2H), 3.69 (s, 3H), 2.89 (dt, J=15.2, 7.6 Hz, 1H), 2.79 (ddd, J=15.3, 8.3, 4.9 Hz, 1H), 2.68 (ddd, J=13.0, 8.3, 5.0 Hz, 1H), 2.22-2.09 (m, 2H), 1.88 (ddd, J=12.4, 8.3, 6.9 Hz, 1H), 1.47 (s, 3H); MS (ESI) m/z 458.1 (M+H)⁺.

Example 49

3-{(2R,4R)-4-[2-methyl-2-(2-methylphenyl)propanamido]-3,4-dihydro-2H-1-benzopyran-2-yl}benzoic acid Example 49 was prepared using the conditions described in Example 46E, substituting 2-methyl-2-(o-tolyl)propanoic acid for Example 46D. ¹H NMR (400 MHz, DMSO-d$_6$) δ 8.01 (d, J=1.7 Hz, 1H), 7.91 (dt, J=7.8, 1.4 Hz, 1H), 7.65 (dt, J=7.7, 1.5 Hz, 1H), 7.52 (t, J=7.7 Hz, 1H), 7.44 (d, J=8.8 Hz, 1H), 7.37 (dd, J=7.3, 1.4 Hz, 1H), 7.21-7.09 (m, 4H), 7.05 (dt, J=7.8, 1.4 Hz, 1H), 6.89 (td, J=7.5, 1.3 Hz, 1H), 6.82 (dd, J=8.2, 1.2 Hz, 1H), 5.47-5.35 (m, 2H), 2.27 (s, 3H), 2.12-2.03 (m, 2H), 1.49 (d, J=11.0 Hz, 6H); MS (ESI) m/z 430 (M+H)⁺.

Example 50

3-[(2R,4R)-4-{[(1R)-7-methoxy-1-methyl-2,3-dihydro-1H-indene-1-carbonyl]amino}-3,4-dihydro-2H-1-benzopyran-2-yl]benzoic acid Example 50A (R)-7-methoxy-1-methyl-2,3-dihydro-1H-indene-1-carboxylic acid Example 50A was isolated as the first eluting enantiomer from the supercritical fluid chromatography as described in Example 46D.

Example 50B

3-[(2R,4R)-4-{[(1R)-7-methoxy-1-methyl-2,3-dihydro-1H-indene-1-carbonyl]amino}-3,4-dihydro-2H-1-benzopyran-2-yl]benzoic acid Example 50B was prepared using the conditions described in Example 46E, substituting Example 50A for Example 46D. ¹H NMR (400 MHz, DMSO-d$_6$) δ 8.05 (t, J=1.8 Hz, 1H), 7.92 (dt, J=7.7, 1.5 Hz, 1H), 7.69 (dt, J=7.7, 1.5 Hz, 1H), 7.54 (t, J=7.7 Hz, 1H), 7.46 (d, J=8.9 Hz, 1H), 7.16 (td, J=7.7, 1.8 Hz, 3H), 6.93 (td, J=7.5, 1.2 Hz, 1H), 6.88-6.78 (m, 2H), 6.77 (d, J=8.1 Hz, 1H), 5.43 (ddd, J=13.2, 9.8, 4.8 Hz, 2H), 3.71 (s, 3H), 2.92 (dd, J=8.2, 6.6 Hz, 2H), 2.45 (dt, J=12.5, 8.1 Hz, 1H), 2.25-2.05 (m, 2H), 1.93 (dt, J=12.7, 6.5 Hz, 1H), 1.41 (s, 3H); MS (ESI) m/z 458 (M+H)⁺.

Example 51

3-[(2R,4R)-4-{2-methyl-2-[4-(trifluoromethyl)phenyl]propanamido}-3,4-dihydro-2H-1-benzopyran-2-yl]benzoic acid The title compound was prepared using the conditions described in Example 55E, substituting 2-methyl-2-(4-(trifluoromethyl)phenyl)propanoic acid for Example 55D. ¹H NMR (400 MHz, DMSO-d$_6$) δ 8.03 (t, J=1.8 Hz, 1H), 7.92 (dt, J=7.7, 1.5 Hz, 1H), 7.77 (d, J=8.8 Hz, 1H), 7.73-7.63 (m, 3H), 7.62-7.49 (m, 3H), 7.13 (td, J=7.7, 1.6 Hz, 1H), 6.91 (dt, J=7.9, 1.5 Hz, 1H), 6.87-6.78 (m, 2H), 5.42 (td, J=11.2, 3.1 Hz, 2H), 2.18-2.09 (m, 1H), 2.07 (dt, J=13.0, 10.1 Hz, 1H), 1.54 (d, J=1.5 Hz, 6H); MS (ESI−) m/z 458 (M−H)⁻.

Example 52

3-{(2R,4R)-4-[2-(2,4-dichlorophenyl)-2-methylpropanamido]-3,4-dihydro-2H-1-benzopyran-2-yl}benzoic acid Example 52 was prepared using the conditions described in Example 55E, substituting 2-(2,4-dichlorophenyl)-2-methylpropanoic acid for Example 55D. ¹H NMR (400 MHz, DMSO-d$_6$) δ ppm 13.10 (br s, 1H), 8.02 (t, J=1.7 Hz, 1H), 7.92 (td, J=1.4, 7.7 Hz, 1H), 7.65 (d, J=7.8 Hz, 1H), 7.59 (d, J=8.9 Hz, 1H), 7.55-7.51 (m, 3H), 7.42 (dd, J=2.3, 8.5 Hz, 1H), 7.16 (dd, J=7.7, 13.3 Hz, 2H), 6.92 (dt, J=1.2, 7.5 Hz, 1H), 6.84 (dd, J=1.0, 8.1 Hz, 1H), 5.45-5.38 (m, 2H), 2.13-1.99 (m, 2H), 1.56 (s, 3H), 1.52 (s, 3H); MS (ESI+) m/z 484 (M+H)⁺.

Example 53

3-[(2R,4R)-4-{[(1R)-6-chloro-1-methyl-2,3-dihydro-1H-inden-1-carbonyl]amino}-3,4-dihydro-2H-1-benzopyran-2-yl]benzoic acid

Example 53A methyl 6-chloro-2,3-dihydro-1H-indene-1-carboxylate

To a stirred solution of 6-chloro-2,3-dihydro-1H-indene-1-carboxylic acid (1 g, 5.10 mmol) in methanol (10 mL) at room temperature was added concentrated sulfuric acid (2 drops). The resultant solution was stirred at 70° C. for 18 hours. The reaction mixture was neutralized with saturated NaHCO$_3$ and was diluted with dichloromethane. The layers were separated and the aqueous layer was re-extracted with dichloromethane. The combined organic layers were passed through a hydrophobic frit and the filtrate was concentrated under reduced pressure to provide the title compound. $^1$H NMR (400 MHz, CDCl$_3$) δ ppm 7.35 (s, 1H), 7.19-7.13 (m, 2H), 4.05-4.00 (1H, m), 3.76 (s, 3H), 3.09-3.01 (m, 1H), 2.91-2.82 (m, 1H), 2.51-2.30 (m, 2H).

Example 53B methyl 6-chloro-1-methyl-2,3-dihydro-1H-indene-1-carboxylate

To a stirred solution of Example 53A (1 g, 4.76 mmol) in anhydrous tetrahydrofuran (26 mL) under a nitrogen atmosphere was added iodomethane (2.08 mL, 33.3 mmol). The resultant reaction mixture was cooled to −78° C. To the resultant reaction mixture was added portion wise potassium tert-butoxide (1.07 g, 9.52 mmol). The reaction mixture turned into a dark red suspension on addition. The resultant reaction mixture was allowed to warm to room temperature and was stirred at room temperature for 18 hours. The reaction mixture was diluted with dichloromethane and was quenched with aqueous ammonium chloride. The layers were separated and the aqueous layer was re-extracted with dichloromethane. The combined organic layers were passed through a hydrophobic frit and the filtrate was concentrated under reduced pressure. The residue was purified by flash chromatography, using Biotage® SNAP 25 g silica column, eluted with 0-10% ethyl acetate in iso-hexane to provide the title compound. $^1$H NMR (400 MHz, CDCl$_3$) δ ppm 7.28-7.27 (m, 1H), 7.19-7.11 (m, 2H), 3.68 (s, 3H), 3.05-2.84 (m, 2H), 2.77-2.69 (m, 1H), 2.01-1.92 (m, 1H), 1.53 (s, 3H).

Example 53C 6-chloro-1-methyl-2,3-dihydro-1H-indene-1-carboxylic acid

To a stirred solution of Example 53B (917 mg, 4.09 mmol) in methanol (4 mL) was added an aqueous solution of 2M sodium hydroxide (4 mL). On addition the reaction mixture turned into a white suspension. The resultant reaction mixture was stirred at 45° C. for 3.5 hours. The organics were concentrated under reduced pressure and ethyl acetate was added. The layers were separated and the organic layer was washed with water. The combined aqueous layers were acidified to pH 1 with aqueous 3M hydrochloric acid solution and extracted with ethyl acetate (2×). The combined organic layers were passed through a hydrophobic frit and the filtrate was concentrated under reduced pressure to provide the title compound. $^1$H NMR (400 MHz, CDCl$_3$) δ ppm 7.31 (d, J=1.5 Hz, 1H), 7.20-7.12 (m, 2H), 3.08-2.99 (m, 1H), 2.93-2.84 (m, 1H), 2.77-2.70 (m, 1H), 2.03-1.94 (m, 1H), 1.56 (s, 3H).

Example 53D (S)-6-chloro-1-methyl-2,3-dihydro-1H-indene-1-carboxylic acid

Example 53C (819 mg, 3.90 mmol) was dissolved in iso-propanol (40 mL) and was purified by supercritical fluid chromatography using a stacker 5 mL loop. 42 injections were carried out using a YMC amylose-C column, 5% iso-propanol in CO$_2$, at a 100 mL/minute flow rate, 120 bar and 40° C. The title compound was obtained as the first eluted enantiomer. $^1$H NMR (400 MHz, CDCl$_3$) δ ppm 7.31 (d, J=1.6 Hz, 1H), 7.20-7.12 (m, 2H), 3.08-2.98 (m, 1H), 2.93-2.84 (m, 1H), 2.77-2.69 (m, 1H), 2.02-1.94 (m, 1H), 1.55 (s, 3H); 100% ee.

Example 53E (R)-6-chloro-1-methyl-2,3-dihydro-1H-indene-1-carboxylic acid

Example 53E was obtained as the second eluted enantiomer from the supercritical fluid chromatography as described in Example 53D. Chirality was confirmed by obtaining X-ray diffraction study. $^1$H NMR (400 MHz, CDCl$_3$) δ ppm 7.31 (d, J=1.9 Hz, 1H), 7.20-7.13 (m, 2H), 3.08-2.98 (m, 1H), 2.93-2.84 (m, 1H), 2.77-2.69 (m, 1H), 2.02-1.94 (m, 1H), 1.55 (s, 3H); 92.5% ee.

Example 53F

3-[(2R,4R)-4-{[(1R)-6-chloro-1-methyl-2,3-dihydro-1H-inden-1-carbonyl]amino}-3,4-dihydro-2H-1-benzopyran-2-yl]benzoic acid The title compound was prepared using the conditions described in Example 55E, substituting Example 53E for Example 55D. $^1$H NMR (400 MHz, DMSO-d$_6$) δ 8.05 (t, J=1.8 Hz, 1H), 7.96-7.86 (m, 2H), 7.66 (dt, J=7.7, 1.5 Hz, 1H), 7.52 (t, J=7.7 Hz, 1H), 7.43 (d, J=1.6 Hz, 1H), 7.29-7.17 (m, 2H), 7.16 (tt, J=6.7, 2.5 Hz, 1H), 6.90-6.80 (m, 3H), 5.47-5.34 (m, 2H), 3.00-2.79 (m, 2H), 2.68 (ddd, J=13.0, 8.3, 5.0 Hz, 1H), 2.22-2.05 (m, 2H), 1.92 (ddd, J=12.6, 8.4, 7.1 Hz, 1H), 1.50 (s, 3H); MS (ESI+) m/z 462 (M+H)$^+$.

Example 54

3-[(2R,4R)-4-{[(1S)-6-chloro-1-methyl-2,3-dihydro-1H-inden-1-carbonyl]amino}-3,4-dihydro-2H-1-benzopyran-2-yl]benzoic acid The title compound was prepared using the conditions described in Example 55E, substituting Example 53D for Example 54D. $^1$H NMR (400 MHz, DMSO-d$_6$) δ 8.04 (d, J=1.8 Hz, 1H), 7.92 (dt, J=7.7, 1.5 Hz, 1H), 7.82 (d, J=8.8 Hz, 1H), 7.68 (dt, J=7.7, 1.5 Hz, 1H), 7.53 (t, J=7.7 Hz, 1H), 7.41 (d, J=1.9 Hz, 1H), 7.27-7.12 (m, 3H), 7.08 (dt, J=7.8, 1.3 Hz, 1H), 6.96-6.83 (m, 2H), 5.48-5.36 (m, 2H), 2.89 (td, J=8.9, 6.4 Hz, 2H), 2.63 (ddd, J=12.7, 8.3, 5.9 Hz, 1H), 2.20-2.09 (m, 2H), 1.96 (ddd, J=12.8, 8.2, 6.5 Hz, 1H), 1.48 (s, 3H); MS (ESI+) m/z 462 (M+H)+.

Example 55

3-[(2R,4R)-4-{[1-methyl-5-(trifluoromethoxy)-2,3-dihydro-1H-indene-1-carbonyl]amino}-3,4-dihydro-2H-1-benzopyran-2-yl]benzoic acid

Example 55A 5-(trifluoromethoxy)-2,3-dihydro-1H-inden-1-one

A solution of 3-(3-(trifluoromethoxy)phenyl)propanoic acid (12.4 g, 0.053 mmol) was diluted with trifluoromethanesulfonic acid (37 mL) at 5° C. and then left to stir at room temperature for 17 hours. The mixture was then concentrated under reduced pressure and the crude oil was dissolved in diethyl ether, and washed with an aqueous solution of 1M potassium carbonate, then with water and brine, dried (MgSO$_4$), filtered, and concentrated under reduced pressure to provide the title compound. $^1$H NMR (400 MHz, DMSO-d$_6$) δ ppm 7.76 (dd, J=0.3, 8.4 Hz, 1H), 7.60 (s, 1H), 7.41-7.37 (m, 1H), 3.17-3.13 (m, 2H), 2.70-2.67 (m, 2H).

Example 55B 5-(trifluoromethoxy)-2,3-dihydro-1H-indene-1-carbonitrile

Example 55B was prepared using the conditions described in Example 7A, substituting Example 55A for 5-methyl-2,3-dihydro-1H-inden-1-one. $^1$H NMR (400 MHz, CDCl$_3$) δ ppm 7.44 (d, J=8.8 Hz, 1H), 7.12 (m, 2H), 4.11 (t, J=8.2 Hz, 1H), 3.16-3.08 (m, 1H), 3.04-2.95 (m, 1H), 2.68-2.59 (m, 1H), 2.49-2.39 (m, 1H).

Example 55C 1-methyl-5-(trifluoromethoxy)-2,3-dihydro-1H-indene-1-carbonitrile Example 55C was prepared using the conditions described in Example 7B, substituting Example 55B for Example 7A. $^1$H NMR (400 MHz, CDCl$_3$) δ ppm 7.39 (d, J=8.0 Hz, 1H), 7.14-7.11 (m, 2H), 3.15-2.97 (m, 2H), 2.71 (ddd, J=6.3, 8.3, 13.0 Hz, 1H), 2.22 (ddd, J=6.2, 8.0, 13.0 Hz, 1H), 1.66 (s, 3H).

Example 55D 1-methyl-5-(trifluoromethoxy)-2, 3-dihydro-1H-indene-1-carboxylic acid To a solution of Example 55C (2.50 g, 10.4 mmol) in methanol (10 mL) was added a 4M aqueous solution of sodium hydroxide (10 mL) and the resulting mixture was heated at 80° C. for 46 hours. The methanol was then removed under reduced pressure and the mixture was acidified to pH 1-2, extracted with ethyl acetate (2×), dried (MgSO$_4$), filtered, and concentrated under reduced pressure to provide the title compound. $^1$H NMR (400 MHz, CDCl$_3$) δ ppm 7.33 (d, J=8.2 Hz, 1H), 7.06-7.03 (m, 2H), 3.08 (ddd, J=8.1, 8.1, 16.3 Hz, 1H), 2.93 (ddd, J=4.5, 8.7, 16.2 Hz, 1H), 2.76 (ddd, J=4.6, 8.5, 13.0 Hz, 1H), 2.00 (ddd, J=7.6, 8.7, 13.0 Hz, 1H), 1.56 (s, 3H).

Example 55E

3-[(2R,4R)-4-{[1-methyl-5-(trifluoromethoxy)-2,3-dihydro-1H-indene-1-carbonyl]amino}-3,4-dihydro-2H-1-benzopyran-2-yl]benzoic acid To a stirred solution of Example 26F (49 mg, 0.173 mmol) and Example 55D (45 mg, 0.17 mmol) in dichloromethane (1 mL) was added N,N-diisopropylethylamine (0.089 mL, 0.50 mmol) followed by 1-[Bis(dimethylamino)methylene]-1H-1,2,3-triazolo[4,5-b]pyridinium 3-oxid hexafluorophosphate (97 mg, 0.26 mmol) and the reaction mixture was stirred at room temperature for 18 hours. The reaction mixture was diluted with dichloromethane and saturated sodium bicarbonate aqueous solution was added. The phases were separated and the aqueous phase was extracted with dichloromethane. The combined organic layers were passed through a hydrophobic frit and the filtrate was concentrated under reduced pressure. The crude residue was purified by reversed-phase HPLC on a Waters Sunfire™ C18 column (150×19 mm id, 10 μm), eluted using a gradient of about 5-100% acetonitrile in 0.1% aqueous formic acid at a flow rate of 20 mL/minute for a total run time of 28 minutes. The ester protected product was dissolved in tetrahydrofuran (0.5 mL) and water (0.5 mL) and LiOH.H$_2$O (12 mg, 0.30 mmol) was added. The resultant suspension was stirred at 45° C. for 18 hours. The organic solvent was removed under reduced pressure and the residue was diluted with dichloromethane and washed with aqueous 3M hydrochloric acid solution. The aqueous layer was re-extracted with dichloromethane. The combined organic layers were passed through a hydrophobic frit and the filtrate was concentrated under reduced pressure. The residue was purified by reversed-phase HPLC on a Waters Sunfire™ C18 column (150×19 mm id 10 μm), eluted using a gradient of about 5-80% acetonitrile in 10 mM aqueous ammonium bicarbonate at a flow rate of 20 mL/minute (the gradient began with 5-20% acetonitrile over 1 minute; held at 20% for 2.5 minutes, 20-80% acetonitrile over 12.5 minutes; held at 80% for 7.5 minutes; 80-5% over 1.5 minute; held at 5% for 3 minutes) to provide the title compound. $^1$H NMR (400 MHz, DMSO-d$_6$) δ ppm 8.06-8.04 (m, 1H), 7.94-7.91 (m, 1H), 7.86 (dd, J=2.2, 8.8 Hz, 1H), 7.68-7.65 (m, 1H), 7.56-7.50 (m, 1H), 7.45 (d, J=8.3 Hz, 1H), 7.22 (d, J=4.9 Hz, 1H), 7.19-7.15 (m, 2H), 7.07 (d, J=7.7 Hz, 1H), 6.93-6.85 (m, 2H), 5.45-5.38 (m, 2H), 3.03-2.90 (m, 2H), 2.71-2.62 (m, 1H), 2.20-2.12 (m, 2H), 2.02-1.95 (m, 1H), 1.49 (d, J=7.9 Hz, 3H); MS (ESI) m/z 510 (M−H)−.

Example 56

3-{(2R,4R)-4-[(6-methoxy-3-methyl-2,3-dihydro-1-benzofuran-3-carbonyl)amino]-3,4-dihydro-2H-1-benzopyran-2-yl}benzoic acid

Example 56A methyl 2-((2-iodo-5-methoxyphenoxy)methyl)acrylate

To a solution of 2-iodo-5-methoxyphenol (1.00 g, 4.00 mmol) and methyl 2-(bromomethyl)acrylate (0.802 g, 4.48 mmol) in acetonitrile (4.00 mL) was added cesium carbonate (1.955 g, 6.00 mmol) and stirred at room temperature for 18 hours. The reaction mixture was partitioned between ethyl acetate and water, the organic extract was separated and dried over anhydrous sodium sulfate then filtered and concentrated in vacuo to give a crude oil, which was purified via flash chromatography, eluting with 0:100 to 15:85 methyl tert-butyl ether:heptanes on a 40 g silica gel column to give the title compound (1.15 g, 82%). $^1$H NMR (501 MHz, CDCl$_3$) δ ppm 3.80 (s, 3H), 3.83 (s, 3H), 4.78 (d, J=1.8 Hz, 2H), 6.28 (dd, J=2.3, 1.2 Hz, 1H), 6.36 (dd, J=8.7, 2.7 Hz, 1H), 6.47 (dd, J=4.6, 2.2 Hz, 2H), 7.64 (d, J=8.6 Hz, 1H); MS (ESI+) m/z 348.7 (M+H)$^+$.

Example 56B methyl 6-methoxy-3-methyl-2,3-dihydrobenzofuran-3-carboxylate

To a solution of tributylamine (1.265 mL, 5.31 mmol) in acetonitrile (10 mL) was added formic acid (0.103 mL, 2.65 mmol) and the reaction mixture was stirred at room temperature for 10 minutes. Example 56A (0.840 g, 2.413 mmol) was added to the reaction mixture and reaction mixture was degassed by nitrogen. Palladium (II) acetate (0.054 g, 0.241 mmol) was added to the reaction mixture and degassing was continued for 2-3 minutes more and then reaction vial was capped and stirred at 60° C. for 17 hours. LC/MS indicated completion of the reaction. The reaction mixture was filtered, then partitioned between ethyl acetate and brine. The organic layer was dried over anhydrous sodium sulfate, filtered, and concentrated in vacuo to give a crude oil, which was purified via flash chromatography, eluting with 0:100 to 20:80 methyl tert-butyl ether:heptanes on a 40 g silica gel column to give 439 mg of the title compound. $^1$H NMR (501 MHz, CDCl$_3$) δ ppm 1.62 (s, 3H), 3.75 (s, 3H), 3.80 (s, 3H), 4.29 (d, J=9.0 Hz, 1H), 5.11 (d, J=9.0 Hz, 1H), 6.42 (d, J=2.3 Hz, 1H), 6.48 (dd, J=8.3, 2.3 Hz, 1H), 7.21 (d, J=8.3 Hz, 1H); MS (ESI+) m/z 222.9 (M+H)$^+$.

Example 56C 6-methoxy-3-methyl-2,3-dihydrobenzofuran-3-carboxylic acid

To a solution of Example 56B (0.159 g, 0.715 mmol) in tetrahydrofuran (4.0 mL) was added potassium trimethylsilanolate (0.110 g, 0.859 mmol), and the reaction mixture was stirred at 50° C. for 1 hour. The reaction was cooled to room temperature and partitioned between methyl tert-butyl ether and water. The aqueous layer was acidified by concentrated HCl solution to pH=2, and the product was extracted into CH$_2$Cl$_2$, and the organic extracts were separated and dried over sodium sulfate, filtered, and concentrated in vacuo. The resulting residue was triturated with hexanes to give a white solid material that was removed via filtration and dried to constant weight in a vacuum oven at 50° C. to give the title compound (118 mg, 79%). $^1$H NMR (501 MHz, CDCl$_3$) δ ppm 1.45 (s, 3H), 3.67 (s, 3H), 4.21 (d, J=9.0 Hz, 1H), 4.90 (d, J=9.0 Hz, 1H), 6.37 (d, J=2.2 Hz, 1H), 6.41 (dd, J=8.3, 2.3 Hz, 1H), 7.12 (d, J=8.3 Hz, 1H), 12.73 (s, 1H); MS (ESI+) m/z 209.0 (M+H)$^+$.

Example 56D

Methyl 3-{(2R,4R)-4-[(6-methoxy-3-methyl-2,3-dihydro-1-benzofuran-3-carbonyl)amino]-3,4-dihydro-2H-1-benzopyran-2-yl}benzoate To a solution of Example 56C (0.0627 g, 0.301 mmol) in N,N-dimethylformamide (1.5 mL) was added HATU (0.172 g, 0.452 mmol), and the reaction mixture was stirred at room temperature for 15 minutes. Example 26F (0.096 g, 0.301 mmol) was added to the reaction mixture, followed by addition of diisopropylethylamine (0.210 mL, 1.205 mmol), which resulted in a light yellow color. The reaction mixture was stirred at room temperature for 1 hour and the reaction mixture was partitioned between ethyl acetate and water. The organic extract was separated and dried over anhydrous sodium sulfate, filtered, and concentrated in vacuo. The resulting residue was purified by flash chromatography, eluting with 0:100 to 60:40 methyl tert-butyl ether:heptanes on a 25 g silica gel column to give the title compound (99 mg, 69%). $^1$H NMR (501 MHz, CDCl$_3$) δ ppm 1.61 (s, 2H), 1.71 (s, 1H), 1.84 (dtd, J=13.2, 11.3, 6.9 Hz, 1H), 2.54 (dddd, J=13.3, 12.1, 6.1, 2.0 Hz, 1H), 3.79 (s, 3H), 3.95 (d, J=5.8 Hz, 3H), 4.34 (dd, J=23.0, 9.1 Hz, 1H), 4.83 (d, J=9.2 Hz, 1H), 4.99 (d, J=9.0 Hz, 1H), 5.27 (ddd, J=11.4, 4.9, 1.9 Hz, 1H), 5.43-5.55 (m, 1H), 5.77 (dd, J=14.7, 8.8 Hz, 1H), 6.39-6.54 (m, 2H), 6.89-6.98 (m, 2H), 6.98-7.04 (m, 1H), 7.03-7.14 (m, 1H), 7.21 (ddddd, J=10.0, 8.0, 7.1, 1.7, 0.8 Hz, 1H), 7.48 (dt, J=15.5, 7.7 Hz, 1H), 7.59-7.67 (m, 1H), 8.03 (ddt, J=13.5, 7.9, 1.5 Hz, 1H), 8.12 (dt, J=14.4, 1.8 Hz, 1H); MS (ESI+) m/z 474.0 (M+H)$^+$.

Example 56E

3-{(2R,4R)-4-[(6-methoxy-3-methyl-2,3-dihydro-1-benzofuran-3-carbonyl)amino]-3,4-dihydro-2H-1-benzopyran-2-yl}benzoic acid To a solution of Example 56D (0.0969 g, 0.205 mmol) in tetrahydrofuran (2.046 mL) was added potassium trimethylsilanolate (0.029 g, 0.225 mmol), and the reaction mixture was stirred at 50° C. for 1 hour. The reaction was cooled to room temperature and the reaction mixture was partitioned between methyl tert-butyl ether and water. The aqueous layer was separated, acidified with concentrated HCl solution to pH=2, and the product was extracted into dichloromethane. The organic extract was separated and dried over anhydrous sodium sulfate then concentrated in vacuo to give the title compound (83 mg, 89% yield). $^1$H NMR (501 MHz, CDCl$_3$) δ ppm 1.69 (dd, J=26.1, 1.5 Hz, 3H), 1.85 (dtd, J=13.5, 11.3, 3.9 Hz, 1H), 2.53-2.68 (m, 1H), 3.79 (d, J=1.4 Hz, 3H), 4.35 (dd, J=18.5, 9.2 Hz, 1H), 4.76-5.07 (m, 1H), 5.26-5.37 (m, 1H), 5.56 (p, J=7.9 Hz, 1H), 5.83 (dd, J=11.6, 8.8 Hz, 1H), 6.41-6.54 (m, 2H), 6.89-6.99 (m, 2H), 6.99-7.04 (m, 1H), 7.04-7.16 (m, 1H), 7.22 (q, J=8.3 Hz, 1H), 7.52 (ddd, J=12.6, 8.6, 7.0 Hz, 1H), 7.64-7.74 (m, 1H), 8.10 (ddt, J=10.9, 7.6, 1.5 Hz, 1H), 8.24 (dt, J=12.7, 1.8 Hz, 1H). MS (ESI+); m/z 459.9 (M+H)$^+$ Example 57 methyl 3-[(2R,4R)-7-methoxy-4-{[1-methyl-6-(trifluoromethoxy)-2,3-dihydro-1H-indene-1-carbonyl]amino}-3,4-dihydro-2H-1-benzopyran-2-yl]benzoate Example 57A 6-(trifluoromethoxy)-2,3-dihydro-1H-indene-1-carbonitrile To a stirred suspension of 6-(trifluoromethoxy)-2,3-dihydro-1H-inden-1-one (1.08 g, 5.00 mmol) and 1-((isocyanomethyl)sulfonyl)-4-methylbenzene (1.37 g, 7.02 mmol) in 1,2-dimethoxyethane (20 mL) cooled to 0° C. with an ice bath, was added dropwise a warm solution of sodium ethoxide in ethanol (5.6 mL, 21 wt %, 15.00 mmol) in over about 10 minutes. The ice bath was allowed to expire and the reaction was stirred at ambient temperature for 16 hours. The reaction was cooled to 0° C. with an ice bath. Water (50 mL) was added and the reaction was acidified to pH about 3 with (1 M HCl). The reaction mixture was extracted with dichloromethane (3×50 mL). The combined organic layers were washed with brine (50 mL), dried over $Na_2SO_4$, filtered and concentrated. The residue was purified by silica gel chromatography (dichloromethane, $R_f$=0.47) to provide the title compound (849.1 mg, 75%). $^1H$ NMR (400 MHz, DMSO-$d_6$) δ 7.44 (d, J=8.3 Hz, 1H), 7.41 (s, 1H), 7.29 (d, J=8.3 Hz, 1H), 4.52 (t, J=7.9 Hz, 1H), 3.09-2.98 (m, 1H), 2.98-2.86 (m, 1H), 2.64-2.52 (m, 1H), 2.37-2.23 (m, 1H); MS (ESI−) m/z 226.1 (M+H)$^+$.

Example 57B 1-methyl-6-(trifluoromethoxy)-2,3-dihydro-1H-indene-1-carbonitrile To a stirred solution of Example 57A (831.0 mg, 3.66 mmol) in anhydrous N,N-dimethylformamide (5 mL) was added sodium hydride (230.5 mg, 60 wt %, 5.76 mmol). The mixture was stirred at ambient temperature for 30 minutes. Methyl iodide (0.70 mL, 11.19 mmol) was added and the reaction was stirred at ambient temperature for 17 hours. The reaction was poured into ethyl acetate (150 mL) and washed with 1 M HCl (50 mL), saturated $NaHCO_3$ (50 mL) and brine (50 mL). The organic layer was dried over $Na_2SO_4$, filtered, and concentrated. The residue was purified by silica gel chromatography (heptane/dichloromethane 1:1, $R_f$=0.54) to afford the title compound (747.0 mg, 85%): $^1H$ NMR (400 MHz, DMSO-$d_6$) δ 7.50 (s, 1H), 7.45 (d, J=8.3 Hz, 1H), 7.34-7.28 (m, 1H), 3.01 (t, J=7.2 Hz, 2H), 2.62 (dt, J=13.3, 6.8 Hz, 1H), 2.23 (dt, J=13.0, 7.5 Hz, 1H), 1.66 (s, 3H).

Example 57C 1-methyl-6-(trifluoromethoxy)-2, 3-dihydro-1H-indene-1-carboxylic acid A suspension of Example 57B (725.2 mg, 3.01 mmol) and potassium hydroxide (777.7 mg, 87 wt %, 12.06 mmol) in diethylene glycol (5 mL) and water (5 mL) was stirred at 140° C. for 17 hours. The reaction was poured into water (50 mL) and washed with dichloromethane (50 mL). The aqueous layer was acidified to pH about 3 with 1 M HCl. The product was extracted with dichloromethane (2×50 mL). The combined organic layers was washed with brine (50 mL), dried over $Na_2SO_4$, filtered, and concentrated to provide the title compound (715.8 mg, 91%): $^1H$ NMR (400 MHz, DMSO-$d_6$) δ 12.51 (s, 1H), 7.34 (d, J=8.2 Hz, 1H), 7.22 (d, J=2.2 Hz, 1H), 7.20-7.15 (m, 1H), 3.01-2.85 (m, 2H), 2.61 (ddd, J=13.3, 8.1, 5.4 Hz, 1H), 2.00-1.89 (m, 1H), 1.46 (s, 3H); MS (ESI−) m/z 259 (M+H)$^+$.

Example 57D 1-methyl-6-(trifluoromethoxy)-2,3-dihydro-1H-indene-1-carbonyl chloride The product of Example 57C (684.5 mg, 2.63 mmol) was dissolved in dichloromethane (10 mL). Oxalyl chloride (350 μL, 4.00 mmol) was added followed by N,N-dimethylformamide (25 μL, 0.323 mmol). The reaction was stirred at ambient temperature for 2 hours. The reaction was concentrated and used without additional purification (715.8 mg, 91%). $^1H$ NMR (400 MHz, DMSO-$d_6$) δ 12.51 (s, 1H), 7.34 (d, J=8.2 Hz, 1H), 7.22 (d, J=2.2 Hz, 1H), 7.20-7.15 (m, 1H), 3.01-2.85 (m, 2H), 2.61 (ddd, J=13.3, 8.1, 5.4 Hz, 1H), 2.00-1.89 (m, 1H), 1.46 (s, 3H); MS (ESI−) m/z 259 (M+H)$^+$.

Example 57E methyl 3-[(2R,4R)-7-methoxy-4-{[1-methyl-6-(trifluoromethoxy)-2, 3-dihydro-1H-indene-1-carbonyl]amino}-3,4-dihydro-2H-1-benzopyran-2-yl]benzoate The product of Example 57D (32.1 mg, 0.115 mmol) was dissolved in dichloromethane (1 mL) and pyridine (0.5 mL). Example 8C (34.4 mg, 0.098 mmol) was added and the reaction mixture was stirred at 60° C. for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (22.1 mg, 39%). $^1H$ NMR (400 MHz, DMSO-$d_6$) δ 8.06 (dt, J=7.3, 1.7 Hz, 1H), 7.95 (ddd, J=6.6, 3.4, 1.6 Hz, 1H), 7.82 (dd, J=26.6, 8.8 Hz, 1H), 7.76-7.67 (m, 1H), 7.57 (td, J=7.7, 4.8 Hz, 1H), 7.39-7.28 (m, 2H), 7.20-7.09 (m, 1H), 6.87 (dd, J=81.4, 8.5 Hz, 1H), 6.54-6.38 (m, 2H), 5.45-5.28 (m, 2H), 3.87 (d, J=2.0 Hz, 3H), 3.70 (d, J=2.0 Hz, 3H), 3.04-2.81 (m, 2H), 2.75-2.61 (m, 1H), 2.24-1.89 (m, 3H), 1.49 (d, J=4.9 Hz, 3H); 1.50 (s, 3H); MS (ESI−) m/z 554 (M−H)$^−$.

Example 58

3-[(2R,4R)-7-methoxy-4-{[1-methyl-6-(trifluoromethoxy)-2,3-dihydro-1H-indene-1-carbonyl]amino}-3,4-dihydro-2H-1-benzopyran-2-yl]benzoic acid Example 57D (23.0 mg, 0.036 mmol) and potassium trimethylsilanolate (16.4 mg, 90% purity, 0.115 mmol) were dissolved in tetrahydrofuran (1 mL) and stirred at ambient temperature for 16 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (13.5 mg, 71%). $^1H$ NMR (400 MHz, DMSO-$d_6$) δ 13.03 (s, 1H), 8.05 (dt, J=6.7, 1.8 Hz, 1H), 7.96-7.89 (m, 1H), 7.83 (dd, J=27.0, 8.8 Hz, 1H), 7.69 (ddt, J=9.1, 7.7, 1.4 Hz, 1H), 7.54 (td, J=7.7, 4.9 Hz, 1H), 7.39-7.28 (m, 2H), 7.20-7.10 (m, 1H), 6.97 (dd, J=8.3, 1.0 Hz, 1H), 5.43-5.29 (m, 2H), 3.70 (d, J=1.7 Hz, 3H), 3.17 (s, 2H), 3.04-2.82 (m, 2H), 2.73-2.62 (m, 1H), 2.23-1.89 (m, 3H), 1.49 (d, J=5.9 Hz, 3H); MS (ESI−) m/z 540 (M−H)$^−$.

Example 59 methyl 4-[(2R,4R)-4-{[(2R)-6-chloro-2-methyl-3,4-dihydro-2H-1-benzopyran-2-carbonyl]amino}-3,4-dihydro-2H-1-benzopyran-2-yl]benzoate

Example 59A methyl 6-chloro-3,4-dihydro-2H-1-benzopyran-2-carboxylate

To a stirred solution of 6-chlorochroman-2-carboxylic acid (500 mg, 2.35 mmol) in methanol (7 mL) at room temperature was added concentrated sulfuric acid (2 drops). The resultant solution was stirred at 70° C. for 18 hours. The reaction mixture was neutralized with saturated NaHCO$_3$ and was diluted with dichloromethane. The layers were separated and the aqueous layer was re-extracted with dichloromethane. The combined organic layers were passed through a hydrophobic frit and the filtrate was concentrated under reduced pressure to provide the title compound. $^1$H NMR (400 MHz, CDCl$_3$) δ ppm 6.89-6.79 (m, 2H), 6.74 (dd, J=2.9, 8.8 Hz, 1H), 4.71 (dd, J=3.6, 7.4 Hz, 1H), 3.79 (s, 3H), 2.86-2.69 (m, 2H), 2.31-2.12 (m, 2H).

Example 59B methyl 6-chloro-2-methyl-3,4-dihydro-2H-1-benzopyran-2-carboxylate To a stirred solution of Example 59A (505 mg, 2.22 mmol) in anhydrous tetrahydrofuran (10 mL) under a nitrogen atmosphere was added iodomethane (1 mL, 16.06 mmol). The resultant reaction mixture was cooled to −78° C. To the resultant reaction mixture was added portion wise potassium tert-butoxide (500 mg, 4.46 mmol). The resultant reaction mixture was allowed to warm to room temperature and was stirred at room temperature for 18 hours. The reaction mixture was diluted with dichloromethane and was quenched with aqueous ammonium chloride. The layers were separated and the aqueous layer was re-extracted with dichloromethane. The combined organic layers were passed through a hydrophobic frit and the filtrate was concentrated under reduced pressure to provide the title compound. $^1$H NMR (400 MHz, CDCl$_3$) δ ppm 6.90-6.78 (m, 2H), 6.74-6.70 (m, 1H), 3.71 (s, 3H), 2.72-2.66 (m, 2H), 2.44-2.34 (m, 1H), 1.92-1.83 (m, 1H), 1.61 (s, 3H).

Example 59C 6-chloro-2-methyl-3,4-dihydro-2H-1-benzopyran-2-carboxylic acid

To a stirred solution of Example 59B (205 mg, 0.85 mmol) in methanol (3 mL) was added an aqueous solution of 2M sodium hydroxide (3 mL). The resultant reaction mixture was stirred at 40° C. for 2 hours. The organics were concentrated under reduced pressure and dichloromethane was added. The layers were separated and the organic layer was washed with water. The combined aqueous layers were acidified to pH1 with aqueous 3M hydrochloric acid solution and extracted with dichloromethane. The organic layer was passed through a hydrophobic frit and the filtrate was concentrated under reduced pressure to provide the title compound. $^1$H NMR (400 MHz, CDCl$_3$) δ ppm 7.31 (d, J=1.5 Hz, 1H), 7.20-7.12 (m, 2H), 3.08-2.99 (m, 1H), 2.93-2.84 (m, 1H), 2.77-2.70 (m, 1H), 2.03-1.94 (m, 1H), 1.56 (s, 3H).

Example 59D (2S)-6-chloro-2-methyl-3,4-dihydro-2H-1-benzopyran-2-carboxylic acid Example 59C (3.17 g, 14.0 mmol) was dissolved in methanol (40 mL) and was purified by supercritical fluid chromatography. 183 injections were carried out using a YMC amylose-C column, 5% methanol in CO$_2$, at a 100 mL/minute flow rate, 120 bar and 40° C. The title compound was obtained as the second eluting enantiomer. $^1$H NMR (400 MHz, CDCl$_3$) δ ppm 7.08 (dd, J=2.6, 8.7 Hz, 1H), 7.04-7.02 (m, 1H), 6.84 (d, J=8.7 Hz, 1H), 2.77-2.72 (m, 2H), 2.41-2.34 (m, 1H), 1.98-1.89 (m, 1H), 1.64 (s, 3H).

Example 59E (2R)-6-chloro-2-methyl-3,4-dihydro-2H-1-benzopyran-2-carboxylic acid The title compound was obtained as the first eluting enantiomer from the supercritical fluid chromatography as described in Example 59D. X-ray diffraction studies confirmed the stereochemistry.

Example 59F methyl 4-[(2R,4R)-4-amino-3,4-dihydro-2H-1-benzopyran-2-yl]benzoate Example 59F was synthesized using the procedures as described in Example 8A-8C, substituting 4H-chromen-4-one for Example 7D, and substituting 4-methoxycarbonylphenylboronic acid for 3-methoxycarbonylphenylboronic acid. $^1$H NMR (400 MHz, CDCl$_3$) δ 8.08 (d, J=7.9 Hz, 2H), 7.50 (dd, J=23.2, 7.8 Hz, 3H), 7.20 (t, J=7.8 Hz, 1H), 7.07-6.84 (m, 2H), 5.22 (d, J=11.4 Hz, 1H), 4.36 (dd, J=10.8, 5.8 Hz, 1H), 3.93 (s, 3H), 2.46 (dd, J=13.2, 5.8 Hz, 1H), 2.00-1.85 (m, 1H); MS(ESI+): m/z=267 (M−NH2).

Example 59G methyl 4-[(2R,4R)-4-{[(2R)-6-chloro-2-methyl-3,4-dihydro-2H-1-benzopyran-2-carbonyl]amino}-3,4-dihydro-2H-1-benzopyran-2-yl]benzoate To Example 59E (50 mg, 0.221 mmol) in N,N-dimethylformamide (2 mL) was added HATU (126 mg, 0.331 mmol). The mixture was stirred at ambient for 5 minutes, Example 59F (62.5 mg, 0.221 mmol) was added, following by the addition of N-ethyl-N-isopropylpropan-2-amine (0.154 mL, 0.882 mmol). The mixture was stirred at ambient temperature overnight; LC/MS indicated completion of the reaction. Purification via chromatography on a 12 g silica gel cartridge, eluting with ethyl acetate/heptane at 5-50% gradient yield title compound (52 mg, 47%). $^1$H NMR (400 MHz, CDCl$_3$) δ 8.03 (d, J=8.0 Hz, 2H), 7.46 (d, J=8.1 Hz, 2H), 7.25 (d, J=4.6 Hz, 2H), 7.09-6.86 (m, 4H), 6.70 (d, J=8.3 Hz, 1H), 6.62 (d, J=9.1 Hz, 1H), 5.50 (td, J=10.1, 6.3 Hz, 1H), 5.26 (dd, J=11.1, 2.2 Hz, 1H), 3.90 (s, 3H), 2.69 (q, J=7.5, 6.9 Hz, 2H), 2.47-2.23 (m, 2H), 1.92 (ddd, J=13.8, 8.3, 6.0 Hz, 1H), 1.79 (dt, J=13.3, 11.0 Hz, 1H), 1.58 (s, 3H); MS(ESI−) m/z=490 (M−H)−.

Example 60

4-[(2R,4R)-4-{[(2R)-6-chloro-2-methyl-3,4-dihydro-2H-1-benzopyran-2-carbonyl]amino}-3,4-dihydro-2H-1-benzopyran-2-yl]benzoic acid Example 59G (50 mg, 0.1 mmol) in methanol (2 mL) and 6N LiOH (0.5 mL) was stirred at 35° C. for 4 hours. Solvent was removed under pressure and water (1 mL) was added. The mixture was adjusted pH to about 1 with the addition of 2N HCl. The white solid precipitated was collected by filtration, washed with water, and dried in oven to yield the title compound (37 mg, 77%). $^1$H NMR (400 MHz, CDCl$_3$) δ 8.10 (d, J=8.1 Hz, 2H), 7.50 (d, J=8.1 Hz, 2H), 7.24 (d, J=7.1 Hz, 2H), 7.05-6.99 (m, 3H), 6.98-6.93 (m, 1H), 6.70 (d, J=8.4 Hz, 1H), 6.64 (d, J=9.1 Hz, 1H), 5.52 (td, J=10.0, 6.3 Hz, 1H), 5.28 (dd, J=11.0, 2.0 Hz, 1H), 2.69 (q, J=7.3, 6.7 Hz, 2H), 2.42 (ddd, J=13.4, 6.1, 2.1 Hz, 1H), 2.33 (dt, J=13.4, 6.0 Hz, 1H), 1.93 (ddd, J=13.8, 8.1, 6.0 Hz, 1H), 1.80 (dt, J=13.4, 11.0 Hz, 1H), 1.63 (s, 3H); MS(ESI-): m/z=476 (M-H)$^-$.

Example 61 methyl 4-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoate To Example 59D (50 mg, 0.221 mmol) in N,N-dimethylformamide (2 mL) was added HATU (126 mg, 0.331 mmol). The mixture was stirred at ambient for 5 minutes, added Example 59F (62.5 mg, 0.221 mmol), following by the addition of N-ethyl-N-isopropylpropan-2-amine (0.154 mL, 0.882 mmol). The mixture was stirred overnight. The reaction mixture was concentrated and purified via chromatography on a 12 g silica gel cartridge, eluting with ethyl acetate/heptane at 5-50% gradient to yield the title compound (48 mg, 44.2%). $^1$H NMR (400 MHz, CDCl$_3$) δ 8.10-8.04 (m, 2H), 7.56-7.48 (m, 2H), 7.18-7.08 (m, 2H), 7.09-6.99 (m, 2H), 6.89 (dd, J=8.3, 1.2 Hz, 1H), 6.75-6.68 (m, 2H), 6.50 (d, J=8.9 Hz, 1H), 6.40 (dt, J=7.6, 1.3 Hz, 1H), 5.40 (td, J=10.2, 6.3 Hz, 1H), 5.27 (dd, J=11.3, 2.0 Hz, 1H), 3.93 (s, 3H), 2.90-2.71 (m, 2H), 2.63-2.45 (m, 2H), 1.98-1.87 (m, 2H), 1.54 (s, 3H); MS(ESI-) m/z=490 (M-H)$^-$.

Example 62

4-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoic acid Example 61 (45 mg, 0.092 mmol) in methanol (2 mL) and 6N LiOH (0.5 mL) was stirred at 35° C. for 4 hours. Solvent was removed under pressure and water (1 mL) added, the mixture was adjusted pH to about 1 with the addition of 2N HCl. The white solid precipitated was collected by filtration, washed with water, and dried in oven to yield the title compound (33.5 mg, 76%). $^1$H NMR (400 MHz, CDCl$_3$) δ 8.19-8.10 (m, 2H), 7.55 (d, J=8.1 Hz, 2H), 7.19-7.10 (m, 2H), 7.06 (dd, J=8.5, 2.5 Hz, 1H), 6.90 (d, J=7.8 Hz, 1H), 6.71 (dd, J=10.1, 7.9 Hz, 2H), 6.52 (d, J=9.0 Hz, 1H), 6.40 (d, J=7.7 Hz, 1H), 5.42 (td, J=10.1, 6.1 Hz, 1H), 5.29 (dd, J=11.6, 2.0 Hz, 1H), 2.89-2.72 (m, 2H), 2.65-2.47 (m, 2H), 1.93 (dtd, J=13.6, 10.7, 10.0, 6.5 Hz, 2H), 1.55 (s, 3H); MS (ESI-) m/z=476 (M-H)$^-$.

Example 63 methyl 3-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoate The product of Example 26F (64.5 mg, 0.202 mmol) was dissolved in N,N-dimethylformamide (0.5 mL) and pyridine (0.5 mL). Example 59D (48.3 mg, 0.213 mmol) and 1-(3-dimethylaminopropyl)-3-ethylcarbodiimide hydrochloride (52.8 mg, 0.275 mmol) were added and the reaction mixture was stirred at 60° C. for 4 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (51.8 mg, 52%). $^1$H NMR (501 MHz, DMSO-d$_6$) δ 8.10 (d, J=9.2 Hz, 1H), 8.07 (t, J=1.8 Hz, 1H), 7.95 (dt, J=7.8, 1.4 Hz, 1H), 7.73 (dt, J=7.7, 1.5 Hz, 1H), 7.58 (t, J=7.7 Hz, 1H), 7.23 (d, J=2.6 Hz, 1H), 7.15-7.06 (m, 2H), 6.86-6.79 (m, 2H), 6.63 (td, J=7.5, 1.2 Hz, 1H), 6.42 (dt, J=7.9, 1.4 Hz, 1H), 5.43 (dd, J=11.6, 2.1 Hz, 1H), 5.37 (td, J=10.2, 6.2 Hz, 1H), 3.88 (s, 3H), 2.80-2.72 (m, 2H), 2.38 (dt, J=13.7, 5.3 Hz, 1H), 2.29-2.13 (m, 2H), 1.81 (ddd, J=13.4, 9.2, 7.0 Hz, 1H), 1.48 (s, 3H); MS (ESI+) m/z 492 (M+H)$^-$.

Example 64

3-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoic acid Example 63 (44.2 mg, 0.090 mmol) and potassium trimethylsilanolate (31.2 mg, 90% purity, 0.219 mmol) were dissolved in tetrahydrofuran (1 mL) and stirred at ambient temperature for 17 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (39.8 mg, 93%). $^1$H NMR (400 MHz, DMSO-d$_6$) δ 13.04 (s, 1H), 8.10 (d, J=9.2 Hz, 1H), 8.06 (t, J=1.8 Hz, 1H), 7.93 (dt, J=7.8, 1.5 Hz, 1H), 7.70 (dt, J=7.9, 1.4 Hz, 1H), 7.55 (t, J=7.7 Hz, 1H), 7.23 (d, J=2.6 Hz, 1H), 7.15-7.05 (m, 2H), 6.82 (dd, J=11.8, 8.6 Hz, 2H), 6.63 (td, J=7.5, 1.2 Hz, 1H), 6.42 (d, J=7.6 Hz, 1H), 5.46-5.32 (m, 2H), 2.75 (dd, J=8.8, 5.1 Hz, 2H), 2.38 (dt, J=13.4, 5.1 Hz, 1H), 2.31-2.11 (m, 2H), 1.82 (dt, J=13.5, 8.3 Hz, 1H), 1.48 (s, 3H); MS (ESI+) m/z 478 (M+H)$^+$.

Example 65

3-[(2R,4R)-4-{[(2R)-6-chloro-2-methyl-3,4-dihydro-2H-1-benzopyran-2-carbonyl]amino}-7-methoxy-3,4-dihydro-2H-1-benzopyran-2-yl]benzoic acid Example 65 was prepared according to the procedure described in Example 2, substituting Example 59E for 1-(3,4-dichlorophenyl) cyclopropanecarboxylic acid, and substituting Example 8C for Example 1C. $^1$H NMR (400

MHz, DMSO-$d_6$) δ 8.23 (d, J=9.0 Hz, 1H), 8.04-7.98 (m, 1H), 7.91 (dt, J=7.7, 1.5 Hz, 1H), 7.66 (dt, J=7.8, 1.5 Hz, 1H), 7.53 (t, J=7.7 Hz, 1H), 7.15-7.05 (m, 2H), 6.95 (d, J=8.6 Hz, 1H), 6.87 (d, J=8.7 Hz, 1H), 6.56 (dd, J=8.6, 2.6 Hz, 1H), 6.44 (d, J=2.6 Hz, 1H), 5.30 (dd, J=26.0, 14.1 Hz, 2H), 3.72 (s, 3H), 2.78-2.57 (m, 2H), 2.31-2.20 (m, 1H), 2.17-2.04 (m, 1H), 2.01-1.91 (m, 1H), 1.88-1.75 (m, 1H), 1.53 (s, 3H). MS (APCI+) m/z 522.3 (M+H)$^+$.

Example 66

3-[(2R,4R)-4-{[(2R)-6-chloro-2-methyl-3,4-dihydro-2H-1-benzopyran-2-carbonyl]amino}-3,4-dihydro-2H-1-benzopyran-2-yl]benzoic acid This Example was prepared according to the procedure described in Example 2, substituting Example 59E for 1-(3,4-dichlorophenyl) cyclopropanecarboxylic acid, and substituting Example 26F for Example 1C. $^1$H NMR (400 MHz, DMSO-$d_6$) δ 8.34 (d, J=9.0 Hz, 1H), 8.02 (t, J=1.8 Hz, 1H), 7.92 (dt, J=7.7, 1.5 Hz, 1H), 7.67 (dt, J=7.8, 1.6 Hz, 1H), 7.54 (t, J=7.7 Hz, 1H), 7.26-7.15 (m, 1H), 7.15-7.02 (m, 3H), 7.02-6.91 (m, 1H), 6.89-6.84 (m, 2H), 5.41-5.30 (m, 2H), 2.79-2.57 (m, 2H), 2.27 (dt, J=13.4, 5.6 Hz, 1H), 2.21-2.08 (m, 1H), 2.03-1.92 (m, 1H), 1.88-1.76 (m, 1H), 1.55 (s, 3H). MS (APCI+) m/z 492.3 (M+H)$^+$.

Example 67

4-[(2R,4R)-4-{[(2R)-6-chloro-2-methyl-3,4-dihydro-2H-1-benzopyran-2-carbonyl]amino}-7-methoxy-3,4-dihydro-2H-1-benzopyran-2-yl]benzoic acid This Example was prepared according to the procedure described in Example 2, substituting Example 59E for 1-(3,4-dichlorophenyl) cyclopropanecarboxylic acid. $^1$H NMR (400 MHz, DMSO-$d_6$) δ 8.23 (d, J=9.0 Hz, 1H), 7.97 (d, J=8.8 Hz, 2H), 7.55 (d, J=8.8 Hz, 2H), 7.15-7.05 (m, 2H), 6.96 (dd, J=8.6, 1.0 Hz, 1H), 6.87 (d, J=8.7 Hz, 1H), 6.56 (dd, J=8.6, 2.6 Hz, 1H), 6.45 (d, J=2.5 Hz, 1H), 5.38-5.23 (m, 2H), 3.72 (s, 3H), 2.79-2.58 (m, 2H), 2.32-2.20 (m, 1H), 2.13-2.02 (m, 1H), 2.01-1.92 (m, 1H), 1.87-1.75 (m, 1H), 1.53 (s, 3H). MS (APCI+) m/z 522.3 (M+H)$^+$.

Example 68

4-[(2R,4R)-7-methoxy-4-{[1-methyl-5-(trifluoromethoxy)-2, 3-dihydro-1H-indene-1-carbonyl]amino}-3,4-dihydro-2H-1-benzopyran-2-yl]benzoic acid

Example 68A

Methyl 4-[(2R,4R)-7-methoxy-4-{[1-methyl-5-(trifluoromethoxy)-2,3-dihydro-1H-indene-1-carbonyl]amino}-3,4-dihydro-2H-1-benzopyran-2-yl]benzoate Example 55D (60.0 mg, 0.230 mmol) was dissolved in N,N-dimethylformamide (1 mL) and pyridine (1 mL). Example 1C (70.4 mg, 0.201 mmol) and 1-(3-dimethylaminopropyl)-3-ethylcarbodiimide hydrochloride (84.3 mg, 0.440 mmol) were added and the reaction mixture was stirred at 60° C. for 4 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (56.3 mg, 51%). 1:1 diastereomers $^1$H NMR (501 MHz, DMSO-$d_6$) δ 8.04-7.98 (m, 2H), 7.78 (dd, J=8.8, 2.4 Hz, 1H), 7.60 (dd, J=8.3, 3.2 Hz, 2H), 7.44 (d, J=8.3 Hz, 1H), 7.24-7.18 (m, 1H), 7.17-7.11 (m, 1H), 6.95 (dd, J=8.5, 1.0 Hz, 0.5H), 6.81-6.74 (m, 0.5H), 6.52 (dd, J=8.6, 2.6 Hz, 0.5H), 6.45 (m, J=4.9, 2.2 Hz, 1.5H), 5.44-5.30 (m, 2H), 3.87 (s, 3H), 3.70 (d, J=1.9 Hz, 3H), 2.93 (tdd, J=15.9, 12.3, 6.7 Hz, 2H), 2.65 (dddd, J=13.3, 10.3, 8.3, 5.7 Hz, 1H), 2.22-1.89 (m, 3H), 1.49 (s, 1.5H), 1.47 (s, 1.5H); MS (ESI−) m/z 554 (M−H)$^-$.

Example 68B

4-[(2R,4R)-7-methoxy-4-{[1-methyl-5-(trifluoromethoxy)-2, 3-dihydro-1H-indene-1-carbonyl]amino}-3,4-dihydro-2H-1-benzopyran-2-yl]benzoic acid Example 68A (52.6 mg, 0.095 mmol) and potassium trimethylsilanolate (31.5 mg, 90% purity, 0.221 mmol) were dissolved in tetrahydrofuran (1 mL) and stirred at ambient temperature for 17 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (40.6 mg, 79%). 1:1 diastereomers. $^1$H NMR (400 MHz, DMSO-$d_6$) δ 12.97 (s, 1H), 7.99 (dd, J=8.4, 1.7 Hz, 2H), 7.78 (d, J=8.8 Hz, 1H), 7.57 (dd, J=8.4, 2.4 Hz, 2H), 7.44 (d, J=8.3 Hz, 1H), 7.24-7.18 (m, 1H), 7.15 (dd, J=8.0, 2.5 Hz, 1H), 6.95 (dd, J=8.6, 1.0 Hz, 0.5H), 6.77 (d, J=9.2 Hz, 0.5H), 6.55-6.41 (m, 2H), 5.36 (ddt, J=17.9, 11.6, 4.4 Hz, 2H), 3.70 (d, J=1.6 Hz, 3H), 3.06-2.82 (m, 2H), 2.72-2.57 (m, 1H), 2.26-1.87 (m, 3H), 1.48 (d, J=6.9 Hz, 3H); MS (ESI−) m/z 540 (M−H)$^-$.

Example 69

4-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoic acid

Example 69A

Methy 4-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoate Example 30A (22.6 mg, 0.110 mmol) was dissolved in N,N-dimethylformamide (0.5 mL) and pyridine (0.5 mL). Example 1C (34.8 mg, 0.099 mmol) and 1-(3-dimethylaminopropyl)-3-ethylcarbodiimide hydrochloride (51.7 mg, 0.270 mmol) were added and the reaction mixture was stirred at 60° C. for 4 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10%

A), to provide the title compound (34.3 mg, 69%). ¹H NMR (400 MHz, DMSO-d₆) δ 8.03-7.95 (m, 2H), 7.62-7.55 (m, 2H), 7.52 (d, J=8.9 Hz, 1H), 7.23 (d, J=8.4 Hz, 1H), 6.96 (d, J=8.6 Hz, 1H), 6.77 (d, J=2.3 Hz, 1H), 6.71 (dd, J=8.4, 2.5 Hz, 1H), 6.52 (dd, J=8.5, 2.5 Hz, 1H), 6.45 (d, J=2.5 Hz, 1H), 5.43-5.26 (m, 2H), 3.87 (s, 3H), 3.70 (s, 3H), 3.70 (s, 3H), 2.98-2.73 (m, 2H), 2.62 (ddd, J=12.6, 8.5, 5.5 Hz, 1H), 2.07 (s, 2H), 1.87 (ddd, J=12.6, 8.3, 6.5 Hz, 1H), 1.43 (s, 3H). MS (ESI−) m/z 500 (M−H)⁻.

Example 69B

4-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoic acid Example 69A (31.3 mg, 0.062 mmol) and potassium trimethylsilanolate (26.7 mg, 90% purity, 0.187 mmol) were dissolved in tetrahydrofuran (1 mL) and stirred at ambient temperature for 16 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (22.3 mg, 73%). ¹H NMR (400 MHz, DMSO-d₆) δ 12.95 (s, 1H), 7.98 (d, J=7.9 Hz, 2H), 7.54 (dd, J=14.2, 8.5 Hz, 3H), 7.23 (d, J=8.3 Hz, 1H), 6.96 (d, J=8.6 Hz, 1H), 6.77 (d, J=2.5 Hz, 1H), 6.71 (dd, J=8.3, 2.6 Hz, 1H), 6.52 (dd, J=8.6, 2.7 Hz, 1H), 6.44 (d, J=2.5 Hz, 1H), 5.42-5.24 (m, 2H), 3.70 (d, J=2.5 Hz, 6H), 2.86 (tdd, J=15.6, 12.2, 6.6 Hz, 2H), 2.63 (ddd, J=13.6, 8.5, 5.4 Hz, 1H), 2.07 (td, J=9.3, 8.9, 4.2 Hz, 2H), 1.87 (ddd, J=12.6, 8.3, 6.5 Hz, 1H), 1.44 (s, 3H); MS (ESI−) m/z 486 (M−H)⁻.

Example 70

4-[(2R,4R)-7-methoxy-4-({1-[4-(trifluoromethoxy)phenyl]cyclobutane-1-carbonyl}amino)-3,4-dihydro-2H-1-benzopyran-2-yl]benzoic acid Example 70A methyl 4-[(2R,4R)-7-methoxy-4-({1-[4-(trifluoromethoxy)phenyl]cyclobutane-1-carbonyl}amino)-3,4-dihydro-2H-1-benzopyran-2-yl]benzoate 1-(4-(trifluoromethoxy)phenyl)cyclobutanecarboxylic acid (CAS 151157-53-8, 40.2 mg, 0.154 mmol) was dissolved in N,N-dimethylformamide (0.5 mL) and pyridine (0.5 mL). Example 1C (35.5 mg, 0.101 mmol) and 1-(3-dimethylaminopropyl)-3-ethylcarbodiimide hydrochloride (35.5 mg, 0.188 mmol) were added and the reaction mixture was stirred at 60° C. for 5 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (34.3 mg, 69%). ¹H NMR (400 MHz, DMSO-d₆) δ 7.97 (dd, J=12.5, 8.6 Hz, 3H), 7.60-7.54 (m, 2H), 7.52-7.39 (m, 2H), 7.31 (d, J=8.3 Hz, 2H), 6.47 (dd, J=8.5, 0.9 Hz, 1H), 6.40 (d, J=2.5 Hz, 1H), 6.28 (dd, J=8.5, 2.6 Hz, 1H), 5.36 (dd, J=11.6, 1.8 Hz, 1H), 5.27 (ddd, J=11.5, 9.0, 6.2 Hz, 1H), 3.85 (s, 3H), 3.65 (s, 3H), 2.80 (dddd, J=11.5, 8.5, 5.7, 2.8 Hz, 1H), 2.69 (dddd, J=11.5, 8.6, 5.8, 2.8 Hz, 1H), 2.46-2.37 (m, 1H), 2.37-2.26 (m, 1H), 2.13-2.02 (m, 1H), 1.95 (dt, J=13.0, 11.6 Hz, 1H), 1.89-1.67 (m, 2H); MS (ESI−) m/z 554 (M−H)⁻.

Example 70B

4-[(2R,4R)-7-methoxy-4-({1-[4-(trifluoromethoxy)phenyl]cyclobutane-1-carbonyl}amino)-3,4-dihydro-2H-1-benzopyran-2-yl]benzoic acid Example 70A (25.1 mg, 0.045 mmol) and potassium trimethylsilanolate (21.8 mg, 90% purity, 0.153 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (19.3 mg, 77%). ¹H NMR (400 MHz, DMSO-d₆) δ 12.96 (s, 1H), 7.97 (dd, J=8.8, 2.6 Hz, 3H), 7.60-7.52 (m, 2H), 7.51-7.44 (m, 2H), 7.33 (d, J=8.2 Hz, 2H), 6.49 (d, J=8.6 Hz, 1H), 6.42 (d, J=2.5 Hz, 1H), 6.30 (dd, J=8.6, 2.6 Hz, 1H), 5.36 (dd, J=11.7, 1.9 Hz, 1H), 5.28 (ddd, J=11.3, 8.8, 6.1 Hz, 1H), 3.67 (s, 3H), 2.82 (dddd, J=11.4, 8.5, 5.7, 2.7 Hz, 1H), 2.71 (dddd, J=11.6, 8.6, 5.7, 2.7 Hz, 1H), 2.44 (dt, J=10.6, 7.8 Hz, 1H), 2.33 (ddd, J=11.7, 9.9, 7.6 Hz, 1H), 2.10 (ddd, J=13.8, 6.6, 2.3 Hz, 1H), 1.98 (q, J=12.0 Hz, 1H), 1.91-1.69 (m, 2H); MS (ESI−) m/z 542 (M−H)⁻.

Example 71

4-{(2R,4R)-4-[2-(2,3-dihydro-1-benzofuran-5-yl)-2-methylpropanamido]-7-methoxy-3,4-dihydro-2H-1-benzopyran-2-yl}benzoic acid Example 71A 2-(2,3-dihydrobenzofuran-5-yl)-2-methylpropanoic acid The title compounds was prepared according to the procedure described from Example 1D to 1E, substituting 2-(2,3-dihydrobenzofuran-5-yl)acetonitrile for 2-(2,2-difluorobenzo[d][1,3]dioxol-5-yl)acetonitrile. ¹H NMR (501 MHz, DMSO-d₆) δ 12.17 (s, 1H), 7.20 (d, J=2.0 Hz, 1H), 7.04 (dd, J=8.4, 2.2 Hz, 1H), 6.69 (d, J=8.3 Hz, 1H), 4.49 (t, J=8.7 Hz, 2H), 3.15 (t, J=8.7 Hz, 2H), 1.43 (s, 6H).

Example 71B

Methyl 4-{(2R,4R)-4-[2-(2,3-dihydro-1-benzofuran-5-yl)-2-methylpropanamido]-7-methoxy-3,4-dihydro-2H-1-benzopyran-2-yl}benzoate Example 71A (25.6 mg, 0.124 mmol) was dissolved in N,N-dimethylformamide (0.5 mL) and pyridine (0.5 mL). Example 1C (37.0 mg, 0.106 mmol) and 1-(3-dimethylaminopropyl)-3-ethylcarbodiimide hydrochloride (44.8 mg, 0.234 mmol) were added and the reaction mixture was stirred at 60° C. for 6 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (22.5 mg, 42%). $^1$H NMR (400 MHz, DMSO-$d_6$) δ 8.03-7.96 (m, 2H), 7.62-7.55 (m, 2H), 7.45 (d, J=8.9 Hz, 1H), 7.22 (d, J=2.1 Hz, 1H), 7.05 (dd, J=8.3, 2.1 Hz, 1H), 6.80 (d, J=8.5 Hz, 1H), 6.68 (d, J=8.3 Hz, 1H), 6.47-6.39 (m, 2H), 5.43-5.27 (m, 2H), 4.48 (t, J=8.6 Hz, 2H), 3.86 (s, 3H), 3.69 (s, 3H), 3.14 (t, J=8.7 Hz, 2H), 2.16-1.92 (m, 2H), 1.46 (s, 3H), 1.45 (s, 3H); MS (ESI−) m/z 500 (M−H)⁻.

Example 71C

4-{(2R,4R)-4-[2-(2,3-dihydro-1-benzofuran-5-yl)-2-methylpropanamido]-7-methoxy-3,4-dihydro-2H-1-benzopyran-2-yl}benzoic acid Example 71B (19.5 mg, 0.039 mmol) and potassium trimethylsilanolate (19.2 mg, 90% purity, 0.135 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (16.4 mg, 87%). $^1$H NMR (400 MHz, DMSO-$d_6$) δ 12.97 (s, 1H), 8.01-7.94 (m, 2H), 7.59-7.52 (m, 2H), 7.45 (d, J=8.8 Hz, 1H), 7.22 (d, J=1.9 Hz, 1H), 7.05 (dd, J=8.4, 2.1 Hz, 1H), 6.81 (dd, J=8.4, 1.0 Hz, 1H), 6.69 (d, J=8.3 Hz, 1H), 6.47-6.39 (m, 2H), 5.45-5.27 (m, 2H), 4.48 (t, J=8.6 Hz, 2H), 3.69 (s, 3H), 3.14 (t, J=8.6 Hz, 2H), 2.13-1.96 (m, 2H), 1.46 (s, 3H), 1.45 (s, 3H); MS (ESI−) m/z 486 (M−H)⁻.

Example 72

4-{(2R,4R)-4-[(3,3-difluoro-1-phenylcyclobutane-1-carbonyl)amino]-7-methoxy-3,4-dihydro-2H-1-benzopyran-2-yl}benzoic acid Example 72A Methyl 4-{(2R,4R)-4-[(3,3-difluoro-1-phenylcyclobutane-1-carbonyl)amino]-7-methoxy-3,4-dihydro-2H-1-benzopyran-2-yl}benzoate 3,3-difluoro-1-phenylcyclobutanecarboxylic acid (29.7 mg, 0.140 mmol) was dissolved in N,N-dimethylformamide (0.5 mL) and pyridine (0.5 mL). Example 1C (38.1 mg, 0.109 mmol) and 1-(3-dimethylaminopropyl)-3-ethylcarbodiimide hydrochloride (28.3 mg, 0.148 mmol) were added and the reaction mixture was stirred at 60° C. for 5 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (28.5 mg, 52%). $^1$H NMR (400 MHz, DMSO-$d_6$) δ 8.23 (d, J=8.8 Hz, 1H), 8.02-7.95 (m, 2H), 7.62-7.53 (m, 2H), 7.47-7.33 (m, 4H), 7.33-7.23 (m, 1H), 6.53 (d, J=8.6 Hz, 1H), 6.43 (d, J=2.4 Hz, 1H), 6.34 (dd, J=8.6, 2.5 Hz, 1H), 5.37 (dd, J=11.8, 1.8 Hz, 1H), 5.26 (ddd, J=11.3, 8.7, 6.1 Hz, 1H), 3.86 (s, 3H), 3.68 (s, 3H), 3.44-3.28 (m, 2H), 3.16-2.92 (m, 2H), 2.14-2.02 (m, 1H), 1.91 (q, J=12.0 Hz, 1H); MS (ESI−) m/z 506 (M−H)⁻.

Example 72B

4-{(2R,4R)-4-[(3,3-difluoro-1-phenylcyclobutane-1-carbonyl)amino]-7-methoxy-3,4-dihydro-2H-1-benzopyran-2-yl}benzoic acid Example 72A (25.5 mg, 0.050 mmol) and potassium trimethylsilanolate (17.6 mg, 90% purity, 0.123 mmol) were dissolved in tetrahydrofuran (1 mL) and stirred at ambient temperature for 4 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (20.9 mg, 84%). $^1$H NMR (400 MHz, DMSO-$d_6$) δ 12.95 (s, 1H), 8.23 (d, J=8.8 Hz, 1H), 8.01-7.94 (m, 2H), 7.58-7.51 (m, 2H), 7.46-7.33 (m, 4H), 7.33-7.24 (m, 1H), 6.53 (dd, J=8.6, 1.0 Hz, 1H), 6.43 (d, J=2.5 Hz, 1H), 6.34 (dd, J=8.6, 2.5 Hz, 1H), 5.36 (dd, J=11.6, 1.8 Hz, 1H), 5.25 (ddd, J=11.1, 8.5, 6.0 Hz, 1H), 3.68 (s, 3H), 3.40-3.32 (m, 2H), 3.04 (dqd, J=26.9, 14.2, 3.0 Hz, 2H), 2.14-2.03 (m, 1H), 1.92 (dt, J=13.1, 11.5 Hz, 1H); MS (ESI−) m/z 492 (M−H)⁻.

Example 73

4-{(2R,4R)-4-[2-(3-chlorophenoxy)-2-methylpropanamido]-7-methoxy-3,4-dihydro-2H-1-benzopyran-2-yl}benzoic acid Example 73 was prepared according to the procedure described in Example 2, substituting 2-(3-chlorophenoxy)-2-methyl-propionic acid for 1-(3,4-dichlorophenyl)-cyclopropanecarboxylic acid. $^1$H NMR (400 MHz, DMSO-$d_6$) δ 8.40 (d, J=8.9 Hz, 1H), 8.03-7.93 (m, 2H), 7.61-7.54 (m, 2H), 7.32 (t, J=8.2 Hz, 1H), 7.10-7.03 (m, 1H), 6.94 (t, J=2.2 Hz, 1H), 6.90-6.83 (m, 2H), 6.50-6.40 (m, 2H), 5.36 (td, J=10.4, 9.5, 6.6 Hz, 2H), 3.70 (s, 3H), 2.19-2.08 (m, 2H), 1.56 (s, 3H), 1.49 (s, 3H). MS (APCI+) m/z 496.3 (M+H)⁺.

Example 74

4-[(2R,4R)-7-methoxy-4-{[1-(4-methoxyphenyl)cyclopropane-1-carbonyl]amino}-3,4-dihydro-2H-1-benzopyran-2-yl]benzoic acid Example 74 was prepared according to the procedure described in Example 2, substituting 1-(4-methoxyphenyl)-cyclopropanecarboxylic acid for 1-(3,4-dichlorophenyl)-cyclopropanecarboxylic acid. $^1$H NMR (400 MHz, DMSO-$d_6$) δ 8.01-7.93 (m, 2H), 7.58-7.51 (m, 2H), 7.31-7.23 (m, 2H), 6.96-6.90 (m, 1H), 6.89-6.82 (m, 2H), 6.78 (d, J=8.8 Hz, 1H), 6.53 (dd, J=8.6, 2.6 Hz, 1H), 6.40 (d, J=2.5 Hz, 1H), 5.37-5.22 (m, 2H), 3.71 (s, 3H), 3.69 (s, 3H), 2.18-1.98 (m, 2H), 1.50-1.41 (m, 1H), 1.37-1.27 (m, 1H), 1.05-0.90 (m, 2H). MS (APCI+) m/z 474.4 (M+H)+.

Example 75

4-{(2R,4R)-7-methoxy-4-[(1-phenylcyclopropane-1-carbonyl)amino]-3,4-dihydro-2H-1-benzopyran-2-yl}benzoic acid Example 75 was prepared according to the procedure described in Example 2, substituting 1-phenyl-cyclopropanecarboxylic acid for 1-(3,4-dichlorophenyl)-cyclopropanecarboxylic acid. $^1$H NMR (400 MHz, DMSO-d$_6$) δ 8.00-7.93 (m, 2H), 7.58-7.51 (m, 2H), 7.39-7.29 (m, 4H), 7.29-7.21 (m, 1H), 6.96-6.87 (m, 2H), 6.52 (dd, J=8.6, 2.6 Hz, 1H), 6.40 (d, J=2.6 Hz, 1H), 5.37-5.23 (m, 2H), 3.69 (s, 3H), 2.20-1.97 (m, 2H), 1.53-1.43 (m, 1H), 1.40-1.30 (m, 1H), 1.11-0.95 (m, 2H). MS (APCI+) m/z 444.4 (M+H)+.

Example 76

4-[(2R,4R)-4-{[1-(4-chlorophenyl)cyclobutane-1-carbonyl]amino}-7-methoxy-3,4-dihydro-2H-1-benzopyran-2-yl]benzoic acid Example 76 was prepared according to the procedure described in Example 2, substituting 1-(4-chlorophenyl)cyclobutanecarboxylic acid for 1-(3,4-dichlorophenyl)-cyclopropanecarboxylic acid. $^1$H NMR (400 MHz, DMSO-d$_6$) δ 8.03-7.93 (m, 3H), 7.61-7.54 (m, 2H), 7.39 (s, 4H), 6.59 (dd, J=8.5, 1.0 Hz, 1H), 6.41 (d, J=2.5 Hz, 1H), 6.38 (dd, J=8.5, 2.6 Hz, 1H), 5.34 (dd, J=11.4, 2.0 Hz, 1H), 5.31-5.20 (m, 1H), 3.69 (s, 3H), 2.83-2.64 (m, 2H), 2.46-2.28 (m, 2H), 2.14-1.92 (m, 2H), 1.91-1.69 (m, 2H). MS (APCI+) m/z 492.4 (M+H)+.

Example 77

4-{(2R,4R)-4-[2-(4-chloro-3-methylphenoxy)-2-methylpropanamido]-7-methoxy-3,4-dihydro-2H-1-benzopyran-2-yl}benzoic acid Example 77 was prepared according to the procedure described in Example 2, substituting 2-(4-chloro-3-methylphenoxy)-2-methyl-propionic acid for 1-(3,4-dichlorophenyl)-cyclopropanecarboxylic acid. $^1$H NMR (400 MHz, DMSO-d$_6$) δ 8.31 (d, J=8.9 Hz, 1H), 8.03-7.95 (m, 2H), 7.61-7.54 (m, 2H), 7.29 (d, J=8.8 Hz, 1H), 6.91-6.82 (m, 2H), 6.76 (dd, J=8.8, 3.0 Hz, 1H), 6.46 (dd, J=8.5, 2.6 Hz, 1H), 6.43 (d, J=2.6 Hz, 1H), 5.41-5.29 (m, 2H), 3.70 (s, 3H), 2.25 (s, 3H), 2.18-2.09 (m, 2H), 1.53 (s, 3H), 1.46 (s, 3H). MS (APCI+) m/z 510.4 (M+H)+.

Example 78

4-[(2R,4R)-7-methoxy-4-{2-methyl-2-[3-(trifluoromethyl)phenoxy]propanamido}-3,4-dihydro-2H-1-benzopyran-2-yl]benzoic acid Example 78 was prepared according to the procedure described in Example 2, substituting 2-methyl-2-[3-(trifluoromethyl)phenoxy]propanoic acid for 1-(3,4-dichlorophenyl)-cyclopropanecarboxylic acid. $^1$H NMR (400 MHz, DMSO-d$_6$) δ 8.47 (d, J=8.9 Hz, 1H), 8.02-7.95 (m, 2H), 7.60-7.49 (m, 3H), 7.35 (d, J=7.9 Hz, 1H), 7.24-7.13 (m, 2H), 6.84-6.77 (m, 1H), 6.45-6.38 (m, 2H), 5.42-5.30 (m, 2H), 3.69 (s, 3H), 2.17-1.99 (m, 2H), 1.59 (s, 3H), 1.52 (s, 3H). MS (APCI+) m/z 530.3 (M+H)+.

Example 79

4-[(2R,4R)-4-(2-ethyl-2-phenylbutanamido)-7-methoxy-3,4-dihydro-2H-1-benzopyran-2-yl]benzoic acid Example 79 was prepared according to the procedure described in Example 2, substituting 2-ethyl-2-phenylbutanoic acid for 1-(3,4-dichlorophenyl)-cyclopropanecarboxylic acid. $^1$H NMR (400 MHz, DMSO-d$_6$) δ 8.47 (d, J=8.9 Hz, 1H), 8.02-7.95 (m, 2H), 7.60-7.49 (m, 3H), 7.35 (d, J=7.9 Hz, 1H), 7.24-7.13 (m, 2H), 6.84-6.77 (m, 1H), 6.45-6.38 (m, 2H), 5.42-5.30 (m, 2H), 3.69 (s, 3H), 2.17-1.99 (m, 2H), 1.59 (s, 3H), 1.52 (s, 3H). MS (APCI+) m/z 530.3 (M+H)+.

Example 80

4-{(2R,4R)-4-[(3,3-difluoro-1-phenylcyclopentane-1-carbonyl)amino]-7-methoxy-3,4-dihydro-2H-1-benzopyran-2-yl}benzoic acid Example 80 was prepared according to the procedure described in Example 2, substituting 3,3-difluoro-1-phenylcyclopentanecarboxylic acid for 1-(3,4-dichlorophenyl)-cyclopropanecarboxylic acid. $^1$H NMR (400 MHz, DMSO-d$_6$) δ 8.02-7.91 (m, 3H), 7.56 (d, J=8.0 Hz, 2H), 7.37 (d, J=4.2 Hz, 4H), 7.33-7.24 (m, 1H), 6.49-6.41 (m, 1H), 6.39 (t, J=2.3 Hz, 1H), 6.34-6.25 (m, 1H), 5.37-5.21 (m, 2H), 3.67 (s, 3H), 3.49-3.15 (m, 1H), 2.96-2.73 (m, 1H), 2.62-2.37 (m, 1H), 2.29-1.88 (m, 5H). MS (APCI+) m/z 508.4 (M+H)+.

Example 81

4-[(2R,4R)-4-{[1-(3,4-difluorophenyl)cyclobutane-1-carbonyl]amino}-7-methoxy-3,4-dihydro-2H-1-benzopyran-2-yl]benzoic acid Example 81 was prepared according to the procedure described in Example 2, substituting 1-(3,4-difluorophenyl)cyclobutanecarboxylic acid for 1-(3,4-dichlorophenyl)-cyclopropanecarboxylic acid. $^1$H NMR (400 MHz, DMSO-d$_6$) δ 8.05-7.95 (m, 3H), 7.57 (d, J=8.2 Hz, 2H), 7.44-7.33 (m, 2H), 7.24-7.14 (m, 1H), 6.67-6.55 (m, 1H), 6.45-6.34 (m, 2H), 5.40-5.31 (m, 1H), 5.31-5.21 (m, 1H), 3.69 (s, 3H), 2.82-2.64 (m, 2H), 2.46-2.29 (m, 2H), 2.15-2.04 (m, 1H), 2.03-1.92 (m, 1H), 1.91-1.70 (m, 2H). MS (APCI+) m/z 494.4 (M+H)+.

Example 82

4-[(2R,4R)-7-methoxy-4-({1-[2-(trifluoromethyl)phenyl]cyclobutane-1-carbonyl}amino)-3,4-dihydro-2H-1-benzopyran-2-yl]benzoic acid Example 82 was prepared according to the procedure described in Example 2, substituting 1-[2-(trifluoromethyl)phenyl]cyclobutanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.72-7.59 (m, 1H), 7.59-7.54 (m, 2H), 7.54-7.43 (m, 2H), 7.08 (d, J=8.8 Hz, 1H), 6.89-6.82 (m, 1H), 6.47 (dd, J=8.5, 2.6 Hz, 1H), 6.41 (d, J=2.6 Hz, 1H), 5.39-5.27 (m, 2H), 3.69 (s, 3H), 2.80 (d, J=10.3 Hz, 1H), 2.73-2.43 (m, 3H), 2.24-2.02 (m, 3H), 1.77 (q, J=10.0 Hz, 1H). MS (APCI+) m/z 526.4 (M+H)+.

Example 83

4-[(2R,4R)-7-methoxy-4-({1-[3-(trifluoromethoxy)phenyl]cyclobutane-1-carbonyl}amino)-3,4-dihydro-2H-1-benzopyran-2-yl]benzoic acid Example 83 was prepared according to the procedure described in Example 2, substituting 1-[(3-trifluoromethoxy)phenyl]cyclobutanecarboxylic acid for 1-(3,4-dichlorophenyl)-cyclopropanecarboxylic acid. $^1$H NMR (400 MHz, DMSO-$d_6$) δ 8.08 (d, J=8.9 Hz, 1H), 8.02-7.95 (m, 2H), 7.60-7.53 (m, 2H), 7.49 (t, J=8.0 Hz, 1H), 7.44-7.37 (m, 1H), 7.35-7.29 (m, 1H), 7.28-7.20 (m, 1H), 6.54 (dd, J=8.6, 1.0 Hz, 1H), 6.41 (d, J=2.5 Hz, 1H), 6.32 (dd, J=8.6, 2.6 Hz, 1H), 5.38-5.31 (m, 1H), 5.31-5.21 (m, 1H), 3.68 (s, 3H), 2.87-2.66 (m, 2H), 2.50-2.29 (m, 2H), 2.15-1.70 (m, 4H). MS (APCI+) m/z 542.4 (M+H)+.

Example 84

4-[(2R,4R)-4-{[1-(4-fluorophenyl)cyclopropane-1-carbonyl]amino}-7-methoxy-3,4-dihydro-2H-1-benzopyran-2-yl]benzoic acid Example 84 was prepared according to the procedure described in Example 2, substituting 1-(4-fluorophenyl)cyclopropanecarboxylic acid for 1-(3,4-dichlorophenyl)-cyclopropanecarboxylic acid. $^1$H NMR (400 MHz, DMSO-$d_6$) δ 8.01-7.94 (m, 2H), 7.58-7.51 (m, 2H), 7.45-7.34 (m, 2H), 7.18-7.09 (m, 2H), 7.05 (d, J=8.9 Hz, 1H), 6.93 (dd, J=8.6, 1.0 Hz, 1H), 6.53 (dd, J=8.6, 2.6 Hz, 1H), 6.40 (d, J=2.6 Hz, 1H), 5.37-5.24 (m, 2H), 3.70 (s, 3H), 2.17-1.99 (m, 2H), 1.53-1.43 (m, 1H), 1.41-1.31 (m, 1H), 1.09-0.95 (m, 2H). MS (APCI+) m/z 462.4 (M+H)+.

Example 85

4-[(2R,4R)-4-{[1-(3-fluorophenyl)cyclopropane-1-carbonyl]amino}-7-methoxy-3,4-dihydro-2H-1-benzopyran-2-yl]benzoic acid Example 85 was prepared according to the procedure described in Example 2, substituting 1-(3-fluorophenyl)cyclopropanecarboxylic acid for 1-(3,4-dichlorophenyl)-cyclopropanecarboxylic acid. $^1$H NMR (400 MHz, DMSO-$d_6$) δ 8.01-7.94 (m, 2H), 7.59-7.52 (m, 2H), 7.41-7.31 (m, 1H), 7.26-7.18 (m, 1H), 7.18-7.11 (m, 1H), 7.11-7.00 (m, 1H), 6.94 (dd, J=8.6, 1.0 Hz, 1H), 6.53 (dd, J=8.6, 2.6 Hz, 1H), 6.41 (d, J=2.6 Hz, 1H), 5.38-5.26 (m, 2H), 3.70 (s, 3H), 2.18-1.99 (m, 2H), 1.53-1.43 (m, 1H), 1.41-1.31 (m, 1H), 1.19-0.99 (m, 2H). MS (APCI+) m/z 462.4 (M+H)+.

Example 86

4-[(2R,4R)-7-methoxy-4-{[1-(3-methoxy-4-methylphenyl)cyclopropane-1-carbonyl]amino}-3,4-dihydro-2H-1-benzopyran-2-yl]benzoic acid Example 86 was prepared according to the procedure described in Example 2, substituting 1-(3-methoxy-4-methylphenyl)cyclopropanecarboxylic acid for 1-(3,4-dichlorophenyl)-cyclopropanecarboxylic acid. $^1$H NMR (400 MHz, DMSO-$d_6$) δ 8.01-7.93 (m, 2H), 7.58-7.51 (m, 2H), 7.10-7.02 (m, 1H), 7.02-6.95 (m, 1H), 6.91 (d, J=1.5 Hz, 1H), 6.83 (dd, J=7.5, 1.7 Hz, 1H), 6.53 (dd, J=8.6, 2.6 Hz, 1H), 6.40 (d, J=2.6 Hz, 1H), 5.31 (ddd, J=12.5, 9.7, 4.4 Hz, 2H), 3.76 (s, 3H), 3.69 (s, 3H), 2.17-2.01 (m, 5H), 1.54-1.44 (m, 1H), 1.36-1.25 (m, 1H), 1.13-1.03 (m, 1H), 1.02-0.92 (m, 1H). MS (APCI+) m/z 488.4 (M+H)+.

Example 87

4-[(2R,4R)-4-{[1-(3-cyanophenyl)cyclopropane-1-carbonyl]amino}-7-methoxy-3,4-dihydro-2H-1-benzopyran-2-yl]benzoic acid Example 87 was prepared according to the procedure described in Example 2, substituting 1-(3-cyanophenyl)cyproanecarboxylic acid for 1-(3,4-dichlorophenyl)-cyclopropanecarboxylic acid. $^1$H NMR (400 MHz, DMSO-$d_6$) δ 8.02-7.95 (m, 2H), 7.80-7.75 (m, 1H), 7.71 (dd, J=7.8, 1.8 Hz, 2H), 7.59-7.46 (m, 3H), 7.36 (d, J=8.8 Hz, 1H), 6.95 (d, J=8.6 Hz, 1H), 6.53 (dd, J=8.6, 2.6 Hz, 1H), 6.41 (d, J=2.5 Hz, 1H), 5.38-5.27 (m, 2H), 3.70 (s, 3H), 2.17-1.96 (m, 2H), 1.57-1.47 (m, 1H), 1.44-1.34 (m, 1H), 1.19-1.02 (m, 2H). MS (APCI+) m/z 469.4 (M+H)+.

Example 88

4-[(2R,4R)-4-{[1-(3-bromophenyl)cyclopropane-1-carbonyl]amino}-7-methoxy-3,4-dihydro-2H-1-benzopyran-2-yl]benzoic acid Example 88 was prepared according to the procedure described in Example 2, substituting 1-(3-bromophenyl)cyproanecarboxylic acid for 1-(3,4-dichlorophenyl)-cyclopropanecarboxylic acid. $^1$H NMR (400 MHz, DMSO-$d_6$) δ 8.01-7.94 (m, 2H), 7.59-7.49 (m, 3H), 7.48-7.41 (m, 1H), 7.40-7.24 (m, 3H), 6.98-6.91 (m, 1H), 6.53 (dd, J=8.6, 2.6 Hz, 1H), 6.41 (d, J=2.5 Hz, 1H), 5.37-5.25 (m, 2H), 3.70 (s, 3H), 2.17-1.99 (m, 2H), 1.53-1.43 (m, 1H), 1.39-1.29 (m, 1H), 1.19-1.05 (m, 1H), 1.08-0.97 (m, 1H). MS (APCI+) m/z 522.3 (M+H)+.

Example 89

4-[(2R,4R)-4-{[1-(2-bromophenyl)cyclopropane-1-carbonyl]amino}-7-methoxy-3,4-dihydro-2H-1-benzopyran-2-yl]benzoic acid Example 89 was prepared according to the procedure described in Example 2, substituting 1-(2-bromophenyl)cyclopropanecarboxylic acid for 1-(3,4-dichlorophenyl)-cyclopropanecarboxylic acid. $^1$H NMR (400 MHz, DMSO-$d_6$) δ 8.01-7.94 (m, 2H), 7.59-7.49 (m, 3H), 7.48-7.41 (m, 1H), 7.40-7.24 (m, 3H), 6.98-6.91 (m, 1H), 6.53 (dd, J=8.6, 2.6 Hz, 1H), 6.41 (d, J=2.5 Hz, 1H), 5.37-5.25 (m, 2H), 3.70 (s, 3H), 2.17-1.99 (m, 2H), 1.53-1.43 (m, 1H), 1.39-1.29 (m, 1H), 1.19-1.05 (m, 1H), 1.08-0.97 (m, 1H). MS (APCI+) m/z 522.3 (M+H)+.

Example 90

4-[(2R,4R)-4-{[1-(3-fluorophenyl)cyclopentane-1-carbonyl]amino}-7-methoxy-3,4-dihydro-2H-1-benzopyran-2-yl]benzoic acid Example 90 was prepared according to the procedure described in Example 2, substituting 1-(3-fluorophenyl)cyclopentanecarboxylic acid for 1-(3,4-dichlorophenyl)-cyclopropanecarboxylic acid. $^1$H NMR (400 MHz, DMSO-$d_6$)

δ 8.02-7.95 (m, 2H), 7.80 (d, J=8.9 Hz, 1H), 7.60-7.53 (m, 2H), 7.43-7.32 (m, 1H), 7.25-7.12 (m, 2H), 7.11-7.01 (m, 1H), 6.52 (d, J=8.6 Hz, 1H), 6.40 (d, J=2.5 Hz, 1H), 6.34 (dd, J=8.6, 2.6 Hz, 1H), 5.37-5.21 (m, 2H), 3.68 (s, 3H), 2.70-2.59 (m, 1H), 2.52-2.46 (m, 1H), 2.10-1.72 (m, 4H), 1.71-1.55 (m, 4H). MS (APCI+) m/z 490.4 (M+H)$^+$.

Example 91

4-[(2R,4R)-4-{[1-(2-fluorophenyl)cyclopentane-1-carbonyl]amino}-7-methoxy-3,4-dihydro-2H-1-benzopyran-2-yl]benzoic acid Example 91 was prepared according to the procedure described in Example 2, substituting 1-(2-fluorophenyl)cyclopentanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.59-7.52 (m, 2H), 7.48-7.34 (m, 2H), 7.35-7.24 (m, 1H), 7.22-7.09 (m, 2H), 6.82 (d, J=8.6 Hz, 1H), 6.45 (dd, J=8.6, 2.6 Hz, 1H), 6.40 (d, J=2.6 Hz, 1H), 5.37-5.24 (m, 2H), 3.68 (s, 3H), 2.64-2.54 (m, 1H), 2.32 (dt, J=13.0, 6.4 Hz, 1H), 2.11-1.94 (m, 3H), 1.85-1.54 (m, 5H). MS (APCI+) m/z 490.4 (M+H)$^+$.

Example 92

4-[(2R,4R)-4-{[1-(4-cyanophenyl)cyclopropane-1-carbonyl]amino}-7-methoxy-3,4-dihydro-2H-1-benzopyran-2-yl]benzoic acid Example 92 was prepared according to the procedure described in Example 2, substituting 1-(4-cyanophenyl)cyclopropanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.81-7.72 (m, 2H), 7.59-7.48 (m, 4H), 7.40 (d, J=8.8 Hz, 1H), 6.95 (d, J=8.6 Hz, 1H), 6.54 (dd, J=8.6, 2.6 Hz, 1H), 6.41 (d, J=2.6 Hz, 1H), 5.39-5.27 (m, 2H), 3.70 (s, 3H), 2.18-1.96 (m, 2H), 1.59-1.47 (m, 1H), 1.47-1.36 (m, 1H), 1.19-1.04 (m, 2H). MS (APCI+) m/z 469.4 (M+H)$^+$.

Example 93

4-[(2R,4R)-4-{[1-(4-fluorophenyl)cyclopentane-1-carbonyl]amino}-7-methoxy-3,4-dihydro-2H-1-benzopyran-2-yl]benzoic acid Example 93 was prepared according to the procedure described in Example 2, substituting 1-(4-fluorophenyl)cyclopentanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.75 (d, J=8.9 Hz, 1H), 7.60-7.53 (m, 2H), 7.46-7.35 (m, 2H), 7.19-7.08 (m, 2H), 6.55 (dd, J=8.6, 1.0 Hz, 1H), 6.40 (d, J=2.5 Hz, 1H), 6.36 (dd, J=8.5, 2.6 Hz, 1H), 5.36-5.21 (m, 2H), 3.68 (s, 3H), 2.69-2.58 (m, 1H), 2.53-2.46 (m, 1H), 2.08-1.93 (m, 2H), 1.90-1.56 (m, 5H). MS (APCI+) m/z 490.4 (M+H)$^+$.

Example 94

4-[(2R,4R)-4-{[1-(2-bromophenyl)cyclobutane-1-carbonyl]amino}-7-methoxy-3,4-dihydro-2H-1-benzopyran-2-yl]benzoic acid Example 94 was prepared according to the procedure described in Example 2, substituting 1-(2-bromophenyl)-cyclobutanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.60-7.53 (m, 3H), 7.47 (dd, J=7.8, 1.8 Hz, 1H), 7.39 (td, J=7.5, 1.3 Hz, 1H), 7.19 (td, J=7.6, 1.7 Hz, 1H), 6.96 (dd, J=8.6, 1.0 Hz, 1H), 6.46 (dd, J=8.6, 2.5 Hz, 1H), 6.40 (d, J=2.5 Hz, 1H), 5.39-5.28 (m, 2H), 3.69 (s, 3H), 2.99-2.88 (m, 1H), 2.72-2.63 (m, 1H), 2.52-2.44 (m, 1H), 2.41-2.29 (m, 1H), 2.17-1.99 (m, 3H), 1.82-1.70 (m, 1H). MS (APCI+) m/z 536.3 (M+H)$^+$.

Example 95

4-[(2R,4R)-4-{[1-(3,4-dichlorophenyl)cyclobutane-1-carbonyl]amino}-7-methoxy-3,4-dihydro-2H-1-benzopyran-2-yl]benzoic acid Example 95 was prepared according to the procedure described in Example 2, substituting 1-(3,4-dichlorophenyl)-cyclobutanecarboxylic acid for 1-(3,4-dichlorophenyl)-cyclopropanecarboxylic acid. $^1$H NMR (400 MHz, DMSO-d$_6$) δ 8.07 (d, J=8.8 Hz, 1H), 8.02-7.95 (m, 2H), 7.65-7.54 (m, 4H), 7.34 (dd, J=8.4, 2.2 Hz, 1H), 6.63-6.55 (m, 1H), 6.42 (d, J=2.6 Hz, 1H), 6.38 (dd, J=8.6, 2.5 Hz, 1H), 5.38-5.32 (m, 1H), 5.32-5.21 (m, 1H), 3.69 (s, 3H), 2.83-2.64 (m, 2H), 2.46-2.30 (m, 2H), 2.16-1.70 (m, 4H). MS (APCI+) m/z 526.3 (M+H)$^+$.

Example 96

4-[(2R,4R)-4-{[1-(2-chlorophenyl)cyclobutane-1-carbonyl]amino}-7-methoxy-3,4-dihydro-2H-1-benzopyran-2-yl]benzoic acid Example 96 was prepared according to the procedure described in Example 2, substituting 1-(2-chlorophenyl)-cyclobutanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.59-7.52 (m, 2H), 7.48 (dd, J=7.7, 1.7 Hz, 1H), 7.43-7.31 (m, 2H), 7.31-7.23 (m, 1H), 7.19 (d, J=8.9 Hz, 1H), 6.93-6.86 (m, 1H), 6.46 (dd, J=8.6, 2.6 Hz, 1H), 6.40 (d, J=2.5 Hz, 1H), 5.39-5.27 (m, 2H), 3.69 (s, 3H), 2.95-2.84 (m, 1H), 2.72-2.61 (m, 1H), 2.54-2.44 (m, 1H), 2.40-2.28 (m, 1H), 2.15-1.96 (m, 3H), 1.85-1.71 (m, 1H). MS (APCI+) m/z 492.4 (M+H)$^+$.

Example 97

4-{(2R,4R)-7-methoxy-4-[(1-phenylcyclopentane-1-carbonyl)amino]-3,4-dihydro-2H-1-benzopyran-2-yl}benzoic acid Example 97 was prepared according to the procedure described in Example 2, substituting 1-phenylcyclopentanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.70 (d, J=8.9 Hz, 1H), 7.60-7.52 (m, 2H), 7.42-7.35 (m, 2H), 7.35-7.28 (m, 2H), 7.28-7.19 (m, 1H), 6.53 (dd, J=8.6, 1.0 Hz, 1H), 6.39 (d, J=2.5 Hz, 1H), 6.33 (dd, J=8.6, 2.5 Hz, 1H), 5.38-5.21 (m, 2H), 3.67 (s, 3H), 2.70-2.59 (m, 1H), 2.53-2.46 (m, 1H), 2.05-1.96 (m, 2H), 1.94-1.83 (m, 1H), 1.83-1.72 (m, 1H), 1.70-1.54 (m, 4H). MS (APCI+) m/z 472.4 (M+H)$^+$.

Example 98

4-[(2R,4R)-4-{[1-(4-chlorophenyl)cyclopentane-1-carbonyl]amino}-7-methoxy-3,4-dihydro-2H-1-benzopyran-2-yl]benzoic acid Example 98 was prepared according to the procedure described in Example 2, substituting 1-(4-chlorophenyl)- cyclopentanecarboxylic acid for 1-(3,4-dichlorophenyl)-cyclopropanecarboxylic acid. $^1$H NMR (400 MHz, DMSO-$d_6$) δ 8.02-7.95 (m, 2H), 7.77 (d, J=8.8 Hz, 1H), 7.59-7.52 (m, 2H), 7.43-7.33 (m, 4H), 6.58-6.51 (m, 1H), 6.40 (d, J=2.5 Hz, 1H), 6.36 (dd, J=8.5, 2.6 Hz, 1H), 5.36-5.21 (m, 2H), 3.68 (s, 3H), 2.67-2.57 (m, 1H), 2.53-2.45 (m, 1H), 2.10-1.93 (m, 2H), 1.91-1.72 (m, 2H), 1.71-1.55 (m, 4H). MS (APCI+) m/z 506.4 (M+H)$^+$.

Example 99

4-[(2R,4R)-4-{2-[(2H-1,3-benzodioxol-5-yl)oxy]-2-methylpropanamido}-7-methoxy-3,4-dihydro-2H-1-benzopyran-2-yl]benzoic acid Example 99A methyl 4-[(2R,4R)-4-{2-[(2H-1,3-benzodioxol-5-yl)oxy]-2-methylpropanamido}-7-methoxy-3,4-dihydro-2H-1-benzopyran-2-yl]benzoate Ammonium 2-(1,3-benzodioxol-5-yloxy)-2-methylpropanoate (40.1 mg, 0.166 mmol) was dissolved in N,N-dimethylformamide (0.5 mL) and pyridine (0.5 mL). Example 1C (36.9 mg, 0.105 mmol) and 1-(3-dimethylaminopropyl)-3-ethylcarbodiimide hydrochloride (32.1 mg, 0.167 mmol) were added and the reaction mixture was stirred at 60° C. for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (10.3 mg, 19%). $^1$H NMR (400 MHz, DMSO-$d_6$) δ 8.27 (d, J=8.9 Hz, 1H), 8.06-7.95 (m, 2H), 7.65-7.57 (m, 2H), 6.98-6.90 (m, 1H), 6.79 (d, J=8.5 Hz, 1H), 6.58 (d, J=2.4 Hz, 1H), 6.51 (dd, J=8.5, 2.6 Hz, 1H), 6.46 (d, J=2.6 Hz, 1H), 6.40 (dd, J=8.4, 2.4 Hz, 1H), 5.96 (s, 2H), 5.46-5.28 (m, 2H), 3.87 (s, 3H), 3.71 (s, 3H), 2.26-2.12 (m, 2H), 1.47 (s, 3H), 1.38 (s, 3H); MS (ESI-) m/z 518 (M-H)$^-$.

Example 99B

4-[(2R,4R)-4-{2-[(2H-1,3-benzodioxol-5-yl)oxy]-2-methylpropanamido}-7-methoxy-3,4-dihydro-2H-1-benzopyran-2-yl]benzoic acid Example 99A (7.3 mg, 0.014 mmol) and potassium trimethylsilanolate (7.0 mg, 90% purity, 0.049 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (4.4 mg, 62%). $^1$H NMR (400 MHz, DMSO-$d_6$) δ 12.96 (s, 1H), 8.29 (d, J=9.0 Hz, 1H), 8.02-7.96 (m, 2H), 7.62-7.55 (m, 2H), 6.94 (d, J=8.5 Hz, 1H), 6.80 (d, J=8.5 Hz, 1H), 6.59 (d, J=2.4 Hz, 1H), 6.50 (dd, J=8.5, 2.6 Hz, 1H), 6.45 (d, J=2.5 Hz, 1H), 6.41 (dd, J=8.5, 2.4 Hz, 1H), 5.96 (s, 2H), 5.45-5.31 (m, 2H), 3.71 (s, 3H), 2.27-2.11 (m, 2H), 1.47 (s, 3H), 1.39 (s, 3H); MS (ESI-) m/z 506 (M-H)$^-$.

Example 100

4-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoic acid Example 100A Methyl 4-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoate Example 28C (24.5 mg, 0.119 mmol) was dissolved in N,N-dimethylformamide (0.5 mL) and pyridine (0.5 mL). Example 1C (35.7 mg, 0.102 mmol) and 1-(3-dimethylaminopropyl)-3-ethylcarbodiimide hydrochloride (31.2 mg, 0.163 mmol) were added and the reaction mixture was stirred at 60° C. for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (25.7 mg, 50%). $^1$H NMR (400 MHz, DMSO-$d_6$) δ 8.05-7.96 (m, 2H), 7.60 (d, J=8.1 Hz, 2H), 7.51 (d, J=8.8 Hz, 1H), 7.21 (d, J=8.4 Hz, 1H), 6.81-6.76 (m, 2H), 6.72 (dd, J=8.5, 2.4 Hz, 1H), 6.49-6.41 (m, 2H), 5.43-5.28 (m, 2H), 3.87 (s, 3H), 3.72 (s, 3H), 3.70 (s, 3H), 2.99-2.76 (m, 2H), 2.63 (ddd, J=13.0, 8.3, 5.0 Hz, 1H), 2.20-2.00 (m, 2H), 1.93-1.82 (m, 1H), 1.44 (s, 3H); MS (ESI-) m/z 500 (M-H)$^-$.

Example 100B

4-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoic acid Example 100A (22.5 mg, 0.04 mmol) and potassium trimethylsilanolate (18.0 mg, 90% purity, 0.126 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (18.4 mg, 84%). $^1$H NMR (400 MHz, DMSO-$d_6$) δ 12.95 (s, 1H), 8.02-7.94 (m, 2H), 7.61-7.54 (m, 2H), 7.51 (d, J=8.8 Hz, 1H), 7.21 (d, J=8.3 Hz, 1H), 6.81-6.75 (m, 2H), 6.72 (dd, J=8.4, 2.5 Hz, 1H), 6.49-6.41 (m, 2H), 5.41-5.27 (m, 2H), 3.72 (s, 3H), 3.70 (s, 3H), 2.97-2.77 (m, 2H), 2.63 (ddd, J=13.0, 8.3, 5.0 Hz, 1H), 2.19-2.01 (m, 2H), 1.88 (ddd, J=12.6, 8.3, 7.0 Hz, 1H), 1.44 (s, 3H); MS (ESI-) m/z 486 (M-H)$^-$.

Example 101

4-[(2R,4R)-4-{[1-(3-chlorophenyl)cyclopropane-1-carbonyl]amino}-7-methoxy-3,4-dihydro-2H-1-benzopyran-2-yl]benzoic acid Example 101 was prepared according to the procedure described in Example 2, substituting 1-(3-chlorophenyl)-cyclopropanecarboxylic acid for 1-(3,4-dichlorophenyl)-cyclopropanecarboxylic acid. $^1$H NMR (400 MHz, DMSO-$d_6$) δ 8.02-7.94 (m, 2H), 7.59-7.48 (m, 2H), 7.41-7.26 (m, 5H), 6.98-6.91 (m, 1H), 6.57-6.49 (m, 1H), 6.41 (d, J=2.6 Hz, 1H), 5.38-5.26 (m, 2H), 3.70 (s, 3H), 2.17-1.99 (m, 2H), 1.54-1.44 (m, 1H), 1.40-1.30 (m, 1H), 1.19-1.05 (m, 1H), 1.09-0.98 (m, 1H). MS (APCI+) m/z 478.3 (M+H)$^+$.

Example 102

4-{(2R,4R)-7-methoxy-4-[(1-phenylcyclobutane-1-carbonyl)amino]-3,4-dihydro-2H-1-benzopyran-2-yl}benzoic acid Example 102 was prepared according to the procedure described in Example 2, substituting 1-phenyl-cyclobutanecarboxylic acid for 1-(3,4-dichlorophenyl)-cyclopropanecarboxylic acid. $^1$H NMR (400 MHz, DMSO-$d_6$) δ 8.02-7.95 (m, 2H), 7.90 (d, J=8.9 Hz, 1H), 7.61-7.54 (m, 2H), 7.47-7.30 (m, 4H), 7.29-7.19 (m, 1H), 6.60-6.53 (m, 1H), 6.43-6.30 (m, 2H), 5.38-5.20 (m, 2H), 3.68 (s, 3H), 2.85-2.64 (m, 2H), 2.49-2.29 (m, 2H), 2.13-1.93 (m, 2H), 1.93-1.69 (m, 2H). MS (APCI+) m/z 458.4 (M+H)$^+$.

Example 103

4-[(2R,4R)-7-methoxy-4-{[1-(2-methoxyphenyl)cyclopropane-1-carbonyl]amino}-3,4-dihydro-2H-1-benzopyran-2-yl]benzoic acid Example 103 was prepared according to the procedure described in Example 2, substituting 1-(2-methoxyphenyl)-cyclopropanecarboxylic acid for 1-(3,4-dichlorophenyl)-cyclopropanecarboxylic acid. $^1$H NMR (400 MHz, DMSO-$d_6$) δ 8.02-7.92 (m, 2H), 7.57-7.50 (m, 2H), 7.35-7.18 (m, 2H), 7.01-6.95 (m, 2H), 6.92-6.84 (m, 1H), 6.55 (dd, J=8.6, 2.5 Hz, 1H), 6.38 (d, J=2.6 Hz, 1H), 5.31 (ddd, J=15.1, 10.0, 5.3 Hz, 2H), 3.81 (s, 3H), 3.69 (s, 3H), 2.12-1.97 (m, 2H), 1.62-1.50 (m, 1H), 1.36-1.24 (m, 1H), 1.09-0.97 (m, 1H), 0.86-0.76 (m, 1H). MS (APCI+) m/z 474.4 (M+H)$^+$.

Example 104

4-[(2R,4R)-4-{[1-(4-bromophenyl)cyclobutane-1-carbonyl]amino}-7-methoxy-3,4-dihydro-2H-1-benzopyran-2-yl]benzoic acid Example 104 was prepared according to the procedure described in Example 2, substituting 1-(4-bromophenyl)-cyclobutanecarboxylic acid for 1-(3,4-dichlorophenyl)-cyclopropanecarboxylic acid. $^1$H NMR (400 MHz, DMSO-$d_6$) δ 7.98 (t, J=8.6 Hz, 3H), 7.61-7.48 (m, 4H), 7.38-7.29 (m, 2H), 6.58 (dd, J=8.5, 1.0 Hz, 1H), 6.44-6.34 (m, 2H), 5.38-5.31 (m, 1H), 5.31-5.20 (m, 1H), 3.69 (s, 3H), 2.83-2.64 (m, 2H), 2.46-2.27 (m, 2H), 2.14-1.95 (m, 2H), 1.93-1.69 (m, 2H). MS (APCI+) m/z 536.3 (M+H)$^+$.

Example 105

4-{(2R,4R)-4-[(2,2-difluoro-1-phenylcyclopropane-1-carbonyl)amino]-7-methoxy-3,4-dihydro-2H-1-benzopyran-2-yl}benzoic acid Example 105 was prepared according to the procedure described in Example 2, substituting 2,2-difluoro-1-phenyl-cyclopropanecarboxylic acid for 1-(3,4-dichlorophenyl)-cyclopropanecarboxylic acid. $^1$H NMR (400 MHz, DMSO-$d_6$, mixture of diastereomers) δ 8.57 (d, J=8.8 Hz, 1H), 8.43 (d, J=8.7 Hz, 1H), 8.02-7.93 (m, 2H), 7.61-7.47 (m, 4H), 7.45-7.31 (m, 3H), 6.84-6.77 (m, 1H), 6.73 (d, J=8.0 Hz, 1H), 6.51-6.41 (m, 2H), 5.39-5.34 (m, 1H), 5.36-5.31 (m, 1H), 5.27 (dtd, J=9.5, 7.5, 6.9, 3.4 Hz, 1H), 3.73-3.67 (m, 3H), 2.43-2.29 (m, 1H), 2.21-1.92 (m, 3H). MS (APCI+) m/z 480.3 (M+H)$^+$.

Example 106

4-[(2R,4R)-4-{[1-(2-fluorophenyl)cyclopropane-1-carbonyl]amino}-7-methoxy-3,4-dihydro-2H-1-benzopyran-2-yl]benzoic acid Example 106 was prepared according to the procedure described in Example 2, substituting 1-(2-fluorophenyl)-cyclopropanecarboxylic acid for 1-(3,4-dichlorophenyl)-cyclopropanecarboxylic acid. $^1$H NMR (400 MHz, DMSO-$d_6$) δ 8.01-7.94 (m, 2H), 7.58-7.45 (m, 2H), 7.41-7.27 (m, 2H), 7.20-7.10 (m, 2H), 6.99-6.92 (m, 1H), 6.53 (dd, J=8.6, 2.6 Hz, 1H), 6.40 (d, J=2.6 Hz, 1H), 5.37-5.27 (m, 2H), 3.70 (s, 3H), 2.16-2.02 (m, 2H), 1.62-1.47 (m, 1H), 1.47-1.37 (m, 1H), 1.13-1.03 (m, 1H), 1.05-0.95 (m, 1H). MS (APCI+) m/z 462.4 (M+H)$^+$.

Example 107

4-{(2R,4R)-4-[2-(4-cyanophenoxy)-2-methylpropanamido]-7-methoxy-3,4-dihydro-2H-1-benzopyran-2-yl}benzoic acid Example 107 was prepared according to the procedure described in Example 2, substituting 2-(4-cyanophenoxy)-2-methyl-propionic acid for 1-(3,4-dichlorophenyl)-cyclopropanecarboxylic acid. $^1$H NMR (400 MHz, DMSO-$d_6$) δ 8.43 (d, J=8.9 Hz, 1H), 8.03-7.96 (m, 2H), 7.79-7.71 (m, 2H), 7.61-7.53 (m, 2H), 7.06-6.97 (m, 2H), 6.79 (d, J=8.3 Hz, 1H), 6.48-6.39 (m, 2H), 5.39-5.28 (m, 2H), 3.69 (s, 3H), 2.16-1.96 (m, 2H), 1.62 (s, 3H), 1.55 (s, 3H). MS (APCI+) m/z 487.4 (M+H)$^+$.

Example 108

4-[(2R,4R)-4-{[1-(4-chlorophenyl)cyclopropane-1-carbonyl]amino}-7-methoxy-3,4-dihydro-2H-1-benzopyran-2-yl]benzoic acid Example 108 was prepared according to the procedure described in Example 2, substituting 1-(4-chlorophenyl)-cyclopropanecarboxylic acid for 1-(3,4-dichlorophenyl)-cyclopropanecarboxylic acid. $^1$H NMR (400 MHz, DMSO-$d_6$) δ 8.01-7.94 (m, 2H), 7.58-7.50 (m, 2H), 7.41-7.31 (m, 4H), 7.16 (d, J=8.9 Hz, 1H), 6.98-6.90 (m, 1H), 6.54 (dd, J=8.6, 2.6 Hz, 1H), 6.40 (d, J=2.6 Hz, 1H), 5.37-5.25 (m, 2H), 3.70

(s, 3H), 2.16-2.00 (m, 2H), 1.53-1.44 (m, 1H), 1.44-1.31 (m, 1H), 1.10-0.95 (m, 2H). MS (APCI+) m/z 478.3 (M+H)+.

Example 109

4-[(2R,4R)-7-methoxy-4-{2-methyl-2-[4-(trifluoromethoxy)phenyl]propanamido}-3,4-dihydro-2H-1-benzopyran-2-yl]benzoic acid Example 109 was prepared according to the procedure described in Example 2, substituting 2-methyl-2-[4-(trifluoromethoxy)phenyl]propanoic acid for 1-(3,4-dichlorophenyl)-cyclopropanecarboxylic acid. $^1$H NMR (400 MHz, DMSO-$d_6$) δ 8.03-7.96 (m, 2H), 7.66 (d, J=8.8 Hz, 1H), 7.60-7.54 (m, 2H), 7.51-7.45 (m, 2H), 7.37-7.29 (m, 2H), 6.79-6.72 (m, 1H), 6.41 (d, J=7.7 Hz, 2H), 5.39-5.27 (m, 2H), 3.68 (s, 3H), 2.18-2.08 (m, 1H), 2.09-1.95 (m, 1H), 1.54-1.48 (m, 6H). MS (APCI+) m/z 530.3 (M+H)+.

Example 110

4-{(2R,4R)-4-[2-(4-chlorophenyl)-2-methylpropanamido]-7-methoxy-3,4-dihydro-2H-1-benzopyran-2-yl}benzoic acid Example 110 was prepared according to the procedure described in Example 2, substituting 2-(4-chlorophenyl)-2-methyl-propionic acid for 1-(3,4-dichlorophenyl)-cyclopropanecarboxylic acid. $^1$H NMR (400 MHz, DMSO-$d_6$) δ 8.03-7.96 (m, 2H), 7.65-7.54 (m, 2H), 7.37 (d, J=0.8 Hz, 4H), 6.82 (dd, J=8.6, 1.0 Hz, 1H), 6.47 (dd, J=8.6, 2.6 Hz, 1H), 6.41 (d, J=2.5 Hz, 1H), 5.39-5.28 (m, 2H), 3.69 (s, 3H), 2.18-1.94 (m, 2H), 1.49 (s, 6H). MS (APCI+) m/z 480.3 (M+H)+.

Example 111

4-{(2R,4R)-4-[2-(4-fluorophenyl)-2-methylpropanamido]-7-methoxy-3,4-dihydro-2H-1-benzopyran-2-yl}benzoic acid Example 11 was prepared according to the procedure described in Example 2, substituting 2-(4-fluorophenyl)-2-methyl-propionic acid for 1-(3,4-dichlorophenyl)-cyclopropanecarboxylic acid. $^1$H NMR (400 MHz, DMSO-$d_6$) δ 8.03-7.95 (m, 2H), 7.58 (dd, J=8.6, 4.6 Hz, 3H), 7.43-7.33 (m, 2H), 7.21-7.09 (m, 2H), 6.85-6.77 (m, 1H), 6.46 (dd, J=8.6, 2.6 Hz, 1H), 6.41 (d, J=2.5 Hz, 1H), 5.39-5.27 (m, 2H), 3.69 (s, 3H), 2.17-1.95 (m, 2H), 1.52-1.47 (m, 6H). MS (APCI+) m/z 464.4 (M+H)+.

Example 112

4-{(2R,4R)-4-[2-(2,3-dihydro-1,4-benzodioxin-6-yl)-2-methylpropanamido]-7-methoxy-3,4-dihydro-2H-1-benzopyran-2-yl}benzoic acid

Example 112A

Methyl 4-{(2R,4R)-4-[2-(2,3-dihydro-1,4-benzodioxin-6-yl)-2-methylpropanamido]-7-methoxy-3,4-dihydro-2H-1-benzopyran-2-yl}benzoate 2-(2,3-Dihydrobenzo[b][1,4]dioxin-6-yl)-2-methylpropanoic acid (39.4 mg, 0.177 mmol) was dissolved in N,N-dimethylformamide (0.5 mL) and pyridine (0.5 mL). Example 1C (41.3 mg, 0.118 mmol) and 1-(3-dimethylaminopropyl)-3-ethylcarbodiimide hydrochloride (37.8 mg, 0.197 mmol) were added and the reaction mixture was stirred at 60° C. for 3 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (28.8 mg, 47%): $^1$H NMR (501 MHz, DMSO-$d_6$) δ 8.03-7.97 (m, 2H), 7.61-7.56 (m, 2H), 7.50 (d, J=8.8 Hz, 1H), 6.83-6.76 (m, 4H), 6.45-6.41 (m, 2H), 5.42-5.28 (m, 2H), 4.24-4.15 (m, 4H), 3.87 (s, 3H), 3.69 (s, 3H), 2.13-1.95 (m, 2H), 1.44 (s, 6H); MS (ESI−) m/z 516 (M−H)−.

Example 112B

4-{(2R,4R)-4-[2-(2,3-dihydro-1,4-benzodioxin-6-yl)-2-methylpropanamido]-7-methoxy-3,4-dihydro-2H-1-benzopyran-2-yl}benzoic acid Example 112A (26.4 mg, 0.051 mmol) and potassium trimethylsilanolate (29.6 mg, 90% purity, 0.208 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (16.5 mg, 64%). $^1$H NMR (400 MHz, DMSO-$d_6$) δ 12.95 (s, 1H), 8.02-7.94 (m, 2H), 7.58-7.54 (m, 2H), 7.50 (d, J=8.8 Hz, 1H), 6.84-6.75 (m, 4H), 6.42 (d, J=7.4 Hz, 2H), 5.34 (ddd, J=22.6, 10.6, 4.7 Hz, 2H), 4.25-4.14 (m, 4H), 3.69 (s, 3H), 2.14-1.94 (m, 2H), 1.44 (s, 6H); MS (ESI−) m/z 502 (M−H)−.

Example 113

4-{(2R,4R)-4-[2-(3-fluoro-4-methoxyphenyl)-2-methylpropanamido]-7-methoxy-3,4-dihydro-2H-1-benzopyran-2-yl}benzoic acid Example 113 was prepared according to the procedure described in Example 2, substituting 2-(3-fluoro-4-methoxyphenyl)-2-methyl-propanoic acid for 1-(3,4-dichlorophenyl)-cyclopropanecarboxylic acid. $^1$H NMR (400 MHz, DMSO-$d_6$) δ 8.02-7.95 (m, 2H), 7.61-7.53 (m, 3H), 7.19-7.06 (m, 3H), 6.84-6.76 (m, 1H), 6.45 (dd, J=8.5, 2.6 Hz, 1H), 6.41 (d, J=2.5 Hz, 1H), 5.39-5.26 (m, 2H), 3.81 (s, 3H), 3.69 (s, 3H), 2.14-1.95 (m, 2H), 1.50-1.45 (m, 6H). MS (APCI+) m/z 494.4 (M+H)+.

Example 114

4-[(2R,4R)-7-methoxy-4-{[1-(4-methoxyphenyl)cyclopentane-1-carbonyl]amino}-3,4-dihydro-2H-1-benzopyran-2-yl]benzoic acid Example 114 was prepared according to the procedure described in Example 2, substituting 1-(4-methoxyphenyl)-cyclopentanecarboxylic acid for 1-(3,4-dichlorophenyl)-cyclopropanecarboxylic acid. $^1$H NMR (400 MHz, DMSO-$d_6$)

δ 8.02-7.95 (m, 2H), 7.64 (d, J=8.9 Hz, 1H), 7.60-7.52 (m, 2H), 7.34-7.25 (m, 2H), 6.92-6.83 (m, 2H), 6.59-6.52 (m, 1H), 6.39 (d, J=2.5 Hz, 1H), 6.34 (dd, J=8.6, 2.5 Hz, 1H), 5.38-5.28 (m, 1H), 5.31-5.20 (m, 1H), 3.73 (s, 3H), 3.68 (s, 3H), 2.65-2.54 (m, 1H), 2.51-2.43 (m, 1H), 2.08-1.96 (m, 2H), 1.91-1.79 (m, 1H), 1.83-1.64 (m, 1H), 1.68-1.55 (m, 4H). MS (APCI+) m/z 502.4 (M+H)$^+$.

Example 115

4-[(2R,4R)-7-methoxy-4-{[1-(4-methoxyphenyl)cyclobutane-1-carbonyl]amino}-3,4-dihydro-2H-1-benzopyran-2-yl]benzoic acid Example 115 was prepared according to the procedure described in Example 2, substituting 1-(4-methoxyphenyl)-cyclobutanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.83 (d, J=8.9 Hz, 1H), 7.61-7.53 (m, 2H), 7.35-7.26 (m, 2H), 6.94-6.85 (m, 2H), 6.61 (d, J=8.4, 1.0 Hz, 1H), 6.44-6.33 (m, 2H), 5.34 (dd, J=11.2, 2.2 Hz, 1H), 5.31-5.19 (m, 1H), 3.74 (s, 3H), 3.69 (s, 3H), 2.80-2.61 (m, 2H), 2.44-2.25 (m, 2H), 2.07-1.93 (m, 2H), 1.90-1.68 (m, 2H). MS (APCI+) m/z 488.4 (M+H)$^+$.

Example 116

4-[(2R,4R)-4-{[1-(3,4-dimethoxyphenyl)cyclobutane-1-carbonyl]amino}-7-methoxy-3,4-dihydro-2H-1-benzopyran-2-yl]benzoic acid Example 116 was prepared according to the procedure described in Example 2, substituting 1-(3,4-dimethoxyphenyl)-cyclobutanecarboxylic acid for 1-(3,4-dichlorophenyl)-cyclopropanecarboxylic acid. $^1$H NMR (400 MHz, DMSO-d$_6$) δ 8.02-7.95 (m, 2H), 7.85 (d, J=8.9 Hz, 1H), 7.61-7.53 (m, 2H), 6.98-6.85 (m, 3H), 6.65 (dd, J=8.5, 1.0 Hz, 1H), 6.44-6.34 (m, 2H), 5.38-5.20 (m, 2H), 3.72 (s, 3H), 3.69 (s, 3H), 3.18 (s, 3H), 2.79-2.61 (m, 2H), 2.37 (dq, J=26.2, 9.4, 8.8 Hz, 2H), 2.13-1.93 (m, 2H), 1.90-1.70 (m, 2H). MS (APCI+) m/z 518.4 (M+H)$^+$.

Example 117

4-{(2R,4R)-4-[2-(2-fluoro-4-methoxyphenyl)-2-methylpropanamido]-7-methoxy-3,4-dihydro-2H-1-benzopyran-2-yl}benzoic acid Example 117 was prepared according to the procedure described in Example 2, substituting 2-(2-fluoro-4-methoxy-phenyl)-2-methyl-propanoic acid for 1-(3,4-dichlorophenyl)-cyclopropanecarboxylic acid. $^1$H NMR (400 MHz, DMSO-d$_6$) δ 8.03-7.95 (m, 2H), 7.60-7.53 (m, 2H), 7.42 (d, J=8.9 Hz, 1H), 7.35-7.25 (m, 1H), 6.99 (dd, J=8.6, 1.0 Hz, 1H), 6.80-6.71 (m, 2H), 6.52 (dd, J=8.6, 2.5 Hz, 1H), 6.41 (d, J=2.5 Hz, 1H), 5.39-5.26 (m, 2H), 3.74 (s, 3H), 3.70 (s, 3H), 2.14-1.95 (m, 2H), 1.45 (s, 6H). MS (APCI+) m/z 494.4 (M+H)$^+$.

Example 118

4-{(2R,4R)-4-[2-(4-fluorophenoxy)-2-methylpropanamido]-7-methoxy-3,4-dihydro-2H-1-benzopyran-2-yl}benzoic acid Example 118 was prepared according to the procedure described in Example 2, substituting 2-(4-fluorophenoxy)-2-methyl-propionic acid for 1-(3,4-dichlorophenyl)-cyclopropanecarboxylic acid. $^1$H NMR (400 MHz, DMSO-d$_6$) δ 8.33 (d, J=8.9 Hz, 1H), 8.04-7.96 (m, 2H), 7.63-7.56 (m, 2H), 7.17-7.05 (m, 2H), 7.00-6.87 (m, 3H), 6.50 (dd, J=8.6, 2.6 Hz, 1H), 6.44 (d, J=2.5 Hz, 1H), 5.44-5.30 (m, 2H), 3.71 (s, 3H), 2.21-2.12 (m, 2H), 1.51 (s, 3H), 1.42 (s, 3H). MS (APCI+) m/z 480.4 (M+H)$^+$.

Example 119

4-{(2R,4R)-4-[2-(4-chlorophenoxy)-2-methylpropanamido]-7-methoxy-3,4-dihydro-2H-1-benzopyran-2-yl}benzoic acid Example 119 was prepared according to the procedure described in Example 2, substituting 2-(4-chlorophenoxy)-2-methyl-propionic acid for 1-(3,4-dichlorophenyl)-cyclopropanecarboxylic acid. $^1$H NMR (400 MHz, DMSO-d$_6$) δ 8.35 (d, J=8.9 Hz, 1H), 8.03-7.97 (m, 2H), 7.62-7.55 (m, 2H), 7.37-7.26 (m, 2H), 6.99-6.89 (m, 2H), 6.89-6.77 (m, 1H), 6.47 (dd, J=8.6, 2.6 Hz, 1H), 6.44-6.38 (m, 1H), 5.40-5.31 (m, 2H), 3.70 (s, 3H), 2.19-2.06 (m, 2H), 1.54 (s, 3H), 1.46 (s, 3H). MS (APCI+) m/z 496.3 (M+H)$^+$.

Example 120

4-{(2R,4R)-4-[2-(2H-1,3-benzodioxol-5-yl)-2-methylpropanamido]-7-methoxy-3,4-dihydro-2H-1-benzopyran-2-yl}benzoic acid Example 120A Methyl 4-{(2R,4R)-4-[2-(2H-1,3-benzodioxol-5-yl)-2-methylpropanamido]-7-methoxy-3,4-dihydro-2H-1-benzopyran-2-yl}benzoate 2-(Benzo[d][1,3]dioxol-5-yl)-2-methylpropanoic acid (34.6 mg, 0.166 mmol) was dissolved in N,N-dimethylformamide (0.5 mL) and pyridine (0.5 mL). Example 1C (39.7 mg, 0.113 mmol) and 1-(3-dimethylaminopropyl)-3-ethylcarbodiimide hydrochloride (37.8 mg, 0.197 mmol) were added and the reaction mixture was stirred at 60° C. for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (21.4 mg, 37%). $^1$H NMR (501 MHz, DMSO-d$_6$) δ 8.04-7.97 (m, 2H), 7.62-7.55 (m, 2H), 7.51 (d, J=8.8 Hz, 1H), 6.89 (d, J=1.8 Hz, 1H), 6.87-6.77 (m, 3H), 6.47-6.40 (m, 2H), 5.97-5.95 (m, 2H), 5.41-5.28 (m, 2H), 3.87 (s, 3H), 3.69 (s, 3H), 2.12-2.07 (m, 1H), 2.05-1.95 (m, 1H), 1.46 (d, J=2.2 Hz, 6H); MS (ESI−) m/z 502 (M−H)$^−$.

Example 120B

4-{(2R,4R)-4-[2-(2H-1,3-benzodioxol-5-yl)-2-methylpropanamido]-7-methoxy-3,4-dihydro-2H-1-benzopyran-2-yl}benzoic acid Example 120A (20.1 mg, 0.040 mmol) and potassium trimethylsilanolate (33.3 mg, 90% purity, 0.234 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (18.3 mg, 94%). $^1$H NMR (400 MHz, DMSO-d$_6$) δ 12.95 (s, 1H), 8.01-7.94 (m, 2H), 7.58-7.54 (m, 2H), 7.51 (d, J=8.8 Hz, 1H), 6.90 (d, J=1.7 Hz, 1H), 6.87-6.79 (m, 3H), 6.47-6.37 (m, 2H), 5.96 (s, 2H), 5.41-5.27 (m, 2H), 3.69 (s, 3H), 2.14-1.93 (m, 2H), 1.46 (d, J=2.1 Hz, 6H); MS (ESI−) m/z 488 (M−H)$^-$.

Example 121

4-{(2R,4R)-7-methoxy-4-[2-(4-methoxyphenyl)-2-methylpropanamido]-3,4-dihydro-2H-1-benzopyran-2-yl}benzoic acid Example 121A Methyl 4-{(2R,4R)-7-methoxy-4-[2-(4-methoxyphenyl)-2-methylpropanamido]-3,4-dihydro-2H-1-benzopyran-2-yl}benzoate 2-(4-Methoxyphenyl)-2-methylpropanoic acid (37.1 mg, 0.191 mmol) was dissolved in N,N-dimethylformamide (0.5 mL) and pyridine (0.5 mL). Example 1C (39.8 mg, 0.114 mmol) and 1-(3-dimethylaminopropyl)-3-ethylcarbodiimide hydrochloride (37.7 mg, 0.197 mmol) were added and the reaction mixture was stirred at 60° C. for 4 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (19.7 mg, 35%). $^1$H NMR (501 MHz, DMSO-d$_6$) δ 8.03-7.97 (m, 2H), 7.61-7.56 (m, 2H), 7.48 (d, J=8.8 Hz, 1H), 7.29-7.22 (m, 2H), 6.90-6.85 (m, 2H), 6.80 (dd, J=8.5, 1.0 Hz, 1H), 6.46-6.40 (m, 2H), 5.43-5.27 (m, 2H), 3.87 (s, 3H), 3.72 (s, 3H), 3.69 (s, 3H), 2.13-2.06 (m, 1H), 2.05-1.95 (m, 1H), 1.47 (s, 6H); MS (ESI−) m/z 488 (M−H)$^-$.

Example 121B

4-{(2R,4R)-7-methoxy-4-[2-(4-methoxyphenyl)-2-methylpropanamido]-3,4-dihydro-2H-1-benzopyran-2-yl}benzoic acid Example 121A (17.6 mg, 0.036 mmol) and potassium trimethylsilanolate (18.9 mg, 90% purity, 0.133 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes linear gradient 95-10% A), to provide the title compound (11.4 mg, 67%). $^1$H NMR (400 MHz, DMSO-d$_6$) δ 12.94 (s, 1H), 8.02-7.94 (m, 2H), 7.59-7.53 (m, 2H), 7.48 (d, J=8.8 Hz, 1H), 7.31-7.22 (m, 2H), 6.91-6.84 (m, 2H), 6.80 (d, J=8.4 Hz, 1H), 6.48-6.39 (m, 2H), 5.40-5.27 (m, 2H), 3.72 (s, 3H), 3.69 (s, 3H), 2.14-1.94 (m, 2H), 1.47 (s, 6H); MS (ESI−) m/z 474 (M−H)$^-$.

Example 122

3-{(2R,4R)-4-[(1,5-dimethyl-2,3-dihydro-1H-inden-1-carbonyl)amino]-7-methoxy-3,4-dihydro-2H-1-benzopyran-2-yl}benzoic acid Example 8D (0.107 g, 0.220 mmol) and potassium trimethylsilanolate (0.062 g, 0.485 mmol) were stirred in tetrahydrofuran (3 mL) at room temperature overnight. The mixture was treated with 3 mL CH$_2$Cl$_2$ and 1.5 mL 1N aqueous HCl, and the mixture was stirred vigorously at room temperature for 30 minutes. The mixture was diluted with ethyl acetate, washed twice with water and once with brine, dried over Na$_2$SO$_4$, filtered, and concentrated in vacuo. The residue was purified by reverse-phase preparative HPLC on a Phenomenex® Luna® C8(2) 5 m 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (42 mg, 40% yield). $^1$H NMR (400 MHz, DMSO-d$_6$) δ 12.94 (s, 1H), 7.96 (dd, J=8.2, 3.9 Hz, 2H), 7.61-7.43 (m, 3H), 7.19 (t, J=7.5 Hz, 1H), 7.05-6.89 (m, 2H), 6.57-6.38 (m, 2H), 5.34 (m, 2H), 3.70 (s, 1.5H), 3.69 (s, 1.5H), 2.85 (m, 1H), 2.60 (m, 1H), 2.25 (s, 1.5H), 2.23 (s, 1.5H), 2.09 (m, 1H), 1.86 (m, 1H), 1.42 (s, 3H); MS (ESI$^+$) m/z 471.9 (M+H)$^+$.

Example 123 methyl 3-{(2R,4R)-4-[(1,5-dimethyl-2,3-dihydro-1H-inden-1-carbonyl)amino]-7-methoxy-3,4-dihydro-2H-1-benzopyran-2-yl}benzoate Example 7C (0.133 g, 0.7 mmol), Example 8C (0.282 g, 0.805 mmol), and 1-ethyl-3-[3-(dimethylamino)propyl]-carbodiimide hydrochloride (EDCI, 0.268 g, 1.400 mmol) were stirred in N,N-dimethylformamide (1.7 mL) and pyridine (1.7 mL) at 60° C. overnight. The mixture was concentrated, and the residue was dissolved in ethyl acetate and washed three times with water and once with brine. The organic solution was dried over Na$_2$SO$_4$, filtered, and concentrated in vacuo. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound (107 mg, 32% yield). $^1$H NMR (400 MHz, DMSO-d$_6$) δ 8.05-7.93 (m, 2H), 7.55 (m, 3H), 7.19 (m, 1H), 7.05-6.89 (m, 2.5H), 6.77 (m, 0.5H), 6.57-6.38 (m, 2H), 5.43-5.24 (m, 2H), 3.86 (s, 3H), 3.69 (s, 3H), 2.85 (dq, J=22.8, 9.0, 8.5 Hz, 2H), 2.68-2.55 (m, 1H), 2.25 (s, 1.5H), 2.23 (s, 1.5H), 2.20-1.96 (m, 2H), 1.93-1.77 (m, 1H), 1.42 (s, 3H); MS (ESI$^+$) m/z 485.9 (M+H)$^+$.

Example 124 methyl 4-{(2R,4R)-4-[(1,5-dimethyl-2,3-dihydro-1H-inden-1-carbonyl)amino]-7-methoxy-3,4-dihydro-2H-1-benzopyran-2-yl}benzoate Example 7C (0.057 g, 0.3 mmol), Example 7G (0.121 g, 0.345 mmol), and 1-ethyl-3-[3-(dimethylamino)propyl]-carbodiimide hydrochloride (EDCI, 0.115 g, 0.600 mmol) were stirred in N,N-dimethylformamide (1 mL) and pyridine (1 mL) at 60° C. overnight. The reaction mixture was concentrated in vacuo; and the remaining crude oil was dissolved in ethyl acetate and washed three times with water and once with brine. The organic layer was dried over $Na_2SO_4$, filtered, and concentrated. The residue was purified by silica gel chromatography, eluting with 0 to 40% ethyl acetate/heptanes to provide the title compound as a white solid (0.098 g, 67% yield). $^1$H NMR (400 MHz, $CDCl_3$) δ 8.10-7.96 (m, 2H), 7.52-7.39 (m, 2H), 7.19-6.84 (m, 4H), 6.58-6.38 (m, 2H), 5.46-5.34 (m, 2H), 5.22 (dd, J=11.0, 2.0 Hz, 1H), 3.93 (s, 1.5H), 3.92 (s, 1.5H), 3.76 (s, 1.5H), 3.75 (s, 1.5H), 2.95-2.74 (m, 2H), 2.64 (ddd, J=12.2, 7.6, 4.4 Hz, 1H), 2.67-2.44 (m, 2H), 2.31 (s, 3H), 2.16-1.96 (m, 1H), 1.62 (m, 1H), 1.59 (s, 1.5H), 1.54 (s, 1.5H); MS ($ESI^+$) m/z 485.9 $(M+H)^+$.

Example 125

3-[(2R,4R)-4-{[(1R)-1,5-dimethyl-2,3-dihydro-1H-inden-1-carbonyl]amino}-7-methoxy-3,4-dihydro-2H-1-benzopyran-2-yl]benzoic acid The diethylamine salt of the title compound was obtained as the second eluting isomer from the chiral SFC separation described in Example 8E (18.6 mg, 16% yield). Analytical chiral SFC analysis of the compound thus provided (Whelk-O1 S,S column, eluting with 5 to 50% $CH_3OH$ (0.1% diethylamine):$CO_2$ over 10 minutes, 3 mL/minute, 150 bar) indicated ee=85%. The chirality of the carbon atom bearing the methyl group was assigned arbitrarily. $^1$H NMR (400 MHz, DMSO-$d_6$) δ 7.91 (m, 2H), 7.58-7.41 (m, 3H), 7.19 (d, J=7.8 Hz, 1H), 7.07-6.92 (m, 2H), 6.77 (d, J=8.7 Hz, 1H), 6.44 (m, 2H), 5.32 (m, 2H), 3.69 (s, 3H), 2.86 (m, 1H), 2.67 (m, 4H), 2.61 (m, 1H), 2.27 (s, 3H), 2.10 (m, 1H), 1.86 (m, 1H), 1.43 (s, 3H), 1.06 (t, J=7.2 Hz, 6H); MS ($ESI^+$) m/z 471.9 $(M+H)^+$.

Example 126

4-[(2R,4R)-4-{[(1R)-1,5-dimethyl-2,3-dihydro-1H-inden-1-carbonyl]amino}-7-methoxy-3,4-dihydro-2H-1-benzopyran-2-yl]benzoic acid The title compound was obtained as the second eluting isomer from the chiral SFC separation described in Example 9. Analytical chiral SFC analysis of the compound thus provided (ChiralCel OD-H column, eluting with 5 to 50% $CH_3OH$:$CO_2$ over 10 minutes, 3 mL/minute, 150 bar) indicated ee>99%. The chirality of the carbon bearing the methyl group was assigned arbitrarily. $^1$H NMR (400 MHz, DMSO-$d_6$) δ 7.94 (d, J=7.9 Hz, 2H), 7.50 (m, 3H), 7.19 (d, J=7.7 Hz, 1H), 7.06-6.92 (m, 2H), 6.78 (d, J=8.3 Hz, 1H), 6.57-6.38 (m, 2H), 5.32 (m, 2H), 3.69 (s, 3H), 2.94-2.62 (m, 4H), 2.25 (s, 3H), 2.11 (m, 1H), 1.86 (m, 1H), 1.43 (s, 3H); MS ($ESI^+$) m/z 471.9 $(M+H)^+$.

Determination of Biological Activity

Cellular Assays
Cell Surface Expression-Horse Radish Peroxidase (CSE-HRP) Assay:

A cellular assay for measuring the F508delCFTR cell surface expression after correction with test compounds was developed in human lung derived epithelial cell line (CFBE41o-) (Veit G et al, (2012) Mol Biol Cell. 23(21): 4188-4202). This was achieved by expressing the F508delCFTR mutation along with a horseradish peroxidase (HRP) in the fourth exofacial loop and then measuring the HRP activity using luminescence readout from these cells, CFBE41o-F508delCFTR-HRP, that were incubated overnight with the test corrector compounds. Briefly, for this primary assay, the CFBE41o-F508delCFTR-HRP cells were plated in 384-well plates (Greiner Bio-one; Cat 781080) at 4,000 cells/well along with 0.5 μg/mL doxycycline to induce the F508delCFTR-HRP expression and further incubated at 37° C., 5% $CO_2$ for 72 hours. The test compounds were then added at the required concentrations and further incubated for 18-24 hours at 33° C. The highest concentration tested was 20 μM with an 8-point concentration response curve using a 3-fold dilution. Three replicate plates were run to determine one $EC_{50}$. All plates contained negative controls (dimethyl sulfoxide, DMSO) and positive controls (3 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) as well as on-plate concentration response of the positive control. Post incubation, the plates were washed 5× times with Dulbecco's phosphate buffered saline (DPBS), followed by the addition of the HRP substrate, luminol (50 μL), and measuring the HRP activity using luminescence readout on EnVision® Multilabel Plate Reader (Perkin Elmer; product number 2104-0010). The raw counts from the experiment are analyzed using Accelrys® Assay Explorer v3.3.

Z' greater than 0.5 was used as passing quality control criteria for the plates.

The Z' is defined as:

$$1-[3*SD_{Positive\ Control}+3*SD_{Negative\ Control}]/\text{Absolute} (Mean_{Positive\ Control}-Mean_{Negative\ Control})]$$

wherein "SD" is standard deviation.

The % activity measured at each of the 8 test concentrations of the test compound was normalized to the on-plate positive control using the following formula:

% activity=[(test compound response−DMSO response)/(positive control response−DMSO response)]*100

The maximum % activity achieved for the test compound at any tested concentration is presented in Table 1 along with the $EC_{50}$ calculated using the following general sigmoidal curve with variable Hill slope equation (described as Model 42 in the Accelrys® Assay Explorer v3.3 software):

$$y=(a-d)/(1+(x/c)^b)+d$$

General sigmoidal curve with concentration, response, top, bottom, $EC_{50}$ and Hill slope.

This model describes a sigmoidal curve with an adjustable baseline, a. The equation can be used to fit curves where response is either increasing or decreasing with respect to the independent variable, "x".

"x" is a concentration of drug under test.
"y" is the response.
"a" is the maximum response, and "d" is the minimum response
"c" is the inflection point ($EC_{50}$) for the curve. That is, "y" is halfway between the lower and upper asymptotes when x=c.
"b" is the slope-factor or Hill coefficient. The sign of b is positive when the response increases with increasing dose and is negative when the response decreases with increasing dose (inhibition).

The maximum percent activity and EC$_{50}$ values for compounds tested in the CSE-HRP assay are presented in Table 1.

TABLE 1

| Example | EC$_{50}$ (μM) | Maximum % activity (%) |
|---|---|---|
| 1 | 0.55 | 110.0 |
| 2 | 0.15 | 95.0 |
| 3 | 1.94 | 106.0 |
| 4 | 0.26 | 94.2 |
| 5 | 0.21 | 120.0 |
| 6 | 0.09 | 95.9 |
| 7 | 0.16 | 90.1 |
| 8 | 0.10 | 91.3 |
| 9 | 0.18 | 95.5 |
| 10 | 0.29 | 119.0 |
| 11 | 0.31 | 124.5 |
| 12 | 0.07 | 135.0 |
| 13 | 0.03 | 124.0 |
| 14D | 0.63 | 121.5 |
| 14E | 0.20 | 125.0 |
| 15A | 0.53 | 94.7 |
| 15B | 0.11 | 125.5 |
| 16 | >20 | 4.0 |
| 17 | 3.32 | 27.6 |
| 18 | >20 | 5.5 |
| 19 | 1.27 | 40.8 |
| 20 | 0.89 | 51.1 |
| 21 | 1.14 | 77.8 |
| 22 | 0.99 | 56.6 |
| 23 | 0.23 | 54.0 |
| 24 | 1.16 | 38.3 |
| 25 | 0.23 | 39.5 |
| 26 | >20 | 1.6 |
| 27 | >20 | 7.9 |
| 28 | 2.49 | 21.2 |
| 29 | 1.44 | 37.8 |
| 30 | 0.96 | 48.4 |
| 31 | 0.40 | 63.6 |
| 32 | 1.21 | 20.4 |
| 33 | 0.27 | 25.9 |
| 34 | 0.41 | 52.6 |
| 35 | 0.20 | 57.5 |
| 36 | 0.67 | 31.4 |
| 37 | >20 | 6.1 |
| 38 | 0.16 | 34.4 |
| 39 | 0.87 | 41.7 |
| 40 | 1.70 | 81.0 |
| 41 | 1.67 | 62.2 |
| 42 | 0.28 | 28.3 |
| 43 | 0.28 | 39.1 |
| 44 | 0.10 | 35.3 |
| 45 | >20 | 15.3 |
| 46 | >20 | 1.1 |
| 47 | 1.06 | 38.2 |
| 48 | >20 | 4.5 |
| 49 | >20 | 3.5 |
| 50 | >20 | 4.9 |
| 51 | 2.03 | 57.9 |
| 52 | >20 | 1.8 |
| 53 | >20 | 1.2 |
| 54 | >20 | 10.4 |
| 55 | 2.71 | 49.9 |
| 56 | 1.30 | 71.4 |
| 57 | >20 | 2.3 |
| 58 | 2.22 | 20.4 |
| 59 | >20 | 1.8 |
| 60 | >20 | 2.3 |
| 61 | 5.88 | 20.0 |
| 62 | 2.65 | 22.6 |
| 63 | >20 | 5.1 |
| 64 | >20 | 18.0 |
| 65 | 2.14 | 27.0 |
| 66 | >20 | 4.8 |
| 67 | >20 | 4.7 |
| 68 | 1.31 | 85.0 |
| 69 | 0.10 | 66.1 |
| 70 | 2.21 | 28.0 |
| 71 | 0.12 | 52.0 |
| 72 | >20 | 1.4 |
| 73 | 1.84 | 29.0 |
| 74 | 0.07 | 49.8 |
| 75 | 0.95 | 37.9 |
| 76 | 2.10 | 52.0 |
| 77 | >20 | 8.0 |
| 78 | 2.47 | 32.0 |
| 79 | >20 | −0.3 |
| 80 | >20 | −0.2 |
| 81 | 1.88 | 32.0 |
| 82 | 1.88 | 23.3 |
| 83 | 3.17 | 51.0 |
| 84 | 0.56 | 56.2 |
| 85 | 0.72 | 50.4 |
| 86 | 0.57 | 57.9 |
| 87 | 1.83 | 46.0 |
| 88 | 0.64 | 44.0 |
| 89 | 0.75 | 42.0 |
| 90 | >20 | 8.1 |
| 91 | >20 | 5.0 |
| 92 | 0.35 | 62.0 |
| 93 | >20 | 5.7 |
| 94 | 2.63 | 49.0 |
| 95 | 1.33 | 76.0 |
| 96 | 3.01 | 33.0 |
| 97 | >20 | 2.5 |
| 98 | >20 | 13.0 |
| 99 | >20 | 15.9 |
| 100 | 0.48 | 55.3 |
| 101 | 0.66 | 46.0 |
| 102 | >20 | 18.1 |
| 103 | 4.01 | 29.0 |
| 104 | 1.56 | 71.0 |
| 105 | 1.10 | 32.0 |
| 106 | 1.29 | 46.0 |
| 107 | 1.32 | 22.4 |
| 108 | 0.17 | 77.7 |
| 109 | 1.36 | 93.0 |
| 110 | 0.31 | 85.0 |
| 111 | 0.84 | 47.7 |
| 112 | 0.36 | 59.9 |
| 113 | 0.06 | 43.5 |
| 114 | >20 | 2.2 |
| 115 | 0.63 | 69.8 |
| 116 | 3.25 | 27.6 |
| 117 | 0.35 | 47.0 |
| 118 | >20 | 16.3 |
| 119 | 2.98 | 27.4 |
| 120 | 0.05 | 73.9 |
| 121 | 0.07 | 49.6 |
| 122 | 0.31 | 86.2 |
| 123 | 0.45 | 80.8 |
| 124 | 0.46 | 87.7 |
| 125 | 0.44 | 70.7 |
| 126 | 0.65 | 72.1 |

Transepithelial Clamp Circuit on Human Bronchial Epithelial Cells Conductance Assay:

A cell based assay using the primary human bronchial epithelial cells (hBE) was used as a secondary assay to test novel F508delCFTR correctors for their activity on primary hBE cells with F508del/F508del CFTR mutation. The assay used a TECC-24 (Transepithelial Clamp Circuit for 24 wells) instrument that measures the functionality of the mutated channel by measuring the equivalent short circuit current (Ieq) generated by the polarized epithelial cells. The instrument works by measuring the transepithelial potential difference (Vt) and transepithelial resistance (Rt) in an open circuit format, and the Ieq is calculated by using Ohms law (Ieq=Vt/Rt). The assay was run in a 24-well format and all 24-wells were measured at the same time point giving a higher throughput for this assay.

Primary human bronchial epithelial (hBE) cells from F508del/F508delCFTR patients were expanded from $1 \times 10^6$ to $250 \times 10^6$ cells (Neuberger T, Burton B, Clark H and VanGoor F; *Cystic Fibrosis*, Methods in Mole Biol 741; eds. Amaral M D and Kunzelmann K, 2011). For this purpose, cells isolated from CF patients with the homozygous mutation were seeded onto 24 well Corning (Cat #3378) filter plates that were coated with 3T3 conditioned media and grown at an air-liquid interface for 35 days using an Ultroser® G supplemented differentiation media. Apical surface mucus was removed 72 hours before the experiment using 3 mM dithiothreitol (DTT) in phosphate buffered saline (PBS). The apical surface was washed again 24 hours before the experiment using PBS. The cells were incubated with the desired dose response of the corrector compounds 18-24 hours at 37° C., 5% $CO_2$. The corrector compounds are only added on the basolateral side of the epithelial cells.

On the day of measuring the corrector activity on the TECC, the cells were switched into a bicarbonate and serum free F-12 Coon's medium and allowed to equilibrate for 30 minutes in a $CO_2$ free incubator. At the time of measurement, the apical and basolateral sides of the filter were bathed with the F-12 Coon's modification media (with 20 mM 4-(2-hydroxyethyl)-1-piperazineethanesulfonic acid (HEPES), pH 7.4 (using 1 M tris(hydroxymethyl)aminomethane (Tris)), and the measurements were made at 36.5° C. Transepithelial voltage (Vt) and transepithelial resistance (Rt) were measured using a 24 channel transepithelial current clamp (TECC-24). Current responses to the sequential addition of benzamil (apical 6 μM addition; for inhibiting epithelial ENaC channel), forskolin (apical and basolateral 10 μM addition; for activating the CFTR channel), control potentiator (N-(3-carbamoyl-5,5,7,7-tetramethyl-4,7-dihydro-5H-thieno[2,3-c]pyran-2-yl)-1H-pyrazole-5-carboxamide; apical and basolateral 1 μM addition; for potentiating the CFTR channel) and bumetanide (basolateral 20 μM addition; for inhibiting the Na:2Cl:K co-transporter, an indirect measure of inhibiting the Cl— secretion driven by CFTR channel) were measured.

All plates contained negative controls (dimethyl sulfoxide, DMSO) which coupled with the control potentiator (N-(3-carbamoyl-5,5,7,7-tetramethyl-4,7-dihydro-5H-thieno[2,3-c]pyran-2-yl)-1H-pyrazole-5-carboxamide) sets the null response and positive controls (3 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) coupled with the control potentiator sets the 100% response to measure the correction of the mutated CFTR channel. The maximum percent activity is reported relative to the positive control value.

The % activity measured at each of the 6 test concentrations of the test compound was normalized to the on-plate positive control using the following formula:

% activity=[(test compound response−DMSO response)/(positive control response−DMSO response)]*100

The following log(agonist) vs response using a four parameters variable slope was used to calculate $EC_{50}$ (4 PL in Prism v 5 software):

$F(x)=D+(A-D)/(1+(x/C)^B)$

Where:
"x" is a concentration of drug under test.
"F(x)" is the response.
"A" is the maximum response, and "D" is the minimum response
"C" is the inflection point ($EC_{50}$) for the curve. That is, "F(x)" is halfway between the lower and upper asymptotes when x=C.
"B" is the slope-factor or Hill coefficient. The sign of B is positive when the response increases with increasing dose and is negative when the response decreases with increasing dose (inhibition).

The maximum percent activity and $EC_{50}$ values for compounds tested are presented in Table 2.

TABLE 2

| hBE-TECC data | | |
|---|---|---|
| Example | EC50 (μM) | Maximum % activity (%) |
| 8 | 0.024 | 85.6 |
| 11 | 0.021 | 104.3 |
| 13 | 0.004 | 117.5 |
| 15A | 0.573 | 92.0 |
| 15B | 0.030 | 109.6 |

It is understood that the foregoing detailed description and accompanying examples are merely illustrative and are not to be taken as limitations upon the scope of the invention, which is defined solely by the appended claims and their equivalents. Various changes and modifications to the described embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I) or a pharmaceutically acceptable salt thereof

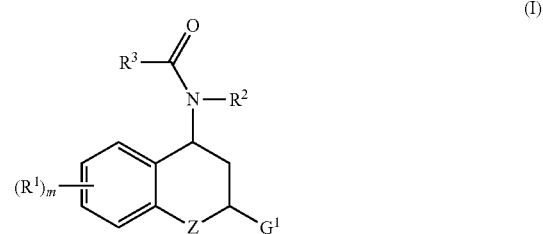

wherein
Z is O;
$R^1$ groups are optional substituents on the benzo ring, and are each independently halogen, —CN, $C_1$-$C_3$ alkyl, $C_1$-$C_3$ haloalkyl, —$OR^j$, or —$SR^j$;
m is 0, 1, 2, 3, or 4;
$R^2$ is hydrogen or $C_1$-$C_3$ alkyl;
$R^3$ is formula (a)

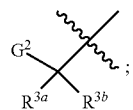

wherein $R^{3a}$ and $R^{3b}$ are each independently $C_1$-$C_3$ alkyl; or $R^{3a}$ and $R^{3b}$ together with the carbon atom to which they are attached, form a cyclopropyl, a cyclobutyl, or a cyclopentyl; wherein the cyclopropyl, the cyclobutyl, and the cyclopentyl are each optionally substituted with 1, 2, 3, or 4 substituents independently selected from the group consisting of $C_1$-$C_3$ alkyl, $C_1$-$C_3$ haloalkyl, and halogen; and $G^2$ is formula (b), phenyl, or —O-phenyl, wherein the phenyl and the phenyl moiety of —O-phenyl are each optionally substituted with 1, 2, 3, or 4 $R^x$ groups;

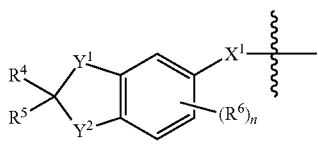

(b)

wherein
each $R^x$ is independently halogen, —CN, $C_1$-$C_6$ alkyl, $C_1$-$C_6$ haloalkyl, —$OR^j$, or —$SR^j$;
$X^1$ is a bond or O;
$Y^1$ is O, $CH_2$, or —O—$CH_2$— wherein the —O—$CH_2$— is connected to the benzo ring via the oxygen atom;
$Y^2$ is O;
$R^4$ and $R^5$ are each independently hydrogen or halogen;
$R^6$ groups are optional substituents on the benzo ring, and are each independently $C_1$-$C_3$ alkyl, $C_1$-$C_3$ haloalkyl, halogen, —CN, —$OR^j$, or —$SR^j$; and
n is 0, 1, 2, or 3;

$G^1$ is phenyl, monocyclic heteroaryl, or $C_3$-$C_6$ cycloalkyl; wherein each $G^1$ is optionally substituted with 1, 2, 3, or 4 $R^9$ groups;

each $R^9$ is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$ alkylenyl)-$OR^j$, —($C_1$-$C_6$ alkylenyl)-$OC(O)R^k$, —($C_1$-$C_6$ alkylenyl)-$OC(O)N(R^j)_2$, —($C_1$-$C_6$ alkylenyl)-$SR^j$, —($C_1$-$C_6$ alkylenyl)-$S(O)_2R^j$, —($C_1$-$C_6$ alkylenyl)-$S(O)_2N(R^j)_2$, —($C_1$-$C_6$ alkylenyl)-$C(O)R^j$, —($C_1$-$C_6$ alkylenyl)-$C(O)OR^j$, —($C_1$-$C_6$ alkylenyl)-$C(O)N(R^j)_2$, —($C_1$-$C_6$ alkylenyl)-$C(O)N(R^j)S(O)_2R^k$, —($C_1$-$C_6$ alkylenyl)-$N(R^j)_2$, —($C_1$-$C_6$ alkylenyl)-$N(R^j)C(O)R^k$, —($C_1$-$C_6$ alkylenyl)-$N(R^j)S(O)_2R^k$, —($C_1$-$C_6$ alkylenyl)-$N(R^j)C(O)O(R^k)$, —($C_1$-$C_6$ alkylenyl)-$N(R^j)C(O)N(R^j)_2$, or —($C_1$-$C_6$ alkylenyl)-CN;

$R^j$, at each occurrence, is independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl;

with the proviso that when $R^2$ is hydrogen, Z is O, $R^3$ is formula (a), $R^{3a}$ and $R^{3b}$ together with the carbon atom to which they are attached form an unsubstituted cyclopropyl, and $G^2$ is formula (b) wherein $Y^1$ is O, $R^4$ and $R^5$ are halogen, $X^1$ is a bond, n is 0 or 1, and $R^6$ is halogen; then $G^1$ is optionally substituted pyrimidinyl, optionally substituted pyridazinyl, optionally substituted pyrazinyl, or

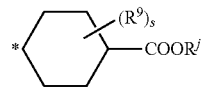

wherein * is the point of connection, $R^9$ is $C_1$-$C_3$ alkyl, $C_1$-$C_3$ haloalkyl, or halogen; and s is 0, 1, 2, or 3.

2. The compound of claim 1 or a pharmaceutically acceptable salt thereof, wherein Z is O and $R^2$ is hydrogen.

3. The compound of claim 1 or a pharmaceutically acceptable salt thereof, wherein $G^1$ is phenyl, pyridinyl, pyrimidinyl, pyridazinyl, pyrazinyl, thiazolyl, thienyl, cyclopropyl, or cyclohexyl; each of which is optionally substituted with 1, 2, 3, or 4 independently selected $R^9$ groups.

4. The compound of claim 1 or a pharmaceutically acceptable salt thereof, wherein $G^1$ is phenyl or cyclohexyl; each of which is substituted with 1, 2, 3, or 4 $R^9$ groups; wherein one of the $R^9$ groups is —$OR^j$ or —$C(O)OR^j$, and the other 1, 2, or 3 optional $R^9$ groups are independently $C_1$-$C_3$ alkyl, halogen, or $C_1$-$C_3$ haloalkyl.

5. The compound of claim 1 or a pharmaceutically acceptable salt thereof, wherein Z is O, $R^2$ is hydrogen;

$G^1$ is phenyl or cyclohexyl; each of which is substituted with 1, 2, 3, or 4 $R^9$ groups; wherein one of the $R^9$ groups is —$C(O)OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl;

m is 0 or 1; and $R^1$ is —$OR^j$ wherein $R^j$ is $C_1$-$C_6$ alkyl or $C_1$-$C_6$ haloalkyl.

6. The compound of claim 1 of formula (I-a) or a pharmaceutically acceptable salt thereof

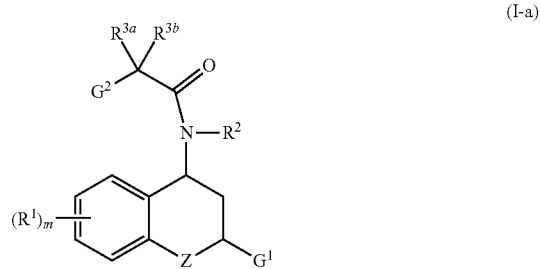

(I-a)

wherein $R^1$, m, Z, $G^1$, $R^2$, $R^{3a}$, and $R^{3b}$ are as set forth in claim 1;

$G^2$ is formula (b), phenyl, or —O-phenyl, wherein the phenyl and the phenyl moiety of —O-phenyl are each optionally substituted with 1, 2, 3, or 4 $R^x$ groups;

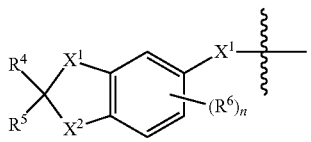
(b)

wherein
each $R^x$ is independently halogen, —CN, $C_1$-$C_6$ alkyl, $C_1$-$C_6$ haloalkyl, —$OR^j$, or —$SR^j$;
$X^1$ is O;
$Y^1$ is O, $CH_2$, or —O—$CH_2$— wherein the —O—$CH_2$— is connected to the benzo ring via the oxygen atom;
$Y^2$ is O;
$R^4$ and $R^5$ are hydrogen or $R^4$ and $R^5$ are halogen;
$R^6$ groups are optional substituents on the benzo ring, and are each independently $C_1$-$C_3$ alkyl, $C_1$-$C_3$ haloalkyl, halogen, —CN, —$OR^j$, or —$SR^j$; and
n is 0, 1, 2, or 3; and
$R^j$, at each occurrence, is independently hydrogen, $C_1$-$C_6$ alkyl, or $C_1$-$C_6$ haloalkyl.

7. The compound of claim 6 or a pharmaceutically acceptable salt thereof, wherein
$G^2$ is phenyl or —O-phenyl, wherein the phenyl and the phenyl moiety of —O-phenyl are each optionally substituted with 1, 2, 3, or 4 $R^x$ groups.

8. The compound of claim 6 or a pharmaceutically acceptable salt thereof, wherein
$G^2$ is phenyl optionally substituted with 1, 2, 3, or 4 $R^x$ groups.

9. The compound of claim 6 or a pharmaceutically acceptable salt thereof, wherein
$G^2$ is formula (b) wherein $Y^1$ is O;
$R^4$ and $R^5$ are hydrogen; and
$R^{3a}$ and $R^{3b}$ are methyl.

10. The compound of claim 6 or a pharmaceutically acceptable salt thereof, wherein
Z is O;
$R^2$ is hydrogen; and
$R^{3a}$ and $R^{3b}$ are each independently $C_1$-$C_3$ alkyl; or $R^{3a}$ and $R^{3b}$ together with the carbon atom to which they are attached, form a cyclopropyl or a cyclobutyl; wherein the cyclopropyl and the cyclobutyl are each optionally substituted with 1, 2, 3, or 4 substituents independently selected from the group consisting of $C_1$-$C_3$ alkyl, $C_1$-$C_3$ haloalkyl, and halogen.

11. The compound of claim 6 or a pharmaceutically acceptable salt thereof, wherein
$G^1$ is phenyl or cyclohexyl; each of which is substituted with 1, 2, 3, or 4 $R^9$ groups; wherein one of the $R^9$ groups is —$OR^j$ or —$C(O)OR^j$, and the other 1, 2, or 3 optional $R^9$ groups are independently $C_1$-$C_3$ alkyl, halogen, or $C_1$-$C_3$ haloalkyl;
m is 0 or 1; and
$R^1$ is —$OR^j$ wherein $R^j$ is $C_1$-$C_6$ alkyl or $C_1$-$C_6$ haloalkyl.

12. The compound of claim 6 or a pharmaceutically acceptable salt thereof, wherein
Z is O;
$R^2$ is hydrogen;
$Y^1$ is O;
$R^{3a}$ and $R^{3b}$ are methyl; or $R^{3a}$ and $R^{3b}$ together with the carbon atom to which they are attached, form a cyclopropyl or a cyclobutyl; wherein the cyclopropyl and the cyclobutyl are each optionally substituted with 1, 2, 3, or 4 substituents independently selected from the group consisting of $C_1$-$C_3$ alkyl, $C_1$-$C_3$ haloalkyl, and halogen;
$G^2$ is phenyl which is optionally substituted with 1, 2, 3, or 4 $R^x$ groups;
$G^1$ is phenyl or cyclohexyl; each of which is substituted with 1, 2, 3, or 4 $R^9$ groups; wherein one of the $R^9$ groups is —$C(O)OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl;
m is 0 or 1; and
$R^1$ is —$OR^j$ wherein $R^j$ is $C_1$-$C_6$ alkyl or $C_1$-$C_6$ haloalkyl.

13. The compound of claim 1 of formula (I-a-i) or a pharmaceutically acceptable salt thereof

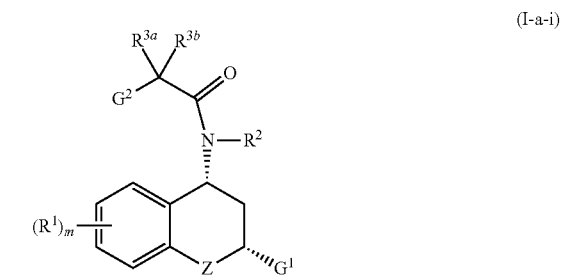
(I-a-i)

wherein
$R^1$, m, $G^1$, $R^{3a}$, and $R^{3b}$ are as set forth in claim 1;
$G^2$ is phenyl which is optionally substituted with 1, 2, 3, or 4 $R^x$ groups;
each $R^x$ is independently halogen, —CN, $C_1$-$C_6$ alkyl, $C_1$-$C_6$ haloalkyl, —$OR^j$, or —$SR^j$;
Z is O;
$R^2$ is hydrogen; and
$R^j$, at each occurrence, is independently hydrogen, $C_1$-$C_6$ alkyl, or $C_1$-$C_6$ haloalkyl.

14. The compound of claim 13 or a pharmaceutically acceptable salt thereof, wherein
$R^{3a}$ and $R^{3b}$ are methyl; or $R^{3a}$ and $R^{3b}$ together with the carbon atom to which they are attached, form a cyclopropyl which is optionally substituted with 1, 2, 3, or 4 substituents independently selected from the group consisting of $C_1$-$C_3$ alkyl, $C_1$-$C_3$ haloalkyl, and halogen.

15. The compound of claim 14 or a pharmaceutically acceptable salt thereof, wherein
$G^1$ is phenyl or cyclohexyl; each of which is substituted with 1, 2, 3, or 4 $R^9$ groups; wherein one of the $R^9$ groups is —$C(O)OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl.

16. The compound of claim 14 or a pharmaceutically acceptable salt thereof, wherein
$G^1$ is

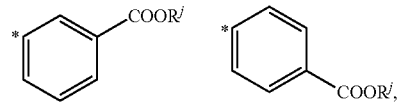

-continued

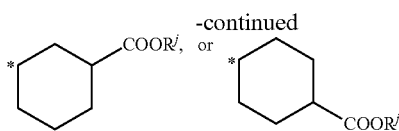

wherein * is the point of connection, and R$^j$ is hydrogen or C$_1$-C$_6$ alkyl.

17. The compound of claim 16 or a pharmaceutically acceptable salt thereof, wherein
m is 0 or 1; and
R$^1$ is —OR$^j$ wherein R$^j$ is C$_1$-C$_6$ alkyl or C$_1$-C$_6$ haloalkyl.

18. The compound of claim 1 of formula (I-a-ii) or a pharmaceutically acceptable salt thereof,

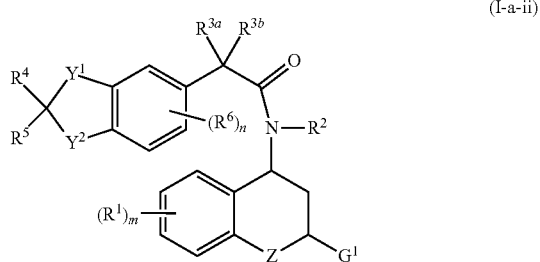

(I-a-ii)

wherein R$^1$, m, Z, G$^1$, R$^2$, R$^{3a}$, R$^{3b}$, R$^6$, n, Y$^1$, and Y$^2$ are as set forth in claim 1; and
R$^4$ and R$^5$ are hydrogen, or R$^4$ and R$^5$ are halogen;
with the proviso that when R$^2$ is hydrogen, Z is O, R$^{3a}$ and R$^{3b}$ together with the carbon atom to which they are attached form an unsubstituted cyclopropyl, Y$^1$ is O, R$^4$ and R$^5$ are halogen, n is 0 or 1, and R$^6$ is halogen, then G$^1$ is optionally substituted pyrimidinyl, optionally substituted pyridazinyl, optionally substituted pyrazinyl, or

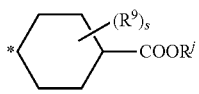

wherein * is the point of connection, R$^9$ is C$_1$-C$_3$ alkyl, C$_1$-C$_3$ haloalkyl, or halogen; and s is 0, 1, 2, or 3.

19. The compound of claim 18 or a pharmaceutically acceptable salt thereof, wherein
Z is O;
R$^2$ is hydrogen; and
R$^{3a}$ and R$^{3b}$ together with the carbon atom to which they are attached, form an unsubstituted cyclopropyl.

20. The compound of claim 19 or a pharmaceutically acceptable salt thereof, wherein
Y$^1$ is O; and
G$^1$ is

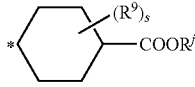

wherein * is the point of connection, R$^j$ is hydrogen or C$_1$-C$_6$ alkyl; R$^9$ is C$_1$-C$_3$ alkyl, C$_1$-C$_3$ haloalkyl, or halogen; and s is 0, 1, 2, or 3.

21. The compound of claim 18 or a pharmaceutically acceptable salt thereof, wherein
Z is O;
R$^2$ is hydrogen; and
R$^{3a}$ and R$^{3b}$ are methyl; or R$^{3a}$ and R$^{3b}$ together with the carbon atom to which they are attached, form a cyclopropyl which is substituted with 1, 2, 3, or 4 substituents independently selected from the group consisting of C$_1$-C$_3$ alkyl, C$_1$-C$_3$ haloalkyl, and halogen.

22. The compound of claim 21 or a pharmaceutically acceptable salt thereof, wherein
G$^1$ is phenyl or cyclohexyl; each of which is substituted with 1, 2, 3, or 4 R$^9$ groups; wherein one of the R$^9$ groups is —OR$^j$ or —C(O)OR$^j$, and the other 1, 2, or 3 optional R$^9$ groups are independently C$_1$-C$_3$ alkyl, halogen, or C$_1$-C$_3$ haloalkyl.

23. The compound of claim 1 of formula (I-a-iii) or a pharmaceutically acceptable salt thereof

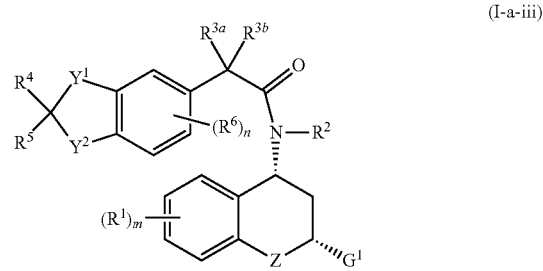

(I-a-iii)

wherein R$^1$, m, G$^1$, R$^{3a}$, R$^{3b}$, R$^6$, and n, are as set forth in claim 1;
Y$^1$ and Y$^2$ are O;
R$^4$ and R$^5$ are hydrogen, or R$^4$ and R$^5$ are halogen;
Z is O; and
R$^2$ is hydrogen;
with the proviso that when R$^{3a}$ and R$^{3b}$ together with the carbon atom to which they are attached form an unsubstituted cyclopropyl, R$^4$ and R$^5$ are halogen, n is 0 or 1, and R$^6$ is halogen, then G$^1$ is optionally substituted pyrimidinyl, optionally substituted pyridazinyl, optionally substituted pyrazinyl, or

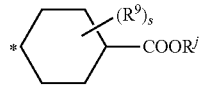

wherein * is the point of connection; R$^9$ is C$_1$-C$_3$ alkyl, C$_1$-C$_3$ haloalkyl, or halogen; and s is 0, 1, 2, or 3.

24. The compound of claim 23 or a pharmaceutically acceptable salt thereof, wherein
R$^{3a}$ and R$^{3b}$ together with the carbon atom to which they are attached, form an unsubstituted cyclopropyl.

25. The compound of claim 24 or a pharmaceutically acceptable salt thereof, wherein
G$^1$ is

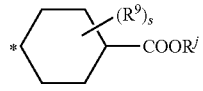

wherein * is the point of connection, $R^j$ is hydrogen or $C_1$-$C_6$ alkyl; $R^9$ is $C_1$-$C_3$ alkyl, $C_1$-$C_3$ haloalkyl, or halogen; and s is 0, 1, 2, or 3.

26. The compound of claim 23 or a pharmaceutically acceptable salt thereof, wherein
$R^{3a}$ and $R^{3b}$ are methyl; or $R^{3a}$ and $R^{3b}$ together with the carbon atom to which they are attached, form a cyclopropyl which is substituted with 1, 2, 3, or 4 substituents independently selected from the group consisting of $C_1$-$C_3$ alkyl, $C_1$-$C_3$ haloalkyl, and halogen.

27. The compound of claim 26 or a pharmaceutically acceptable salt thereof, wherein
$G^1$ is phenyl or cyclohexyl; each of which is substituted with 1, 2, 3, or 4 $R^9$ groups; wherein one of the $R^9$ groups is —C(O)$OR^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl.

28. The compound of claim 1 or a pharmaceutically acceptable salt thereof, wherein the compound is selected from the group consisting of:
4-{(2R,4R)-4-[2-(2,2-difluoro-2H-1,3-benzodioxol-5-yl)-2-methylpropanamido]-7-methoxy-3,4-dihydro-2H-1-benzopyran-2-yl}benzoic acid;
4-[(2R,4R)-4-{[1-(3,4-dichlorophenyl)cyclopropane-1-carbonyl]amino}-7-methoxy-3,4-dihydro-2H-1-benzopyran-2-yl]benzoic acid;
4-[(2R,4R)-7-methoxy-4-({1-[4-(trifluoromethoxy)phenyl]cyclopropane-1-carbonyl}amino)-3,4-dihydro-2H-1-benzopyran-2-yl]benzoic acid;
4-[(2R,4R)-4-{[1-(4-bromophenyl)cyclopropane-1-carbonyl]amino}-7-methoxy-3,4-dihydro-2H-1-benzopyran-2-yl]benzoic acid;
4-[(2R,4R)-7-methoxy-4-({1-[4-(trifluoromethyl)phenyl]cyclopropane-1-carbonyl}amino)-3,4-dihydro-2H-1-benzopyran-2-yl]benzoic acid;
4-[(2R,4R)-7-methoxy-4-{[1-(4-methylphenyl)cyclopropane-1-carbonyl]amino}-3,4-dihydro-2H-1-benzopyran-2-yl]benzoic acid;
ethyl trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylate;
trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylic acid;
ethyl trans-4-[(2R,4R)-4-{[1-(2,2-difluoro-2H-1,3-benzodioxol-5-yl)cyclopropane-1-carbonyl[amino}-7-(trifluoromethoxy)-3,4-dihydro-2H-1-benzopyran-2-yl]cyclohexane-1-carboxylate;
trans-4-[(2R,4R)-4-{[1-(2,2-difluoro-2H-1,3-benzodioxol-5-yl)cyclopropane-1carbonyl]amino}-7-(trifluoromethoxy)-3,4-dihydro-2H-1-benzopyran-2-yl]cyclohexane-1-carboxylic acid;
methyl cis-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylate;
methyl trans-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylate;
cis-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylic acid;
trans-4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylic acid;
N-[2-(3,4-dimethoxyphenyl)-7-methoxy-3,4-dihydro-2H-1-benzopyran-4-yl]-3,3-difluoro-1-phenylcyclobutane-1-carboxamide;
1-(3,4-difluorophenyl)-N-[2-(3,4-dimethoxyphenyl)-7-methoxy-3,4-dihydro-2H-1-benzopyran-4-yl]cyclobutane-1-carboxamide;
2-(4-chlorophenoxy)-N-[2-(3,4-dimethoxyphenyl)-7-methoxy-3,4-dihydro-2H-1-benzopyran-4-yl]-2-methylpropanamide;
N-[2-(3,4-dimethoxyphenyl)-7-methoxy-3,4-dihydro-2H-1-benzopyran-4-yl]-1-(3-fluorophenyl)cyclopropane-1-carboxamide;
N-[2-(3,4-dimethoxyphenyl)-7-methoxy-3,4-dihydro-2H-1-benzopyran-4-yl]-1-(4-fluorophenyl)cyclopropane-1-carboxamide;
1-(4-chlorophenyl)-N-[2-(3,4-dimethoxyphenyl)-7-methoxy-3,4-dihydro-2H-1-benzopyran-4-yl]cyclopropane-1-carboxamide;
2-(4-chlorophenyl)-N-[2-(3,4-dimethoxyphenyl)-7-methoxy-3,4-dihydro-2H-1-benzopyran-4-yl]-2-methylpropanamide;
N-[2-(3,4-dimethoxyphenyl)-7-methoxy-3,4-dihydro-2H-1-benzopyran-4-yl]-2-(4-methoxyphenyl)-2-methylpropanamide;
3-{(2R,4S)-7-methoxy-4-[2-(4-methoxyphenyl)-2-methylpropanamido]-3,4-dihydro-2H-1-benzopyran-2-yl}benzoic acid;
3-{(2R,4R)-7-methoxy-4-[2-(4-methoxyphenyl)-2-methylpropanamido]-3,4-dihydro-2H-1-benzopyran-2-yl}benzoic acid;
3-[(2R,4R)-7-methoxy-4-{2-methyl-2-[4-(2-methylpropoxy)phenyl]propanamido}-3,4-dihydro-2H-1-benzopyran-2-yl]benzoic acid;
3-{(2R,4R)-4-[2-(2H-1,3-benzodioxol-5-yl)-2-methylpropanamido]-7-methoxy-3,4-dihydro-2H-1-benzopyran-2-yl}benzoic acid;
3-{(2R,4R)-4-[2-(2,3-dihydro-1,4-benzodioxin-6-yl)-2-methylpropanamido]-7-methoxy-3,4-dihydro-2H-1-benzopyran-2-yl}benzoic acid;
3-[(2R,4R)-7-methoxy-4-{2-methyl-2-[4-(trifluoromethoxy)phenyl]propanamido}-3,4-dihydro-2H-1-benzopyran-2-yl]benzoic acid;
3-[(2R,4R)-7-methoxy-4-({1-[4-(trifluoromethoxy)phenyl]cyclopropane-1-carbonyl}amino)-3,4-dihydro-2H-1-benzopyran-2-yl]benzoic acid;
3-[(2R,4R)-4-{[1-(4-chlorophenyl)cyclopropane-1-carbonyl]amino}-7-methoxy-3,4-dihydro-2H-1-benzopyran-2-yl]benzoic acid;
3-[(2R,4R)-4-{[1-(4-bromophenyl)cyclopropane-1-carbonyl]amino}-7-methoxy-3,4-dihydro-2H-1-benzopyran-2-yl]benzoic acid;
3-[(2R,4R)-7-methoxy-4-{[1-(4-methoxyphenyl)cyclopropane-1-carbonyl]amino}-3,4-dihydro-2H-1-benzopyran-2-yl]benzoic acid;
3-{(2R,4R)-4-[2-(4-chlorophenoxy)-2-methylpropanamido]-7-methoxy-3,4-dihydro-2H-1-benzopyran-2-yl}benzoic acid;
3-{(2R,4R)-4-[2-methyl-2-(2-methylphenyl)propanamido]-3,4-dihydro-2H-1-benzopyran-2-yl}benzoic acid;
3-[(2R,4R)-4-{2-methyl-2-[4-(trifluoromethyl)phenyl]propanamido}-3,4-dihydro-2H-1-benzopyran-2-yl]benzoic acid;

3-{(2R,4R)-4-[2-(2,4-dichlorophenyl)-2-methylpropanamido]-3,4-dihydro-2H-1-benzopyran-2-yl}benzoic acid;
4-[(2R,4R)-7-methoxy-4-({1-[4-(trifluoromethoxy)phenyl]cyclobutane-1-carbonyl}amino)-3,4-dihydro-2H-1-benzopyran-2-yl]benzoic acid;
4-{(2R,4R)-4-[2-(2,3-dihydro-1-benzofuran-5-yl)-2-methylpropanamido]-7-methoxy-3,4-dihydro-2H-1-benzopyran-2-yl}benzoic acid;
4-{(2R,4R)-4-[(3,3-difluoro-1-phenylcyclobutane-1-carbonyl)amino]-7-methoxy-3,4-dihydro-2H-1-benzopyran-2-yl}benzoic acid;
4-{(2R,4R)-4-[2-(3-chlorophenoxy)-2-methylpropanamido]-7-methoxy-3,4-dihydro-2H-1-benzopyran-2-yl}benzoic acid;
4-[(2R,4R)-7-methoxy-4-{[1-(4-methoxyphenyl)cyclopropane-1-carbonyl]amino}-3,4-dihydro-2H-1-benzopyran-2-yl]benzoic acid;
4-{(2R,4R)-7-methoxy-4-[(1-phenylcyclopropane-1-carbonyl)amino]-3,4-dihydro-2H-1-benzopyran-2-yl}benzoic acid;
4-[(2R,4R)-4-{[1-(4-chlorophenyl)cyclobutane-1-carbonyl]amino}-7-methoxy-3,4-dihydro-2H-1-benzopyran-2-yl]benzoic acid;
4-{(2R,4R)-4-[2-(4-chloro-3-methylphenoxy)-2-methylpropanamido]-7-methoxy-3,4-dihydro-2H-1-benzopyran-2-yl}benzoic acid;
4-[(2R,4R)-7-methoxy-4-{2-methyl-2-[3-(trifluoromethyl)phenoxy]propanamido}-3,4-dihydro-2H-1-benzopyran-2-yl]benzoic acid;
4-[(2R,4R)-4-(2-ethyl-2-phenylbutanamido)-7-methoxy-3,4-dihydro-2H-1-benzopyran-2-yl]benzoic acid;
4-{(2R,4R)-4-[(3,3-difluoro-1-phenylcyclopentane-1-carbonyl)amino]-7-methoxy-3,4-dihydro-2H-1-benzopyran-2-yl}benzoic acid;
4-[(2R,4R)-4-{[1-(3,4-difluorophenyl)cyclobutane-1-carbonyl]amino}-7-methoxy-3,4-dihydro-2H-1-benzopyran-2-yl]benzoic acid;
4-[(2R,4R)-7-methoxy-4-({1-[2-(trifluoromethyl)phenyl]cyclobutane-1-carbonyl}amino)-3,4-dihydro-2H-1-benzopyran-2-yl]benzoic acid;
4-[(2R,4R)-7-methoxy-4-({1-[3-(trifluoromethoxy)phenyl]cyclobutane-1-carbonyl}amino)-3,4-dihydro-2H-1-benzopyran-2-yl]benzoic acid;
4-[(2R,4R)-4-{[1-(4-fluorophenyl)cyclopropane-1-carbonyl]amino}-7-methoxy-3,4-dihydro-2H-1-benzopyran-2-yl]benzoic acid;
4-[(2R,4R)-4-{[1-(3-fluorophenyl)cyclopropane-1-carbonyl]amino}-7-methoxy-3,4-dihydro-2H-1-benzopyran-2-yl]benzoic acid;
4-[(2R,4R)-7-methoxy-4-{[1-(3-methoxy-4-methylphenyl)cyclopropane-1-carbonyl]amino}-3,4-dihydro-2H-1-benzopyran-2-yl]benzoic acid;
4-[(2R,4R)-4-{[1-(3-cyanophenyl)cyclopropane-1-carbonyl]amino}-7-methoxy-3,4-dihydro-2H-1-benzopyran-2-yl]benzoic acid;
4-[(2R,4R)-4-{[1-(3-bromophenyl)cyclopropane-1-carbonyl]amino}-7-methoxy-3,4-dihydro-2H-1-benzopyran-2-yl]benzoic acid;
4-[(2R,4R)-4-{[1-(2-bromophenyl)cyclopropane-1-carbonyl]amino}-7-methoxy-3,4-dihydro-2H-1-benzopyran-2-yl]benzoic acid;
4-[(2R,4R)-4-{[1-(3-fluorophenyl)cyclopentane-1-carbonyl]amino}-7-methoxy-3,4-dihydro-2H-1-benzopyran-2-yl]benzoic acid;
4-[(2R,4R)-4-{[1-(2-fluorophenyl)cyclopentane-1-carbonyl]amino}-7-methoxy-3,4-dihydro-2H-1-benzopyran-2-yl]benzoic acid;
4-[(2R,4R)-4-{[1-(4-cyanophenyl)cyclopropane-1-carbonyl]amino}-7-methoxy-3,4-dihydro-2H-1-benzopyran-2-yl]benzoic acid;
4-[(2R,4R)-4-{[1-(4-fluorophenyl)cyclopentane-1-carbonyl]amino}-7-methoxy-3,4-dihydro-2H-1-benzopyran-2-yl]benzoic acid;
4-[(2R,4R)-4-{[1-(2-bromophenyl)cyclobutane-1-carbonyl]amino}-7-methoxy-3,4-dihydro-2H-1-benzopyran-2-yl]benzoic acid;
4-[(2R,4R)-4-{[1-(3,4-dichlorophenyl)cyclobutane-1-carbonyl]amino}-7-methoxy-3,4-dihydro-2H-1-benzopyran-2-yl]benzoic acid;
4-[(2R,4R)-4-{[1-(2-chlorophenyl)cyclobutane-1-carbonyl]amino}-7-methoxy-3,4-dihydro-2H-1-benzopyran-2-yl]benzoic acid;
4-{(2R,4R)-7-methoxy-4-[(1-phenylcyclopentane-1-carbonyl)amino]-3,4-dihydro-2H-1-benzopyran-2-yl}benzoic acid;
4-[(2R,4R)-4-{[1-(4-chlorophenyl)cyclopentane-1-carbonyl]amino}-7-methoxy-3,4-dihydro-2H-1-benzopyran-2-yl]benzoic acid;
4-[(2R,4R)-4-{2-[(2H-1,3-benzodioxol-5-yl)oxy]-2-methylpropanamido}-7-methoxy-3,4-dihydro-2H-1-benzopyran-2-yl]benzoic acid;
4-[(2R,4R)-4-{[1-(3-chlorophenyl)cyclopropane-1-carbonyl]amino}-7-methoxy-3,4-dihydro-2H-1-benzopyran-2-yl]benzoic acid;
4-{(2R,4R)-7-methoxy-4-[(1-phenylcyclobutane-1-carbonyl)amino]-3,4-dihydro-2H-1-benzopyran-2-yl}benzoic acid;
4-[(2R,4R)-7-methoxy-4-{[1-(2-methoxyphenyl)cyclopropane-1-carbonyl]amino}-3,4-dihydro-2H-1-benzopyran-2-yl]benzoic acid;
4-[(2R,4R)-4-{[1-(4-bromophenyl)cyclobutane-1-carbonyl]amino}-7-methoxy-3,4-dihydro-2H-1-benzopyran-2-yl]benzoic acid;
4-{(2R,4R)-4-[(2,2-difluoro-1-phenylcyclopropane-1-carbonyl)amino]-7-methoxy-3,4-dihydro-2H-1-benzopyran-2-yl}benzoic acid;
4-[(2R,4R)-4-{[1-(2-fluorophenyl)cyclopropane-1-carbonyl]amino}-7-methoxy-3,4-dihydro-2H-1-benzopyran-2-yl]benzoic acid;
4-{(2R,4R)-4-[2-(4-cyanophenoxy)-2-methylpropanamido]-7-methoxy-3,4-dihydro-2H-1-benzopyran-2-yl}benzoic acid;
4-[(2R,4R)-4-{[1-(4-chlorophenyl)cyclopropane-1-carbonyl]amino}-7-methoxy-3,4-dihydro-2H-1-benzopyran-2-yl]benzoic acid;
4-[(2R,4R)-7-methoxy-4-{2-methyl-2-[4-(trifluoromethoxy)phenyl]propanamido}-3,4-dihydro-2H-1-benzopyran-2-yl]benzoic acid;
4-{(2R,4R)-4-[2-(4-chlorophenyl)-2-methylpropanamido]-7-methoxy-3,4-dihydro-2H-1-benzopyran-2-yl}benzoic acid;
4-{(2R,4R)-4-[2-(4-fluorophenyl)-2-methylpropanamido]-7-methoxy-3,4-dihydro-2H-1-benzopyran-2-yl}benzoic acid;
4-{(2R,4R)-4-[2-(2,3-dihydro-1,4-benzodioxin-6-yl)-2-methylpropanamido]-7-methoxy-3,4-dihydro-2H-1-benzopyran-2-yl}benzoic acid;
4-{(2R,4R)-4-[2-(3-fluoro-4-methoxyphenyl)-2-methylpropanamido]-7-methoxy-3,4-dihydro-2H-1-benzopyran-2-yl}benzoic acid;

4-[(2R,4R)-7-methoxy-4-{[1-(4-methoxyphenyl)cyclopentane-1-carbonyl]amino}-3,4-dihydro-2H-1-benzopyran-2-yl]benzoic acid;

4-[(2R,4R)-7-methoxy-4-{[1-(4-methoxyphenyl)cyclobutane-1-carbonyl]amino}-3,4-dihydro-2H-1-benzopyran-2-yl]benzoic acid;

4-[(2R,4R)-4-{[1-(3,4-dimethoxyphenyl)cyclobutane-1-carbonyl]amino}-7-methoxy-3,4-dihydro-2H-1-benzopyran-2-yl]benzoic acid;

4-{(2R,4R)-4-[2-(2-fluoro-4-methoxyphenyl)-2-methylpropanamido]-7-methoxy-3,4-dihydro-2H-1-benzopyran-2-yl}benzoic acid;

4-{(2R,4R)-4-[2-(4-fluorophenoxy)-2-methylpropanamido]-7-methoxy-3,4-dihydro-2H-1-benzopyran-2-yl}benzoic acid;

4-{(2R,4R)-4-[2-(4-chlorophenoxy)-2-methylpropanamido]-7-methoxy-3,4-dihydro-2H-1-benzopyran-2-yl}benzoic acid;

4-{(2R,4R)-4-[2-(2H-1,3-benzodioxol-5-yl)-2-methylpropanamido]-7-methoxy-3,4-dihydro-2H-1-benzopyran-2-yl}benzoic acid;

4-{(2R,4R)-7-methoxy-4-[2-(4-methoxyphenyl)-2-methylpropanamido]-3,4-dihydro-2H-1-benzopyran-2-yl}benzoic acid.

29. A pharmaceutical composition comprising a therapeutically effective amount of a compound of claim 1, or a pharmaceutically acceptable salt thereof, in combination with a pharmaceutically acceptable carrier.

30. A compound of claim 1 or a pharmaceutically acceptable salt thereof, or a pharmaceutical composition of claim 29, for use in medicine.

31. A compound of claim 1 or a pharmaceutically acceptable salt thereof, or a pharmaceutical composition of claim 29, for use in the treatment of cystic fibrosis.

32. A pharmaceutical composition comprising a compound of claim 1 or a pharmaceutically acceptable salt thereof, one potentiator, and one or more additional correctors.

33. A pharmaceutical composition comprising a compound of claim 1 or a pharmaceutically acceptable salt thereof, and one or more additional therapeutic agents.

34. The pharmaceutical composition of claim 33 wherein the additional therapeutic agents are selected from the group consisting of CFTR modulators and CFTR amplifiers.

35. The pharmaceutical composition of claim 33 wherein the additional therapeutic agents are CFTR modulators.

36. A compound of formula (I) or a pharmaceutically acceptable salt thereof

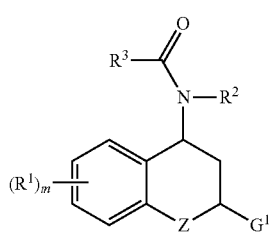

wherein
Z is O;
$R^1$ groups are optional substituents on the benzo ring, and are each independently halogen, —CN, $C_1$-$C_3$ alkyl, $C_1$-$C_3$ haloalkyl, —$OR^j$, or —$SR^j$;
m is 0, 1, 2, 3, or 4;

$R^2$ is hydrogen or $C_1$-$C_3$ alkyl;
$R^3$ is formula (c)

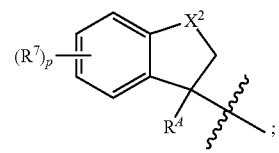

wherein
$X^2$ is O or $CH_2$;
$R^4$ is $C_1$-$C_3$ alkyl;
$R^7$ groups are optional substituents on the benzo ring, and are each independently halogen, —CN, $C_1$-$C_6$ alkyl, $C_1$-$C_6$ haloalkyl, —$OR^j$, or —$SR^j$; and
p is 0, 1, 2, 3, or 4;

$G^1$ is phenyl, monocyclic heteroaryl, or $C_3$-$C_6$ cycloalkyl; wherein each $G^1$ is optionally substituted with 1, 2, 3, or 4 $R^9$ groups;

each $R^9$ is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, k —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$ alkylenyl)—$OR^j$, —($C_1$-$C_6$ alkylenyl)—$OC(O)R^k$, —($C_1$-$C_6$ alkylenyl)—$OC(O)N(R^j)_2$, —($C_1$-$C_6$ alkylenyl)—$SR^j$, —($C_1$-$C_6$ alkylenyl)—$S(O)_2R^j$, —($C_1$-$C_6$ alkylenyl)—$S(O)_2N(R^j)_2$, —($C_1$-$C_6$ alkylenyl)—$C(O)R^j$, —($C_1$-$C_6$ alkylenyl)-$C(O)OR^j$, —($C_1$-$C_6$ alkylenyl)—$C(O)N(R^j)_2$, —($C_1$-$C_6$ alkylenyl)—$C(O)N(R^j)S(O)_2R^k$, —($C_1$-$C_6$ alkylenyl)—$N(R^j)_2$, —($C_1$-$C_6$ alkylenyl)—$N(R^j)C(O)R^k$, —($C_1$-$C_6$ alkylenyl)—$N(R^j)S(O)_2R^k$, —($C_1$-$C_6$ alkylenyl)—$N(R^j)C(O)O(R^k)$, —($C_1$-$C_6$ alkylenyl)—$N(R^j)C(O)N(R^j)_2$, or —($C_1$-$C_6$ alkylenyl)—CN;

$R^j$, at each occurrence, is independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl;

with the proviso that when $R^2$ is hydrogen, Z is O, $R^3$ is formula (a), $R^{3a}$ and $R^{3b}$ together with the carbon atom to which they are attached form an unsubstituted cyclopropyl, and $G^2$ is formula (b) wherein $Y^1$ is O, $R^4$ and $R^5$ are halogen, $X^1$ is a bond, n is 0 or 1, and $R^6$ is halogen; then $G^1$ is optionally substituted pyrimidinyl, optionally substituted pyridazinyl, optionally substituted pyrazinyl, or

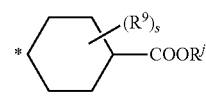

wherein * is the point of connection, $R^9$ is $C_1$-$C_3$ alkyl, $C_1$-$C_3$ haloalkyl, or halogen; and s is 0, 1, 2, or 3.

37. A compound of formula (I) or a pharmaceutically acceptable salt thereof

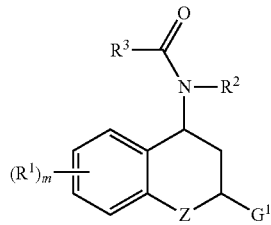

(I)

wherein
Z is O;
$R^1$ groups are optional substituents on the benzo ring, and are each independently halogen, —CN, $C_1$-$C_3$ alkyl, $C_1$-$C_3$ haloalkyl, —$OR^j$, or —$SR^j$;
m is 0, 1, 2, 3, or 4;
$R^2$ is hydrogen or $C_1$-$C_3$ alkyl;
$R^3$ is formula (d)

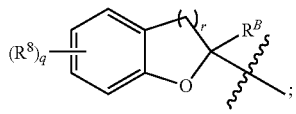

(d)

wherein
r is 1 or 2;
q is 0, 1, 2, 3, or 4;
$R^B$ is $C_1$-$C_3$ alkyl;
$R^8$ groups are optional substituents on the benzo ring, and are each independently halogen, —CN, $C_1$-$C_6$ alkyl, $C_1$-$C_6$ haloalkyl, —$OR^j$, or —$SR^j$;
$G^1$ is phenyl, monocyclic heteroaryl, or $C_3$-$C_6$ cycloalkyl; wherein each $G^1$ is optionally substituted with 1, 2, 3, or 4 $R^9$ groups;
each $R^9$ is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$ alkylenyl)—$OR^j$, —($C_1$-$C_6$ alkylenyl)—$OC(O)R^k$, —($C_1$-$C_6$ alkylenyl)—$OC(O)N(R^j)_2$, —($C_1$-$C_6$ alkylenyl)—$SR^j$, —($C^1$$C_6$ alkylenyl)—$S(O)_2R^j$, —($C_1$-$C_6$ alkylenyl)—$S(O)_2N(R^j)_2$, —($C_1$-$C_6$ alkylenyl)—$C(O)R^j$, —($C_1$-$C_6$ alkylenyl)—$C(O)OR^j$, —($C_1$-$C_6$ alkylenyl)—$C(O)N(R^j)_2$, —($C_1$-$C_6$ alkylenyl)—$C(O)N(R)S(O)_2R^k$, —($C_1$-$C_6$ alkylenyl)—$N(R^j)_2$, —($C_1$-$C_6$ alkylenyl)—$N(R^j)C(O)R^k$, —($C_1$-$C_6$ alkylenyl)—$N(R^j)S(O)_2R^k$, —($C_1$-$C_6$ alkylenyl)—$N(R^j)C(O)O(R^k)$, —($C_1$-$C_6$ alkylenyl)—$N(R^j)C(O)N(R^j)_2$, or —($C_1$-$C_6$ alkylenyl)—CN;
$R^j$, at each occurrence, is independently hydrogen, $C_1$-$C_6$ alkyl, or $C_1$-$C_6$ haloalkyl; and
$R^k$, at each occurrence, is independently $C_1$-$C_6$ alkyl or $C_1$-$C_6$ haloalkyl;
with the proviso that when $R^2$ is hydrogen, Z is O, $R^3$ is formula (a), $R^{3a}$ and $R^{3b}$ together with the carbon atom to which they are attached form an unsubstituted cyclopropyl, and $G^2$ is formula (b) wherein $Y^1$ is O, $R^4$ and $R^5$ are halogen, $X^1$ is a bond, n is 0 or 1, and $R^6$ is halogen; then $G^1$ is optionally substituted pyrimidinyl, optionally substituted pyridazinyl, optionally substituted pyrazinyl, or

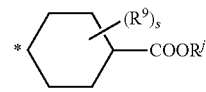

wherein * is the point of connection, $R^9$ is $C_1$-$C_3$ alkyl, $C_1$-$C_3$ haloalkyl, or halogen; and s is 0, 1, 2, or 3.

38. The compound of claim 36 or a pharmaceutically acceptable salt thereof, wherein the compound is selected from the group consisting of:
4-{(2R,4R)-4-[(1,5-dimethyl-2,3-dihydro-1H-indene-1-carbonyl)amino]-7-methoxy-3,4-dihydro-2H-1-benzopyran-2-yl}benzoic acid;
3-[(2R, 4R)-4-{[(1S)-1,5-dimethyl-2,3-dihydro-1H-indene-1-carbonyl]amino}-7-methoxy-3,4-dihydro-2H-1-benzopyran-2-yl]benzoic acid;
4-[(2R,4R)-4-{[(1S)-1,5-dimethyl-2,3-dihydro-1H-indene-1-carbonyl]amino}-7-methoxy-3,4-dihydro-2H-1-benzopyran-2-yl]benzoic acid;
3-[(2R, 4R)-4-{ [(2R)-5-chloro-2-methyl-2,3-dihydro-1-benzofuran-2-carbonyl]amino}-3,4-dihydro-2H-1-benzopyran-2-yl]benzoic acid;
3-[(2R, 4R)-4-{[(2S)-5-chloro-2-methyl-2,3-dihydro-1-benzofuran-2-carbonyl]amino}-3,4-dihydro-2H-1-benzopyran-2-yl]benzoic acid;
methyl 3-[(2R,4R)-4-{[(1R)-5-methoxy-1-methyl-2,3-dihydro-1H-indene-1-carbonyl]amino}-3,4-dihydro-2H-1-benzopyran-2-yl]benzoate;
methyl 3-[(2R,4R)-7-methoxy-4-{[(1R)-5-methoxy-1-methyl-2,3-dihydro-1H-indene-1-carbonyl]amino}-3,4-dihydro-2H-1-benzopyran-2-ylThenzoate;
methyl 3-[(2R,4R)-4-{[(1S)-5-methoxy-1-methyl-2,3-dihydro-1H-indene-1-carbonyl]amino}-3,4-dihydro-2H-1-benzopyran-2-yl]benzoate;
methyl 3-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoate;
3-[(2R,4R)-4-{[(1R)-5-methoxy-1-methyl-2,3-dihydro-1H-indene-1-carbonyl]amino}-3,4-dihydro-2H-1-benzopyran-2-yl]benzoic acid;
3-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoic acid;
3-[(2R,4R)-4-{[(1S)-5-methoxy-1-methyl-2,3-dihydro-1H-indene-1-carbonyl]amino}-3,4-dihydro-2H-1-benzopyran-2-yl]benzoic acid;
3-[(2R,4R)-7-methoxy-4-{[(1S)-5-methoxy-1-methyl-2,3-dihydro-1H-indene-1-carbonyl]amino}-3,4-dihydro-2H-1-benzopyran-2-yl]benzoic acid;
3-{(2R,4R)-4-[(5-chloro-1-methyl-2,3-dihydro-1H-indene-1-carbonyl)amino]-7-methoxy-3,4-dihydro-2H-1-benzopyran-2-yl}benzoic acid;
3-[(2R,4R)-4-{[(1S)-7-methoxy-1-methyl-2,3-dihydro-1H-indene-1-carbonyl]amino}-3,4-dihydro-2H-1-benzopyran-2-yl]benzoic acid;

3-[(2R,4R)-4-{[(1S)-6-methoxy-1-methyl-2,3-dihydro-1H-indene-1-carbonyl]amino}-3,4-dihydro-2H-1-benzopyran-2-yl]benzoic acid;
3-[(2R,4R)-4-{[(1R)-6-methoxy-1-methyl-2,3-dihydro-1H-indene-1-carbonyl]amino}-3,4-dihydro-2H-1-benzopyran-2-yl]benzoic acid;
3-[(2R,4R)-4-{[(1R)-7-methoxy-1-methyl-2,3-dihydro-1H-indene-1-carbonyl]amino}-3,4-dihydro-2H-1-benzopyran-2-yl]benzoic acid;
3-[(2R,4R)-4-{[(1R)-6-chloro-1-methyl-2,3-dihydro-1H-indene-1-carbonyl]amino}-3,4-dihydro-2H-1-benzopyran-2-yl]benzoic acid;
3-[(2R,4R)-4-{[(1S)-6-chloro-1-methyl-2,3-dihydro-1H-indene-1-carbonyl]amino}-3,4-dihydro-2H-1-benzopyran-2-yl]benzoic acid;
3-[(2R,4R)-4-{[1-methyl-5-(trifluoromethoxy)-2,3-dihydro-1H-indene-1-carbonyl]amino}-3,4-dihydro-2H-1-benzopyran-2-yl]benzoic acid;
3-{(2R,4R)-4-[(6-methoxy-3-methyl-2,3-dihydro-1-benzofuran-3-carbonyl)amino]-3,4-dihydro-2H-1-benzopyran-2-yl}benzoic acid;
methyl 3-[(2R,4R)-7-methoxy-4-{[1-methyl-6-(trifluoromethoxy)-2,3-dihydro-1H-indene-1-carbonyl]amino}-3,4-dihydro-2H-1-benzopyran-2-yl]benzoate;
3-[(2R,4R)-7-methoxy-4-{[1-methyl-6-(trifluoromethoxy)-2,3-dihydro-1H-indene-1-carbonyl]amino}-3,4-dihydro-2H-1-benzopyran-2-yl]benzoic acid;
4-[(2R,4R)-7-methoxy-4-{[(1S)-5-methoxy-1-methyl-2,3-dihydro-1H-indene-1carbonyl]amino}-3,4-dihydro-2H-1-benzopyran-2-yl]benzoic acid;
4-[(2R,4R)-7-methoxy-4-{[(1R)-5-methoxy-1-methyl-2,3-dihydro-1H-indene-1-carbonyl]amino}-3,4-dihydro-2H-1-benzopyran-2-yl]benzoic acid;
3-{(2R,4R)-4-[(1,5-dimethyl-2,3-dihydro-1H-indene-1-carbonyl)amino]-7-methoxy-3,4-dihydro-2H-1-benzopyran-2-yl}benzoic acid;
methyl 3-{(2R,4R)-4-[(1,5-dimethyl-2,3-dihydro-1H-indene-1-carbonyl)amino]-7-methoxy-3,4-dihydro-2H-1-benzopyran-2-yl}benzoate;
methyl 4-{(2R,4R)-4-[(1,5-dimethyl-2,3-dihydro-1H-indene-1-carbonyl)amino]-7-methoxy-3,4-dihydro-2H-1-benzopyran-2-yl}benzoate;
3-[(2R,4R)-4-{[(1R)-1,5-dimethyl-2,3-dihydro-1H-indene-1-carbonyl]amino}-7-methoxy-3,4-dihydro-2H-1-benzopyran-2-yl]benzoic acid; and
4-[(2R,4R)-4-{[(1R)-1,5-dimethyl-2,3-dihydro-1H-indene-1-carbonyl]amino}-7-methoxy-3,4-dihydro-2H-1-benzopyran-2-yl]benzoic acid.

39. The compound of claim 37 or a pharmaceutically acceptable salt thereof, wherein the compound is selected from the group consisting of:
methyl 4-[(2R,4R)-4-{[(2R)-6-chloro-2-methyl-3,4-dihydro-2H-1-benzopyran-2-carbonyl]amino}-3,4-dihydro-2H-1-benzopyran-2-yl]benzoate;
4-[(2R, 4R)-4-{[(2R)-6-chloro-2-methyl-3,4-dihydro-2H-1-benzopyran-2-carbonyl]amino}-3,4-dihydro-2H-1-benzopyran-2-yl]benzoic acid;
methyl 4-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoate;
4-[(2R, 4R)-4-{[(2S)-6-chloro-2-methyl-3,4-dihydro-2H-1-benzopyran-2-carbonyl]amino}-3,4-dihydro-2H-1-benzopyran-2-yl]benzoic acid;
methyl 3-[(2R,4R)-4-{[(2S)-6-chloro-2-methyl-3,4-dihydro-2H-1-benzopyran-2-carbonyl]amino}-3,4-dihydro-2H-1-benzopyran-2-yl]benzoate;
3-[(2R, 4R)-4-{[(2S)-6-chloro-2-methyl-3,4-dihydro-2H-1-benzopyran-2-carbonyl]amino}-3,4-dihydro-2H-1-benzopyran-2-yl]benzoic acid;
3-[(2R,4R)-4-{[(2R)-6-chloro-2-methyl-3,4-dihydro-2H-1-benzopyran-2-carbonyl]amino}-7-methoxy-3,4-dihydro-2H-1-benzopyran-2-yl]benzoic acid;
3-[(2R, 4R)-4-{[(2R)-6-chloro-2-methyl-3,4-dihydro-2H-1-benzopyran-2-carbonyl]amino}-3,4-dihydro-2H-1-benzopyran-2-yl]benzoic acid; and
4-[(2R,4R)-4-{[(2R)-6-chloro-2-methyl-3,4-dihydro-2H-1-benzopyran-2-carbonyl]amino}-7-methoxy-3,4-dihydro-2H-1-benzopyran-2-yl]benzoic acid.

40. The compound of claim 36 of formula (I-c) or a pharmaceutically acceptable salt thereof,

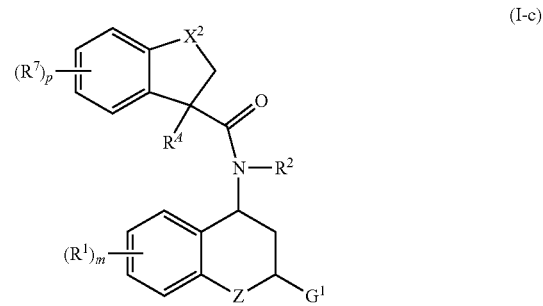

(I-c)

wherein $R^1$, m, Z, $G^1$, $R^2$, $X^2$, $R^A$, $R^7$, and p are as set forth in claim 36.

41. The compound of claim 40 or a pharmaceutically acceptable salt thereof, wherein
Z is O;
$R^2$ is hydrogen; and
$R^A$ is methyl.

42. The compound of claim 41 or a pharmaceutically acceptable salt thereof, wherein
$G^1$ is phenyl, pyridinyl, pyrimidinyl, pyridazinyl, pyrazinyl, thiazolyl, thienyl, cyclopropyl, or cyclohexyl; each of which is optionally substituted with 1, 2, 3, or 4 independently selected $R^9$ groups.

43. The compound of claim 41 or a pharmaceutically acceptable salt thereof, wherein
$G^1$ is phenyl or cyclohexyl; each of which is substituted with 1, 2, 3, or 4 $R^9$ groups; wherein one of the $R^9$ groups is —$OR^j$ or —$C(O)OR^j$, and the other 1, 2, or 3 optional $R^9$ groups are independently $C_1$-$C_3$ alkyl, halogen, or $C_1$-$C_3$ haloalkyl;
m is 0 or 1; and
$R^1$ is —$OR^j$ wherein $R^j$ is $C_1$-$C_6$ alkyl or $C_1$-$C_6$ haloalkyl.

44. The compound of claim 36 of formula (I-c-i) or a pharmaceutically acceptable salt thereof,

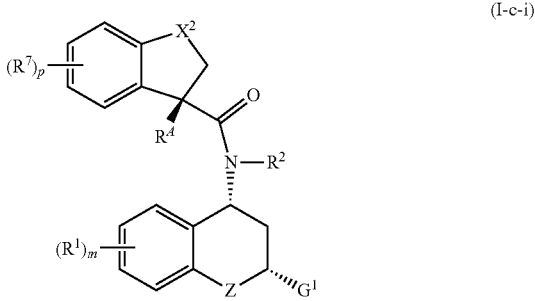

(I-c-i)

wherein $R^1$, m, $G^1$, $X^2$, $R^7$, and p are as set forth in claim 36;

Z is O;

$R^2$ is hydrogen; and $R^A$ is methyl.

45. The compound of claim 44 or a pharmaceutically acceptable salt thereof, wherein $G^1$ is phenyl or cyclohexyl; each of which is substituted with 1, 2, 3, or 4 $R^9$ groups; wherein one of the $R^9$ groups is —C(O)O$R^j$ wherein $R^j$ is hydrogen or $C_1$-$C_6$ alkyl, and the other 1, 2, or 3 optional $R^9$ groups are independently $C_1$-$C_3$ alkyl, halogen, or $C_1$-$C_3$ haloalkyl.

46. The compound of claim 44 or a pharmaceutically acceptable salt thereof, wherein $G^1$ is

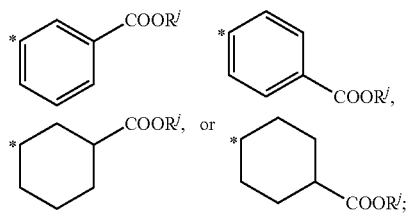

wherein * is the point of connection; and $R^j$ is hydrogen or $C_1$-$C_6$ alkyl;

m is 0 or 1; and $R^1$ is —O$R^j$ wherein $R^j$ is $C_1$-$C_6$ alkyl or $C_1$-$C_6$ haloalkyl.

47. The compound of claim 37 of formula (I-d) or a pharmaceutically acceptable salt thereof,

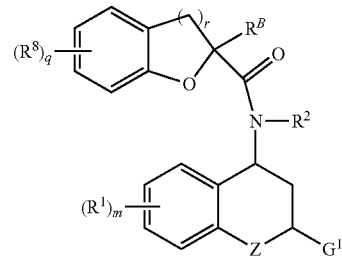

(I-d)

wherein $R^1$, m, Z, $G^1$, $R^2$, $R^B$, $R^8$, q, and r are as set forth in claim 37.

48. The compound of claim 47 or a pharmaceutically acceptable salt thereof, wherein Z is O;

$R^2$ is hydrogen; and $R^B$ is methyl.

49. The compound of claim 48 or a pharmaceutically acceptable salt thereof, wherein $G^1$ is phenyl, pyridinyl, pyrimidinyl, pyridazinyl, pyrazinyl, thiazolyl, thienyl, cyclopropyl, or cyclohexyl; each of which is optionally substituted with 1, 2, 3, or 4 independently selected $R^9$ groups.

50. The compound of claim 48 or a pharmaceutically acceptable salt thereof, wherein $G^1$ is phenyl or cyclohexyl; each of which is substituted with 1, 2, 3, or 4 $R^9$ groups; wherein one of the $R^9$ groups is —O$R^j$ or —C(O)O$R^j$, and the other 1, 2, or 3 optional $R^9$ groups are independently $C_1$-$C_3$ alkyl, halogen, or $C_1$-$C_3$ haloalkyl;

m is 0 or 1; and $R^1$ is —O$R^j$ wherein $R^j$ is $C_1$-$C_6$ alkyl or $C_1$-$C_6$ haloalkyl.

* * * * *